(12) United States Patent
Ohlmeyer et al.

(10) Patent No.: US 9,540,358 B2
(45) Date of Patent: Jan. 10, 2017

(54) TRICYCLIC COMPOUNDS AS ANTICANCER AGENTS

(75) Inventors: Michael Ohlmeyer, Plainsboro, NJ (US); Goutham Narla, Beachwood, OH (US); Neil Dhawan, New York, NY (US); David Kastrinsky, Fair Lawn, NJ (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 136 days.

(21) Appl. No.: 14/238,511

(22) PCT Filed: Aug. 16, 2012

(86) PCT No.: PCT/US2012/051097
§ 371 (c)(1),
(2), (4) Date: Mar. 27, 2014

(87) PCT Pub. No.: WO2013/025882
PCT Pub. Date: Feb. 21, 2013

(65) Prior Publication Data
US 2014/0213578 A1 Jul. 31, 2014

Related U.S. Application Data

(60) Provisional application No. 61/523,897, filed on Aug. 16, 2011.

(51) Int. Cl.
| | | |
|---|---|---|
| *A61K 31/55* | (2006.01) | |
| *C07D 223/26* | (2006.01) | |
| *C07D 223/28* | (2006.01) | |
| *C07D 401/12* | (2006.01) | |
| *C07D 409/12* | (2006.01) | |
| *C07D 417/12* | (2006.01) | |
| *C07D 417/06* | (2006.01) | |
| *C07D 279/28* | (2006.01) | |
| *C07C 311/20* | (2006.01) | |
| *C07D 207/26* | (2006.01) | |
| *C07D 211/76* | (2006.01) | |
| *C07D 307/94* | (2006.01) | |
| *C07D 311/96* | (2006.01) | |
| *C09B 21/00* | (2006.01) | |

(52) U.S. Cl.
CPC ........... *C07D 409/12* (2013.01); *C07C 311/20* (2013.01); *C07D 207/26* (2013.01); *C07D 211/76* (2013.01); *C07D 223/28* (2013.01); *C07D 279/28* (2013.01); *C07D 307/94* (2013.01); *C07D 311/96* (2013.01); *C07D 401/12* (2013.01); *C07D 417/06* (2013.01); *C09B 21/00* (2013.01)

(58) Field of Classification Search
CPC ..... A61K 31/55; C07D 223/26; C07D 223/28; C07D 401/12; C07D 407/12; C07D 409/12; C07D 417/12
USPC ......................... 514/217; 540/589, 591, 592
See application file for complete search history.

(56) References Cited

U.S. PATENT DOCUMENTS

| | | | |
|---|---|---|---|
| 4,668,671 A | 5/1987 | Gribble et al. | |
| 4,882,351 A | 11/1989 | Oshima et al. | |

FOREIGN PATENT DOCUMENTS

| | | |
|---|---|---|
| EP | 0679641 A1 | 11/1995 |
| WO | WO2004052847 A2 | 6/2004 |
| WO | WO2006116157 A3 | 11/2006 |
| WO | WO2006117183 A1 | 11/2006 |

OTHER PUBLICATIONS

PubChemCompound, URL: http://pubchem.ncbi.nlm.nih.gov/search/search.cgi 2013.

(Continued)

*Primary Examiner* — Brenda Coleman
(74) *Attorney, Agent, or Firm* — Heslin, Rothenberg, Farley & Mesiti, P.C.

(57) ABSTRACT

Tricyclic chemical modulators of FOXO transcription factor proteins are disclosed. The compounds are useful to treat cancer, age-onset proteotoxicity, stress-induced depression, inflammation, and acne. The compounds are of the following phenothiazine, dibenzoazepine and annulene and similar genera:

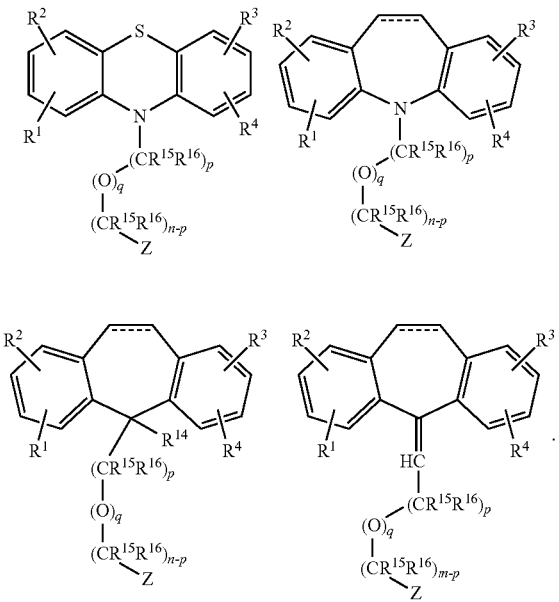

20 Claims, No Drawings

(56) References Cited

OTHER PUBLICATIONS

Cui-Feng Yang et al; "Catalytic decarboxylative alkylation of B-keto acids with sulfonamides via the cleavage of carbon-nitrogen and carbon-carbon bonds," Chemical Communications, 2011 (published on Web: Jun. 22, 2011), vol. 47, No. 29, pp. 8343-8345.
Magnus A. Azuine et al; "Cancer chemopreventive effect of phenothiazines and related tri-heterocyclic analogues in the 12-0-tetradecanoylphorbol-13-acetate promoted Epstein-Barr virus early antigen activation and the mouse skin two-stage carcinogenes is models," Pharmacological Research, 2004, vol. 49, No. 2, pp. 161-169.
Etsuo Ohshima, et al; "Non-Prostanoid Thromboxane $A_2$ Receptor Antagonists with a Dibenzoxepin Ring System. 2" J. Med. Chem, 1992, 35, 3402-3413.
RN 1350122-38-1 CAS Registry Dec. 7, 2011.
International Search Report for PCT/US2012/051097 dated Feb. 20, 2013.
Hadrich, et al., "Synthesis and Characterization of Fluorescent Ligands for the Norepinephrine Transporter: Potential Neuroblastoma Imaging Agents", J. Med. Chem., 1999, (published on web Jul. 16, 1999).
Runyon, et al., "Influence of Chain Length and N-Alkylation on the Selective Serotonin Receptor Ligand 9(Aminomethyl)-9,10-dihydroanthracene", Bioorganic & Medicinal Chemistry Letters 11 (2001), 655-658.
Van Dort, et al., Synthesis of $^{11}$C-Labeled Desipramine and its Metabolite 2-Hydroxydesipramine: Potential Radiotracers for PET Studies of the Norepinephrine Transporter, Nuclear Medicine & Biology, vol. 24, pp. 707-711, 1997.
Ilies, et al., "Protease Inhibitors: Synthesis of Bacterial Collagenase and Matrix Metalloproteinase Inhibitors Incorporating Arylsulfonylureido and 5-Dibenzo-suberenyl/suberyl Moieties", Bioorganic & Medicinal Chemistry, 11 (2003) 2227-2239.
Extended EP Search Report for EP 1223881.3 dated Mar. 3, 2015.
Gunnel Alfredsson et al., "Mass Fragmentographic Analysis of Clomipramine and Its Mono-Demethylated Metabolite in Human Plasma" Psychopharmacology, 52, 25-30 (1977).
I. Midgley et al., "Synthesis of [13$C_2$]-Amitriptyline, Nortriptyline and Desmethylnortriptyline" Journal of Labelled Compounds and Radiopharmaceuticals, vol. XV, p. 511-521 (1978).

TRICYCLIC COMPOUNDS AS ANTICANCER AGENTS

CROSS REFERENCE TO RELATED APPLICATIONS

This application is a national phase filing under 35 U.S.C. §371 of PCT International Application PCT/US2012/051097, filed Aug. 16, 2012, and published under PCT Article 21(2) in English as WO 2013/025882 on Feb. 21, 2013. PCT/US2012/051097 claims priority from U.S. provisional application 61/523,897, filed Aug. 16, 2011, the entire contents of which are incorporated herein by reference.

FIELD OF THE INVENTION

The invention relates to the use of tricyclic chemical modulators of FOXO transcription factor proteins to treat cancer, age-onset proteotoxicity, stress-induced, depression, inflammation, and acne.

BACKGROUND

The FOXO (Forkhead transcription factors, Class O) proteins are a group of transcription factors involved in control of a variety of physiological, metabolic and developmental pathways. They are downstream effectors in a number of signaling pathways including insulin and growth factor signaling; they are also regulated by oxidative stress and nutrient deprivation. Cellular processes affected by FOXO activity include cell cycle control, differentiation, proliferation and apoptosis. Disregulation of FOXO mediated processes has been implicated in a number of pathologies including tumorigenesis, inflammation, diabetes and neurodegenerative conditions amongst others. Activity of FOXO transcription factors are controlled in part by their sub-cellular localization, in particular their localization to the nucleus from the cytosol, and their subsequent transcriptional activation.

Four FOXO proteins designated FOXO1, FOXO3a, FOXO4 and FOXO6 are present in human cells and their activity is controlled by a variety of mechanisms including stability (proteolytic cleavage), sub-cellular localization and transcriptional activation. Activity of the first three members of the family, and in particular FOXO1, is controlled by cytosolic-nuclear translocation with nuclear FOXO1 exerting its actions either directly by transcriptional activation of its target genes or indirectly by interaction with other nuclear transcription factors.

The compounds described herein, which are based on tricyclic scaffolds, exhibit anti-proliferative effects and are useful as monotherapy in cancer treatment. Additionally, they can be used in combination with other drugs to restore sensitivity to chemotherapy where resistance has developed.

SUMMARY OF THE INVENTION

A genus of tricyclics has now been found that induce FOXO1 transcription factor translocation to the nucleus. The compounds described herein also retain anti-proliferative effects, but have significantly reduced dopamine binding and are thus likely to have reduced GPCR mediated CNS and CV side effects. These agents are useful in the treatment of a variety of disorders, including as a monotherapy in cancer treatment, or used in combination with other drugs to restore sensitivity to chemotherapy where resistance has developed.

In a first aspect the invention relates to compounds of formula (I):

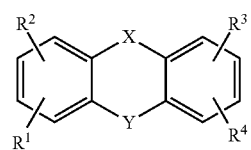

wherein:
X is selected from the group consisting of: —S—, —(CH$_2$—CH$_2$)—, and —CH=CH—;
Y is selected from the group consisting of:

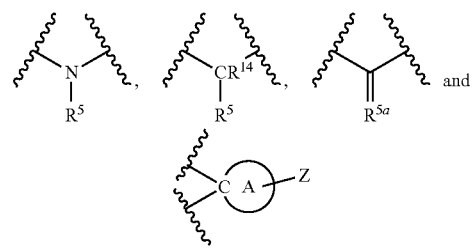

A is a three to six membered aliphatic carbocycle or heterocycle attached at Y as a spiro ring, and A may be additionally substituted with one or two substituents chosen from OH, F, cyano, amino, (C$_1$-C$_3$)alkylamino, (C$_1$-C$_3$)dialkylamino, (C$_1$-C$_3$)alkyl, (C$_1$-C$_3$)haloalkyl, (C$_1$-C$_3$)haloalkoxy, and (C$_1$-C$_3$)alkoxy;

R$^1$, R$^2$, R$^3$, and R$^4$ are independently selected from the group consisting of: H, halo, —N$_3$, —NR$^6$R$^7$, (C$_1$-C$_6$)alkyl, (C$_1$-C$_6$)haloalkyl, —OR$^6$, —C(O)R$^6$, —OC(O)R$^6$, —C(O)NR$^6$R$^7$, —C(O)OR$^6$, —SR$^6$, —SO$_2$R$^6$, and —SO$_2$NR$^6$R$^7$;

R$^5$ is —(CR$^{15}$R$^{16}$)$_p$-Q$_q$(CR$^{15}$R$^{16}$)$_{n-p}$—Z or

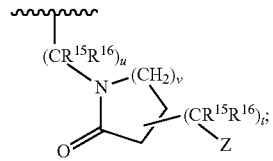

R$^{5a}$ is =CR$^{14}$(CR$^{15}$R$^{16}$)$_p$-Q$_q$-(CR$^{15}$R$^{16}$)$_{m-p}$—Z;
Q is chosen from —O—, —NR$^{14}$— and

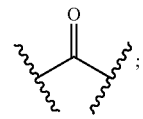

each R$^6$ and R$^7$ is independently selected from the group consisting of: H and (C$_1$-C$_6$)alkyl;
R$^{14}$ is H or (C$_1$-C$_3$)alkyl;
R$^{15}$ and R$^{16}$, in each occurrence are chosen independently from H, OH, cyano, amino, (C$_1$-C$_3$)alkylamino, (C$_1$-

C$_3$)dialkylamino, (C$_1$-C$_3$)alkyl, (C$_1$-C$_3$)haloalkyl, (C$_1$-C$_3$)haloalkoxy, and (C$_1$-C$_3$)alkoxy, or, taken together, two of R$^{14}$, R$^{15}$ and R$^{16}$ may form a three to seven membered carbocycle or heterocycle wherein said three to seven membered carbocycle or heterocycle may be additionally substituted with one or two substituents chosen from OH, F, cyano, amino, (C$_1$-C$_3$)alkylamino, (C$_1$-C$_3$)dialkylamino, (C$_1$-C$_3$)alkyl, (C$_1$-C$_3$)haloalkyl, (C$_1$-C$_3$)haloalkoxy, and (C$_1$-C$_3$)alkoxy;

m is an integer from 1 to 3;
n is an integer from 2 to 4;
p is zero, 1 or 2;
q is zero or 1;
t is zero, 1 or 2;
u is zero, 1 or 2, with the proviso that when Y is

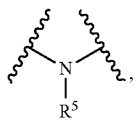

u is 2;
v is 1, 2 or 3;
with the proviso that when q is zero and R$^{15}$ and R$^{16}$, in all of their occurrences are H, n is not 4;
Z is selected from the group consisting of: —NHSO$_2$R$^{17}$, —NHC(O)NR$^8$R$^9$, —NHC(O)OR$^8$, —S(O)$_2$NR$^8$R$^9$, substituted or unsubstituted cyclic carbamate; substituted or unsubstituted cyclic urea, cyclic imide, cyanoguanidine;
R$^8$ and R$^9$ are independently selected from H, substituted or unsubstituted (C$_1$-C$_6$)alkyl, and substituted or unsubstituted (C$_3$-C$_7$) cycloalkyl; and
R$^{17}$ is chosen from phenyl and monocyclic heteroaryl, said phenyl and monocyclic heteroaryl optionally substituted with one or two substituents chosen from OH, halogen, cyano, nitro, (C$_1$-C$_3$)alkylamino, (C$_1$-C$_3$)dialkylamino, (C$_1$-C$_3$)acylamino, (C$_1$-C$_3$)alkylsulfonyl, (C$_1$-C$_3$)alkylthio, (C$_1$-C$_3$)alkyl, (C$_1$-C$_3$)haloalkyl, (C$_1$-C$_3$)haloalkoxy, and (C$_1$-C$_3$)alkoxy.

In a second aspect, the invention relates to methods and uses of the above-described compounds in medicine, particularly for the treatment of a disease chosen from: (a) cancer; (b) diabetes; (c) autoimmune disease; (d) age onset proteotoxic disease; (e) mood disorder; (f) acne vulgaris; (g) solid organ transplant rejection; (h) graft vs host disease; and (i) cardiac hypertrophy.

In a third aspect, the invention relates to pharmaceutical compositions comprising the above-described compounds.

DETAILED DESCRIPTION OF THE INVENTION

Substituents are generally defined when introduced and retain that definition throughout the specification and in all independent claims.

In a composition aspect, the invention relates to compounds of formula (I):

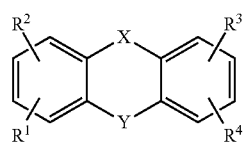

as described above. Subgenera of the formula I include the following:

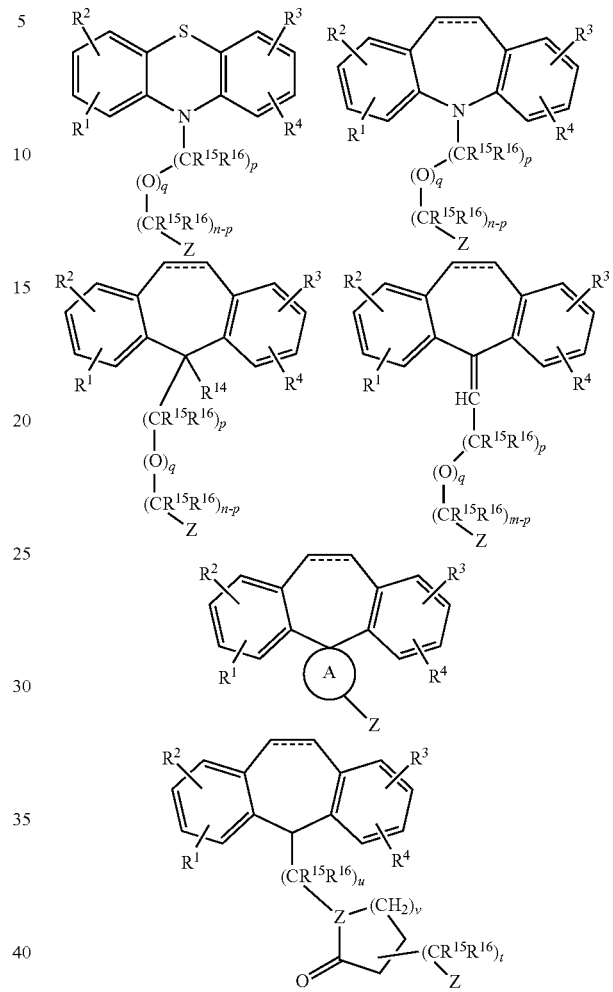

in which the dashed line represents an optional double bond.

In some subgenera, Z is selected from —NHSO$_2$R$^{17}$, —NHC(O)NR$^8$R$^9$, and —NHC(O)OR$^8$.

In the subgenus in which Z is —NHSO$_2$R$^{17}$, some compounds are of formula:

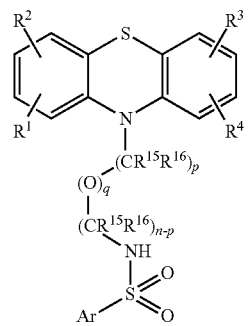

wherein Ar is a substituted or unsubstituted phenyl, thienyl, furanyl or pyrrolyl. And, in particular, they may be of formula (IA) or (IA'):

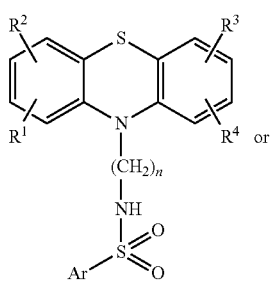

IA

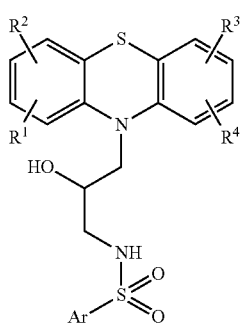

IA' in which R¹ and R³ are independently selected from H and halo; and R² and R⁴ are H.

Other compounds in the genus in which Z is —NHSO₂R¹⁷ are in subgenera of formulae:

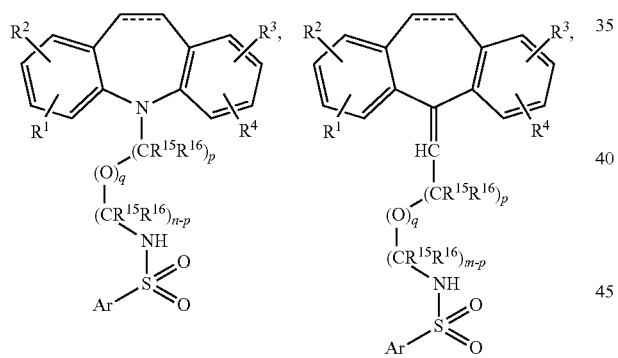

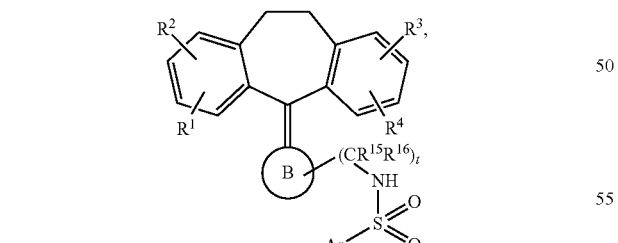

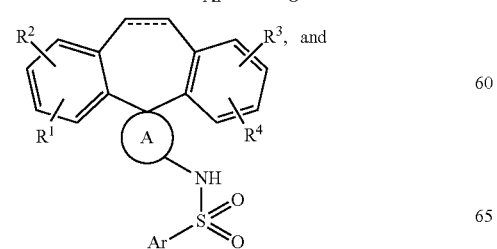

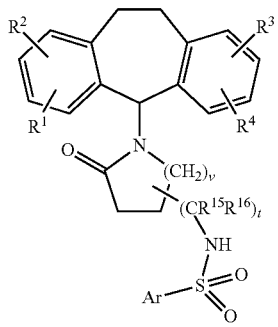

-continued wherein Ar is a substituted or unsubstituted phenyl, thienyl, furanyl or pyrrolyl and B is a three to seven membered carbocycle or heterocycle. Ring B may be additionally substituted with one or two substituents chosen from OH, F, cyano, amino, (C₁-C₃)alkylamino, (C₁-C₃)dialkylamino, (C₁-C₃)alkyl, (C₁-C₃)haloalkyl, (C₁-C₃)haloalkoxy, and (C₁-C₃)alkoxy.

Narrower subgenera of the foregoing are:

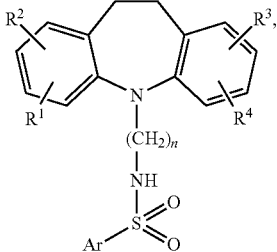

ID

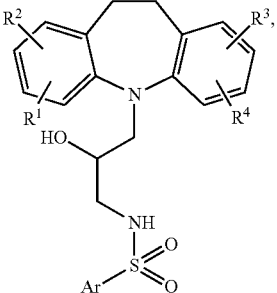

ID'

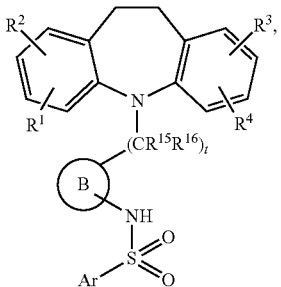

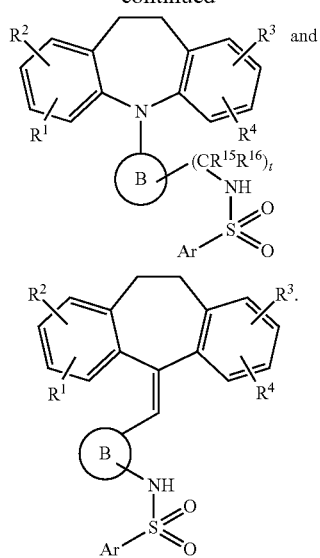
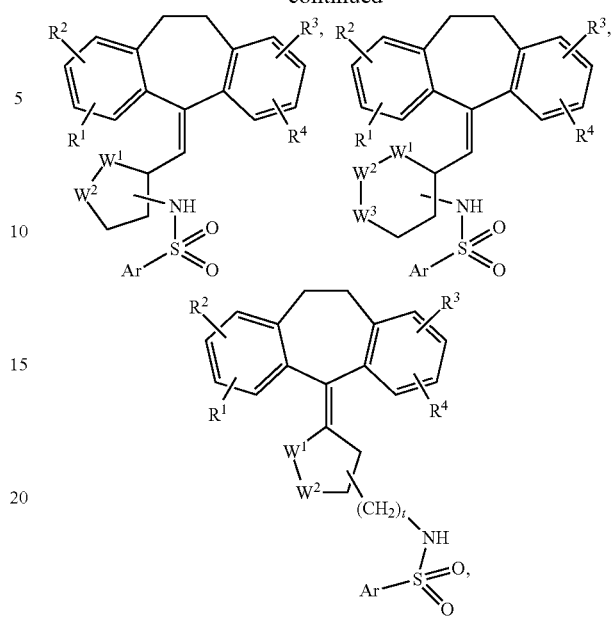
Particular embodiments of the A and B rings in the foregoing subgenera are, for example:
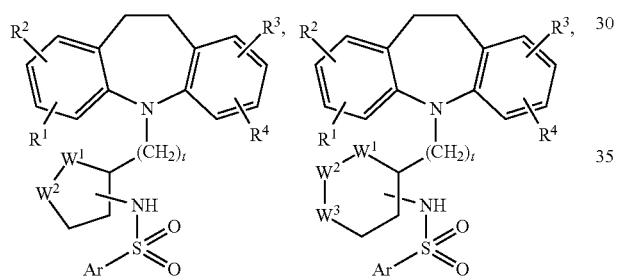
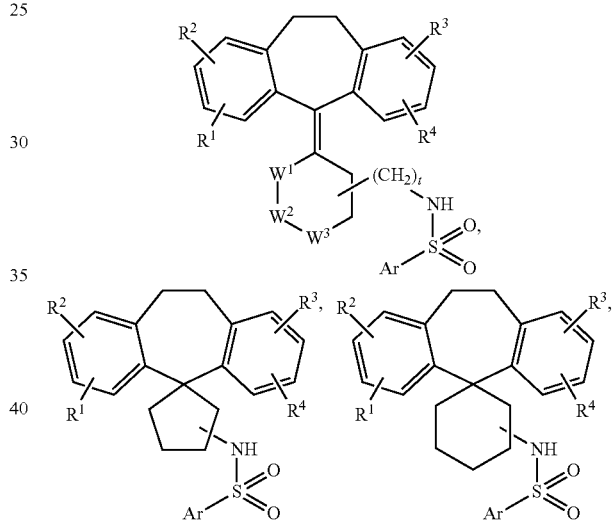
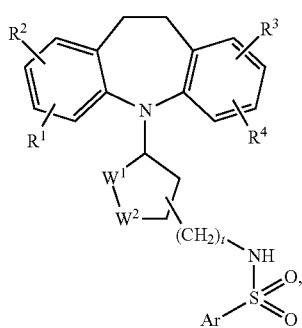
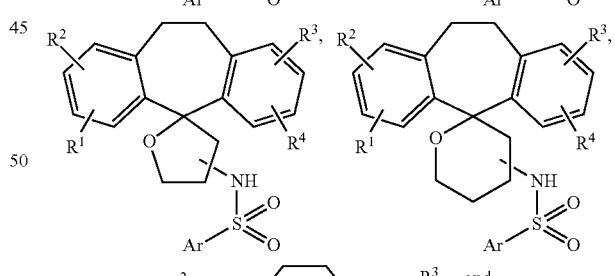
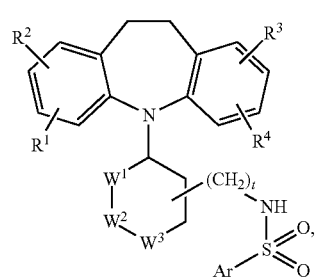
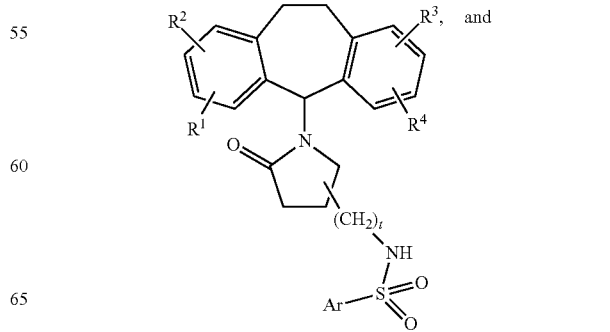

-continued

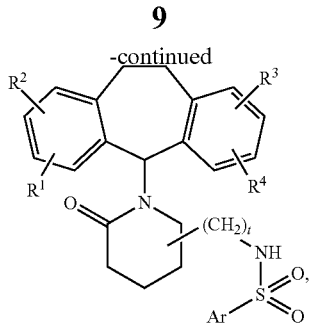

in which W¹ W² and W³ are selected from among —CH₂—, —O—, and —CH(OH)—.

In certain embodiments, t is zero. In certain embodiments Ar is phenyl or thienyl, optionally substituted with one or two substituents chosen from methyl, halogen, cyano, nitro, trifluoromethyl, methylsulfonyl, trifluoromethoxy, and acetylamino. In compounds of the invention, Ar is restricted to monocyclic aryl and heteroaryl because, in the bicyclic examples tested little or no activity was observed. In some of these embodiments the one or two substituents are located at positions that are not adjacent to the point of attachment of Ar to the sulfonamide. For example, when Ar is thienyl, 3-chloro-2-thienyl has a halogen substituent adjacent the point of attachment, whereas 4-chloro-2-thienyl does not. In certain embodiments, Ar is phenyl, optionally substituted at the 3, 4 or 5 positions with one or two substituents chosen from methyl, halogen, cyano, trifluoromethyl and trifluoromethoxy. In embodiments in which $R^5$ is —$(CR^{15}R^{16})_p$-$Q_q$-$(CR^{15}R^{16})_{n-p}$—Z and in which p and q are zero, when $R^{15}$ and $R^{16}$ are H in all occurrences, n may be 2 or 3.

In the subgenera in which Z is chosen from —NHC(O)NR⁸R⁹ and —NHC(O)OR⁸, some compounds are of formulae:

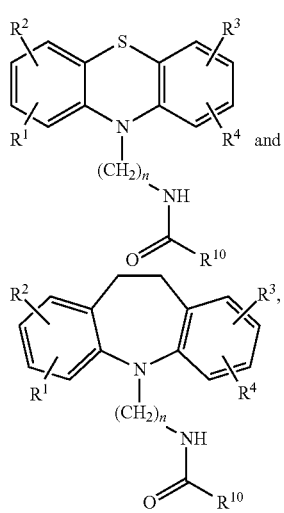

in which $R^{10}$ is selected from $OR^{11}$ and $NHR^{11}$, and $R^{11}$ is selected from the group consisting of substituted or unsubstituted ($C_1$-$C_6$)alkyl, substituted or unsubstituted ($C_3$-$C_7$) cycloalkyl, and substituted or unsubstituted ($C_5$-$C_{14}$)aryl. In certain embodiments $R^{11}$ is ($C_1$-$C_6$)alkyl.

In many embodiments $R^1$ and $R^3$ are independently selected from the group consisting of H and halo and $R^2$ and $R^4$ are H.

All the members of the genus described above exhibit biological activity in screens that are predictive of utility. However, certain species appear from a preliminary search of the literature to be unpatentable to applicants. Thus, for example,

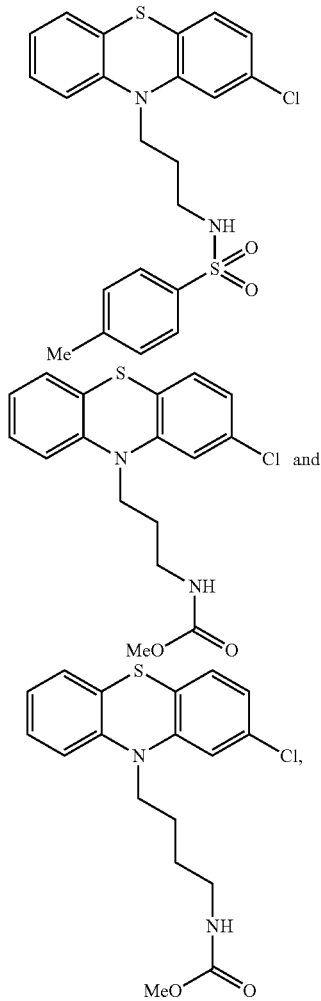

while they are part of the inventive concept, have been excluded from the claims to compounds. It may be found upon examination that methods employing certain members of the excluded genera are patentable to the inventors in this application or that additional species and genera not presently excluded are not patentable to the inventors in this application. In either case, the exclusion of species and genera in applicants' claims are to be considered artifacts of patent prosecution and not reflective of the inventors' concept or description of their invention, which encompasses all members of the genus that are not in the public's possession.

As used herein, and as would be understood by the person of skill in the art, the recitation of "a compound"—unless expressly further limited—is intended to include salts of that compound. Thus, for example, the recitation "a compound of formula"

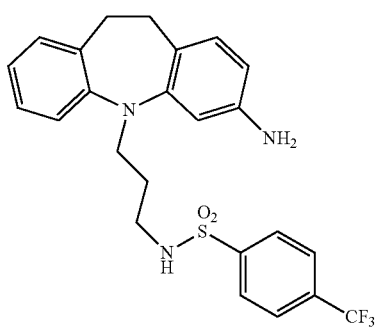 [SMILES: Nc1ccc2c(c1)N(CCCNS(=O)(=O)c1ccc(C(F)(F)F)cc1)c1ccccc1CC2]

as depicted above, in which $R^4$ is $NH_2$, would include salts in which $R^4$ is $NH_3^+X^-$, wherein $X^-$ is any counterion. In a particular embodiment, the term "compound of formula I" refers to the compound or a pharmaceutically acceptable salt thereof. Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion. Unless otherwise stated, all tautomeric forms of the compounds of the invention are within the scope of the invention.

Also provided herein is a pharmaceutical composition comprising a compound of formula (I), or a pharmaceutically acceptable salt form thereof, and a pharmaceutically acceptable carrier or diluent.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^{2}$H, $^{3}$H, $^{13}$C, $^{14}$C, $^{15}$N, $^{35}$S, $^{18}$F, and $^{36}$Cl, respectively. Compounds that contain those radioisotopes and/or other radioisotopes of other atoms are within the scope of this invention. Tritiated, i.e. $^{3}$H, and carbon-14, i.e., $^{14}$C, radioisotopes are particularly preferred for their ease in preparation and detectability. Compounds that contain isotopes $^{11}$C, $^{13}$N, $^{15}$O and $^{18}$F are well suited for positron emission tomography. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

The compounds provided herein can be used for treating cancer in a patient, the method comprising administering to the patient a therapeutically effective amount of a compound of formula (I), or a pharmaceutically acceptable salt form thereof. In some embodiments, the cancer is characterized by dysregulation of the PI3K-AKT-FOXO signaling pathway. For example, the cancer can be selected from the group consisting of: ovarian, pancreatic, renal cell, breast, prostate, lung, hepatocellular carcinoma, glioma, leukemia, lymphoma, colorectal cancers, and sarcomas.

In some embodiments, the method further comprises administering one or more cancer chemotherapeutic agents. In some embodiments, the one or more cancer chemotherapeutic agents are EGFR inhibitors. For example, the chemotherapeutic agent may be erlotinib or gefitinib.

In some embodiments, the cancer is chemotherapy resistant cancer. In some embodiments, the method further comprises administering one or more cancer chemotherapeutic agents. In some embodiments, the one or more cancer chemotherapeutic agents are EGFR inhibitors. For example, the chemotherapeutic agent is erlotinib or gefitinib.

In some embodiments, administration of a compound of formula (I) or a pharmaceutically acceptable salt form thereof, can restore sensitivity to one or more chemotherapeutic agents in a patient wherein the patient has developed a resistance to the one or more chemotherapeutic agents.

Also provided herein is a method for treating diabetes in a patient, the method comprising administering to the patient a therapeutically effective amount of a compound of formula (I), or a pharmaceutically acceptable salt form thereof.

Further provided herein is a method for treating an autoimmune disease in a patient, the method comprising administering to the patient a therapeutically effective amount of a compound of formula (I). The autoimmune disease an be, for example, inflammatory bowel disease (IBD). Immune responses are constantly and tightly regulated and one important cellular component in maintaining self tolerance (ie prevention of autoimmunity) and tolerance of benign commensal gut flora are regulatory T cells (Treg). Treg can be subdivided into multiple phenotypes, but the most common are CD4+CD25+ T cells that express the transcription factor Foxp3. Foxp3 is a direct transcriptional target of FOXO proteins, particularly FOXO1 and FOXO3. Thus activation of FOXO proteins in naïve T-cells promotes and directs differentiation to maintain a population of Treg cells.

Acute immune mediated rejection and chronic immune mediated rejection are key obstacles to successful solid organ transplantation. It is believed that these forms of rejection can be prevented/overcome by amplifying Treg number and or function. Similarly, a common and morbid complication of allogeneic hematopoietic cell transplants (Allo-HCT) used to treat various malignant and non-malignant conditions, is graft versus host disease, in which the transplanted immune cells from the donor damage multiple organs in the recipient (most notably skin, gut, and liver). Increasing experimental and clinical data indicate that Tregs can be harnessed to prevent and or treat this disease process.

Thus compounds of the present invention are useful in treatment of autoimmune and related diseases, by activating FOXO proteins and inducing T cell differentiation to Tregs. Compounds may be administered therapeutically to subjects directly, or alternatively, T cells may be collected from a subject and differentiated ex vivo to Tregs as described by Taylor et al. [*Blood* 99, 3493-3499 (2002)]. Compounds of the present invention may be used alone or in combination with conventional immunosuppressive drugs such as cyclosporine, FK506 or rapamycin and its analogs. In addition compounds of the present invention may be co-administered with histone deacetylase inhibitors (HDACi) which have been shown to enhance Treg function by maintaining Foxp3 acetylation and activity.

Aspects of the invention include methods for treatment of autoimmune disease characterized by deficiency in Treg function comprising administering a therapeutically useful amount of compound of Formula I, optionally in combination with an HDAC inhibitor. The method can also include extraction of naïve T-cells from a patient, differentiation of T-cells to Tregs ex vivo by treatment with a compound of Formula I, optionally supplemented with an HDACi, followed by administration of Tregs to patient with optional separation of compound of Formula I from Tregs prior to their administration. As stated above, autoimmune diseases that can be so treated include IBD, solid organ transplant rejection, and GvHD in allo-HCT. by treatment of donor cell inoculum with a therapeutically useful amount of compound of Formula I.

In some embodiments, the compounds can be administered to a patient to treat an autoimmune disorder, for example, Addison's disease, Amyotrophic Lateral Sclerosis, celiac disease, Crohns disease, diabetes, eosinophilic fasciitis, Guillain-Barré syndrome (GBS), Graves' disease, Lupus erythematosus, Miller-Fisher syndrome, psoriasis, rheumatoid arthritis, ulcerative colitis, and vasculitis.

In some embodiments, the compound provided herein can be used for treating a disease or disorder in a patient wherein the disease or disorder involves excessive or unregulated cellular proliferation, the method comprising administering to the patient a therapeutically effective amount of a compound of formula (I). Also provided herein is a method for treating a disease or disorder in a patient where the disease or disorder involves the dysregulation of the pi3K-AKT-FOXO signaling pathway, the method comprising administering to the patient a therapeutically effective amount of a compound of formula (I).

Further provided herein is a method for treating a disease in a patient wherein the disease is characterized by age onset proteotoxicity, the method comprising administering to the patient a therapeutically effective amount of a compound of formula (I). In some embodiments, the disease is selected from the group consisting of: Alzheimer's disease, Parkinson's disease, Huntington's disease, and amyotrophic lateral sclerosis.

The compounds provided herein may further be used in a method for treating a mood disorder in a patient, the method comprising administering to the patient a therapeutically effective amount of a compound of formula (I). In some embodiments, the mood disorder is stress induced depression.

Also provided herein is a method for treating acne vulgaris in a patient, the method comprising administering to the patient a therapeutically effective amount of a compound of formula (I).

Further provided herein is a method for treating cardiac hypertrophy in a patient, the method comprising administering to the patient a therapeutically effective amount of a compound of formula (I). In some embodiments, the cardiac hypertrophy is associated with a disease selected from hypertension, myocardial infarction, and valvular heart disease.

The compounds are described herein induce FOXO1 transcription factor translocation to the nucleus. They exhibit anti-proliferative effects, but minimal dopamine binding and are thus likely to have reduced GPCR-mediated CNS and CV side effects. These agents are useful in the treatment of a variety of disorders, including as a monotherapy in cancer treatment, or used in combination with other drugs to restore sensitivity to chemotherapy where resistance has developed.

More particularly, cancers that may be treated by the compounds, compositions and methods described herein include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue.

The compounds described herein can also be administered in combination with existing methods of treating cancers, for example by chemotherapy, irradiation, or surgery. Thus, there is further provided a method of treating cancer comprising administering an effective amount of a compound according to formula (I), or a pharmaceutically acceptable salt form thereof, to a patient, wherein a therapeutically effective amount of one or more additional cancer chemotherapeutic agents are administered to the patient. Examples of suitable chemotherapeutic agents include EGFR inhibitors such as erlotinib or gefitinib.

Unless defined otherwise, all technical and scientific terms used herein have the same meaning as is commonly understood by one of ordinary skill in the art to which this disclosure belongs. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In the event that there is a plurality of definitions for terms cited herein, those in this section prevail unless otherwise stated.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof, but only if the additional features, integers, steps, components or groups thereof do not materially alter the basic and novel characteristics of the claimed composition or method.

A "patient," as used herein, includes both humans and other animals, particularly mammals. Thus the methods are applicable to both human therapy and veterinary applications. In some embodiments, the patient is a mammal, for example, a primate. In some embodiments, the patient is a human.

Treatment can involve administering a compound described herein to a patient diagnosed with a disease, and may involve administering the compound to a patient who does not have active symptoms. Conversely, treatment may involve administering the compositions to a patient at risk of developing a particular disease, or to a patient reporting one or more of the physiological symptoms of a disease, even though a diagnosis of this disease may not have been made.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The term "modulate" with respect to a FOXO transcription factor protein refers to activation of the FOXO transcription factor protein and its biological activities associated with the FOXO pathway. Modulation of FOXO transcription factor proteins includes upregulation (i.e., agonizing, activation or stimulation). The mode of action of a FOXO modulator can be direct, e.g., through binding to the FOXO transcription factor protein as a ligand. The modulation can also be indirect, e.g., through binding to and/or modifying another molecule which otherwise binds to and activates the FOXO transcription factor protein.

Unless otherwise specified, alkyl is intended to include linear, branched, or cyclic hydrocarbon structures and combinations thereof. Straight-chain alkyl groups include methyl, ethyl, n-propyl, n-butyl, n-pentyl, n-hexyl, n-heptyl, n-octyl, n-nonyl, and n-decyl and branched-chain alkyl groups include isopropyl, tert-butyl, isobutyl, sec-butyl, and neopentyl. A combination would be, for example, cyclopropylmethyl. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like. In certain embodiments, a straight chain or branched chain alkyl has 6 or fewer carbon atoms in its backbone (e.g., $C_{1-6}$ for straight chain, $C_{3-6}$ for branched chain). The term $C_{1-6}$ includes alkyl groups containing 1 to 6 carbon atoms. In some embodiments, cycloalkyls have from 3-8 carbon atoms in their ring structure, for example, they can have 3, 4, 5 or 6 carbons in the ring structure.

$C_1$ to $C_{20}$ hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. Hydrocarbon refers to any substituent comprised of hydrogen and carbon as the only elemental constituents.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles.

Alkoxy or alkoxyl refers to groups of from 1 to 8 carbon atoms of a straight, branched or cyclic configuration and combinations thereof attached to the parent structure through an oxygen. Examples include methoxy, ethoxy, propoxy, isopropoxy, cyclopropyloxy, cyclohexyloxy and the like.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. The double bonded oxygen, when referred to as a substituent itself is called "oxo".

Aryl and heteroaryl mean (i) a phenyl group (or benzene) or a monocyclic 5- or 6-membered heteroaromatic ring containing 1-4 heteroatoms selected from O, N, or S; (ii) a bicyclic 9- or 10-membered aromatic or heteroaromatic ring system containing 0-4 heteroatoms selected from O, N, or S; or (iii) a tricyclic 13- or 14-membered aromatic or heteroaromatic ring system containing 0-5 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. In one embodiment, the alkyl group of an arylalkyl or a heteroarylalkyl is an alkyl group of from 1 to 6 carbons. Examples include, e.g., pyridinylmethyl, pyrimidinylethyl and the like.

Heterocycle means a cycloaliphatic or aryl carbocycle residue in which from one to four carbons is replaced by a heteroatom selected from the group consisting of N, O and S. The nitrogen and sulfur heteroatoms may optionally be oxidized, and the nitrogen heteroatom may optionally be quaternized. Unless otherwise specified, a heterocycle may be non-aromatic or aromatic. Examples of heterocycles include pyrrolidine, pyrazole, pyrrole, indole, quinoline, isoquinoline, tetrahydroisoquinoline, benzofuran, benzodioxan, benzodioxole, tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. Oxygen heteroaryl is a subset of oxygen heterocycle; examples include furan and oxazole. Sulphur heteroaryl is a subset of sulphur heterocycle; examples include thiophene and thiazine. A nitrogen heterocycle is a heterocycle containing at least one nitrogen in the ring; it may contain additional nitrogens, as well as other heteroatoms. Examples include piperidine, piperazine, morpholine, pyrrolidine and thiomorpholine. Nitrogen heteroaryl is a subset of nitrogen heterocycle; examples include pyridine, pyrrole and thiazole.

As used herein, the term "optionally substituted" may be used interchangeably with "unsubstituted or substituted". The term "substituted" refers to the replacement of one or more hydrogen atoms in a specified group with a specified radical. "Oxo" may also be included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(O)alkoxy, respectively.

The term "halogen" means fluorine, chlorine, bromine or iodine. In one embodiment, halogen may be fluorine or chlorine.

Preparation of compounds can involve the protection and deprotection of various chemical groups. The need for protection and deprotection, and the selection of appropriate protecting groups, can be readily determined by one skilled in the art. Suitable groups for that purpose are discussed in standard textbooks in the field of chemistry, such as Protective Groups in Organic Synthesis by T. W. Greene and P. G. M. Wuts [John Wiley & Sons, New York, 1999], in *Protecting Group Chemistry*, 1st Ed., Oxford University Press, 2000; and in *March's Advanced Organic chemistry: Reactions, Mechanisms, and Structure*, 5th Ed., Wiley-Interscience Publication, 2001.

For example, compounds according to formulas (1G), (1H), and (1J) can be prepared as shown in Schemes 1, 2 and 3

Scheme 1 General Scheme

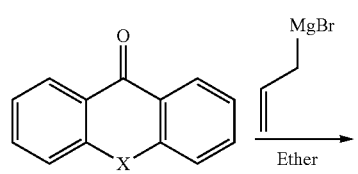

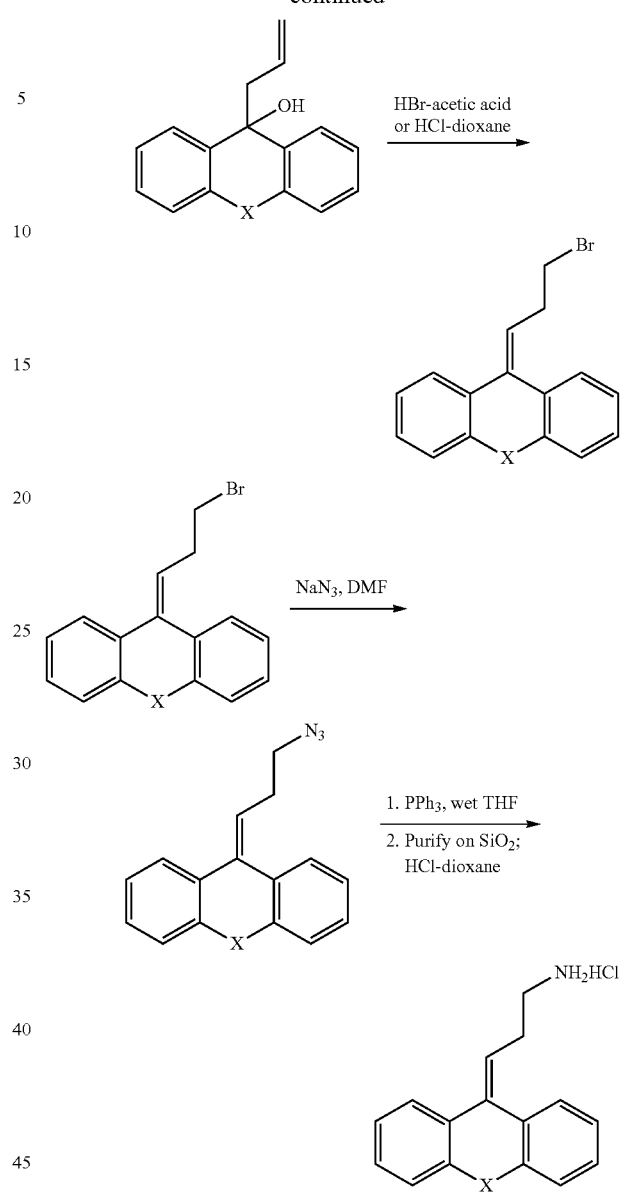

Scheme 2 Thioxanthene Scheme

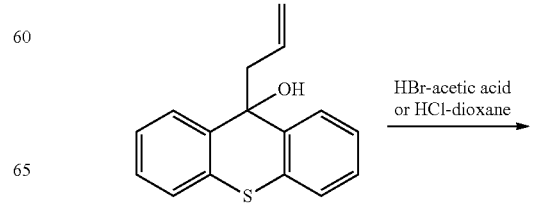

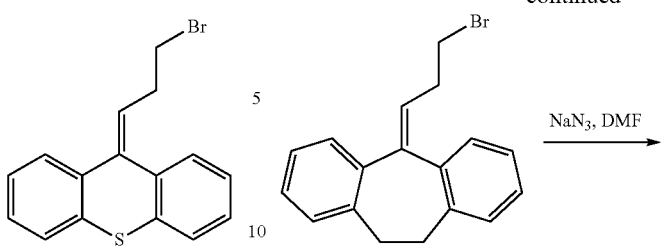
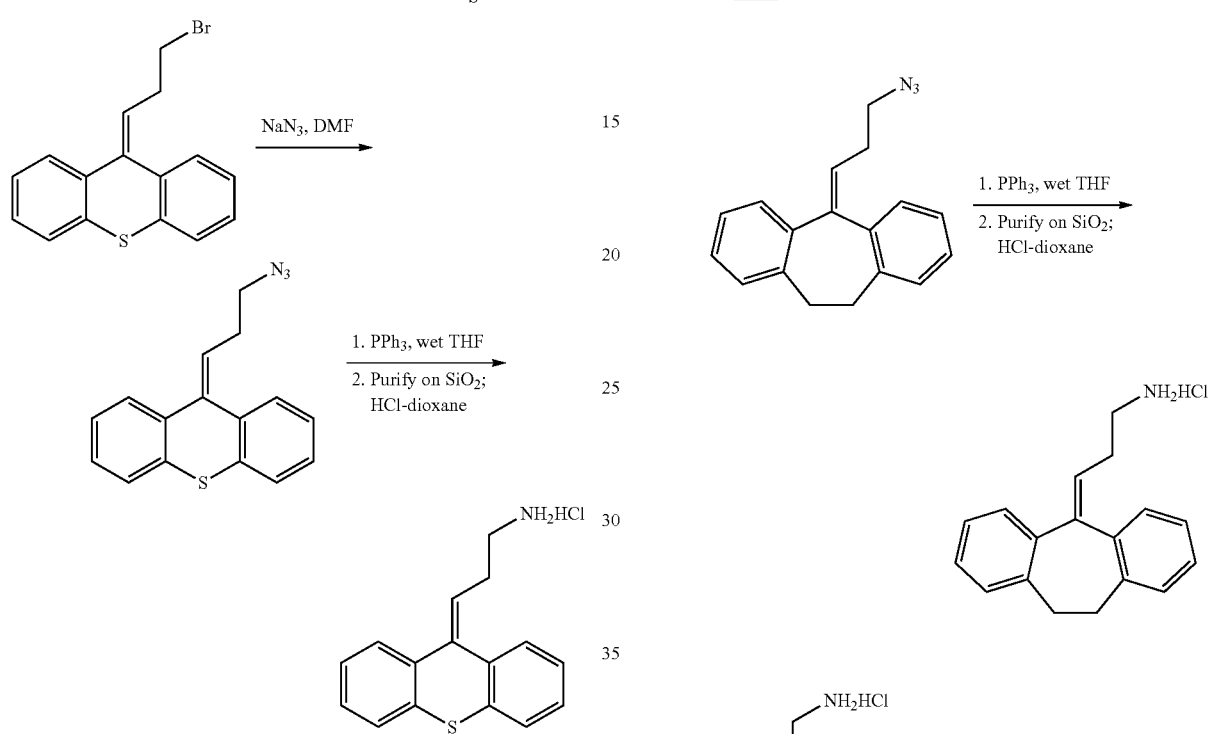
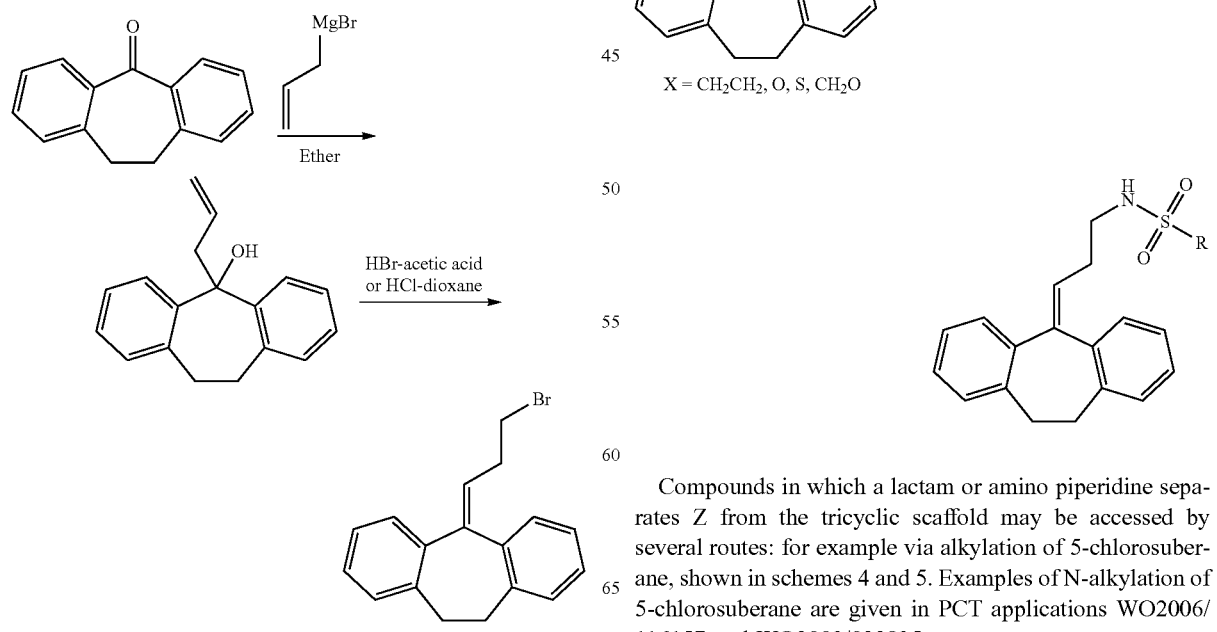
Compounds in which a lactam or amino piperidine separates Z from the tricyclic scaffold may be accessed by several routes: for example via alkylation of 5-chlorosuberane, shown in schemes 4 and 5. Examples of N-alkylation of 5-chlorosuberane are given in PCT applications WO2006/116157 and WO2003/022835

Scheme 4

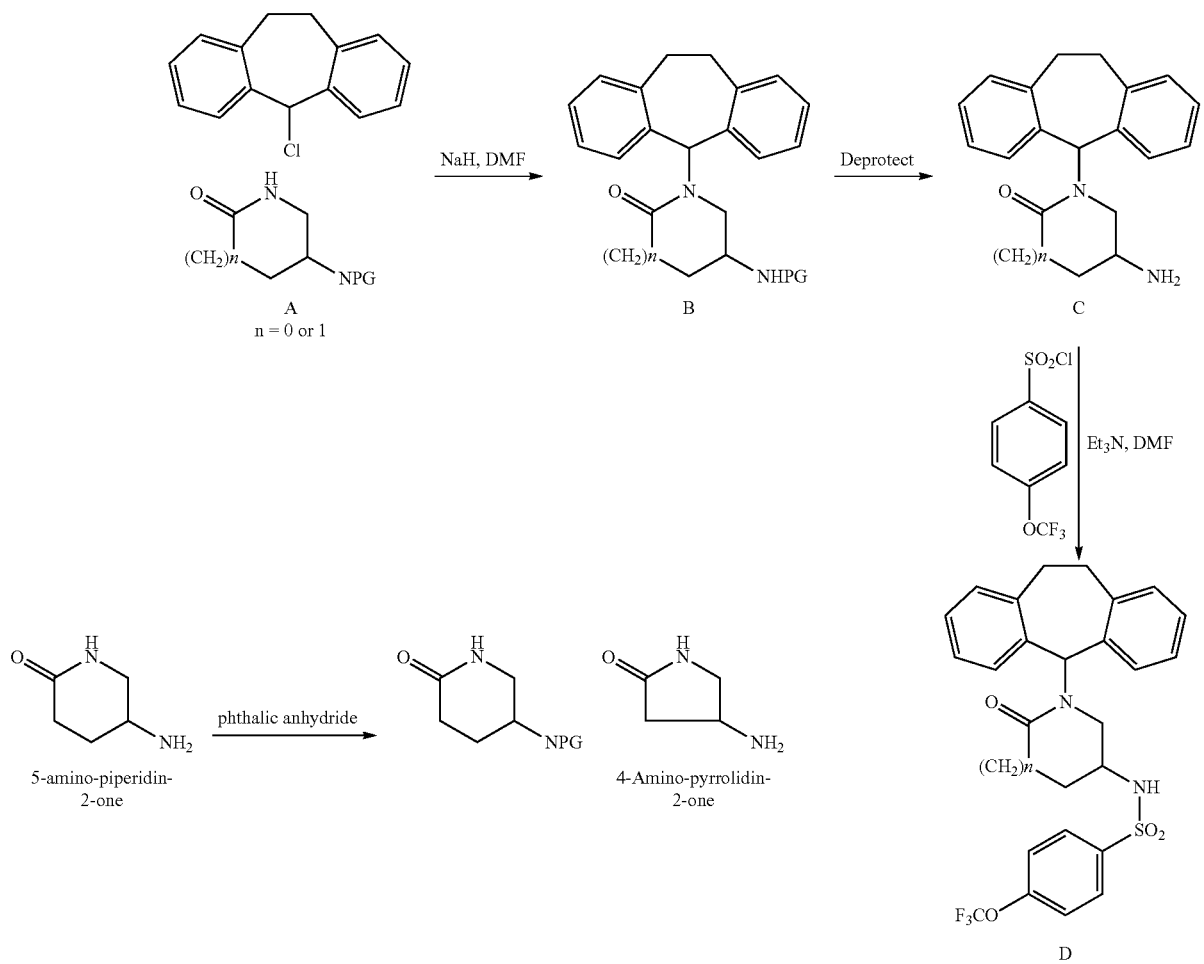

Available amino lactams, eg 5-aminopiperidin-2-one or 4-aminopyrrolidinone-2-one are protected with a group such as phthaloyl (PG=phthaloyl) on the exocyclic nitrogen to give intermediates A. The protected aminolactam, A, is then deprotonated with a strong base such as sodium hydride, LDA or KN(TMS)2, then treated with 5-chlorosuberane to yield protected intermediate B. The exocyclic ring nitrogen is deprotected, for example by treatment with hydrazine where PG=phthaloyl to yield intermediate C. The exocyclic amine is then reacted under standard conditions with an aromatic sulfonyl chloride, such as 4-trifluoromethoxyphenylsulfonyl chloride, to yield the products, for example D.

Synthesis of amino piperidines proceeds in an analogous fashion as shown in Scheme 5 starting from the available N-Boc protected amino piperidine or pyrrolidine:

Scheme 5

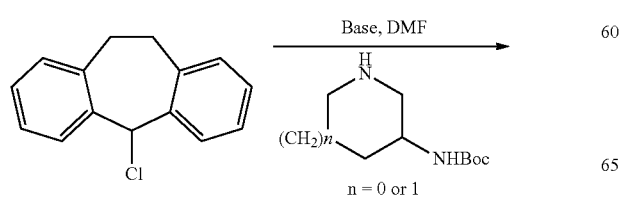

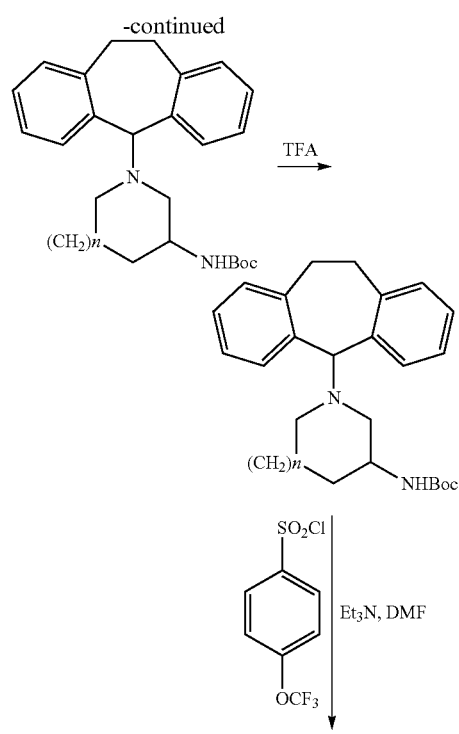

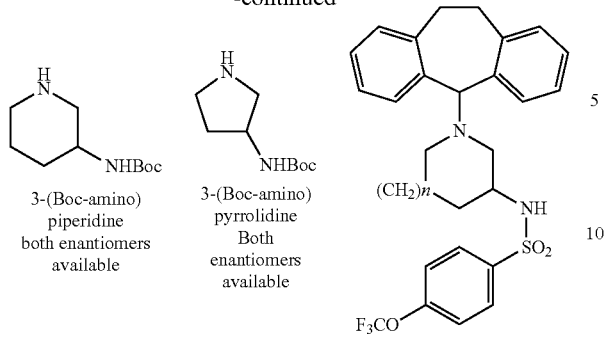
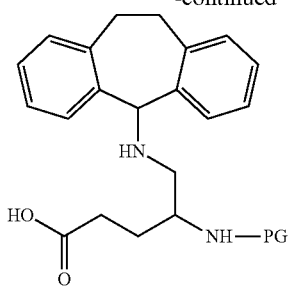

A second route into the constrained lactams involves construction of the ring starting from glutamic or aspartic acids, which are available in optically pure form, as shown in Scheme 6. t-Butyl ester side chain protected a-amino protected (for example Cbz or Fmoc) aldehyde derivative of glutamic or aspartic acid is reacted under standard reductive amination conditions (sodium cyanoborohydride or sodium acetoxyborohydride with catalytic acid) with 5-aminosuberane to give secondary amine intermediates A'. The side chain t-butyl ester is deprotected under standard acidic conditions (eg trifluoroacetic acid in dichloromethane) to give intermediates B' and intramolecular amide bond formation (for example with carbodiimide acid activation) gives protected cyclic intermediates C'. These are deprotected under standard conditions (hydrogenolysis for Cbz or piperidine-DMF for Fmoc) to liberate the free exo-cyclic primary intermediates D' which are reacted with aryl sulfonyl chlorides, for example 4-trifluoromethoxyphenylsulfonyl chloride, to give the products E'.

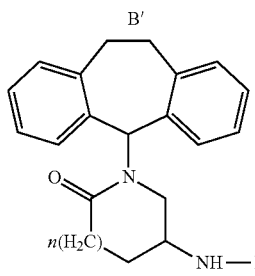
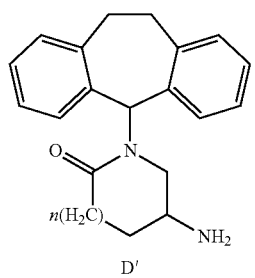

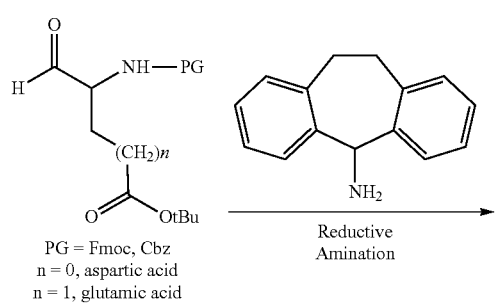

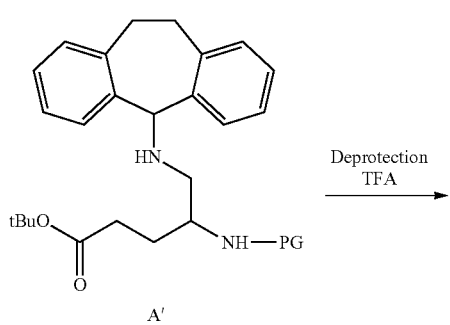

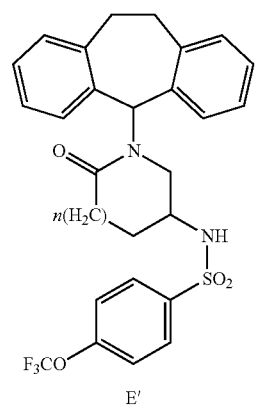

Spiro-attached oxygen-containing rings A may be attached as follows:

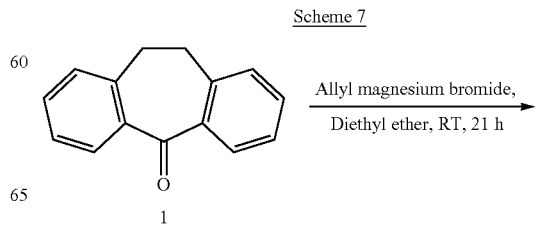

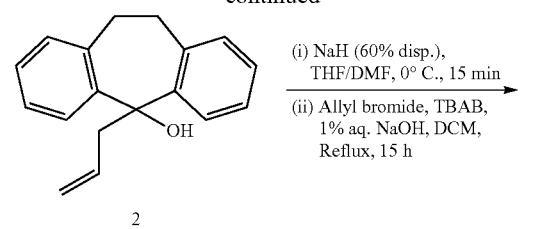

2

(i) NaH (60% disp.),
THF/DMF, 0° C., 15 min
(ii) Allyl bromide, TBAB,
1% aq. NaOH, DCM,
Reflux, 15 h

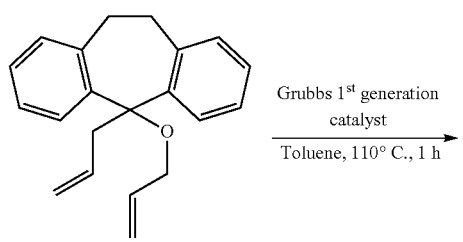

3

Grubbs 1st generation catalyst
Toluene, 110° C., 1 h

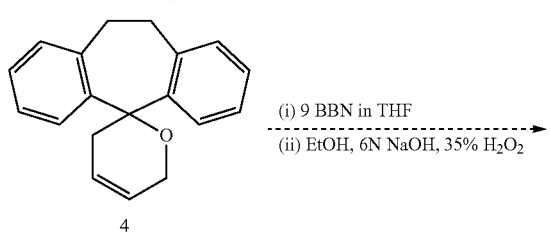

4

(i) 9 BBN in THF
(ii) EtOH, 6N NaOH, 35% H$_2$O$_2$

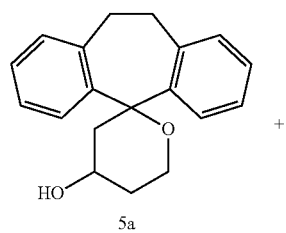

5a

+

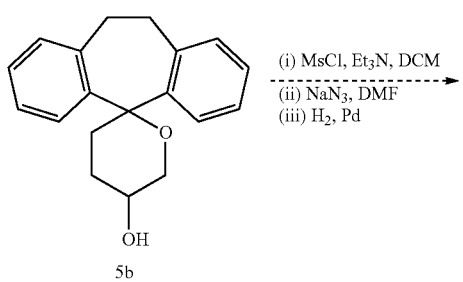

5b (i) MsCl, Et$_3$N, DCM
(ii) NaN$_3$, DMF
(iii) H$_2$, Pd

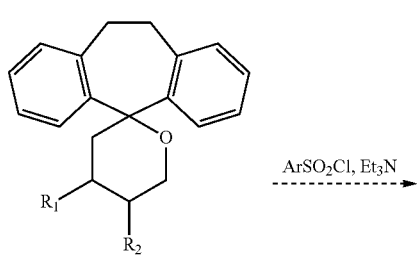

6a R$_1$ = NH$_2$, R$_2$ = H
6b R$_1$ = H, R$_2$ = NH$_2$

ArSO$_2$Cl, Et$_3$N

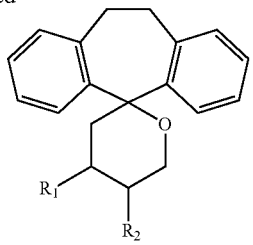

7a R$_1$ = NHSO$_2$Ar, R$_2$ = H
7b R$_1$ = H, R$_2$ = NHSO$_2$Ar

Ar = 4-ClPh, 4-OCF$_3$Ph

The synthesis was commenced by a grignard reaction of allylmagnesium bromide with commercially available dibenzosuberone 1 to afford allyl carbinol 2 in 81% yield (J. Heterocycl. Chem. 1995, 32, 1027-1032). A sodium hydride induced alkylation of 2 with allyl bromide in presence of tetrabutylammonium bromide furnished double allylated product 3 in 74% yield (Tetrahedron 2012, 68, 747-753). A ring closing methathesis (RCM) reaction of 3 by Grubbs' first generation catalyst in dry toluene afforded spiro compound 4 in 62% yield (ARKIVOC. 2003, (iii), 67-76). Compound 4 is converted to the regioisomers—5a and 5b by a Brown hydroboration-oxidation reaction (J. Am. Chem. Soc. 1974, 96(25), 7765-7770). Sequential mesylation (Org. Lett. 2006, 8(10), 2175-2178), azide displacement (Bioorg. Med. Chem. 2004, 12(23), 6301-6315) and reduction of 5a and 5b affords 6a and 6b respectively. Sulfonamides 7a and 7b are synthesized by treating 6a and 6b respectively with arylsulfonyl chlorides (Tetrahedron: Asymmetry 1994, 5(10), 1869-72).

Spiro-attached carbocycles A may be attached as shown in Scheme 8:

Scheme 8

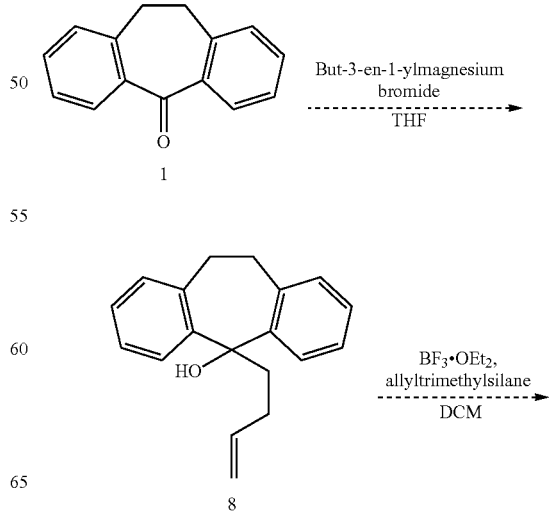

-continued

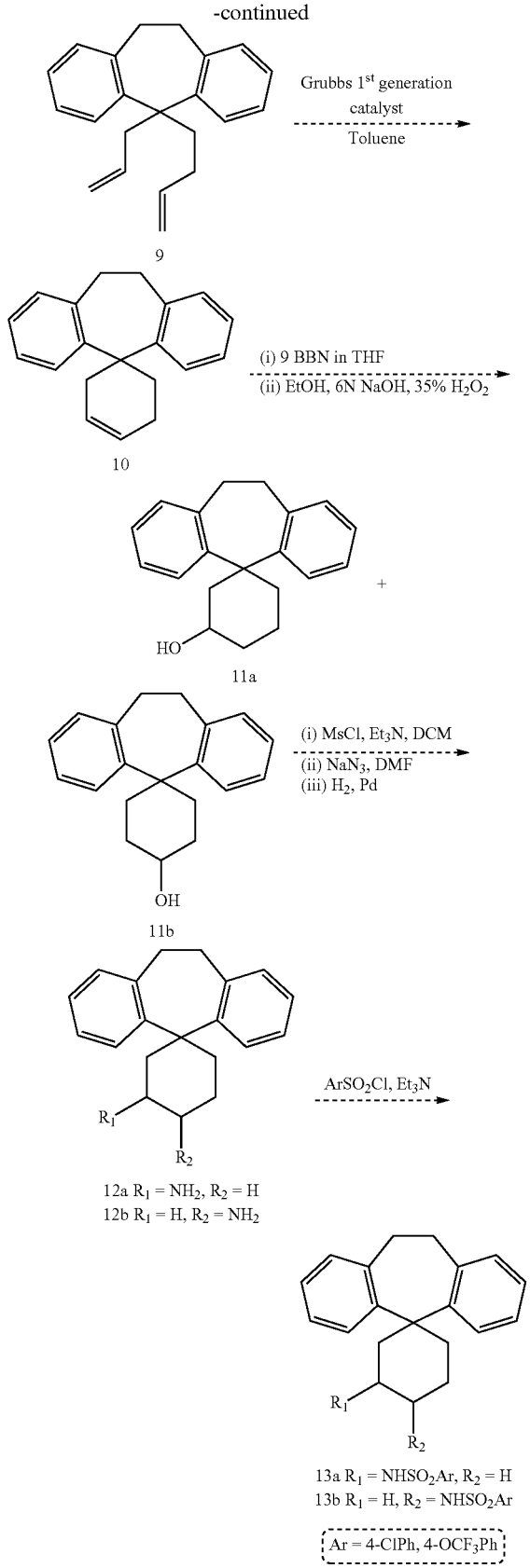

12a R₁ = NH₂, R₂ = H
12b R₁ = H, R₂ = NH₂

13a R₁ = NHSO₂Ar, R₂ = H
13b R₁ = H, R₂ = NHSO₂Ar

Ar = 4-ClPh, 4-OCF₃Ph

The synthesis is commenced by a grignard reaction of but-3-en-1-ylmagnesium bromide with commercially available dibenzosuberone 1 to afford homo allyl carbinol 8. Allylation of 8 with allyltrimethylsilane and $BF_3 \cdot OEt_2$ in DCM furnishes the allyl-homoallyl system 9 (Adv. Synth. Catal. 2008, 350, 1419-1424). A ring closing methathesis (RCM) reaction of 9 by Grubbs' first generation catalyst in dry toluene affords spiro compound 10. Compound 10 is converted to the regioisomers—11a and 11b by a Brown hydroboration-oxidation reaction. Sequential mesylation, azide displacement and reduction of 11a and 11b affords 12a and 12b respectively. Sulfonamides 13a and 13b are synthesized by treating 12a and 12b respectively with arylsulfonyl chlorides.

EXAMPLES

Example 1

Synthesis of 2-(4-(2-chloro-10H-phenothiazin-10-yl)butyl)isoindoline-1,3-dione

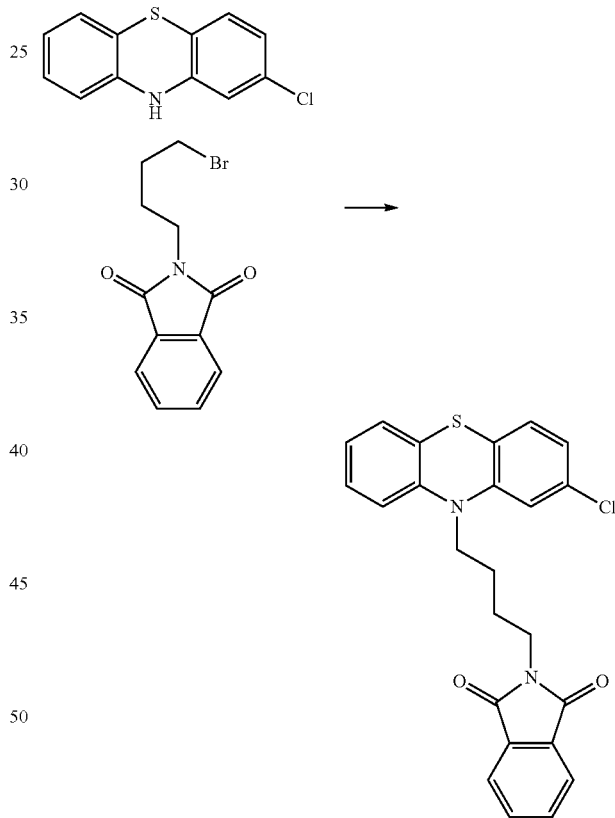

A solution of 2-chloro-10H-phenothiazine (3.00 g, 12.8 mmol), in DMF (50 mL) was cooled to 0° C., treated with NaH (60% dispersion in mineral oil, 0.616 g, 15.4 mmol), and stirred for 0.5 h at 0° C. N-(4-bromobutyl)phthalimide (3.98 g, 14.1 mmol) in DMF (10 mL) was added dropwise and the combined solution was warmed to 25° C. and stirred for 2 h. The mixture was poured over saturated aqueous NH₄Cl solution (200 mL) and extracted with ethyl acetate (3×200 mL). The combined extracts were washed with saturated aqueous NaCl (3×200 mL), dried (Na₂SO₄), concentrated in vacuo, and the residue was purified by flash chromatography (SiO₂, 0-40% Ethyl acetate-hexanes) to provide a beige solid (4.10 g, 73%). $^1$H NMR (600 MHz, CDCl$_3$) δ 7.81 (2H, dd, J=5.4, 3.1 Hz), 7.70 (2H, dd, J=5.4, 3.0 Hz), 7.12 (1H, t, J=7.4 Hz), 7.09 (1H, d, J=7.6 Hz), 6.98 (1H, d, J=8.1 Hz), 6.88 (1H, t, J=7.4 Hz), 6.84 (1H, d, J=8.0 Hz), 6.83 (1H, dd, J=8.1, 1.9 Hz), 6.79 (1H, d, J=1.8 Hz), 3.89 (2H, t, J=5.8 Hz), 3.70 (2H, t, J=5.8 Hz), 1.84 (4H, br s). $^{13}$C NMR (150 MHz, CDCl$_3$) δ 168.6, 146.6, 144.6, 134.1, 133.4, 132.2, 128.1, 127.7, 127.6, 125.4, 124.1, 123.4, 123.1, 122.5, 116.08, 116.06, 46.8, 37.6, 25.9, 24.1; LCMS m/z 435.1578 ([M+H$^+$], C$_{24}$H$_{19}$ClN$_2$O$_2$S requires 435.0929).

Example 2

Synthesis of 4-(2-chloro-10H-phenothiazin-10-yl)butan-1-amine hydrochloride

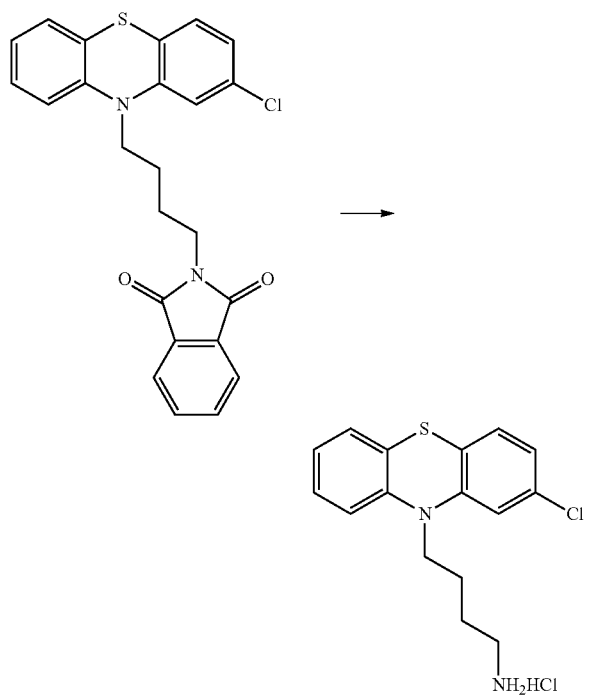

A solution of 2-(4-(2-chloro-10H-phenothiazin-10-yl)butyl)isoindoline-1,3-dione (2.00 g, 4.60 mmol) in EtOH (10.0 mL) was treated with hydrazine hydrate (0.25 mL, 5.05 mmol) and heated to 90° C. for 1 h. The mixture was cooled to 25° C., filtered to remove the white solid that had formed, and concentrated. The residue was dissolved in 1:1 EtOH-ethyl acetate (10 mL), the solution filtered, and treated with aqueous 1 M HCl (5.0 mL). The combined solution was concentrated to dryness to afford a gray solid (0.672 g, 42%). $^1$H NMR (600 MHz, CD$_3$OD) δ 7.22 (1H, td, J=8.4, 1.3 Hz), 7.14 (1H, dd, J=7.6, 1.3 Hz), 7.09 (1H, d, J=8.2 Hz), 7.03 (1H, d, J=8.1 Hz). 7.01 (1H, d, J=1.9 Hz), 6.98 (1H, d, J=7.6 Hz), 6.95 (1H, dd, J=8.3, 2.0 Hz), 3.99 (2H, t, J=6.3 Hz), 2.91 (2H, t, J=7.7 Hz), 1.86 (2H, quintet, J=6.7 Hz), 1.76 (2H, quintet, J=7.0 Hz); $^{13}$C NMR (150 MHz, CD$_3$OD) δ; LCMS m/z 305.1087 ([M+H$^+$], C$_{16}$H$_{17}$ClN$_2$S requires 305.0874).

Example 3

Synthesis of N-(3-(2-chloro-10H-phenothiazin-10-yl)propyl)-4-methylbenzenesulfonamide

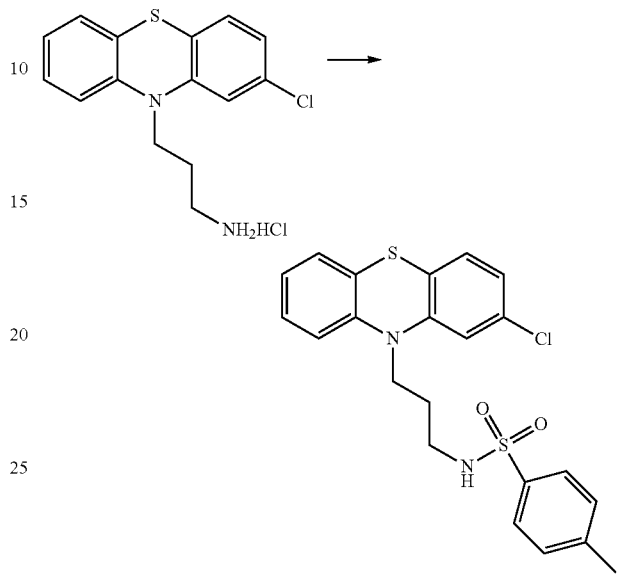

A solution of 3-(2-chloro-10H-phenothiazin-10-yl)propan-1-amine hydrochloride (0.100 g, 0.306 mmol) (prepared according to methods described in *International Journal of Antimicrobial Agents* (2000) 14:203-207) in DMF (1.0 mL) was cooled to 0° C. and treated sequentially with triethylamine (89 µL, 0.643 mmol) and p-toluenesulfonyl chloride (0.0736 g, 0.336 mmol). The solution was warmed to 25° C. and stirred for 2 h. The mixture was poured over saturated aqueous NaCl (20 mL) and extracted with ethyl acetate (3×50 mL). The combined organic layers were washed with saturated aqueous NaCl (3×50 mL), dried (Na$_2$SO$_4$), concentrated in vacuo, and the residue was purified by flash chromatography (SiO$_2$, 10-30% EtOAc-hexanes). The purified fractions were combined, concentrated in vacuo, and the residue was suspended in a minimal amount of ethyl ether, and precipitated by the addition of hexanes to afford the title compound as a white solid (0.0945 g, 69%) that was collected by filtration.

Example 4

Synthesis of Methyl (3-(2-chloro-10H-phenothiazin-10-yl)propyl)carbamate

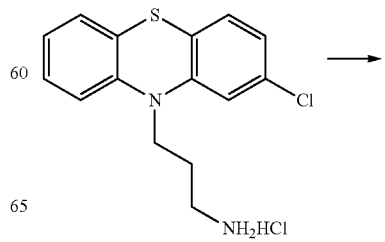

-continued

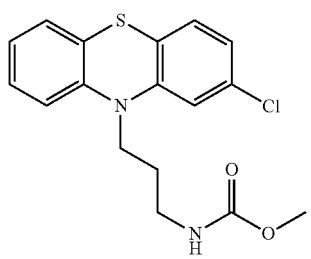

A solution of 3-(2-chloro-10H-phenothiazin-10-yl)propan-1-amine hydrochloride (0.100 g, 0.306 mmol) (prepared according to methods described in *International Journal of Antimicrobial Agents* (2000) 14:203-207) in DMF (1.0 mL) was cooled to 0° C. and treated sequentially with triethylamine (89 µL, 0.643 mmol) and methyl chloroformate (26 µL, 0.336 mmol). The solution was warmed to 25° C. and stirred for 2 h. The mixture was poured over saturated aqueous NaCl (20 mL) and extracted with ethyl acetate (3×50 mL). The combined organic layers were washed with saturated aqueous NaCl (3×50 mL), dried (Na$_2$SO$_4$), concentrated in vacuo, and the residue was purified by flash chromatography (SiO$_2$, 10-30% EtOAc-hexanes) to afford the title compound as a clear oil (0.0875 g, 82%).

Example 5

Synthesis of 2-Chloro-1-(3-chloro-10,11-dihydro-5H-dibenzo[b,f]azepin-5-yl)ethanone

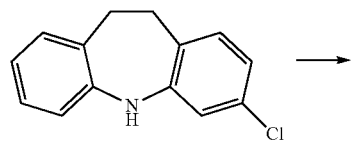

A solution of 3-chloro-10,11-dihydro-5H-dibenzo[b,f]azepine (2.00 g, 8.70 mmol) (*The Journal of Biological Chemistry* (2009) 285, 11, 8363-8374) in toluene (vv20.0 mL) was treated with chloroacetyl chloride (0.72 mL, 9.14 mmol) and heated to 100° C. for 1 h. The mixture was cooled to 25° C., concentrated under N$_2$ stream, taken up in a minimal amount of toluene and purified by flash chromatography (SiO$_2$, 5-20% Ethyl acetate-hexanes) to afford the title compound as an off-white solid (2.33 g, 87%).

Example 6

Synthesis of 3-(3-chloro-10,11-dihydro-5H-dibenzo[b,f]azepin-5-yl)-3-oxopropanenitrile

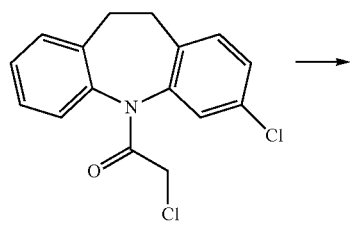

A solution of 2-chloro-1-(3-chloro-10,11-dihydro-5H-dibenzo[b,f]azepin-5-yl)ethanone (2.39 g, 7.81 mmol) (ref) in CH$_2$Cl$_2$ (20.0 mL) was cooled to 0° C. and treated with tetrabutylammonium cyanide (0.72 mL, 9.14 mmol) in portions. The mixture was warmed to 25° C. and stirred for 0.5 h. The solution was diluted with CH$_2$Cl$_2$ (200 mL) and the organic layer was washed with H$_2$O (2×100 mL), saturated aqueous NaCl (100 mL), dried (Na$_2$SO$_4$), and concentrated in vacuo. The residue was taken up in a minimal amount of CH$_2$Cl$_2$ and purified by flash chromatography (SiO$_2$, 10-30% Ethyl acetate-hexanes) to afford the title compound as an off-white solid (1.41 g, 61%). $^1$H NMR (600 MHz, CDCl$_3$) δ (as a mixture of rotamers) (1H, [7.76, s; 7.58, d, J=7.6 Hz; 7.48, s]), 7.34-7.39 (2H, m), 7.28-7.32 (2H, m), 7.23-7.25 (2H, m), (2H, [4.08, d, J=19.0 Hz; 3.97, d, J=19.0 Hz; 3.72, d, J=18.9 Hz; 3.64, d, J=19.0 Hz], 3.36 (1H, m), 3.27 (1H, m), 2.78 (1H, m), 2.51 (1H, m); LCMS m/z 297.1281 ([M+H$^+$], C$_{17}$H$_{13}$ClN$_2$O requires 297.0789).

Example 7

Synthesis of 3-(3-chloro-10,11-dihydro-5H-dibenzo[b,f]azepin-5-yl)propan-1-amine

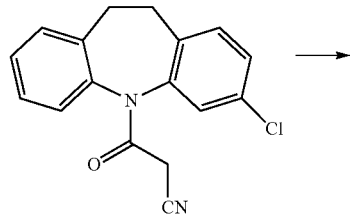

-continued

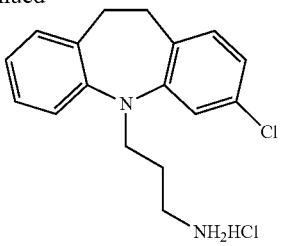

3-(3-chloro-10,11-dihydro-5H-dibenzo[V]azepin-5-yl)propan-1-amine was prepared according to methods in The Journal of Biological Chemistry (2010) 285, 11, 8363-8374) $^1$H NMR (600 MHz, CD$_3$OD) δ 7.17 (1H, m), 7.16 (1H, br s), 7.14 (1H, d, J=8.1 Hz), 7.13 (1H, d, J=1.9 Hz), 7.04 (1H, d, J=8.2 Hz), 6.99 (1H, m), 6.88 (1H, dd, J=8.2, 2.0 Hz) 3.84 (2H, t, J=6.6 Hz), 3.13 (2H, m), 3.09 (2H, m), 2.95 (2H, t, J=9.4 Hz), 1.92 (2H, quintet, J=6.6 Hz). $^{13}$C NMR (150 MHz, CD$_3$OD) δ 149.4, 148.0, 135.9, 132.1, 131.92, 131.85, 129.7, 127.1, 124.1, 122.6, 120.7, 119.7, 47.6, 38.1, 32.3, 31.4, 26.1; LCMS m/z 287.1783 ([M+H$^+$], C$_{17}$H$_{19}$ClN$_2$ requires 287.1310).

Example 8

Synthesis of N-(3-(3-chloro-10,11-dihydro-5H-dibenzo[b,f]azepin-5-yl)propyl)-4-methylbenzenesulfonamide

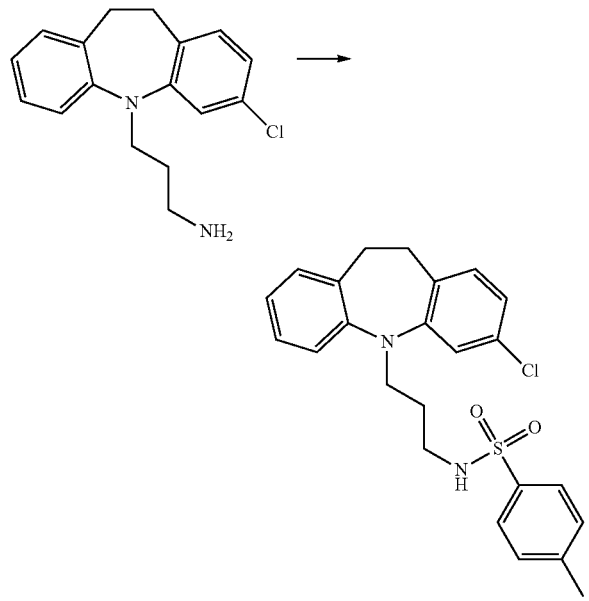

A solution of 3-(3-chloro-10,11-dihydro-5H-dibenzo[b,f]azepin-5-yl)propan-1-amine (0.0952 g, 0.332 mmol) (prepared according to methods described in The Journal of Biological Chemistry (2009) 285(11):8363-8374) in DMF (1.0 mL) was cooled to 0° C. and treated sequentially with triethylamine (97 µL, 0.643 mmol) and p-toluenesulfonyl chloride (0.0700 g, 0.365 mmol). The solution was warmed to 25° C. and stirred for 2 h. The mixture was poured over saturated aqueous NaCl (20 mL) and extracted with ethyl acetate (3×50 mL). The combined organic layers were washed with saturated aqueous NaCl (3×50 mL), dried (Na$_2$SO$_4$), concentrated in vacuo, and the residue was purified by flash chromatography (SiO$_2$, 5-20% EtOAc-hexanes) to afford the title compound as a clear oil (0.0968 g, 66%). $^1$H NMR (600 MHz, CDCl$_3$) δ 7.63 (2H, t, J=8.1 Hz), 7.23 (2H, d, J=8.0 Hz), 7.12 (1H, t, J=7.5 Hz), 7.10 (1H, d, J=7.2 Hz), 6.96 (3H, m), 6.93 (1H, d, J=1.6 Hz), 6.88 (1H, dd, J=6.4, 1.7 Hz), 4.49 (1H, br m), 3.66 (2H, t, J=6.4 Hz), 3.04 (4H, br s), 2.95-3.00 (2H, m), 2.41 (3H, s), 1.70 (2H, quintet, J=6.5 Hz). LCMS m/z 441.1408 ([M+H$^+$], C$_{24}$H$_{25}$ClN$_2$O$_2$S requires 441.1398).

Example 9

Synthesis of Methyl (3-(3-chloro-10,11-dihydro-5H-dibenzo[b,f]azepin-5-yl)propyl)carbamate

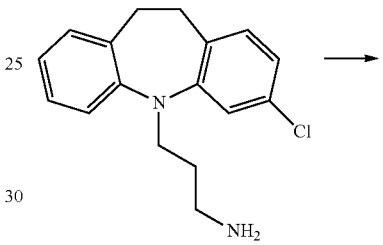

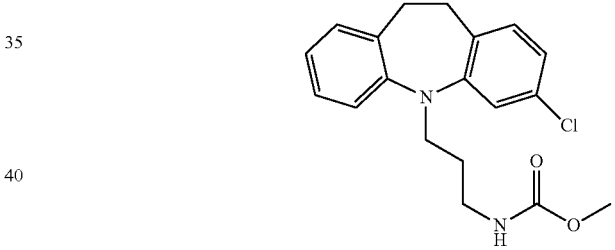

A solution of 3-(3-chloro-10,11-dihydro-5H-dibenzo[b,f]azepin-5-yl)propan-1-amine (0.100 g, 0.349 mmol) (prepared according to methods in The Journal of Biological Chemistry (2009), 285, 11, 8363-8374) in DMF (1.0 mL) was cooled to 0° C. and treated sequentially with triethylamine (102 µL, 0.732 mmol) and methyl chloroformate (30 µL, 0.383 mmol). The solution was warmed to 25° C. and stirred for 2 h. The mixture was poured over saturated aqueous NaCl (20 mL) and extracted with ethyl acetate (3×50 mL). The combined organic layers were washed with saturated aqueous NaCl (3×50 mL), dried (Na$_2$SO$_4$), concentrated in vacuo, and the residue was purified by flash chromatography (SiO$_2$, 5-20% EtOAc-hexanes) to afford the title compound as a clear oil (0.0765 g, 64%). $^1$H NMR (600 MHz, CDCl$_3$) δ 7.16 (1H, t, J=7.9 Hz), 7.12 (1H, d, J=7.4 Hz), 7.06 (1H, d, J=8.0 Hz), 7.04 (1H, s), 6.97-7.01 (2H, m), 6.88 (1H, dd, J=6.2, 1.9 Hz), 4.68 (1H, br s), 3.75 (2H, t, J=6.6 Hz), 3.63 (2H, s), 3.20 (2H, d, J=6.1 Hz), 3.12 (4H, br m), 1.78 (2H, quintet, J=6.4 Hz). LCMS m/z 345.1589 ([M+H$^+$], C$_{19}$H$_{21}$ClN$_2$O$_2$ requires 345.1364).

Example 10

Synthesis of 3-(3-(3-chloro-10,11-dihydro-5H-dibenzo[b,f]azepin-5-yl)propyl)-1,1-dimethylurea

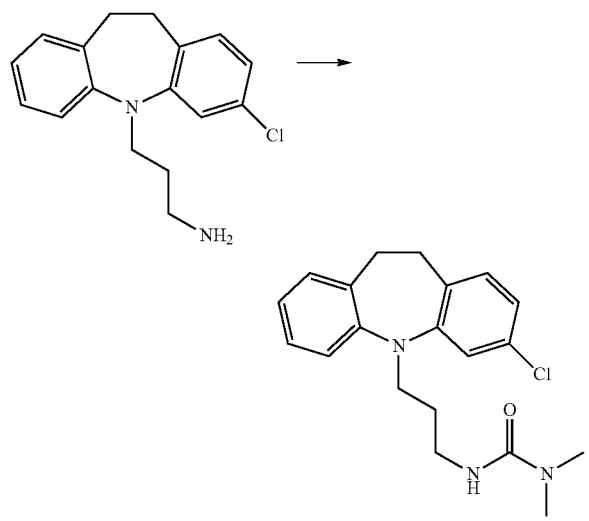

A solution of 3-(3-chloro-10,11-dihydro-5H-dibenzo[b,f]azepin-5-yl)propan-1-amine (0.0850 g, 0.296 mmol) (prepared according to methods in *The Journal of Biological Chemistry* (2009), 285, 11, 8363-8374) in DMF (1.0 mL) was cooled to 0° C. and treated sequentially with triethylamine (86.0 μL, 0.622 mmol) and dimethylcarbamyl chloride (30.0 μL, 0.326 mmol). The solution was warmed to 25° C. and stirred for 2 h. The mixture was poured over saturated aqueous NaCl (20 mL) and extracted with ethyl acetate (3×50 mL). The combined organic layers were washed with saturated aqueous NaCl (3×50 mL), dried ($Na_2SO_4$), concentrated in vacuo, and the residue was purified by flash chromatography ($SiO_2$, 50-75% Ethyl acetate-hexanes) to afford the title compound as a clear oil (0.0931 g, 88%). $^1$H NMR (600 MHz, $CDCl_3$) δ 7.16 (1H, t, J=7.6 Hz), 7.12 (1H, d, J=7.4 Hz), 7.08 (1H, d, J=8.0 Hz), 7.05 (1H, s), 6.96-7.00 (2H, m), 6.87 (1H, dd, J=8.0, 1.7 Hz), 4.32 (1H, br s), 3.76 (2H, t, J=6.7 Hz), 3.25 (2H, dd, J=12.0, 6.4 Hz), 3.12 (4H, m), 2.83 (6H, s), 1.79 (2H, quintet, J=6.8 Hz). LCMS m/z 358.1854 ([M+H$^+$], $C_{20}H_{24}ClN_3O$ requires 358.1681).

Example 11

Synthesis of N-(3-(2-chloro-10H-phenothiazin-10-yl)propyl)-4-methoxybenzenesulfonamide

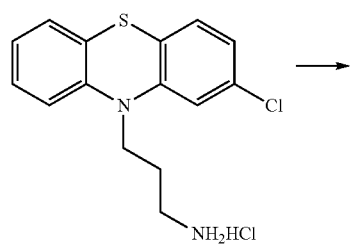

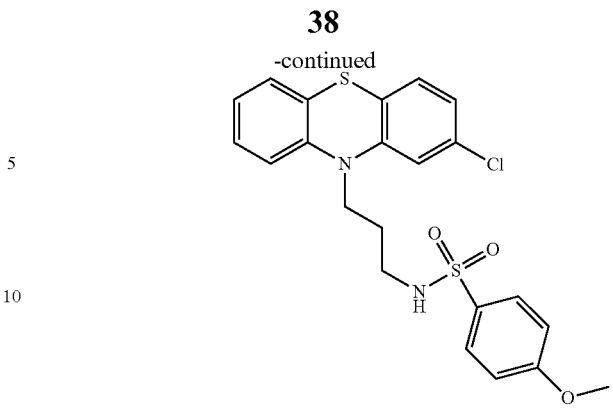

A solution of 3-(2-chloro-10H-phenothiazin-10-yl)propan-1-amine hydrochloride (0.100 g, 0.306 mmol) in DMF (1.0 mL) was cooled to 0° C. and treated sequentially with triethylamine (89.0 μL, 0.641 mmol) and 4-methoxybenzenesulfonyl chloride (0.0690 g, 0.336 mmol). The solution was warmed to 25° C. and stirred for 2 h. The mixture was poured over saturated aqueous NaCl (20 mL) and extracted with ethyl acetate (3×50 mL). The combined organic layers were washed with saturated aqueous NaCl (3×50 mL), dried ($Na_2SO_4$), concentrated in vacuo, and the residue was purified by flash chromatography ($SiO_2$, 10-30% Ethyl acetate-hexanes) to afford the title compound as a clear oil (0.138 g, 98%). $^1$H NMR (600 MHz, $CDCl_3$) δ 7.61 (2H, d, J=8.8 Hz), 7.19 (2H, d, J=7.3 Hz), 7.09 (1H, d, J=8.1 Hz), 7.00 (1H, br m), 6.96 (1H, br m), 6.86 (2H, d, J=8.9 Hz), 8.85 (1H, br m), 6.80 (1H, br s), 4.74 (1H, t, J=5.9 Hz), 3.90 (2H, br m), 3.86 (3H, s), 3.07 (2H, m), 1.93 (2H, t, J=5.5 Hz); $^{13}$C NMR (150 MHz, $CDCl_3$) δ LCMS m/z 461.0690 ([M+H$^+$], $C_{22}H_{21}ClN_2O_3S_2$ requires 461.0755).

Example 12

Synthesis of N-(3-(3-chloro-10,11-dihydro-5H-dibenzo[b,f]azepin-5-yl)propyl)-2-methylbenzenesulfonamide

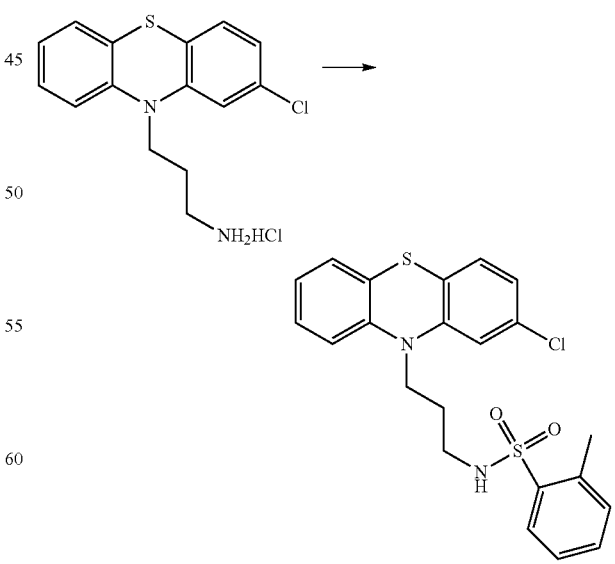

A solution of 3-(2-chloro-10H-phenothiazin-10-yl)propan-1-amine hydrochloride (0.100 g, 0.306 mmol) in DMF (1.5 ml) was cooled to 0° C., treated with Et₃N (89.0 μL, 0.513 mmol), and 2-methylbenzenesulfonyl chloride (48.0 μL, 0.336 mmol). The mixture was warmed to 25° C., and stirred for 2 h. The mixture was poured over saturated aqueous NaCl (50 mL), and extracted with Ethyl acetate (3×50 mL). The combined organic extracts were washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-35% hexanes-Ethyl acetate) to afford the title compound as a white solid triturated from diethyl ether-hexanes (0.0500 g, 37%). $^1$H NMR (600 MHz, CDCl₃) δ 7.87 (1H, d, J=7.8 Hz), 7.42 (1H, t, J=7.6 Hz), 7.23 (1H, d, J=7.5 Hz), 7.26 (1H, m), 7.18 (2H, m), 7.07 (1H, d, J=8.0 Hz), 6.97 (1H, br m), 6.93 (1H, br m), 6.84 (1H, br m), 6.80 (1H, br m), 4.78 (1H, t, J=6.1 Hz), 3.88 (2H, br m), 3.06 (2H, br m), 2.47 (3H, s), 1.98 (2H, br m); LCMS m/z 445.1444 ([M+H$^+$], C₂₂H₂₁ClN₂O₂S₂ requires 445.0806).

Example 13

Synthesis of N-(3-(3-chloro-10,11-dihydro-5H-dibenzo[b,f]azepin-5-yl)propyl)-3,5-difluorobenzenesulfonamide A solution of 3-(2-chloro-10H-phenothiazin-10-yl)propan-1-amine hydrochloride (0.0800 g, 0.244 mmol) in DMF (1.5 ml) was cooled to 0° C., treated with Et₃N (71 mL, 0.513 mmol), and 3,5-difluorobenzenesulfonyl chloride (0.057 g, 0.268 mmol). The mixture was warmed to 25° C., and stirred for 2 h. The mixture was poured over saturated aqueous NaCl (50 mL), and extracted with Ethyl acetate (3×50 mL). The combined organic extracts were washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-35% hexanes-Ethyl acetate) to afford the title compound as a white solid triturated from diethyl ether-hexanes (0.0736 g, 65%). $^1$H NMR (600 MHz, CDCl₃) δ 7.17-7.22 (4H, m), 7.11 (1H, d, J=8.2 Hz), 7.01 (1H, t, J=7.6 Hz), 6.95 (2H, m), 6.85 (1H, d, J=8.1 Hz), 6.81 (1H, s), 5.23 (1H, t, J=5.9 Hz), 3.93 (2H, t, J=5.8 Hz), 3.13 (2H, dd, J=12.2, 6.1 Hz), 1.97 (2H, quintet, J=5.9 Hz); $^{13}$C NMR (150 MHz, CDCl₃) δ 163.7 (d, J=48.0 Hz), 162.0 (d, J=44.2 Hz), 146.5, 144.5, 143.4 (t, J=34.3 Hz), 133.8, 128.6, 128.2, 127.9, 126.0, 124.8, 123.9, 123.3, 116.4, 116.3, 110.6 (dd, J=85.3, 26.0 Hz), 108.3 (t, J=100.6 Hz), 45.3, 42.0, 26.3, problem with carbon; LCMS m/z 467.1119 ([M+H$^+$], C₂₁H₁₇ClF₂N₂O₂S₂ requires 467.0461).

Example 14

Synthesis of N-(3-(2-chloro-10H-phenothiazin-10-yl)propyl)-4-cyanobenzenesulfonamide

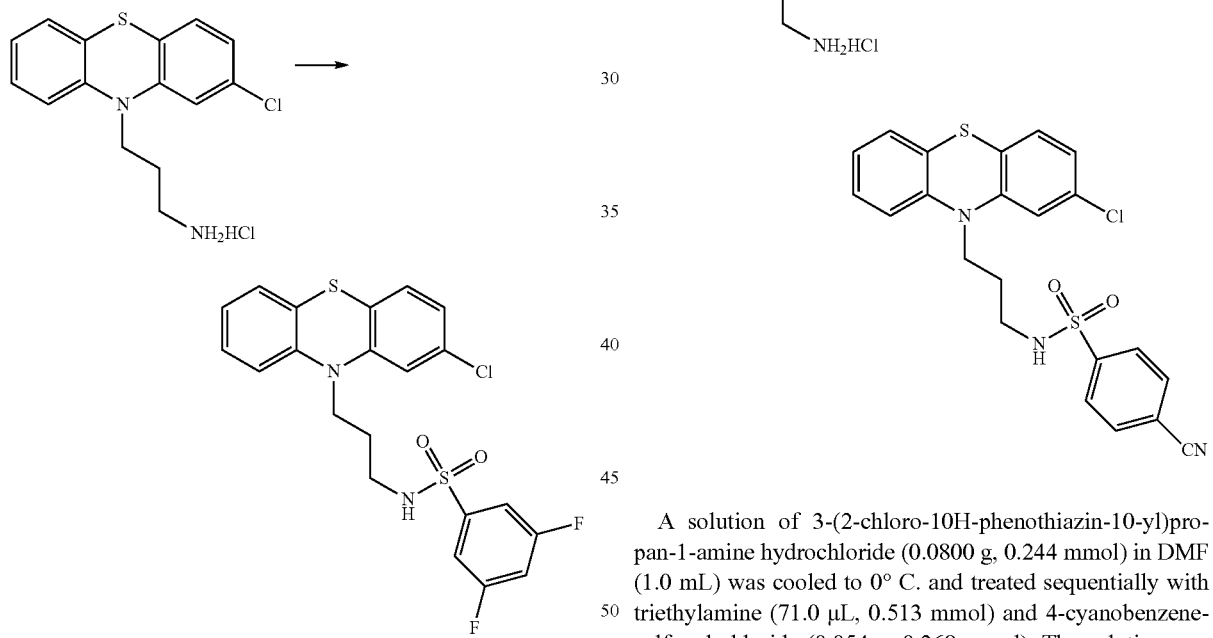

A solution of 3-(2-chloro-10H-phenothiazin-10-yl)propan-1-amine hydrochloride (0.0800 g, 0.244 mmol) in DMF (1.0 mL) was cooled to 0° C. and treated sequentially with triethylamine (71.0 μL, 0.513 mmol) and 4-cyanobenzenesulfonyl chloride (0.054 g, 0.268 mmol). The solution was warmed to 25° C. and stirred for 2 h. The mixture was poured over saturated aqueous NaCl (20 mL) and extracted with ethyl acetate (3×50 mL). The combined organic layers were washed with saturated aqueous NaCl (3×50 mL), dried (Na₂SO₄), concentrated in vacuo, and the residue was purified by flash chromatography (SiO₂, 10-30% Ethyl acetate-hexanes) to afford the title compound as a clear oil (0.0620 g, 55%). $^1$H NMR (600 MHz, CDCl₃) δ 7.72 (2H, d, J=8.3 Hz), 7.64 (2H, d, J=8.3 Hz), 7.26 (1H, d, J=7.3 Hz), 7.21 (1H, br m), 7.14 (1H, d, J=8.2 Hz), 7.05 (1H, br m), 7.02 (1H, br m), 6.85 (1H, br m), 6.81 (1H, br m), 5.15 (1H, t, J=5.7 Hz), 3.92 (2H, br m), 3.15 (2H, m), 1.94 (2H, br m); $^{13}$C NMR (600 MHz, CDCl₃) δ LCMS m/z 456.1231 ([M+H$^+$], C₂₂H₁₈ClN₃O₂S₂ requires 456.0602).

Example 15

Synthesis of 4-Chloro-N-(3-(2-chloro-10H-phenothiazin-10-yl)propyl)benzenesulfonamide

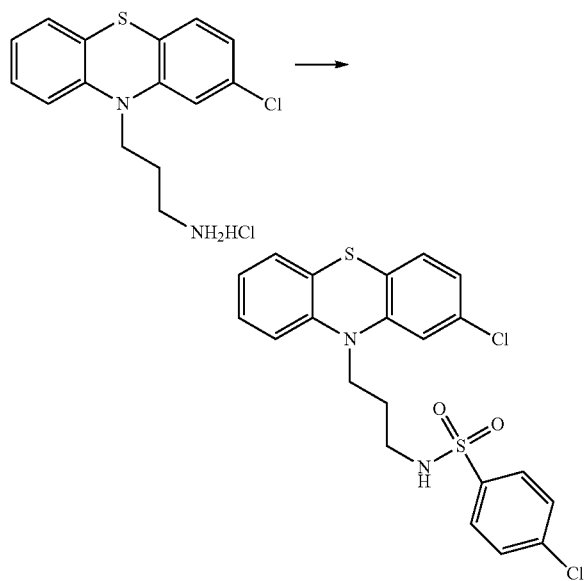

A solution of 3-(2-chloro-10H-phenothiazin-10-yl)propan-1-amine hydrochloride (0.0800 g, 0.244 mmol) in DMF (1.5 ml) was cooled to 0° C., treated with Et₃N (71 mL, 0.513 mmol), and 4-chlorosulfonyl chloride (0.057 g, 0.268 mmol). The mixture was warmed to 25° C., and stirred for 2 h. The mixture was poured over saturated aqueous NaCl (50 mL), and extracted with EtOAc (3×50 mL). The combined organic extracts were washed with saturated aqueous NaCl (2×50 mL), dried (Na₂SO₄), and concentrated in vacuo. The residue was dissolved in a minimal amount of CH₂Cl₂ and purified by flash chromatography (SiO₂, 20-35% hexanes-EtOAc) to afford the title compound as a beige solid triturated from diethyl ether-hexanes (0.0896 g, 79%). ¹H NMR (600 MHz, CDCl₃) δ 7.58 (2H, d, J=8.5 Hz), 7.35 (2H, d, J=8.5 Hz), 7.22 (1H, d, J=7.7 Hz), 7.20 (1H, m), 7.12 (1H, d, J=8.2 Hz), 7.03 (1H, br s), 6.99 (1H, br s), 6.85 (1H, br m), 6.81 (1H, br s), 4.92 (1H, t, J=6.2 Hz), 3.92 (2H, br s), 3.11 (2H, m), 1.94 (2H, t, J=5.5 Hz); ¹³C NMR (150 MHz, CDCl₃) δ 146.5, 144.4, 139.1, 138.4, 133.7, 129.5, 128.53, 128.51, 128.1, 127.9, 126.0, 124.7, 123.7, 123.1, 116.3, 116.2, 45.1, 41.7, 26.2; LCMS m/z 465.0916 ([M+H⁺], requires C₂₁H₁₈Cl₂N₂O₂S₂ requires 465.0260.

Example 16

Synthesis of N-(4-(2-chloro-10H-phenothiazin-10-yl)butyl)-4-methylbenzenesulfonamide

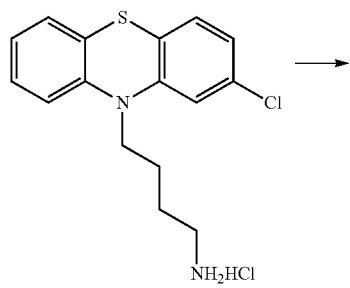

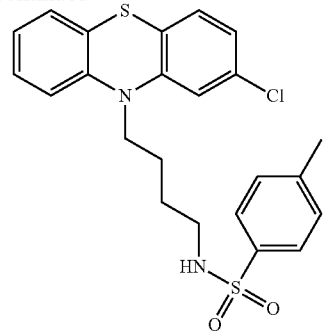

A solution of 4-(2-chloro-10H-phenothiazin-10-yl)butan-1-amine hydrochloride (0.0800 g, 0.234 mmol) in DMF (1.0 mL) was cooled to 0° C. and treated sequentially with triethylamine (68.0 µL, 0.513 mmol) and p-toluenesulfonyl chloride (0.0490 g, 0.257 mmol). The solution was warmed to 25° C. and stirred for 2 h. The mixture was poured over saturated aqueous NaCl (20 mL) and extracted with ethyl acetate (3×50 mL). The combined organic layers were washed with saturated aqueous NaCl (3×50 mL), dried (Na₂SO₄), concentrated in vacuo, and the residue was purified by flash chromatography (SiO₂, 10-30% ethyl acetate-hexanes) to afford the title compound as a white solid (0.0533 g, 50%). ¹H NMR (600 MHz, CDCl₃) δ 7.66 (2H, d, J=8.2 Hz), 7.26 (2H, d, J=7.8 Hz), 7.25 (1H, m), 7.14 (2H, m), 7.03 (1H, d, J=7.8 Hz), 6.92 (1H, br m), 6.81 (1H, br m), 6.78 (1H, br m), 4.27 (1H, t, J=6.4 Hz), 3.82 (2H, br m) 2.92 (2H, q, J=6.6 Hz), 2.41 (3H, s), 1.77 (2H, br m), 1.58 (2H, br m); ¹³C NMR (150 MHz, CDCl₃) δ; LCMS m/z 459.1552 ([M+H⁺], C₂₃H₂₃ClN₂O₂S₂ requires 459.0962).

Example 17

Synthesis of 3-(3-(2-Chloro-10H-phenothiazin-10-yl)propyl)-1,1-dimethylurea

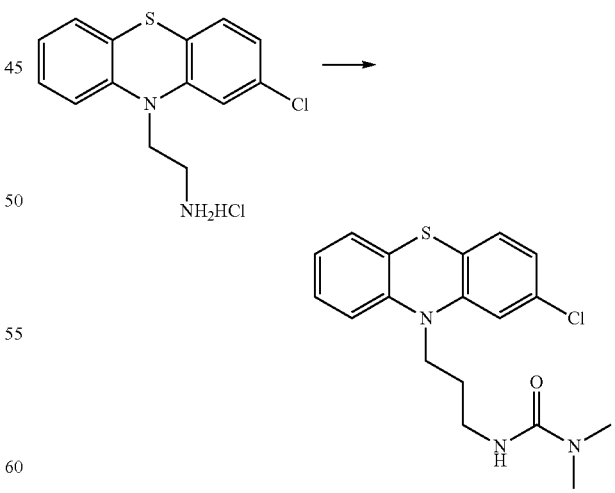

A solution of 3-(2-chloro-10H-phenothiazin-10-yl)propan-1-amine hydrochloride (0.100 g, 0.306 mmol) in DMF (1.0 mL) was cooled to 0° C. and treated sequentially with triethylamine (0.643 mmol) and dimethylcarbamyl chloride (26.0 µL, 0.336 mmol). The solution was warmed to 25° C.

and stirred for 2 h. The mixture was poured over saturated aqueous NaCl (20 mL) and extracted with ethyl acetate (3×50 mL). The combined organic layers were washed with saturated aqueous NaCl (3×50 mL), dried (Na₂SO₄), concentrated in vacuo, and the residue was purified by flash chromatography (SiO₂, 10-30% ethyl acetate-hexanes) to afford the title compound as a clear oil (0.0875 g, 82%). $^1$H NMR (600 MHz, CDCl₃) δ 7.18 (1H, t, J=7.7 Hz), 7.14 (1H, t, J=7.6 Hz), 7.04 (1H, t, J=8.2 Hz), 6.96 (1H, t, J=7.3 Hz), 6.91 (1H, t, J=8.1 Hz), 6.87 (1H, s), 4.52 (1H, t, J=5.2 Hz), 3.93 (2H, t, J=5.6 Hz), 3.33 (2H, dd, J=12.2, 5.9 Hz), 2.78 (6H, s), 2.03 (2H, quintet, J=6.1 Hz); $^{13}$C NMR (150 MHz, CDCl₃) δ 158.6, 146.8, 144.8, 133.6, 128.2, 127.82, 127.81, 125.3, 124.1, 123.3, 122.7, 116.25, 116.24, 45.1, 38.8, 36.2, 27.2; LCMS m/z 362.1469 ([M+H$^+$], $C_{18}H_{20}ClN_3OS$ requires 362.1088).

Example 18

Synthesis of N-(2-(2-chloro-10H-phenothiazin-10-yl)ethyl)-4-methylbenzenesulfonamide

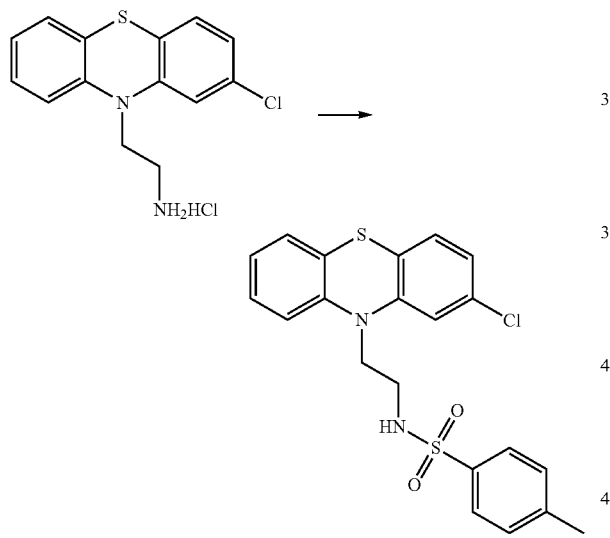

A solution of 2-(2-chloro-10H-phenothiazin-10-yl)ethanamine hydrochloride (0.060 g, 0.192 mmol) in DMF (1.0 mL) was cooled to 0° C., treated with Et₃N (55.0 µL, 0.403 mmol), and p-toluenesulfonyl chloride (0.040 g, 0.211 mmol). The mixture was warmed to 25° C., and stirred for 2 h. The mixture was partitioned between saturated aqueous NaCl (100 mL), and CH₂Cl₂ (400 mL). The organic layer was washed with saturated aqueous NaCl (3×100 mL), dried (Na₂SO₄), and concentrated in vacuo. The residue was dissolved in a minimal amount of CH₂Cl₂ and purified by flash chromatography (SiO₂, 0-25% hexanes-ethyl acetate) to afford the title compound as a white solid (0.038 g, 46%). $^1$H NMR (600 MHz, CDCl₃) δ 7.58 (2H, d, J=6.9 Hz), 7.18 (1H, d, J=7.6 Hz), 7.14 (1H, t, J=7.6 Hz), 7.08 (3H, m), 7.00 (1H, t, J=7.3 Hz), 6.93 (1H, d, J=7.9 Hz), 6.75 (1H, d, J=7.9 Hz), 6.63 (1H, s), 4.71 (1H, br s), 3.89 (2H, br s), 3.36 (2H, br m), 2.36 (3H, s); $^{13}$C NMR (150 MHz, CDCl₃) δ; LCMS m/z 431.1244 ([M+H$^+$], $C_{21}H_{19}ClN_2O_2S_2$ requires 431.0649).

Example 19

Synthesis of 3-(10,11-dihydro-5H-dibenzo[b,f]azepin-5-yl)propan-1-aminium chloride

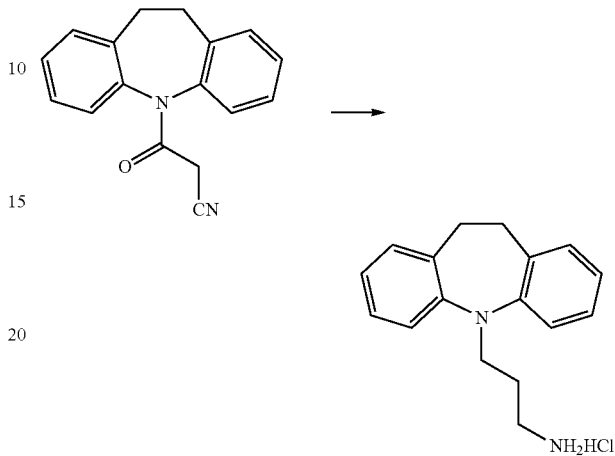

Compound was prepared as described in J. Med. Chem. 2001, 44, 2152-2163.

Example 20

Synthesis of N-(3-(3-chloro-10,11-dihydro-5H-dibenzo[b,f]azepin-5-yl)propyl)-4-fluorobenzenesulfonamide

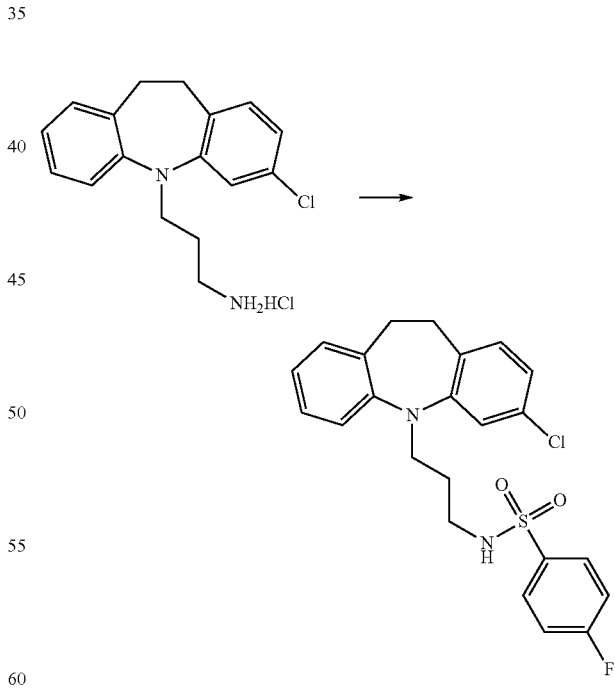

A solution of 3-(3-chloro-10,11-dihydro-5H-dibenzo[b,f]azepin-5-yl)propan-1-amine hydrochloride (0.0800 g, 0.247 mmol) in DMF (1.0 mL) was cooled to 0° C., treated with Et₃N (72 µL, 0.520 mmol), and 4-fluorosulfonyl chloride (0.052 g, 0.272 mmol). The mixture was warmed to 25° C., and stirred for 2 h. The mixture was partitioned between saturated aqueous NaCl (50 mL) and CH₂Cl₂ (100 mL). The organic layer was washed with saturated aqueous NaCl (2×50 mL), dried (Na₂SO₄), and concentrated in vacuo. The residue was dissolved in a minimal amount of CH₂Cl₂ and purified by flash chromatography (SiO₂, 20-35% hexanes-EtOAc) to afford the title compound as a clear oil (0.0696 g, 63%). $^1$H NMR (600 MHz, CDCl₃) δ 7.74 (2H, dd, J=3.6, 5.0 Hz), 7.14 (1H, t, J=7.3 Hz), 7.08-7.12 (3H, m), 6.99 (3H, m), 6.94 (1H, s), 6.89 (1H, d, J=8.3 Hz), 4.37 (1H, t, J=6.0 Hz), 3.68 (1H, t, J=6.3 Hz), 3.01 (4H, br s), 2.99 (2H, m), 1.71 (2H, quintet, J=6.4 Hz); LCMS m/z 445.1707 ([M+H⁺], C₂₃H₂₂ClFN₂O₂S requires 445.1147).

Example 21

Synthesis of N-(3-(3-chloro-10,11-dihydro-5H-dibenzo[b,f]azepin-5-yl)propyl)-4-(trifluoromethyl)benzenesulfonamide

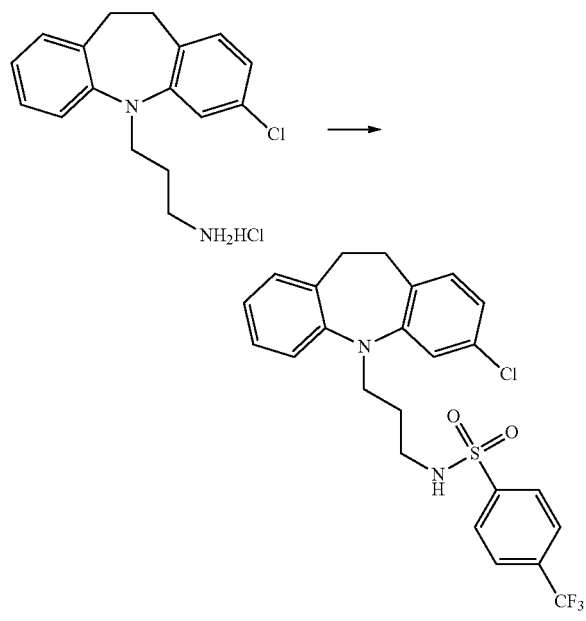

A solution of 3-(3-chloro-10,11-dihydro-5H-dibenzo[b,f]azepin-5-yl)propan-1-amine hydrochloride (0.0800 g, 0.247 mmol) in DMF (1.0 mL) was cooled to 0° C., treated with Et₃N (72.0 μL, 0.520 mmol), and 4-trifluoromethylbenzenesulfonyl chloride (0.066 g, 0.272 mmol). The mixture was warmed to 25° C., and stirred for 2 h. The mixture was partitioned between saturated aqueous NaCl (50 mL), and CH₂Cl₂ (100 mL). The organic layer was washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-25% hexanes-Ethyl acetate) to afford the title compound as a clear film (0.0975 g, 80%). $^1$H NMR (600 MHz, CDCl₃) δ 7.84 (2H, d, J=8.1 Hz), 7.69 (2H, d, J=8.2 Hz), 7.13 (1H, t, J=7.4 Hz), 7.11 (1H, d, J=7.9 Hz), 6.97-7.00 (3H, m), 6.95 (1H, br s), 6.89 (1H, d, J=8.1 Hz), 4.49 (1H, t, J=5.8 Hz), 3.69 (2H, t, J=6.2 Hz), 3.06 (2H, q, J=6.7 Hz), 3.03 (4H, br s), 1.73 (2H, quintet, J=6.5 Hz); $^{13}$C NMR (150 MHz, CDCl₃) δ 148.8, 147.4, 143.6, 135.1, 134.4 (q, J=132 Hz), 131.83, 131.79, 131.6, 129.9, 127.6, 126.9, 126.4 (q, J=13.7 Hz), 124.3, 123.9, 122.8, 120.3, 119.8, 47.5, 41.4, 32.1, 31.5, 27.5; LCMS m/z 495.1716 ([M+H⁺], C₂₄H₂₂ClF₃N₂O₂S requires 495.1115).

Example 22

Synthesis of N-(3-(3-chloro-10,11-dihydro-5H-dibenzo[b,f]azepin-5-yl)propyl)-4-cyanobenzenesulfonamide

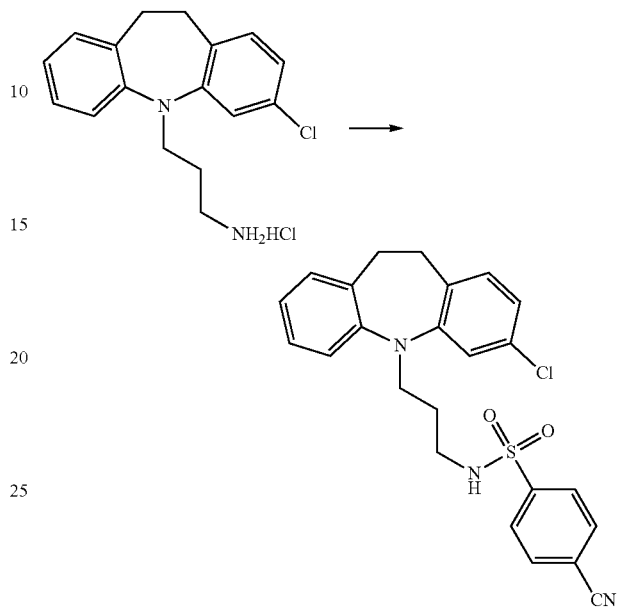

A solution of 3-(3-chloro-10,11-dihydro-5H-dibenzo[b,f]azepin-5-yl)propan-1-amine hydrochloride (0.0800 g, 0.247 mmol) in DMF (1.0 mL) was cooled to 0° C., treated with Et₃N (72.0 μL, 0.520 mmol), and 4-cyanobenzenesulfonyl chloride (0.0550 g, 0.272 mmol). The mixture was warmed to 25° C., and stirred for 2 h. The mixture was partitioned between saturated aqueous NaCl (50 mL), and CH₂Cl₂ (100 mL). The organic layer was washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-25% hexanes-Ethyl acetate) to afford the title compound as a clear film (0.0832 g, 75%). $^1$H NMR (600 MHz, CDCl₃) δ 7.82 (2H, d, J=8.2 Hz), 7.68 (2H, d, J=8.2 Hz), 7.13-7.16 (2H, m), 7.01 (2H, d, J=6.9 Hz), 6.97 (1H, d, J=8.0 Hz), 6.92 (2H, m), 4.55 (1H, t, J=5.9 Hz), 3.67 (2H, t, J=6.2 Hz), 3.08 (2H, m), 3.05 (4H, br s), 1.72 (2H, quintet, J=6.4 Hz); $^{13}$C NMR (150 MHz, CDCl₃) δ; LCMS m/z 452.0861 ([M+H⁺], C₂₄H₂₂ClN₃O₂S requires 452.1194).

Example 23

Synthesis of 4-Chloro-N-(3-(3-chloro-10,11-dihydro-5H-dibenzo[b,f]azepin-5-yl)propyl)benzenesulfonamide

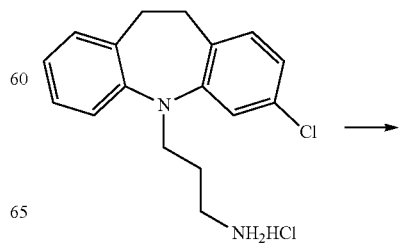

47
-continued

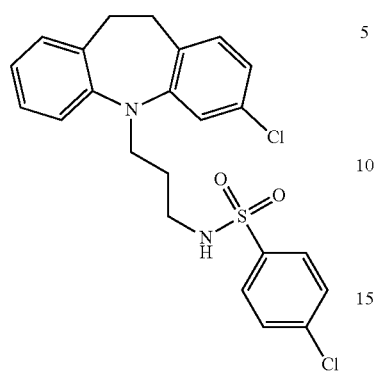

A solution of 3-(3-chloro-10,11-dihydro-5H-dibenzo[b] azepin-5-yl)propan-1-amine hydrochloride (0.0800 g, 0.247 mmol) in DMF (1.0 mL) was cooled to 0° C., treated with Et$_3$N (72 µL, 0.520 mmol), and 4-chlorosulfonyl chloride (0.057 g, 0.272 mmol). The mixture was warmed to 25° C., and stirred for 2 h. The mixture was partitioned between saturated aqueous NaCl (50 mL) and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 20-35% hexanes-EtOAc) to afford the title compound as a clear film (0.100 g, 88%). $^1$H NMR (600 MHz, CDCl$_3$) δ 7.67 (2H, d, J=8.5 Hz), 7.39 (2H, d, J=8.5 Hz), 7.14 (1H, t, J=7.7 Hz), 7.11 (1H, d, J=7.5 Hz), 6.99 (3H, td, J=5.2, 2.5), 6.95 (1H, s), 6.90 (1H, dd, J=6.3, 1.8 Hz), 4.41 (1H, t, J=6.0 Hz), 3.69 (2H, t, J=6.3 Hz), 3.02 (4H, br s), 3.00 (2H, m), 1.72 (2H, quintet, J=6.7 Hz). $^{13}$C NMR (150 MHz, CDCl$_3$) δ 47.5, 41.3, 32.1, 31.5, 27.5; LCMS m/z 461.0501 ([M+H$^+$], C$_{23}$H$_{22}$Cl$_2$N$_2$O$_2$S requires 461.0852).

Example 24

Synthesis of N-(3-(3-chloro-10,11-dihydro-5H-dibenzo[b,f]azepin-5-yl)propyl)-4-(methylsulfonyl)benzenesulfonamide 48
-continued A solution of 3-(3-chloro-10,11-dihydro-5H-dibenzo[b,f] azepin-5-yl)propan-1-amine hydrochloride (0.0800 g, 0.247 mmol) in DMF (1.0 mL) was cooled to 0° C., treated with Et$_3$N (72 µL, 0.520 mmol), and 4-(methylsulfonyl)benzenesulfonyl chloride (0.0690 g, 0.272 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-25% hexanes-Ethyl acetate) to afford the title compound as a white solid (0.1170 g, 94%). $^1$H NMR (600 MHz, CDCl$_3$) δ 8.01 (2H, d, J=7.9 Hz), 7.91 (2H, d, J=7.67 Hz), 7.13-7.17 (2H, m), 7.00 (3H, m), 6.97 (1H, s), 6.91 (1H, d, J=8.2 Hz), 4.57 (1H, br s), 3.72 (2H, t, J=5.8 Hz), 3.10 (3H, br s), 3.08 (2H, m), 3.06 (4H, br s), 1.76 (2H, quintet, J=6.2 Hz); $^{13}$C NMR (150 MHz, CDCl$_3$) δ 148.8, 147.4, 145.5, 144.3, 135.1, 131.84, 131.83, 131.7, 130.0, 128.5, 128.1, 127.0, 124.0, 122.8, 120.2, 119.7, 47.5, 44.5, 41.5, 32.1, 31.5, 27.6; LCMS m/z 505.0598 ([M+H$^+$], C$_{24}$H$_{25}$ClN$_2$O$_4$S$_2$ requires 505.1017).

Example 25

Synthesis of N-(3-(3-chloro-10,11-dihydro-5H-dibenzo[b,f]azepin-5-yl)propyl)-4-methoxybenzenesulfonamide

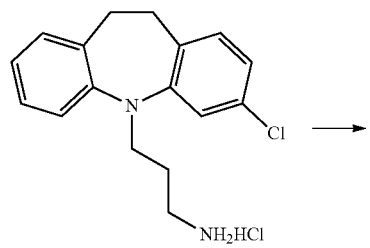

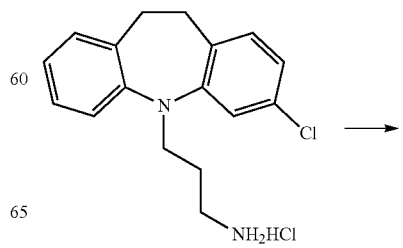

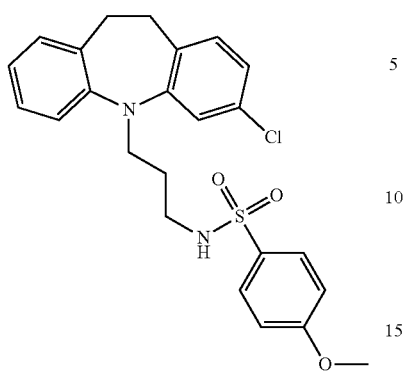

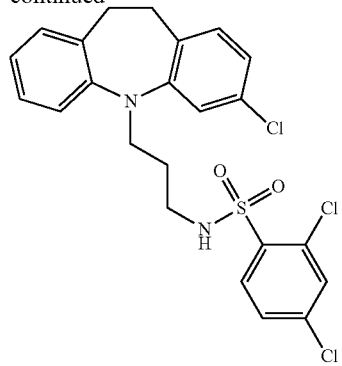

A solution of 3-(3-chloro-10,11-dihydro-5H-dibenzo[b]azepin-5-yl)propan-1-amine hydrochloride (0.0800 g, 0.247 mmol) in DMF (1.0 mL) was cooled to 0° C., treated with Et₃N (72.0 µL, 0.520 mmol), and 4-methoxybenzenesulfonyl chloride (0.0560 g, 0.272 mmol). The mixture was warmed to 25° C., and stirred for 2 h. The mixture was partitioned between saturated aqueous NaCl (50 mL), and CH₂Cl₂ (100 mL). The organic layer was washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-25% hexanes-Ethyl acetate) to afford the title compound as a clear oil (0.1072 g, 95%). $^1$H NMR (600 MHz, CDCl₃) δ 8.01 (1H, br s), 7.68 (2H, d, J=7.2 Hz), 7.12 (1H, t, J=7.8 Hz), 7.09 (1H, d, J=7.5 Hz), 6.96-6.98 (3H, m), 6.94 (1H, s), 6.88 3H, m) 4.75 (1H, br s), 3.86 (3H, s), 3.66 (2H, t, J=6.3 Hz); 3.03 (2H, m), (1.69 (2H, quintet, J=6.4 Hz); $^{13}$C NMR (150 MHz, CDCl₃) δ 162.9, 148.9, 147.6, 135.1, 131.8, 131.7, 131.6, 131.5, 129.8, 129.3, 126.8, 123.7, 122.6, 120.4, 119.8, 114.3, 55.8, 47.6, 41.2, 32.1, 31.5, 27.5; LCMS m/z 457.1008 ([M+H$^+$], C₂₄H₂₅ClN₂O₃S requires 457.1347).

Example 26

Synthesis of 2,4-dichloro-N-(3-(3-chloro-10,11-dihydro-5H-dibenzo[b,f]azepin-5-yl)propyl)benzenesulfonamide

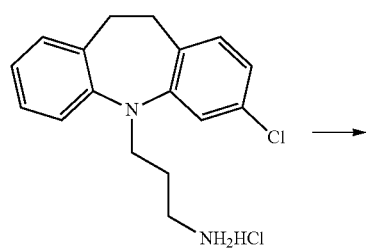 →

A solution of 3-(3-chloro-10,11-dihydro-5H-dibenzo[b,f]azepin-5-yl)propan-1-amine hydrochloride (0.0800 g, 0.247 mmol) in DMF (1.0 mL) was cooled to 0° C., treated with Et₃N (72.0 µL, 0.520 mmol), and 2,4-dichlorobenzenesulfonyl chloride (0.0670 g, 0.272 mmol). The mixture was warmed to 25° C., and stirred for 2 h. The mixture was partitioned between saturated aqueous NaCl (50 mL), and CH₂Cl₂ (100 mL). The organic layer was washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-25% hexanes-Ethyl acetate) to afford the title compound as a clear oil (0.1072 g, 88%). $^1$H NMR (600 MHz, CDCl₃) δ 7.92 (1H, d, J=8.5 Hz), 7.40 (1H, s), 7.33 (1H, d, J=8.5 Hz), 7.14 (1H, t, J=7.7 Hz), 7.10 (1H, d, J=7.3 Hz), 6.99 (3H, m), 6.94 (1H, s), 6.89 (1H, d, J=8.1 Hz), 4.91 (1H, t, J=5.3 Hz), 3.69 (2H, t, J=6.1 Hz), 3.01 (4H, s), 2.99 (2H, m), 1.73 (2H, quintet, J=6.3 Hz); LCMS m/z 497.0025 ([M+H$^+$], C₂₃H₂₁Cl₃N₂O₂S requires 497.0438).

Example 27

Synthesis of 4-chloro-N-(2-(2-chloro-10H-phenothiazin-10-yl)ethyl)benzenesulfonamide

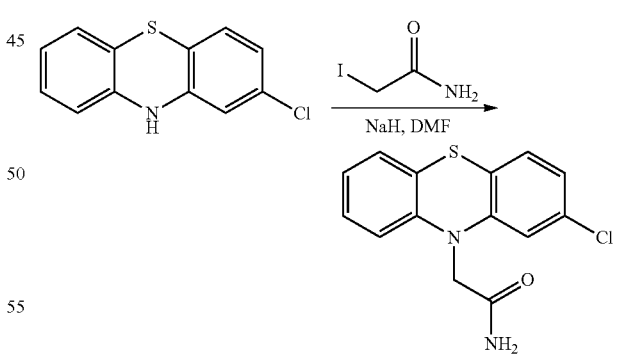

2-(2-chloro-10H-phenothiazin-10-yl)acetamide. A solution of 2-chloro-10H-phenothiazine (5.00 g, 21.4 mmol) in DMF (50.0 mL) was cooled to 0° C., treated with NaH (60% dispersion in mineral oil, 1.03 g, 25.6 mmol), and iodoacetamide (4.35 g, 23.5 mmol). The mixture was warmed to 25° C., and stirred for 2 h. The mixture was poured over a solution of saturated aqueous NaCl (200 mL) and the solid that had formed was collected by filtration. The solid was suspended in a minimal amount of CH₂Cl₂ and purified by flash chromatography (SiO$_2$, 20-50% hexanes-EtOAc) to afford the title compound as a purple solid (0.373 g, 6%). $^1$H NMR (600 MHz, CD$_3$OD) δ 7.14 (1H, td, J=7.4, 1.5 Hz), 7.08 (1H, dd, J=7.6, 1.5 Hz), 7.03 (1H, d, J=8.2 Hz), 6.95 (1H, dd, J=7.6, 1.0 Hz), 6.92 (1H, dd, J=8.2, 2.0 Hz), 6.80 (1H, d, J=8.2 Hz), 6.77 (1H, d, J=2.0 Hz), 4.48 (2H, s); LCMS m/z 291.1279 ([M+H$^+$], C$_{14}$H$_{11}$ClN$_2$OS requires 291.0353).

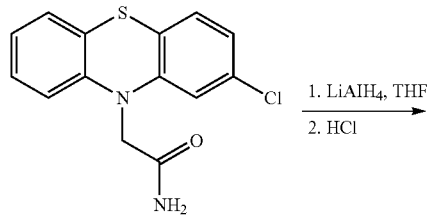

2-(2-chloro-10H-phenothiazin-10-yl)ethanamine hydrochloride. A solution of 2-(2-chloro-10H-phenothiazin-10-yl)acetamide (0.570 g, 1.94 mmol) in anhydrous THF (10.0 mL) was cooled to 0° C., and treated with LiAlH$_4$ (0.222 g, 5.83 mmol) in 50 mg portions. The mixture was warmed to 70° C. and stirred for 3 h. The mixture was cooled to 0° C., and treated dropwise with a solution of aqueous 4 N NaOH (1.5 mL) and then H$_2$O (1.5 mL). The mixture was suspended in THF (100 mL), filtered, and concentrated in vacuo. The residue was suspended in a minimal amount of CH$_2$Cl$_2$ and purified by flash chromatography (SiO$_2$, 3% MeOH—CH$_2$Cl$_2$ followed by 17:2:1 CH$_2$Cl$_2$-MeOH-conc. NH$_4$OH). The combined fractions were concentrated to dryness, taken up in a minimal amount of ether, and treated with a solution of 4 N HCl in dioxane (0.5 mL). The beige solid that had formed was collect by filtration to afford the title compound (0.142 g, 23%). $^1$H NMR (600 MHz, CD$_3$OD) δ 7.14 (1H, td, J=7.4, 1.5 Hz), 7.08 (1H, dd, J=7.6, 1.5 Hz), 7.03 (1H, d, J=8.2 Hz), 6.95 (1H, dd, J=7.6, 1.0 Hz), 6.92 (1H, dd, J=8.2, 2.0 Hz), 6.80 (1H, d, J=8.2 Hz), 6.77 (1H, d, J=2.0 Hz), 4.48 (2H, s); LCMS m/z 291.1279 ([M+H$^+$], C$_{14}$H$_{11}$ClN$_2$OS requires 291.0353).

Azide Route

2-Chloro-1-(2-chloro-10H-phenothiazin-10-yl)ethanone. A solution of 2-chloro-10H-phenothiazine (4.00 g, 17.1 mmol) (The Journal of Biological Chemistry (2009) 285, 11, 8363-8374) in toluene (20.0 mL) was treated with chloroacetyl chloride (1.43 mL, 18.0 mmol) and heated to 100° C. for 1 h. The mixture was cooled to 25° C., concentrated in vacuo, taken up in a minimal amount of toluene and purified by flash chromatography (SiO$_2$, 5-20% ethyl acetate-hexanes) to afford the title compound as an off-white solid (4.01 g, 76%). $^1$H NMR (600 MHz, CDCl$_3$) δ (mixture of rotamers) 7.65 (1H, s), 7.55 (1H, d, J=7.8 Hz), 7.47 (1H, d, J=7.8 Hz), 7.36 (2H, m), 7.30 (1H, q, J=7.2 Hz) 7.26 (1H, m), 4.22 (1H, m), 4.15 (1H, m); $^{13}$C NMR (150 MHz, CDCl$_3$) δ 165.6, 139.1, 137.7, 133.3, 128.8, 128.6, 128.0, 127.9, 127.75, 127.30, 127.28, 126.50, 126.49, 41.8; LCMS m/z 309.9605 ([M+H$^+$], C$_{14}$H$_9$Cl$_2$NOS requires 309.9855).

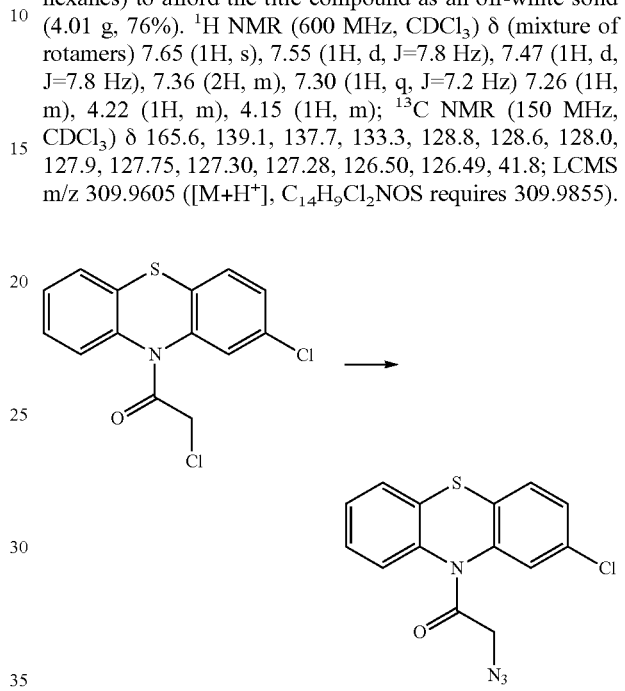

2-Azido-1-(2-chloro-10H-phenothiazin-10-yl)ethanone. A solution of 2-chloro-1-(2-chloro-10H-phenothiazin-10-yl)ethanone (4.40 g, 14.2 mmol) in DMF (50 mL) was treated with sodium azide (2.77 g, 42.6 mmol) and stirred at 25° C. for 14 h. The solution was diluted with CH$_2$Cl$_2$ (500 mL) and the organic layer was washed with H$_2$O (2×100 mL), saturated aqueous NaCl (100 mL), dried (Na$_2$SO$_4$), and concentrated in vacuo. The residue was taken up in a minimal amount of CH$_2$Cl$_2$ and purified by flash chromatography (SiO$_2$, 10-30% ethyl acetate-hexanes) to afford the title compound as a white solid (4.30 g, 96%). $^1$H NMR (600 MHz, CDCl$_3$) δ (mixture of rotamers) 7.59 (1H, br s), 7.48 (1H, d, J=6.6 Hz), 7.45 (1H, m), 7.36 (2H, m), 7.30 (1H, q, J=7.2 Hz) 7.25 (1H, m), 4.03 (1H, br s), 3.91 (1H, br s); $^{13}$C NMR (150 MHz, CDCl$_3$) δ 166.8, 138.8, 137.2, 133.3, 128.9, 128.6, 128.0, 127.83, 127.77, 127.35, 127.31, 126.62, 126.60, 51.1; LCMS m/z 316.9987 ([M+H$^+$], C$_{14}$H$_9$ClN$_4$OS requires 317.0258).

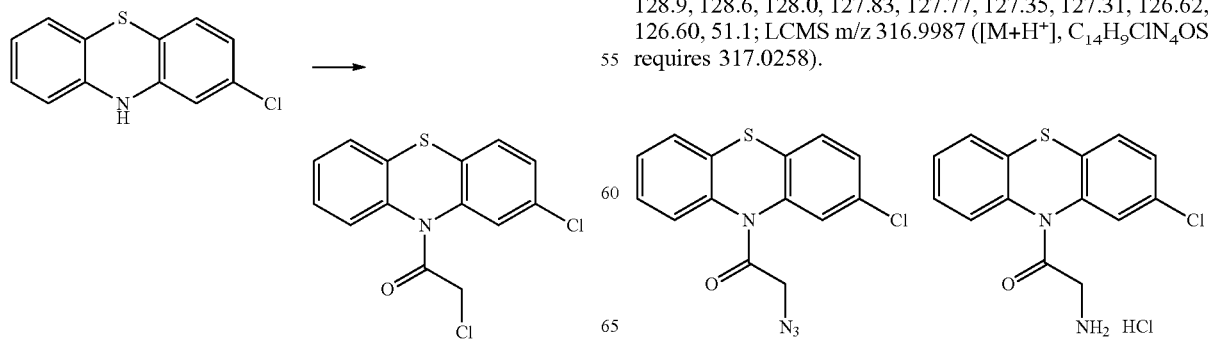

2-(2-Chloro-10H-phenothiazin-10-yl)ethanamine hydrochloride. A solution of 2-azido-1-(2-chloro-10H-phenothiazin-10-yl)ethanone (3.80 g, 12.0 mmol) in THF (10.0 mL) was cooled to 0° C. and treated with a BH$_3$-THF (1 M solution in THF, 48.0 mL, 48.0 mmol). The flask was sealed, heated to 70° C. for 5 h, and then cooled to 0° C. The solution was treated slowly, dropwise with a solution of aqueous 1 M HCl (96 mL), stirred for an additional 0.5 h, and then heated to 70° C. for 1 h. The mixture was cooled to 25° C., treated with aqueous 4 M NaOH until pH>8, and then extracted with ethyl acetate (3×200 mL). The combined extracts were washed with saturated aqueous NaCl (100 mL), dried (Na$_2$SO$_4$), and concentrated in vacuo. The residue was dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$:MeOH:NH$_4$OH to elute the product). The combined fractions of pure product were concentrated, dried azeotropically with toluene, and then suspended in Et$_2$O (100 mL) and treated dropwise with a 4 N HCl-dioxane solution (3.0 mL). The white solid that had precipitated was collected by filtration to afford the title compound (3.15 g, 84%) which proved identical to the compound produced above by all methods of characterization.

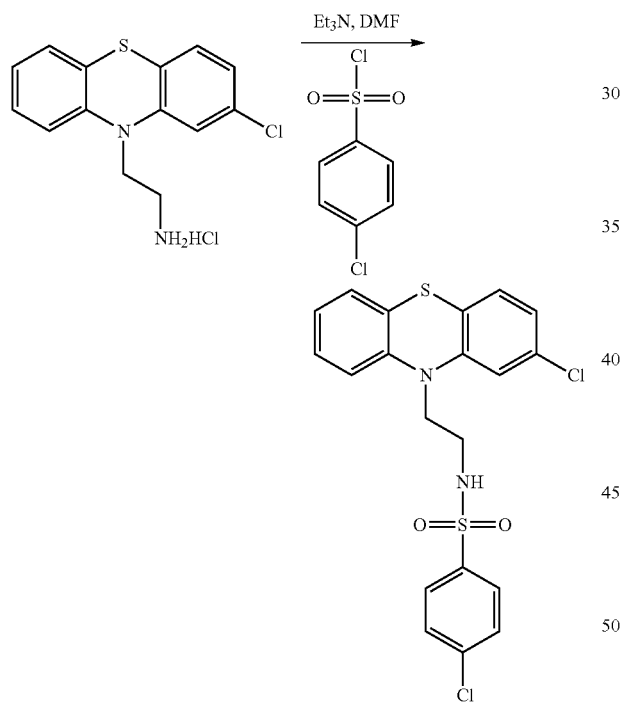

4-Chloro-N-(2-(2-chloro-10H-phenothiazin-10-yl)ethyl)benzenesulfonamide. A solution of 2-(2-chloro-10H-phenothiazin-10-yl)ethanamine hydrochloride (1.26 g, 4.02 mmol) in DMF (10.0 mL) was cooled to 0° C., treated with triethylamine (1.17 mL, 8.44 mmol), and 4-chlorobenzenesulfonyl chloride (0.934 g, 4.42 mmol). The mixture was warmed to 25° C., and stirred for 2 h. The mixture was partitioned between saturated aqueous NaCl (100 mL), and CH$_2$Cl$_2$ (400 mL). The organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-25% ethyl acetate-hexanes) to afford the title compound as a white solid (1.25 g, 69%). $^1$H NMR (600 MHz, CDCl$_3$) δ 7.62 (2H, d, J=8.3 Hz), 7.22 (2H, d, J=8.3 Hz), 7.17 (1H, d, J=7.6 Hz), 7.14 (1H, t, J=7.5 Hz), 7.06 (1H, d, J=8.2 Hz), 6.99 (1H, t, J=7.5 Hz) 6.94 (1H, d, J=8.2 Hz), 6.73 (1H, d, J=8.0 Hz), 6.66 (1H, s), 4.85 (1H, t, J=5.2 Hz), 3.93 (2H, t, J=5.7 Hz), 3.36 (2H, q, J=5.7 Hz); $^{13}$C NMR (150 MHz, CDCl$_3$) δ 145.7, 143.7, 139.3, 137.9, 133.7, 129.4, 128.5, 128.2, 128.1, 127.9, 126.4, 125.2, 124.0, 123.5, 116.4, 116.2, 46.0, 39.5; LCMS m/z 450.9783 ([M+H]$^+$, C$_{20}$H$_{16}$Cl$_2$N$_2$O$_2$S$_2$ requires 451.0103). Anal. Calcd for C$_{20}$H$_{16}$Cl$_2$N$_2$O$_2$S$_2$: C, 53.22; H, 3.57; N, 6.21; S, 14.21. Found: C, 53.05; H, 3.90; N, 6.45; S, 13.97.

Example 28

Synthesis of N-(3-(3-chloro-10,11-dihydro-5H-dibenzo[b,f]azepin-5-yl)propyl)-4-chloro-2-fluorobenzenesulfonamide

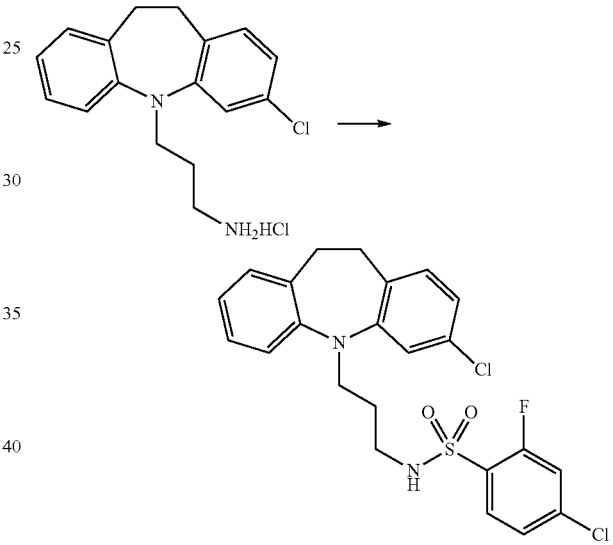

A solution of 3-(3-chloro-10,11-dihydro-5H-dibenzo[b,f]azepin-5-yl)propan-1-amine hydrochloride (0.0800 g, 0.247 mmol) in DMF (1.0 mL) was cooled to 0° C., treated with Et$_3$N (72 μL, 0.520 mmol), and 4-fluorosulfonyl chloride (0.052 g, 0.272 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 20-35% hexanes-Ethyl acetate) to afford the title compound as a clear film (0.0962 g, 81%). $^1$H NMR (600 MHz, CDCl$_3$) δ 7.74 (1H, t, J=8.0 Hz), 7.20 (1H, d, J=8.3 Hz), 7.14 (1H, t, J=7.9 Hz), 7.08-7.11 (2H, m), 6.98-7.00 (3H, m), 6.96 (1H, s), 6.89 (1H, d, J=8.0 Hz), 4.76 (1H, t, J=5.5 Hz), 3.70 (2H, t, J=6.2 Hz), 3.06 (2H, t, J=6.5 Hz), 3.04 (4H, br s), 1.74 (2H, quintet, J=6.4 Hz); $^{13}$C NMR (150 MHz, CDCl$_3$) δ 159.5, 148.8, 147.4, 135.2, 131.9, 131.8, 131.6, 131.2, 129.9, 126.9, 125.20, 125.18, 123.9, 122.7, 120.3, 119.7, 118.0, 117.8, 47.3, 41.2, 32.1, 31.5, 27.7; LCMS m/z 479.0417 ([M+H]$^+$, C$_{23}$H$_{21}$Cl$_2$FN$_2$O$_2$S requires 479.0758).

Example 29

Synthesis of 3,4-dichloro-N-(3-(3-chloro-10,11-dihydro-5H-dibenzo[b,f]azepin-5-yl)propyl)benzenesulfonamide

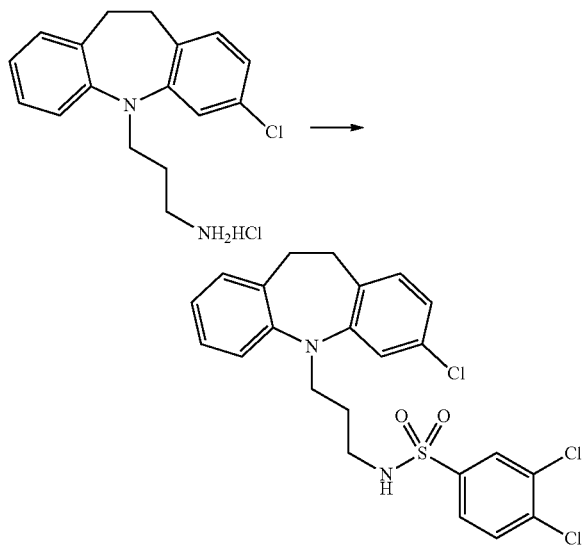

A solution of 3-(3-chloro-10,11-dihydro-5H-dibenzo[b,f]azepin-5-yl)propan-1-amine hydrochloride (0.0800 g, 0.247 mmol) in DMF (1.0 mL) was cooled to 0° C., treated with Et$_3$N (72 µL, 0.520 mmol), and 3,4-dichlorosulfonyl chloride (25.0 µL, 0.272 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-25% hexanes-Ethyl acetate) to afford the title compound as a clear oil (0.0907 g, 74%). $^1$H NMR (600 MHz, CDCl$_3$) δ 7.87 (1H, d, J=2.0 Hz), 7.51 (1H, dd, J=6.3, 2.0 Hz), 7.46 (1H, d, J=8.4 Hz), 7.14 (1H, t, J=8.1 Hz), 7.11 (1H, d, J=6.4 Hz), 6.97-7.00 (4H, m), 6.95 (1H, d, J=1.9 Hz), 6.88 (1H, dd, J=6.1, 2.0 Hz), 4.67 (1H, t, J=6.1 Hz), 3.69 (1H, t, J=6.2 Hz), 3.03 (4H, br s), 3.01 (2H, m), 1.74 (2H, quintet, J=6.5 Hz); LCMS m/z 496.9990 ([M+H$^+$], C$_{23}$H$_{21}$Cl$_3$N$_2$O$_2$S requires 497.0438).

Example 30

Synthesis of N-(3-(3-chloro-10,11-dihydro-5H-dibenzo[b,f]azepin-5-yl)propyl)-4-(trifluoromethoxy)benzenesulfonamide

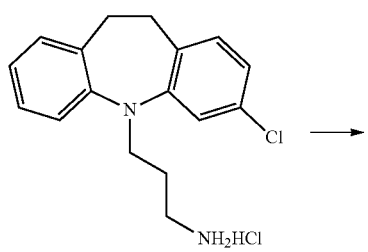

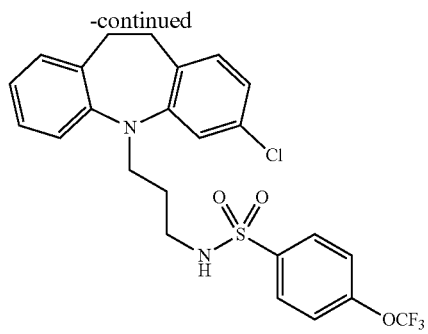

A solution of 3-(3-chloro-10,11-dihydro-5H-dibenzo[b,f]azepin-5-yl)propan-1-amine hydrochloride (0.0800 g, 0.247 mmol) in DMF (1.0 mL) was cooled to 0° C., treated with Et$_3$N (72.0 µL, 0.520 mmol), and 4-trifluoromethoxybenzenesulfonyl chloride (0.0700 g, 0.272 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-25% hexanes-Ethyl acetate) to afford the title compound as a white solid (0.0860 g, 68%). Mp. 119-121° C. (ether-hexanes); $^1$H NMR (600 MHz, CDCl$_3$) δ 7.76 (2H, d, J=8.8 Hz), 7.24 (2H, d, J=8.5 Hz), 7.12 (1H, t, J=7.6 Hz), 7.10 (1H, d, J=7.7 Hz), 6.98 (2H, d, J=7.6 Hz), 6.97 (1H, d, J=8.1 Hz), 6.95 (1H, s), 6.88 (1H, dd, J=8.2, 1.7 Hz), 4.66 (1H, t, J=6.1 Hz), 3.68 (1H, t, J=6.3 Hz), 3.02 (4H, br s), 3.00 (2H, q, J=6.5 Hz), 1.72 (2H, quintet, J=6.5 Hz); $^{13}$C NMR (600 MHz, CDCl$_3$) δ 151.6, 148.1, 146.8, 137.7, 134.4, 131.2, 131.1, 130.9, 129.3, 128.6, 126.3, 123.3, 122.1, 120.44, 120.43, 119.7, 119.1, 46.8, 40.7, 31.4, 40.8, 26.4; LCMS m/z 511.0821 ([M+H$^+$], C$_{24}$H$_{22}$ClF$_3$N$_2$O$_3$S requires 511.1065). Anal. Calcd for C$_{24}$H$_{22}$ClF$_3$N$_2$O$_3$S: C, 56.42; H, 4.34; N, 5.48; S, 6.28. Found: C, 56.15; H, 4.59; N, 5.60; S, 6.24.

Example 31

Synthesis of 2-Azido-1-(3-chloro-10,11-dihydro-5H-dibenzo[b,f]azepin-5-yl)ethanone

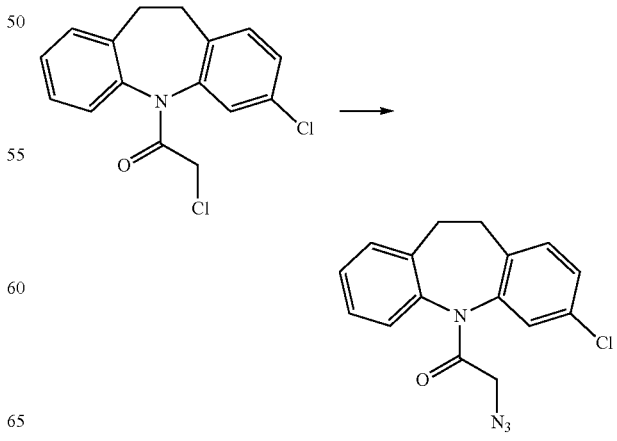

A solution of 2-chloro-1-(3-chloro-10,11-dihydro-5H-dibenzo[b,f]azepin-5-yl)ethanone (3.00 g, 13.1 mmol) in DMF (60.0 mL) was cooled to 0° C. and treated with NaN₃ (2.55 g, 39.3 mmol). The mixture was warmed to 25° C. and stirred for 14 h. The mixture was partitioned between saturated aqueous NaCl (250 mL), and CH₂Cl₂ (200 mL). The aqueous layer was extracted with CH₂Cl₂ (2×200 mL). The combined organic layers were washed with saturated aqueous NaCl (3×100 mL), dried (Na₂SO₄), and concentrated in vacuo. The residue was dissolved in a minimal amount of CH₂Cl₂ and purified by flash chromatography (SiO₂, 0-25% hexanes-Ethyl acetate) to afford the title compound as a white solid (3.04 g, 74%). ¹H NMR (600 MHz, CDCl₃) δ (mixture of rotamers) 7.41 (1H, br s), 7.31 (1H, br s), 7.24 (3H, br m), 7.16 (1H, br s), 7.07 (1H, d, J=6.4 Hz), 3.94 (1H, m), 3.56 (1H, m), 3.31 (2H, m), 2.82 (2H, m); LCMS m/z 313.1115 ([M+H⁺], C₁₆H₁₃ClN₄O requires 313.0851).

Example 32

Synthesis of 2-(3-chloro-10,11-dihydro-5H-dibenzo[b,f]azepin-5-yl)ethanamine hydrochloride

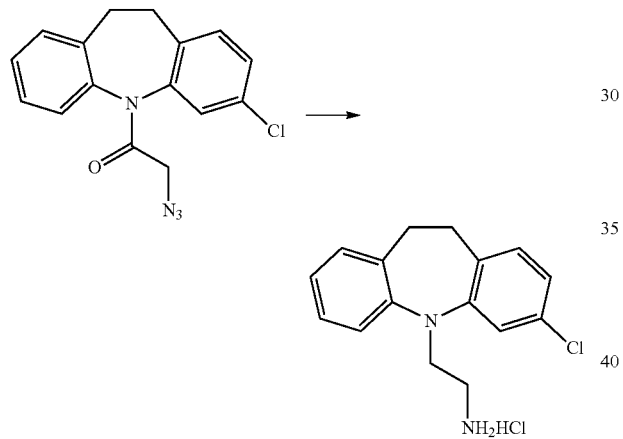

A solution of 2-azido-1-(3-chloro-10,11-dihydro-5H-dibenzo[b,f]azepin-5-yl)ethanone (2.50 g, 8.00 mmol) in THF (10.0 mL) was cooled to 0° C. and treated with a BH₃-THF (1 M solution in THF, 32 mL, 32 mmol). The flask was sealed, heated to 70° C. for 5 h, and then cooled to 0° C. The solution was treated slowly, dropwise with a solution of aqueous 1 M HCl (64 mL), stirred for an additional 0.5 h, and then heated to 70° C. for 1 h. The mixture was cooled to 25° C., treated with aqueous 4 M NaOH until pH>8, and then the mixture was extracted with Ethyl acetate (3×200 mL). The combined extracts were washed with saturated aqueous NaCl (100 mL), dried (Na₂SO₄), and concentrated in vacuo. The residue was dissolved in a minimal amount of CH₂Cl₂ and purified by flash chromatography (SiO₂, 0-50% hexanes-Ethyl acetate to remove nonpolar impurities followed by 17:2:1 CH₂Cl₂:MeOH:NH₄OH to elute the product). The combined fractions of pure product were concentrated, dried azeotropically with toluene, and then suspended in Et₂O (100 mL) and treated dropwise with a 4 N HCl-dioxane solution (2.0 mL). The white solid that had precipitated was collected by filtration to afford the title compound (1.41 g, 57%). ¹H NMR (600 MHz, CD₃OD) δ 7.18 (2H, m), 7.17 (2H, m), 7.08 (1H, d, J=8.1 Hz), 7.02 (1H, m), 6.93 (1H, dd, J=8.1, 1.9 Hz), 4.05 (2H, t, J=6.5 Hz), 3.17 (2H, m), 3.13 (2H, m), 3.11 (2H, t, J=6.5 Hz); ¹³C NMR (150 MHz, CD₃OD) δ 149.0, 147.6, 136.0, 132.8, 132.0, 130.1, 129.1, 127.2, 124.6, 123.3, 120.2, 119.5, 48.1, 37.5, 32.0, 31.1; LCMS m/z 273.1754 ([M+H⁺], C₁₆H₁₇ClN₂ requires 273.1153).

Example 33

Synthesis of 4-chloro-N-(2-(3-chloro-10,11-dihydro-5H-dibenzo[b,f]azepin-5-yl)ethyl)benzenesulfonamide

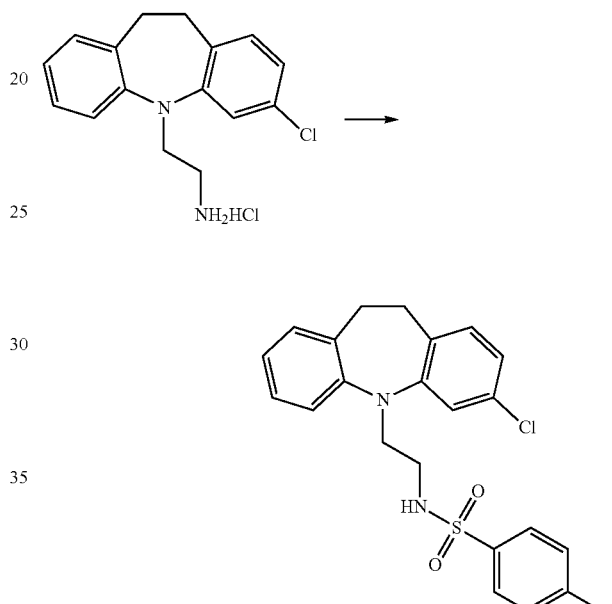

A solution of 2-(3-chloro-10,11-dihydro-5H-dibenzo[b,f]azepin-5-yl)ethanamine hydrochloride (0.08000 g, 0.259 mmol) in DMF (1.0 mL) was cooled to 0° C. and treated sequentially with triethylamine (75.0 μL, 0.543 mmol) and 4-chlorobenzenesulfonyl chloride (0.0600 g, 0.284 mmol). The solution was warmed to 25° C. and stirred for 2 h. The mixture was partitioned between saturated aqueous NaCl (50 mL), and CH₂Cl₂ (100 mL). The organic layer was washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-20% hexanes-Ethyl acetate) to afford the title compound as a white solid (0.0987 g, 85%). ¹H NMR (600 MHz, CDCl₃) δ 7.61 (2H, d, J=8.5 Hz), 7.30 (2H, d, J=8.5 Hz), 7.11 (2H, m), 7.00 (1H, d, J=7.0 Hz), 6.97 (1H, d, J=8.0 Hz), 6.93 (1H, d, J=7.9 Hz), 6.90 (2H, m), 4.55 (1H, br m), 3.79 (2H, t, J=5.7 Hz), 3.16 (2H, m), 3.06 (4H, m); ¹³C NMR (600 MHz, CDCl₃) δ 147.9, 146.6, 139.4, 138.1, 135.1, 132.0, 131.8, 131.6, 130.1, 129.5, 128.4, 127.1, 124.4, 123.2, 120.3, 119.7, 49.4, 40.7, 32.2, 31.7; LCMS m/z 447.0405 ([M+H⁺], C₂₂H₂₀Cl₂N₂O₂S requires 447.0695).

Example 34

Synthesis of N-(2-(3-chloro-10,11-dihydro-5H-dibenzo[b,f]azepin-5-yl)ethyl)-4-(trifluoromethyl)benzenesulfonamide

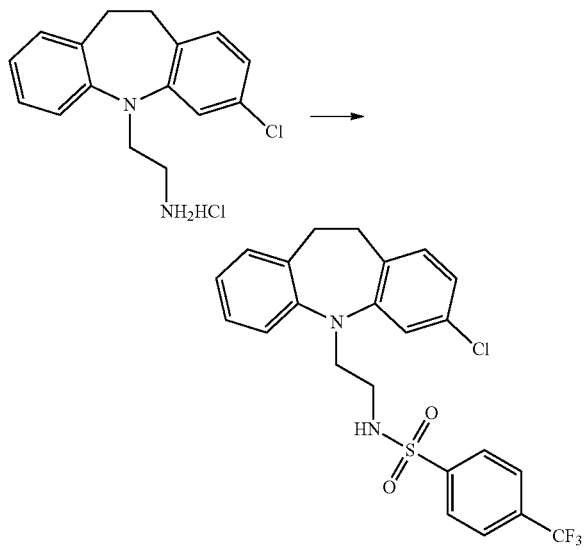

A solution of 2-(3-chloro-10,11-dihydro-5H-dibenzo[b,f]azepin-5-yl)ethanamine hydrochloride (0.0800 g, 0.259 mmol) in DMF (1.0 mL) was cooled to 0° C. and treated sequentially with triethylamine (75.0 μL, 0.543 mmol) and 4-trifluoromethylbenzenesulfonyl chloride (0.069 g, 0.284 mmol). The solution was warmed to 25° C. and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% hexanes-Ethyl acetate) to afford the title compound as a white solid (0.0987 g, 85%). $^1$H NMR (600 MHz, CDCl$_3$) δ 7.81 (2H, d, J=7.9 Hz), 7.60 (2H, d, J=7.9 Hz), 7.08 (2H, m), 6.98 (1H, d, J=7.4 Hz), 6.95 (1H, d, J=7.7 Hz), 6.92 (1H, d, J=8.0 Hz), 6.89 (2H, m), 4.66 (1H, br s), 3.81 (2H, br s), 3.19 (2H, m), 3.06 (4H, m); $^{13}$C NMR (600 MHz, CDCl$_3$) δ 147.9, 146.5, 143.2, 135.0, 134.6, 134.3, 132.0, 131.8, 131.6, 130.1, 127.4, 127.1, 126.3 (q, J=15.0 Hz), 124.5, 123.2, 120.2, 119.6, 49.3, 40.7, 32.2, 31.7; LCMS m/z 481.0950 ([M+H$^+$], C$_{23}$H$_{20}$ClF$_3$N$_2$O$_2$S requires 481.0959).

Example 35

Synthesis of 4-chloro-N-(3-(10,11-dihydro-5H-dibenzo[b,f]azepin-5-yl)propyl)benzenesulfonamide

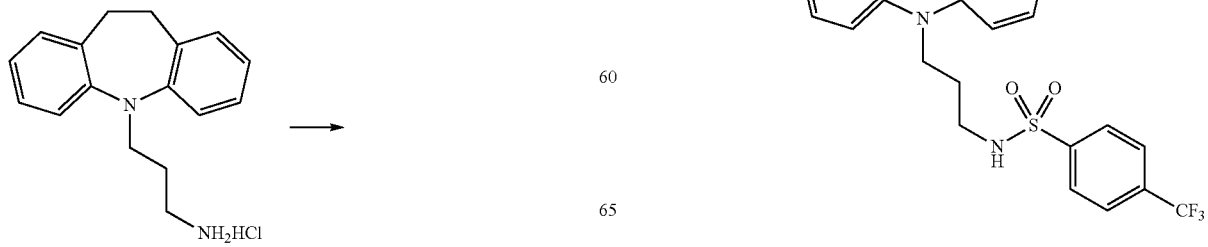

A solution of 3-(10,11-dihydro-5H-dibenzo[b,f]azepin-5-yl)propan-1-amine hydrochloride (0.0800 g, 0.277 mmol) in DMF (1.0 mL) was cooled to 0° C., treated with Et$_3$N (79.0 μL, 0.582 mmol), and 4-chlorobenzenesulfonyl chloride (0.064 g, 0.304 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% hexanes-Ethyl acetate) to afford the title compound as a white solid (0.0960 g, 81%). $^1$H NMR (600 MHz, CDCl$_3$) δ 7.81 (2H, d, J=7.9 Hz), 7.60 (2H, d, J=7.9 Hz), 7.08 (2H, m), 6.98 (1H, d, J=7.4 Hz), 6.95 (1H, d, J=7.7 Hz), 6.92 (1H, d, J=8.0 Hz), 6.89 (2H, m), 4.66 (1H, br s), 3.81 (2H, br s), 3.19 (2H, m), 3.06 (4H, m); $^{13}$C NMR (600 MHz, CDCl$_3$) δ 147.9, 146.5, 143.2, 135.0, 134.6, 134.3, 132.0, 131.8, 131.6, 130.1, 127.4, 127.1, 126.3 (q, J=15.0 Hz), 124.5, 123.2, 120.2, 119.6, 49.3, 40.7, 32.2, 31.7; LCMS m/z 481.0950 ([M+H$^+$], C$_{23}$H$_{20}$ClF$_3$N$_2$O$_2$S requires 481.0959).

Example 36

Synthesis of N-(3-(10,11-dihydro-5H-dibenzo[b,f]azepin-5-yl)propyl)-4-(trifluoromethyl)benzenesulfonamide

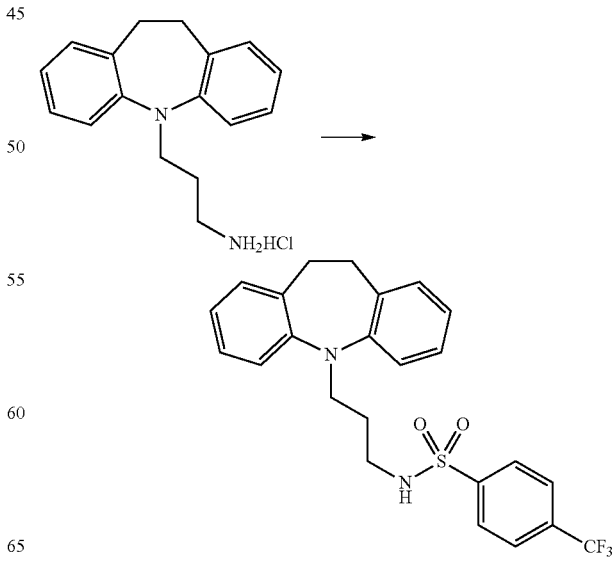

A solution of 3-(3-chloro-10,11-dihydro-5H-dibenzo[b,f]azepin-5-yl)propan-1-amine hydrochloride (0.0800 g, 0.277 mmol) in DMF (1.0 mL) was cooled to 0° C., treated with Et₃N (79.0 µL, 0.582 mmol), and 4-trifluoromethylbenzenesulfonyl chloride (0.0740 g, 0.304 mmol). The mixture was warmed to 25° C., and stirred for 2 h. The mixture was partitioned between saturated aqueous NaCl (50 mL), and CH₂Cl₂ (100 mL). The organic layer was washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-20% hexanes-Ethyl acetate) to afford the title compound as a clear oil (0.103 g, 81%). ¹H NMR (600 MHz, CDCl₃) δ 7.84 (2H, d, J=8.0 Hz), 7.68 (2H, d, J=8.0 Hz), 7.11 (4H, m), 6.99 (2H, d, J=7.9 Hz), 6.95 (2H, t, J=7.3 Hz), 4.68 (1H, br s), 3.73 (2H, t, J=6.0 Hz), 3.07 (4H, br s), 3.05 (2H, m), 1.74 (2H, quintet, J=6.3 Hz); ¹³C NMR (150 MHz, CDCl₃) δ 147.9, 143.7, 134.5, 134.35, 134.32, 130.3, 127.7, 126.8, 126.4 (q, J=13.7 Hz), 123.2, 119.8, 47.5, 41.6, 32.2, 27.6; LCMS m/z 461.1244 ([M+H⁺], C₂₄H₂₃F₃N₂O₂S requires 461.1505).

Example 37

Synthesis of N-(2-(3-chloro-10,11-dihydro-5H-dibenzo[b,f]azepin-5-yl)ethyl)-4-(trifluoromethoxy)benzenesulfonamide

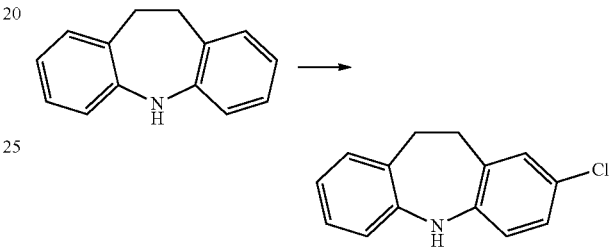

A solution of 2-(3-chloro-10,11-dihydro-5H-dibenzo[b,f]azepin-5-yl)ethanamine hydrochloride (0.0800 g, 0.259 mmol) in DMF (1.0 mL) was cooled to 0° C., treated with Et₃N (75.0 µL, 0.543 mmol), and 4-trifluoromethoxybenzenesulfonyl chloride (0.0740 g, 0.284 mmol). The mixture was warmed to 25° C., and stirred for 2 h. The mixture was partitioned between saturated aqueous NaCl (50 mL), and CH₂Cl₂ (100 mL). The organic layer was washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-20% hexanes-Ethyl acetate) to afford the title compound as a white solid (0.0859 g, 81%). ¹H NMR (600 MHz, CDCl₃) δ 7.74 (2H, d, J=8.6 Hz), 7.18 (2H, d, J=8.3 Hz), 7.10 (3H, m), 6.98 (2H, m), 6.94 (2H, d, J=8.1 Hz), 6.93 (1H, s), 6.89 (1H, d, J=8.1 Hz), 4.70 (1H, t, J=5.3 Hz), 3.81 (2H, t, J=5.6 Hz), 3.16 (2H, dd, 11.4, 5.6 Hz), 3.07 (4H, m); ¹³C NMR (150 MHz, CDCl₃) δ 152.2, 148.0, 146.6, 137.99, 137.97, 135.1, 132.0, 131.74, 131.70, 130.0, 129.1, 127.0, 124.4, 123.2, 120.9, 120.3, 119.7, 49.5, 40.8, 32.2, 31.6; LCMS m/z 497.0918 ([M+H⁺], C₂₃H₂₀ClF₃N₂O₃S requires 497.0918).

Example 38

Synthesis of N-(3-(2-chloro-10,11-dihydro-5H-dibenzo[b,f]azepin-5-yl)propyl)-4-(trifluoromethyl)benzenesulfonamide

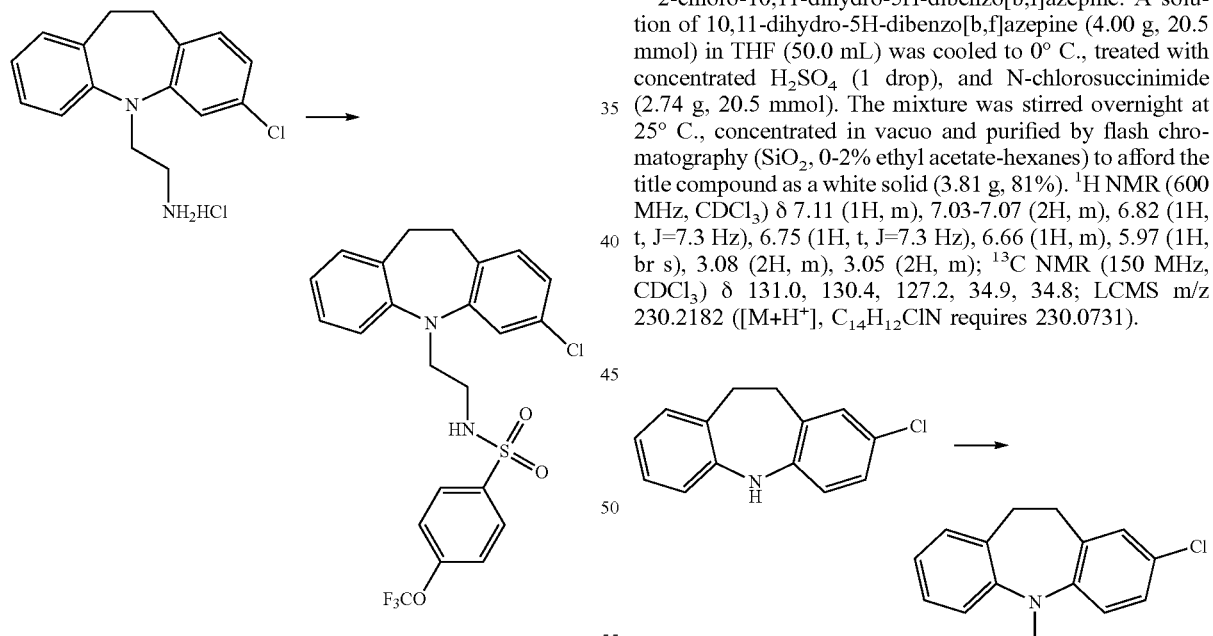

2-chloro-10,11-dihydro-5H-dibenzo[b,f]azepine. A solution of 10,11-dihydro-5H-dibenzo[b,f]azepine (4.00 g, 20.5 mmol) in THF (50.0 mL) was cooled to 0° C., treated with concentrated H₂SO₄ (1 drop), and N-chlorosuccinimide (2.74 g, 20.5 mmol). The mixture was stirred overnight at 25° C., concentrated in vacuo and purified by flash chromatography (SiO₂, 0-2% ethyl acetate-hexanes) to afford the title compound as a white solid (3.81 g, 81%). ¹H NMR (600 MHz, CDCl₃) δ 7.11 (1H, m), 7.03-7.07 (2H, m), 6.82 (1H, t, J=7.3 Hz), 6.75 (1H, t, J=7.3 Hz), 6.66 (1H, m), 5.97 (1H, br s), 3.08 (2H, m), 3.05 (2H, m); ¹³C NMR (150 MHz, CDCl₃) δ 131.0, 130.4, 127.2, 34.9, 34.8; LCMS m/z 230.2182 ([M+H⁺], C₁₄H₁₂ClN requires 230.0731).

2-chloro-1-(2-chloro-10,11-dihydro-5H-dibenzo[b,f]azepin-5-yl)ethanone. A solution of 2-chloro-10,11-dihydro-5H-dibenzo[b,f]azepine (2.00 g, 8.71 mmol) (*The Journal of Biological Chemistry* (2009) 285, 11, 8363-8374) in toluene (10.0 mL) was treated with chloroacetyl chloride (0.73 mL, 9.14 mmol) and heated to 100° C. for 1 h. The mixture was cooled to 25° C., concentrated under N₂ stream, taken up in a minimal amount of toluene and purified by flash chromatography (SiO₂, 5-20% ethyl acetate-hexanes) to afford the title compound as an off-white solid (2.06 g, 77%). ¹H NMR (600 MHz, CDCl₃) δ (mixture of rotamers); LCMS m/z 306.1044 ([M+H⁺], $C_{16}H_{13}Cl_2NO$ requires 306.0447).

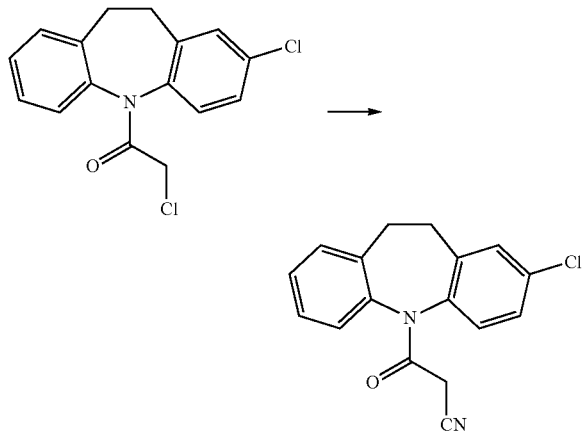

3-(2-chloro-10,11-dihydro-5H-dibenzo[b,f]azepin-5-yl)-3-oxopropanenitrile. A solution of 2-chloro-1-(2-chloro-10,11-dihydro-5H-dibenzo[b,f]azepin-5-yl)ethanone (2.06 g, 6.72 mmol) (ref) in DMF (5.0 mL) was cooled to 0° C. and treated with tetrabutylammonium iodide (0.248 g, 0.672 mmol) and sodium cyanide (0.353 g, 7.40 mmol) in portions. The mixture was warmed to 25° C. and stirred for 14 h. The solution was diluted with CH₂Cl₂ (200 mL) and the organic layer was washed with H₂O (2×100 mL), saturated aqueous NaCl (100 mL), dried (Na₂SO₄), and concentrated in vacuo. The residue was taken up in a minimal amount of CH₂Cl₂ and purified by flash chromatography (SiO₂, 10-30% ethyl acetate-hexanes) to afford the title compound as a tan oil (1.21 g, 61%). ¹H NMR (600 MHz, CDCl₃) δ (as a mixture of rotamers); LCMS m/z 306.1044 ([M+H⁺], $C_{16}H_{13}Cl_2NO$ requires 306.0447).

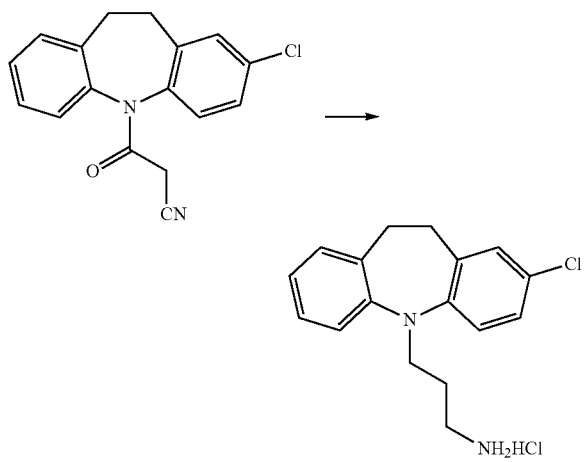

3-(2-chloro-10,11-dihydro-5H-dibenzo[b,f]azepin-5-yl)propan-1-amine hydrochloride. A solution of 3-(2-chloro-10,11-dihydro-5H-dibenzo[b,f]azepin-5-yl)-3-oxopropanenitrile (1.30 g, 4.38 mmol) in THF (10.0 mL) was cooled to 0° C. and treated with a BH₃-THF (1 M solution in THF, 17.5 mL, 17.5 mmol). The flask was sealed, heated to 70° C. for 5 h, and then cooled to 0° C. The solution was treated slowly, dropwise with a solution of aqueous 1 M HCl (35 mL), stirred for an additional 0.5 h, and then heated to 70° C. for 1 h. The mixture was cooled to 25° C., treated with aqueous 4 M NaOH until pH>8, and then the mixture was extracted with ethyl acetate (3×200 mL). The combined extracts were washed with saturated aqueous NaCl (100 mL), dried (Na₂SO₄), and concentrated in vacuo. The residue was dissolved in a minimal amount of CH₂Cl₂ and purified by flash chromatography (SiO₂, 0-50% ethyl acetate-hexanes to remove nonpolar impurities followed by 17:2:1 CH₂Cl₂:MeOH:NH₄OH to elute the product). The combined fractions of pure product were concentrated, dried azeotropically with toluene, and then suspended in Et₂O (100 mL) and treated dropwise with a 4 N HCl-dioxane solution (1.1 mL). The white solid that had precipitated was collected by filtration to afford the title compound (1.36 g, 58%). ¹H NMR (600 MHz, CD₃OD) δ; ¹³C NMR (150 MHz, CD₃OD) δ; LCMS m/z 287.2472 ([M+H⁺], $C_{17}H_{19}ClN_2$ requires 287.1310).

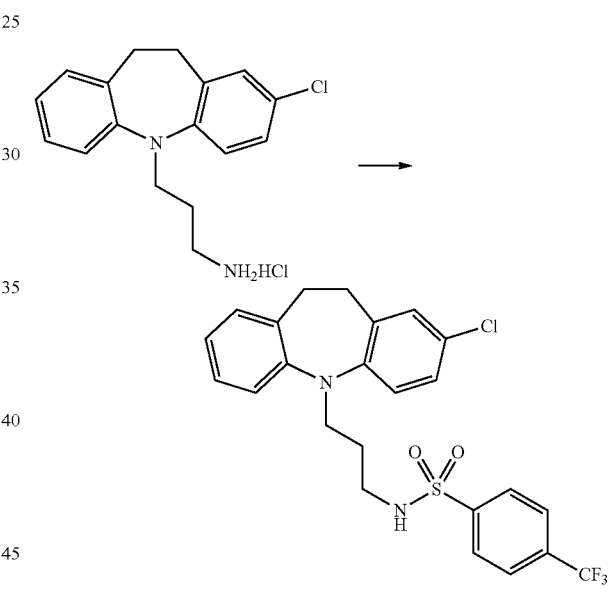

N-(3-(2-chloro-10,11-dihydro-5H-dibenzo[b,f]azepin-5-yl)propyl)-4-(trifluoromethyl)benzenesulfonamide. A solution of 3-(2-chloro-10,11-dihydro-5H-dibenzo[b,f]azepin-5-yl)propan-1-amine hydrochloride (0.310 g, 0.958 mmol) in DMF (1.0 mL) was cooled to 0° C., treated with Et₃N (280 µL, 2.01 mmol), and 4-trifluoromethylbenzenesulfonyl chloride (0.273 g, 0.284 mmol). The mixture was warmed to 25° C., and stirred for 2 h. The mixture was partitioned between saturated aqueous NaCl (50 mL), and CH₂Cl₂ (100 mL). The organic layer was washed with saturated aqueous NaCl (2×50 mL), dried (Na₂SO₄), and concentrated in vacuo. The residue was dissolved in a minimal amount of CH₂Cl₂ and purified by flash chromatography (SiO₂, 0-20% hexanes-Ethyl acetate) to afford the title compound as a clear film (0.233 g, 49%). ¹H NMR (600 MHz, CDCl₃) δ 7.85 (2H, d, J=8.0 Hz), 7.70 (2H, d, J=8.0 Hz), 7.13 (1H, t, J=7.7 Hz), 7.10 (1H, d, J=8.0 Hz), 7.07 (1H, s), 7.06 (1H, m), 6.97 (2H, m), 6.90 (1H, d, J=8.2 Hz), 4.67 (1H, t, J=5.2 Hz), 3.69 (2H, t, J=6.2 Hz), 3.04 (4H, m), 1.71 (2H, quintet, J=6.4 Hz); $^{13}$C NMR (150 MHz, CDCl$_3$) δ 147.6, 146.5, 143.7, 135.9, 134.6, 134.4, 134.3, 130.2, 130.1, 128.1, 127.6, 126.9, 126.6, 126.5 (q, J=13.6 Hz), 123.6, 121.1, 119.9, 47.5, 41.5, 32.1, 31.7, 27.6; LCMS m/z 495.0705 ([M+H$^+$], C$_{24}$H$_{22}$ClF$_3$N$_2$O$_2$S requires 495.1115).

Example 39

Synthesis of N-(3-(3-chloro-10,11-dihydro-5H-dibenzo[b,f]azepin-5-yl)propyl)-3-trifluoromethyl-benzenesulfonamide

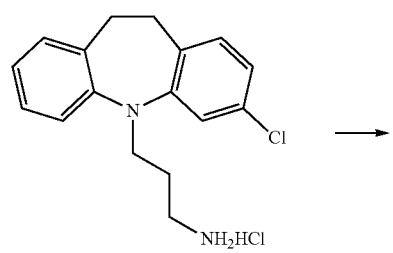

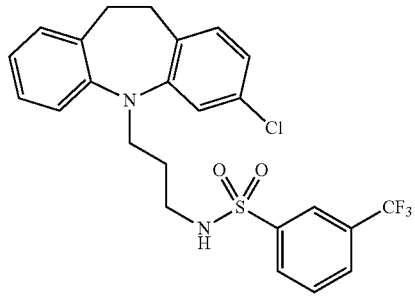

A solution of 3-(3-chloro-10,11-dihydro-5H-dibenzo[b,f]azepin-5-yl)propan-1-amine hydrochloride (0.080 g, 0.259 mmol) in DMF (1.0 mL) was cooled to 0° C., treated with Et$_3$N (75.0 μL, 0.543 mmol), and 3-trifluoromethylbenzenesulfonyl chloride (0.069 g, 0.284 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-50% hexanes-Ethyl acetate) to afford the title compound as a white solid (0.085 g, 66%). $^1$H NMR (600 MHz, CDCl$_3$) δ 8.08 (1H, s), 7.91 (1H, d, J=7.9 Hz), 7.79 (1H, d, J=7.7 Hz), 7.55 (1H, d, J=7.8 Hz), 7.14 (1H, t, J=8.2 Hz), 7.09 (1H, d, J=7.4 Hz), 6.94-6.99 (4H, m), 6.88 (1H, dd, J=8.1, 1.9 Hz) 4.86 (1H, t, J=6.1 Hz), 3.68 (2H, t, J=6.4 Hz), 3.02 (4H, s), 3.00 (2H, dd, J=13.1, 6.7 Hz), 1.73 (2H, quintet, J=6.5 Hz); $^{13}$C NMR (150 MHz, CDCl$_3$) δ 148.8, 147.5, 141.3, 135.1, 132.0, 131.8, 131.6, 130.4, 130.2, 129.9, 129.5 (q, J=12.7 Hz), 126.9, 124.3 (q, J=16.7 Hz), 123.9, 122.8, 120.4, 119.8, 47.4, 41.3, 32.1, 31.5, 27.6; LCMS m/z 495.1228 ([M+H$^+$], C$_{24}$H$_{22}$ClF$_3$N$_2$O$_2$S requires 495.1115).

Example 40

Synthesis of N-(3-(3-chloro-10,11-dihydro-5H-dibenzo[b,f]azepin-5-yl)propyl)-4-nitrobenzenesulfonamide

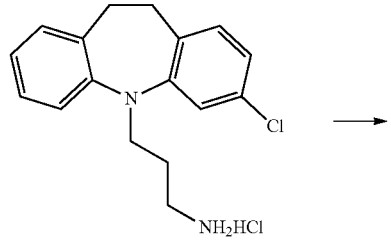

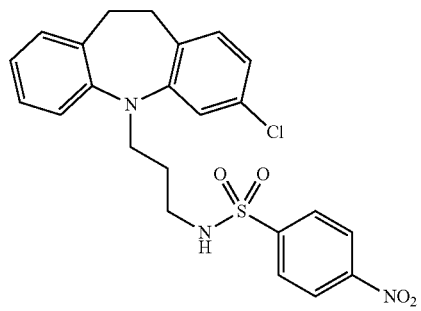

A solution of 3-(3-chloro-10,11-dihydro-5H-dibenzo[b,f]azepin-5-yl)propan-1-amine hydrochloride (0.400 g, 1.24 mmol) in DMF (1.0 mL) was cooled to 0° C., treated with Et$_3$N (0.360 mL, 2.60 mmol), and 4-nitrobenzenesulfonyl chloride (0.301 g, 1.36 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-50% hexanes-Ethyl acetate) to afford the title compound as a white solid (0.459 g, 78%). $^1$H NMR (600 MHz, CDCl$_3$) δ 8.21 (2H, d, J=8.8 Hz), 7.88 (2H, d, J=8.8 Hz), 7.12 (1H, d, J=7.6 Hz), 7.11 (1H, d, J=6.6 Hz), 7.00 (2H, m), 6.96 (1H, d, J=8.0 Hz), 6.91 (1H, d, J=1.8 Hz), 6.88 (1H, dd, J=8.1, 1.9 Hz), 4.76 (1H, t, J=6.1 Hz), 3.66 (2H, t, J=6.1 Hz), 3.08 (2H, dd, J=13.0, 6.6 Hz), 3.04 (4H, m), 1.71 (2H, quintet, J=6.5 Hz); $^{13}$C NMR (150 MHz, CDCl$_3$) δ 150.2, 148.6, 147.4, 146.0, 135.1, 131.9, 131.71, 131.67, 130.0, 128.3, 127.0, 124.5, 124.1, 122.9, 120.3, 119.7, 47.3, 41.4, 32.1, 31.5, 27.5; LCMS m/z ([M+H$^+$], C$_{23}$H$_{22}$ClFN$_2$O$_2$S requires 472.1092).

Example 41

Synthesis of 4-trifluoromethyl-N-(2-(2-chloro-10H-phenothiazin-10-yl)ethyl)benzenesulfonamide

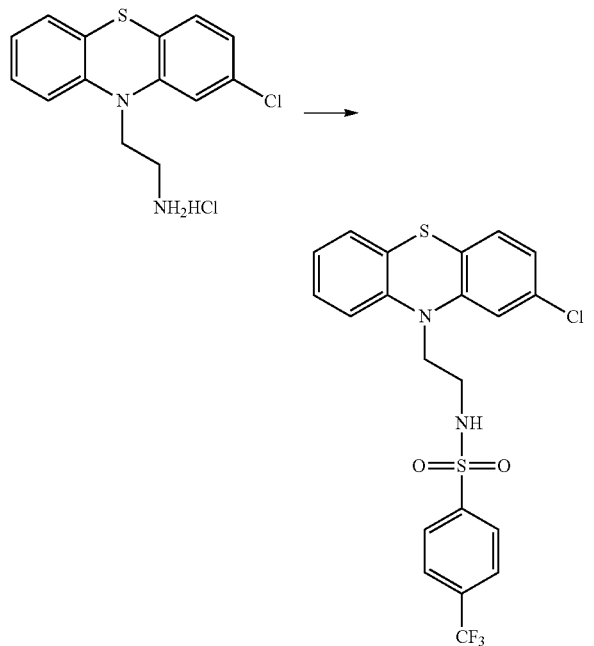

A solution of 2-(2-chloro-10H-phenothiazin-10-yl)ethanamine hydrochloride (0.090 g, 0.287 mmol) in DMF (1.0 mL) was cooled to 0° C., treated with Et$_3$N (84.0 µL, 0.603 mmol), and 4-trifluoromethylbenzenesulfonyl chloride (0.077 g, 0.316 mmol). The mixture was warmed to 25° C., and stirred for 2 h. The mixture was partitioned between saturated aqueous NaCl (100 mL), and CH$_2$Cl$_2$ (100 mL). The organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-25% ethyl acetate-hexanes) to afford the title compound as a clear film (0.092 g, 66%). $^1$H NMR (600 MHz, CDCl$_3$) δ 7.80 (2H, d, J=8.2 Hz), 7.52 (2H, d, J=8.3 Hz), 7.14 (1H, d, J=7.6 Hz), 7.09 (1H, t, J=7.4 Hz), 7.04 (1H, t, J=8.2 Hz), 6.97 (1H, t, J=7.4 Hz), 6.91 (1H, dd, J=8.2, 1.4 Hz), 6.70 (1H, d, J=8.2 Hz), 6.69 (1H, d, J=1.7 Hz), 5.07 (1H, t, J=5.6 Hz), 3.92 (2H, t, J=5.8 Hz), 3.36 (2H, dd, J=11.6, 5.8 Hz); $^{13}$C NMR (150 MHz, CDCl$_3$) δ 145.6, 143.7, 143.0, 134.2 (q, J=131.2 Hz), 133.6, 128.5, 128.1, 127.9, 127.4, 126.3, 126.2 (q, J=13.2, Hz), 125.1, 124.2, 124.1, 123.5, 116.4, 116.2, 46.1, 39.5; LCMS m/z 485.0002 ([M+H$^+$], C$_{21}$H$_{16}$ClF$_3$N$_2$O$_2$S$_2$ requires 485.0637).

Example 42

Synthesis of 4-trifluoromethoxy-N-(2-(2-chloro-10H-phenothiazin-10-yl)ethyl)benzenesulfonamide

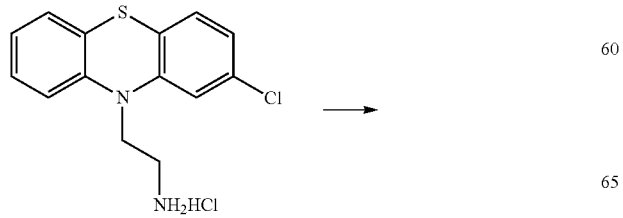

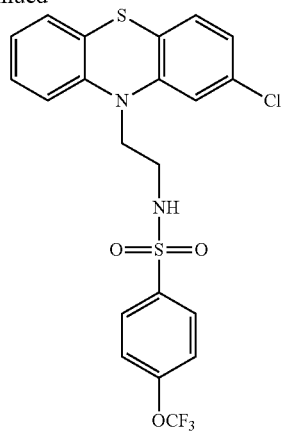

A solution of 2-(2-chloro-10H-phenothiazin-10-yl)ethanamine hydrochloride (0.090 g, 0.287 mmol) in DMF (1.0 mL) was cooled to 0° C., treated with Et$_3$N (84.0 µL, 0.603 mmol), and 4-trifluoromethoxybenzenesulfonyl chloride (0.082 g, 0.316 mmol). The mixture was warmed to 25° C., and stirred for 2 h. The mixture was partitioned between saturated aqueous NaCl (100 mL), and CH$_2$Cl$_2$ (100 mL). The organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-25% hexanes-Ethyl acetate) to afford the title compound as a clear film (0.096 g, 67%). $^1$H NMR (600 MHz, CDCl$_3$) δ 7.74 (2H, d, J=8.8 Hz), 7.18 (1H, d, J=7.6 Hz), 7.12 (3H, m), 7.08 (1H, d, J=8.2 Hz), 6.99 (1H, br s), 6.96 (1H, br s), 6.75 (1H, d, J=7.4 Hz), 6.73 (1H, br s), 4.85 (1H, t, J=5.3 Hz), 3.97 (2H, br s), 3.36 (2H, dd, J=11.1, 5.5 Hz), 3.92 (2H, t, J=5.8 Hz), 3.36 (2H, dd, J=11.6, 5.8 Hz); $^{13}$C NMR (150 MHz, CDCl$_3$) δ 151.5, 145.1, 143.1, 137.1, 133.1, 129.6, 128.4, 127.9, 127.49, 127.2, 125.9, 124.6, 123.4, 122.9, 120.1, 115.8, 115.7, 45.6, 38.8; LCMS m/z 500.9960 ([M+H$^+$], C$_{21}$H$_{16}$ClF$_3$N$_2$O$_3$S$_2$ requires 501.0316).

Example 43

Synthesis of N-(3-(3-amino-10,11-dihydro-5H-dibenzo[b,f]azepin-5-yl)propyl)-4-(trifluoromethyl)benzenesulfonamide

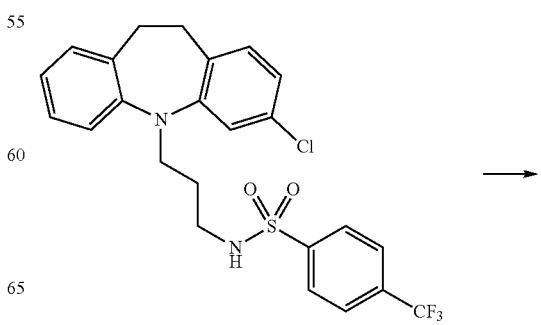

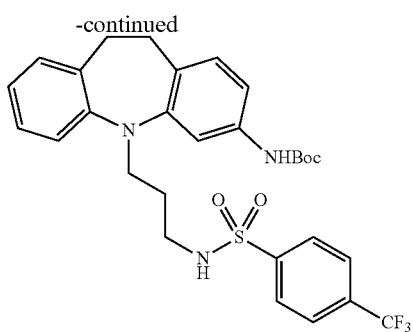

tert-Butyl (5-(3-(4-(trifluoromethyl)phenylsulfonamido)propyl)-10,11-dihydro-5H-dibenzo[b,f]azepin-3-yl)carbamate. A solution of N-(3-(3-chloro-10,11-dihydro-5H-dibenzo[b,f]azepin-5-yl)propyl)-4-(trifluoromethyl)benzenesulfonamide (0.250 g, 0.506 mmol) in dioxane (1.5 mL) was treated with tert-butyl carbamate (0.071 g, 0.606 mmol), palladium acetate (0.0033 g, 0.0151 mmol), X-Phos (0.021 g, 0.0454 mmol), and cesium carbonate (0.231 g, 0.708 mmol), degassed with argon and then the vial was sealed. The solution was heated to 100° C. for 24 h, cooled to 25° C., and partitioned between $CH_2Cl_2$ (200 mL) and saturated aqueous NaCl (200 mL). The organic layer was dried ($Na_2SO_4$), concentrated, and the residue purified by flash chromatography ($SiO_2$, 0-20% ethyl acetate-hexanes) to provide a white solid (0.300 g, 99%). $^1$H NMR (600 MHz, $CDCl_3$) δ 7.90 (2H, d, J=8.2 Hz), 7.71 (2H, d, J=8.2 Hz), 7.32 (1H, br s), 7.12 (1H, d, J=7.7 Hz), 7.10 (2H, d, J=7.3 Hz), 6.96 (2H, m), 6.61 (1H, d, J=8.1 Hz), 6.44 (1H, br s), 5.22 (1H, br s), 3.73 (2H, t, J=6.7 Hz), 3.06 (2H, m), 3.05 (2H, m), 3.02 (2H, m), 1.78 (2H, quintet, J=6.4 Hz), 1.54 (9H, s); $^{13}$C NMR (150 MHz, $CDCl_3$) δ 153.2, 148.7, 147.5, 144.0, 136.7, 135.2, 134.4, 134.2, 130.9, 129.7, 128.1, 127.7, 126.8, 126.4 (q, J=13.4 Hz), 123.6, 120.4, 112.9, 110.7, 80.9, 47.9, 41.6, 32.1, 31.9, 28.6, 27.3; LCMS m/z ([M+H$^+$], $C_{23}H_{22}ClFN_2O_2S$ requires 445.1147).

N-(3-(3-amino-10,11-dihydro-5H-dibenzo[b,f]azepin-5-yl)propyl)-4-(trifluoromethyl)benzenesulfonamide. A solution of tert-butyl (5-(3-(4-(trifluoromethyl)phenylsulfonamido)propyl)-10,11-dihydro-5H-dibenzo[b,f]azepin-3-yl)carbamate (0.300 g, mmol) in $CH_2Cl_2$ (1.5 mL) was cooled to 0° C. and treated with TFA (0.30 mL). The solution was warmed to 25° C., stirred for 1 h, then concentrated with a stream of $N_2$. The residue was dissolved $CH_2Cl_2$ (15 mL) washed with saturated aqueous bicarbonate (15 mL), dried ($Na_2SO_4$), concentrated and purified by flash chromatography ($SiO_2$, 0-50% ethyl acetate-hexanes) to provide a white solid ( ). $^1$H NMR (600 MHz, $CDCl_3$) δ 7.82 (2H, d, J=8.2 Hz), 7.68 (2H, d, J=8.2 Hz), 7.09 (2H, m), 6.95 (2H, m), 6.86 (1H, d, J=8.0 Hz), 6.36 (1H, s), 6.30 (1H, d, J=6.4 Hz), 4.78 (1H, t, J=5.9 Hz), 3.68 (2H, t, J=6.1 Hz), 3.04 (2H, dd, J=13.0, 6.5 Hz), 3.02 (2H, m), 2.95 (2H, m), 1.72 (2H, quintet, J=6.4 Hz); $^{13}$C NMR (150 MHz, $CDCl_3$) δ 148.5, 148.1, 145.1, 143.7, 135.0, 134.5, 134.3, 131.2, 130.2, 127.7, 126.7, 126.4 (q, J=13.9 Hz), 124.0, 123.4, 119.9, 110.3, 106.7, 47.4, 41.7, 32.3, 31.4, 28.6, 27.5; LCMS m/z ([M+H$^+$], $C_{23}H_{22}ClFN_2O_2S$ requires 445.1147).

Example 44

Synthesis of N-(3-(3-azido-10,11-dihydro-5H-dibenzo[b,f]azepin-5-yl)propyl)-4-(trifluoromethyl)benzenesulfonamide

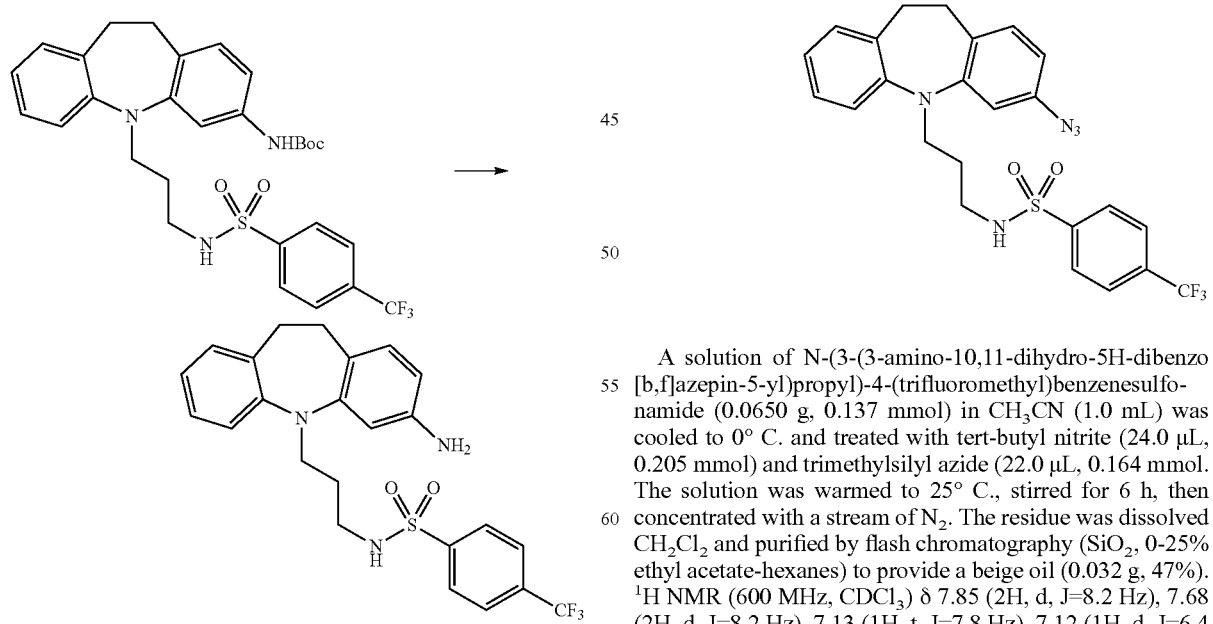

A solution of N-(3-(3-amino-10,11-dihydro-5H-dibenzo[b,f]azepin-5-yl)propyl)-4-(trifluoromethyl)benzenesulfonamide (0.0650 g, 0.137 mmol) in $CH_3CN$ (1.0 mL) was cooled to 0° C. and treated with tert-butyl nitrite (24.0 μL, 0.205 mmol) and trimethylsilyl azide (22.0 μL, 0.164 mmol. The solution was warmed to 25° C., stirred for 6 h, then concentrated with a stream of $N_2$. The residue was dissolved $CH_2Cl_2$ and purified by flash chromatography ($SiO_2$, 0-25% ethyl acetate-hexanes) to provide a beige oil (0.032 g, 47%). $^1$H NMR (600 MHz, $CDCl_3$) δ 7.85 (2H, d, J=8.2 Hz), 7.68 (2H, d, J=8.2 Hz), 7.13 (1H, t, J=7.8 Hz), 7.12 (1H, d, J=6.4 Hz), 7.04 (1H, t, J=8.0 Hz), 6.98 (2H, m), 6.63 (1H, d, J=8.2 Hz), 6.61 (1H, s), 4.75 (1H, t, J=5.9 Hz), 3.69 (2H, t, J=6.2 Hz), 3.04 (6H, m), 1.73 (2H, quintet, J=6.5 Hz); $^{13}$C NMR (150 MHz, CDCl$_3$) δ 149.0, 147.5, 143.7, 138.3, 135.2, 134.6, 134.4, 131.8 130.1, 130.0, 127.6, 127.0, 126.5 (q, J=13.4 Hz), 123.9, 120.3, 113.1, 110.4, 47.4, 41.4, 32.1, 31.6, 27.6; LCMS m/z 502.1497 ([M+H$^+$], C$_{24}$H$_{22}$F$_3$N$_5$O$_2$S requires 502.1519).

Example 45

Synthesis of N-(3-(3-chloro-10,11-dihydro-5H-dibenzo[b,f]azepin-5-yl)propyl)benzenesulfonamide

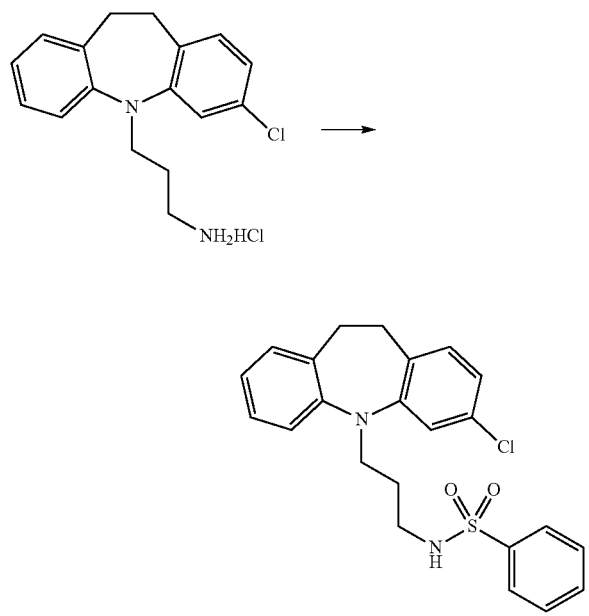

A solution of 3-(3-chloro-10,11-dihydro-5H-dibenzo[b,f]azepin-5-yl)propan-1-amine hydrochloride (0.0870 g, 0.270 mmol) in DMF (1.0 mL) was cooled to 0° C., treated with triethylamine (78.0 µL, 0.565 mmol), and benzenesulfonyl chloride (37.0 µL, 0.296 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a clear film (0.0949 g, 82%). $^1$H NMR (600 MHz, CDCl$_3$) δ 7.78 (2H, d, J=7.8 Hz), 7.53 (1H, t, J=7.8 Hz), 7.43 (2H, t, J=7.8 Hz), 7.12 (1H, t, J=7.2 Hz), 7.10 (1H, d, J=7.2 Hz), 6.97-6.99 (3H, m), 6.95 (1H, d, J=1.2 Hz), 6.88 (1H, dd, J=7.8, 1.8 Hz), 4.94 (1H, t, J=6.0 Hz), 3.65 (2H, t, J=6.0 Hz), 3.00 (4H, s), 3.01 (2H, q, J=6.6 Hz), 1.70 (2H, quintet, J=6.6 Hz); $^{13}$C NMR (150 MHz, CDCl$_3$) δ 148.9, 147.5, 139.8, 135.1, 132.7, 131.74, 131.66, 131.5, 129.8, 129.2, 127.1, 126.8, 123.7, 122.5, 120.3, 119.7, 47.5, 41.2, 32.0, 31.4, 27.5; LCMS m/z 427.1248 ([M+H$^+$], C$_{23}$H$_{23}$ClN$_2$O$_2$S requires 427.1242).

Example 46

Synthesis of N-(2-(10H-phenothiazin-10-yl)ethyl)-4-trifluoromethoxybenzenesulfonamide

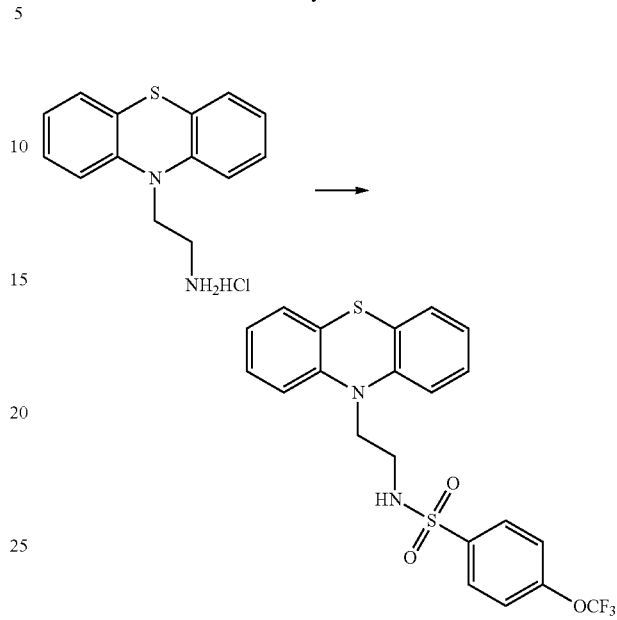

A solution of 2-(10H-phenothiazin-10-yl)ethanamine hydrochloride (0.080 g, 0.287 mmol) in DMF (1.0 mL) was cooled to 0° C., treated with triethylamine (84.0 µL, 0.603 mmol), and 4-trifluoromethoxybenzenesulfonyl chloride (0.082 g, 0.316 mmol). The mixture was warmed to 25° C., and stirred for 2 h. The mixture was partitioned between saturated aqueous NaCl (100 mL), and CH$_2$Cl$_2$ (100 mL). The organic layer was washed with saturated aqueous NaCl (3×100 mL), dried (Na$_2$SO$_4$), and concentrated in vacuo. The residue was dissolved in a minimal amount of CH$_2$Cl$_2$ and purified by flash chromatography (SiO$_2$, 0-25% ethyl acetate-hexanes) to afford the title compound as a clear film (0.121 g, 90%). $^1$H NMR (600 MHz, CDCl$_3$) δ 7.70 (2H, d, J=8.4 Hz), 7.19 (2H, d, J=7.8 Hz), 7.10 (2H, t, J=7.2 Hz), 7.06 (2H, t, J=7.8 Hz), 6.97 (2H, m), 6.74 (2H, d, J=7.8 Hz), 5.00 (1H, s), 3.98 (2H, s), 3.34 (2H, d, J=5.4 Hz); $^{13}$C NMR (150 MHz, CDCl$_3$) δ 152.0, 144.4, 137.8, 129.0, 128.0, 127.7, 126.9, 123.7, 120.8, 119.5, 116.1, 46.0, 39.6; LCMS m/z 467.0703 ([M+H$^+$], C$_{21}$H$_{17}$F$_3$N$_2$O$_3$S$_2$ requires 467.0705).

Example 47

Synthesis of N-(2-(10H-phenothiazin-10-yl)ethyl)-4-chlorobenzenesulfonamide

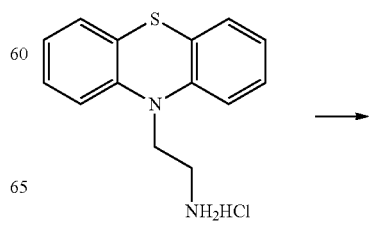

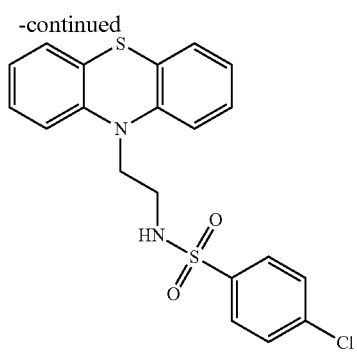

A solution of 2-(10H-phenothiazin-10-yl)ethanamine hydrochloride (0.080 g, 0.287 mmol) in DMF (1.0 mL) was cooled to 0° C., treated with triethylamine (84.0 µL, 0.603 mmol), and 4-chlorobenzenesulfonyl chloride (0.067 g, 0.316 mmol). The mixture was warmed to 25° C., and stirred for 2 h. The mixture was partitioned between saturated aqueous NaCl (100 mL), and $CH_2Cl_2$ (100 mL). The organic layer was washed with saturated aqueous NaCl (3×100 mL), dried ($Na_2SO_4$), and concentrated in vacuo. The residue was dissolved in a minimal amount of $CH_2Cl_2$ and purified by flash chromatography ($SiO_2$, 0-25% ethyl acetate-hexanes) to afford the title compound as a clear film (0.0993 g, 83%). $^1$H NMR (600 MHz, $CDCl_3$) δ 7.59 (2H, d, J=8.4 Hz), 7.17-7.19 (4H, m), 7.11 (2H, t, J=7.2 Hz), 6.98 (2H, t, J=7.2 Hz), 6.71 (2H, d, J=7.8 Hz), 4.91 (1H, br s), 3.93 (2H, br s), 3.34 (2H, d, J=5.4 Hz); $^{13}$C NMR (150 MHz, $CDCl_3$) δ 144.4, 139.1, 138.0, 129.3, 128.2, 128.1, 127.7, 126.8, 123.6, 116.1, 45.8, 39.6; LCMS m/z 417.0482 ([M+H$^+$], $C_{20}H_{17}ClN_2O_2S_2$ requires 417.0493).

Example 48

Synthesis of N-(3-(9H-thioxanthen-9-ylidene)propyl)-4-chlorobenzenesulfonamide

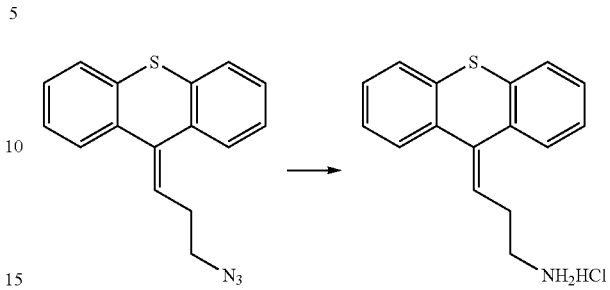

9-(3-azidopropylidene)-9H-thioxanthene. A solution of 9-(3-bromopropylidene)-9H-thioxanthene (0.245 g, 0.772 mmol) prepared according to methods described in (Dansk Patent NR. 88606) was dissolved in DMF (5.0 mL), treated with $NaN_3$ (0.107 g, 1.54 mmol), and stirred for 14 h at 25° C. The mixture was treated with saturated aqueous NaCl (100 mL), and extracted with hexanes (3×50 mL). The combined organic layers were washed with saturated aqueous NaCl (2×50 mL), dried ($Na_2SO_4$), and concentrated in vacuo. The residue was dissolved in a minimal amount of $CH_2Cl_2$ and purified by flash chromatography ($SiO_2$, 0-5% ethyl acetate-hexanes) to afford the title compound as a purple oil (0.177 g, 82%). $^1$H NMR (600 MHz, $CDCl_3$) δ 7.74 (1H, d, J=7.2 Hz), 7.72 (1H, d, J=6.6 Hz), 7.67 (1H, d, J=7.8 Hz), 7.64 (1H, d, J=7.2 Hz), 7.52 (2H, m), 7.47 (2H, m), 6.01 (1H, t, J=7.2 Hz), 3.65 (2H, t, J=7.2 Hz), 2.96 (2H, q, J=7.2 Hz); $^{13}$C NMR (150 MHz, $CDCl_3$) δ 138.2, 138.1, 133.9, 133.3, 131.8, 128.6, 127.5, 127.3, 127.1 (2C), 127.0, 126.1, 125.9, 125.8, 51.4, 29.5.

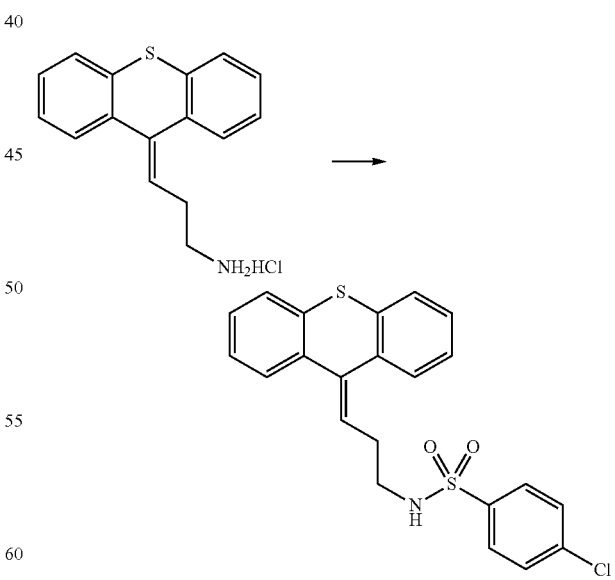

3-(9H-thioxanthen-9-ylidene)propan-1-amine hydrochloride. A solution of 9-(3-azidopropylidene)-9H-thioxanthene (0.177 g, 0.634 mmol) in THF (5.0 mL) was cooled to 0° C., treated with $PPh_3$ (0.183 g, 0.696 mmol) and stirred for 14 h at 25° C. The solution was concentrated to dryness, dissolved in a minimal amount of $CH_2Cl_2$ and purified by flash chromatography ($SiO_2$, 0-50% ethyl acetate-hexanes to remove nonpolar impurities followed by 17:2:1 $CH_2Cl_2$:MeOH:$NH_4OH$ to elute the product). The combined fractions of pure product were concentrated, dried azeotropically with toluene, and then suspended in $Et_2O$ (100 mL) and treated dropwise with a 4 N HCl-dioxane solution (0.16 mL). The white solid that had precipitated was collected by filtration to afford the title compound (0.167 g, 91%). $^1$H NMR (600 MHz, $CD_3OD$) δ 7.57 (1H, d, J=7.2 Hz), 7.47 (2H, d, J=7.2 Hz), 7.37 (1H, d, J=7.2 Hz), 7.35 (1H, t, J=7.2 Hz), 7.31 (2H, m), 7.26 (1H, t, J=7.2 Hz), 5.88 (1H, t, J=7.2 Hz), 3.10 (2H, t, J=7.2 Hz), 2.85 (2H, q, J=7.2 Hz); $^{13}$C NMR (150 MHz, $CD_3OD$) δ 139.2, 138.3, 134.3, 133.3, 132.1, 128.9, 127.9, 127.5, 127.4, 126.9, 126.5, 125.94, 125.87, 125.79, 39.8, 28.0; LCMS m/z 254.1223 ([M+H$^+$], $C_{16}H_{15}NS$ requires 254.0998).

N-(3-(9H-thioxanthen-9-ylidene)propyl)-4-chlorobenzenesulfonamide. A solution of 3-(9H-thioxanthen-9-ylidene)propan-1-amine hydrochloride (0.050 g, 0.172 mmol) in DMF (1.0 mL) was cooled to 0° C., treated with triethylamine (50.0 µL, 0.362 mmol), and 4-chlorobenzenesulfonyl chloride (0.040 g, 0.190 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a clear film (0.067 g, 91%). $^1$H NMR (600 MHz, CDCl$_3$) δ 7.68 (2H, d, J=8.4 Hz), 7.47 (1H, d, J=7.2 Hz), 7.40 (2H, t, J=8.4 Hz), 7.30 (2H, d, J=7.8 Hz), 7.26 (5H, m), 5.59 (1H, t, J=7.2 Hz), 4.47 (1H, br s), 3.15 (2H, d, J=6.0 Hz), 2.60 (2H, q, J=6.2 Hz), 2.59 (2H, q, J=6.7 Hz); $^{13}$C NMR (150 MHz, CD$_3$OD) δ 139.2, 138.9, 138.6, 138.1, 134.0, 133.1, 131.8, 129.5, 128.7, 128.6, 127.7, 127.3, 127.3, 127.1, 126.9, 126.2, 126.1, 125.7, 43.3, 29.8; LCMS m/z 428.0532 ([M+H$^+$], C$_{22}$H$_{18}$ClNO$_2$S$_2$ requires 428.0540).

Example 49

Synthesis of N-(3-(9H-thioxanthen-9-ylidene)propyl)-4-(trifluoromethoxy)benzenesulfonamide

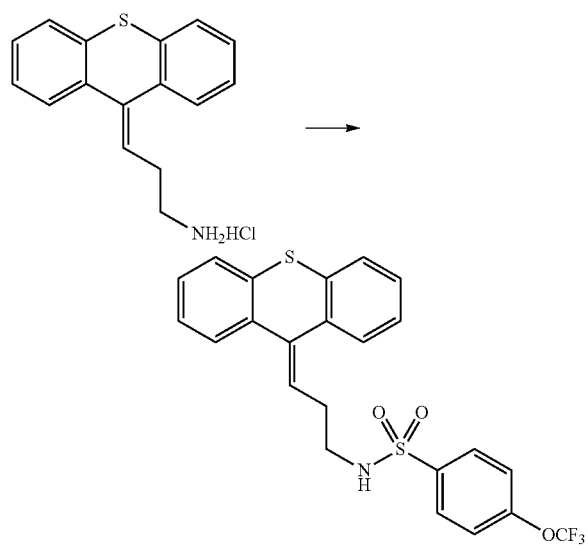

A solution of 3-(9H-thioxanthen-9-ylidene)propan-1-amine hydrochloride (0.050 g, 0.173 mmol) in DMF (1.0 mL) was cooled to 0° C., treated with triethylamine (50.0 μL, 0.362 mmol), and 4-trifluoromethoxybenzenesulfonyl chloride (0.050 g, 0.190 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a clear film (0.0756 g, 92%). $^1$H NMR (600 MHz, CDCl$_3$) δ 7.82 (2H, d, J=8.4 Hz), 7.45 (1H, d, J=7.2 Hz), 7.40 (1H, d, J=7.2 Hz) 7.38 (1H, d, J=7.2 Hz), 7.28 (1H, m), 7.23 (5H, m), 7.18 (2H, d, J=8.4 Hz), 5.63 (1H, t, J=7.2 Hz), 4.86 (1H, br m), 3.12 (2H, q, J=6.6 Hz), 2.61 (2H, q, J=6.6 Hz); $^{13}$C NMR (150 MHz, CDCl$_3$) δ 152.1, 138.6, 138.4, 138.1, 133.9, 133.1, 131.8, 129.3, 128.7, 127.6, 127.3, 127.2, 127.04, 127.01, 126.2, 126.0, 125.7, 121.2, 121.0, 43.2, 29.9; LCMS m/z 478.0750 ([M+H$^+$], C$_{23}$H$_{18}$F$_3$NO$_3$S$_2$ requires 478.0753).

Example 50

Synthesis of 5-(3-Azidopropylidene)-10,11-dihydro-5H-dibenzo[a,d][7]annulene

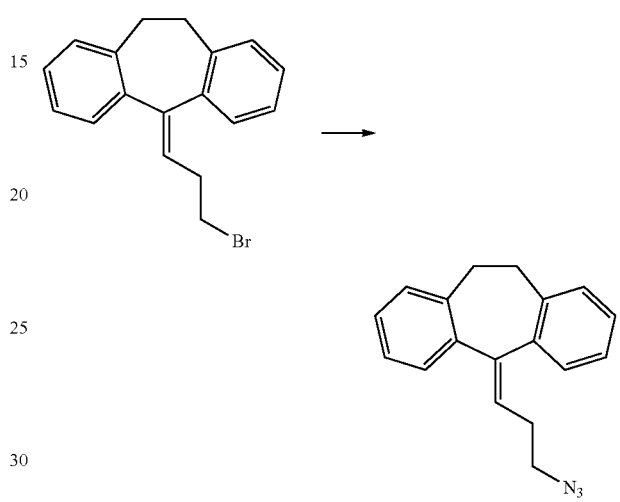

5-(3-Azidopropylidene)-10,11-dihydro-5H-dibenzo[a,d][7]annulene. A solution of 5-(3-bromopropylidene)-10,11-dihydro-5H-dibenzo[a,d][7]annulene (1.40 g, 4.47 mmol) prepared according to methods described in (PCT/US2008/013221 [00212]) was dissolved in DMF (5.0 mL), treated with NaN$_3$ (0.925 g, 13.4 mmol), and stirred for 14 h at 25° C. The mixture was treated with saturated aqueous NaCl (100 mL), and extracted with CH$_2$Cl$_2$ (3×50 mL). The combined organic layers were washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-10% CH$_2$Cl$_2$-hexanes) to afford the title compound as a clear oil (0.890 g, 72%). $^1$H NMR (600 MHz, CDCl$_3$) δ 7.29 (1H, m), 7.23 (2H, m), 7.14-7.21 (4H, m), 7.06 (1H, m), 5.87 (1H, t, J=7.2 Hz), 3.36 (4H, m), 2.99 (1H, br s), 2.81 (1H, br s), 2.44 (2H, d, J=6.0 Hz), $^{13}$C NMR (150 MHz, CDCl$_3$) δ 145.8, 141.1, 139.8, 139.6, 137.4, 130.3, 128.7, 128.4, 128.3, 127.9, 127.5, 127.0, 126.3, 126.1, 51.5, 33.9, 32.2, 29.4.

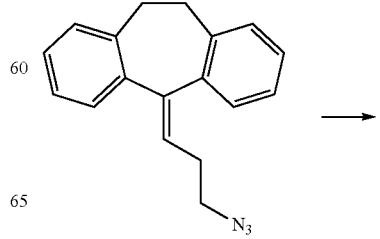

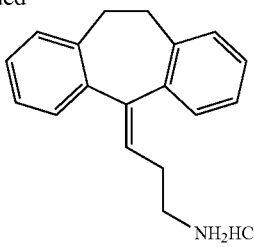

3-(10,11-dihydro-5H-dibenzo[a,d][7]annulen-5-ylidene)propan-1-amine hydrochloride. A solution of 5-(3-azidopropylidene)-10,11-dihydro-5H-dibenzo[a,d][7]annulene (0.890 g, 3.23 mmol) in THF (10.0 mL) was cooled to 0° C., treated with PPh$_3$ (0.931 g, 3.56 mmol) and stirred for 14 h at 25° C. The solution was concentrated to dryness, dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$:MeOH:NH$_4$OH to elute the product). The combined fractions of pure product were concentrated, dried azeotropically with toluene, and then suspended in Et$_2$O (100 mL) and treated dropwise with a 4 N HCl-dioxane solution (0.81 mL). The white solid that had precipitated was collected by filtration to afford the title compound (0.756 g, 82%). $^1$H NMR (600 MHz, CD$_3$OD) δ 7.57 (1H, d, J=7.2 Hz), 7.47 (2H, d, J=7.2 Hz), 7.37 (1H, d, J=7.2 Hz), 7.35 (1H, t, J=7.2 Hz), 7.31 (2H, m), 7.26 (1H, t, J=7.2 Hz), 5.88 (1H, t, J=7.2 Hz), 3.10 (2H, t, J=7.2 Hz), 2.85 (2H, q, J=7.2 Hz); $^{13}$C NMR (150 MHz, CD$_3$OD) δ 139.2, 138.3, 134.3, 133.3, 132.1, 128.9, 127.9, 127.5, 127.4, 126.9, 126.5, 125.94, 125.87, 125.79, 39.8, 28.0; LCMS m/z 250.2414 ([M+H$^+$], C$_{18}$H$_{19}$N requires 250.1590).

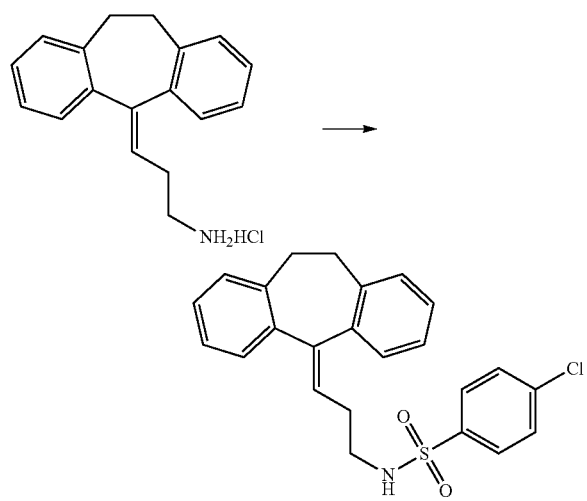

4-Chloro-N-(3-(10,11-dihydro-5H-dibenzo[a,d][7]annulen-5-ylidene)propyl)benzenesulfonamide. A solution of A solution of 3-(10,11-dihydro-5H-dibenzo[a,d][7]annulen-5-ylidene)propan-1-amine hydrochloride (0.150 g, 0.524 mmol) in DMF (1.0 mL) was cooled to 0° C., treated with triethylamine (152 μL, 1.100 mmol), and 4-chlorobenzenesulfonyl chloride (0.122 g, 0.577 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a white solid (0.207 g, 93%). $^1$H NMR (600 MHz, CDCl$_3$) δ 7.70 (2H, d, J=8.4 Hz), 7.40 (2H, d, J=8.4 Hz), 7.21 (2H, m), 7.12-7.17 (4H, t, J=7.2 Hz), 7.04 (1H, d, J=7.2 Hz), 7.01 (1H, d, J=7.2 Hz), 5.68 (1H, t, J=7.2 Hz), 4.36 (1H, t, J=6.0 Hz), 3.03 (2H, br m), 3.03 (2H, br m), 2.96 (1H, br m), 2.79 (1H, br m), 2.28 (2H, t, J=7.2 Hz); $^{13}$C NMR (150 MHz, CDCl$_3$) δ 146.4, 140.7, 139.5, 139.4, 139.3, 138.6, 137.2, 130.3, 129.6, 128.7, 128.6, 128.5, 128.3, 128.0, 127.7, 126.6, 126.4, 126.1, 43.2, 33.9, 32.2, 29.8; LCMS m/z 424.1127 ([M+H$^+$], C$_{24}$H$_{22}$ClNO$_2$S requires 424.1133).

Example 51

N-(3-(10,11-dihydro-5H-dibenzo[a,d][7]annulen-5-ylidene)propyl)-4-(trifluoromethoxy)benzenesulfonamide

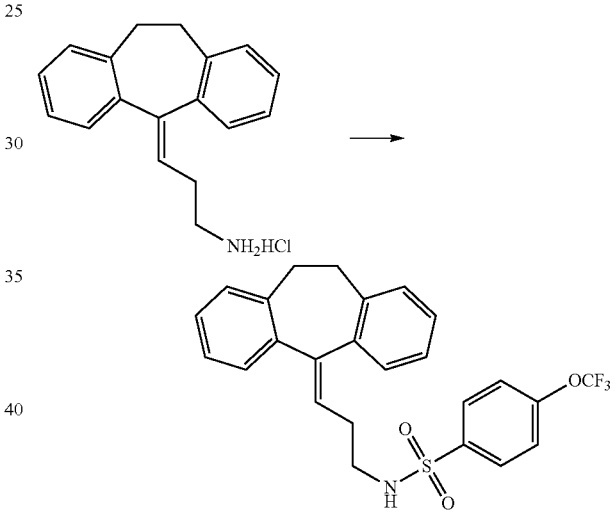

A solution of 3-(10,11-dihydro-5H-dibenzo[a,d][7]annulen-5-ylidene)propan-1-amine hydrochloride (0.150 g, 0.524 mmol) in DMF (1.0 mL) was cooled to 0° C., treated with triethylamine (152 μL, 1.10 mmol), and 4-trifluoromethoxybenzenesulfonyl chloride (0.150 g, 0.577 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a white solid (0.214 g, 86%). $^1$H NMR (600 MHz, CDCl$_3$) δ 7.79 (2H, d, J=8.4 Hz), 7.20 (2H, d, J=8.4 Hz), 7.19 (3H, d, J=4.2 Hz), 7.08-7.14 (3H, m), 7.00 (2H, t, J=10.2 Hz), 5.68 (1H, t, J=7.8 Hz), 4.67 (1H, t, J=6.0 Hz), 3.28 (2H, br m), 3.01 (2H, br m), 2.94 (1H, br m), 2.76 (1H, br s), 2.27 (2H, br s); $^{13}$C NMR (150 MHz, CDCl$_3$) δ 152.2, 146.2, 140.7, 139.6, 139.4, 138.4, 137.2, 130.3, 129.3, 128.6, 128.4, 128.2, 127.9, 127.6, 126.6, 126.3, 126.1, 121.3, 121.1, 43.2, 33.9, 32.2, 29.8; LCMS m/z 474.1346 ([M+H$^+$], C$_{25}$H$_{22}$F$_3$NO$_3$S requires 474.1345).

Example 52

4-Chloro-N-(3-(2,8-dichloro-10,11-dihydro-5H-dibenzo[b,f]azepin-5-yl)propyl)benzenesulfonamide

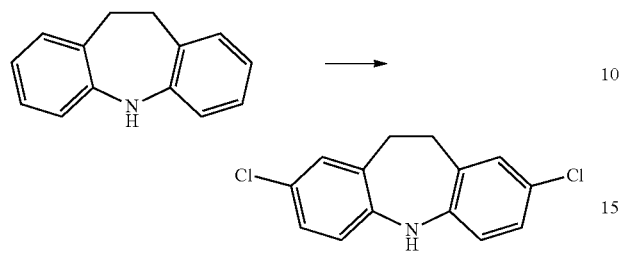

2,8-Dichloro-10,11-dihydro-5H-dibenzo[b,f]azepine. A solution of 10,11-dihydro-5H-dibenzo[b,f]azepine (4.00 g, 20.5 mmol) in THF (50.0 mL) was cooled to 0° C., treated with N-chloro-succinimide (5.47 g, 41.0 mmol), and one drop of concentrated $H_2SO_4$. The solution was warmed to 25° C. and stirred for 14 h. The mixture was partitioned between saturated aqueous NaCl (100 mL), and $CH_2Cl_2$ (300 mL). The organic layer was washed with saturated aqueous NaCl (2×50 mL), dried ($Na_2SO_4$), and concentrated in vacuo. The residue was dissolved in a minimal amount of $CH_2Cl_2$ and purified by flash chromatography ($SiO_2$, 0-5% ethyl acetate-hexanes) to afford the title compound as a green white solid (2.60 g, 48%). $^1$H NMR (600 MHz, $CDCl_3$) δ 7.03 (3H, m), 6.64 (3H, d, J=8.0 Hz), 5.93 (1H, br s), 3.01 (4H, s); $^{13}$C NMR (150 MHz, $CDCl_3$) δ 140.8, 130.4, 130.1, 126.9, 124.5, 119.4, 34.5.

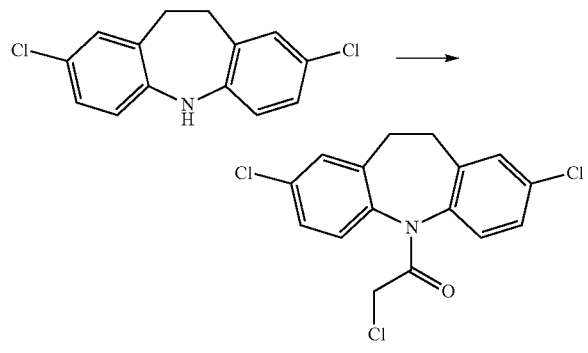

2-Chloro-1-(2,8-dichloro-10,11-dihydro-5H-dibenzo[b,f]azepin-5-yl)ethanone. A solution of 2-2,8-dichloro-10,11-dihydro-5H-dibenzo[b,f]azepine (2.20 g, 9.58 mmol) in toluene (10.0 mL) was treated with chloroacetyl chloride (0.80 mL, 10.1 mmol) and heated to 100° C. for 1 h. The mixture was cooled to 25° C., concentrated under $N_2$ stream, taken up in a minimal amount of toluene and purified by flash chromatography ($SiO_2$, 5-20% ethyl acetate-hexanes) to afford the title compound as a white solid (2.06 g, 77%). $^1$H NMR (600 MHz, $CDCl_3$) δ (mixture of rotamers) 7.26-7.30 (4H, m), 7.16-7.20 (2H, m), 3.99 (2H, d, J=16.8 Hz), 3.42 (1H, br m), 3.33 (1H, br m), 2.79-2.84 (2H, m); $^{13}$C NMR (150 MHz, $CDCl_3$) δ 166.3, 139.7, 139.4, 137.9, 136.2, 135.3, 133.8, 130.8, 130.5, 129.8, 128.6, 128.1, 127.3, 41.6, (30.6, 30.1); LCMS m/z 342.0028 ([M+H$^+$], $C_{16}H_{12}Cl_3NO$ requires 342.0033).

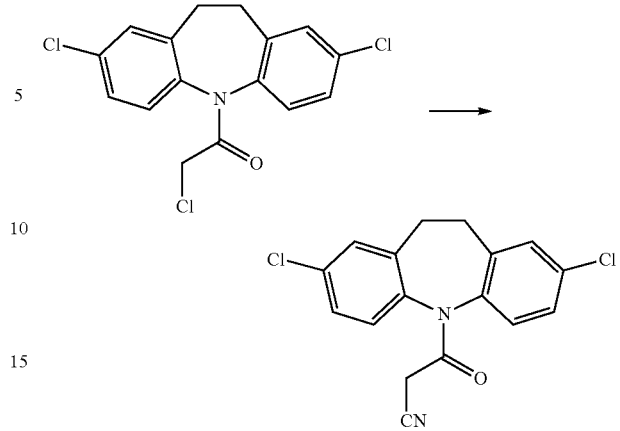

3-(2,8-Dichloro-10,11-dihydro-5H-dibenzo[b,f]azepin-5-yl)-3-oxopropanenitrile. A solution of 2-chloro-1-(2,8-dichloro-10,11-dihydro-5H-dibenzo[b,f]azepin-5-yl)ethanone (2.26 g, 6.63 mmol) (ref) in DMF (10.0 mL) was cooled to 0° C. and treated with sodium cyanide (0.358 g, 7.30 mmol). The mixture was warmed to 25° C. and stirred for 14 h. The solution was diluted with $CH_2Cl_2$ (500 mL) and the organic layer was washed with $H_2O$ (3×200 mL), saturated aqueous NaCl (100 mL), dried ($Na_2SO_4$), and concentrated in vacuo. The residue was taken up in a minimal amount of $CH_2Cl_2$ and purified by flash chromatography ($SiO_2$, 10-30% ethyl acetate-hexanes) to afford the title compound as a white solid (1.30 g, 59%). $^1$H NMR (600 MHz, $CDCl_3$) δ (as a mixture of rotamers) 7.35 (1H, d, J=1.2 Hz), 7.29 (2H, t, J=6.6 Hz), 7.25 (1H, t, J=8.4 Hz), 7.20 (1H, dd, J=8.4, 1.8 Hz), 7.18 (1H, s), 3.47 (1H, d, J=18.0 Hz), 3.39 (1H, m), 3.32 (1H, d, J=18.0 Hz), 3.30-3.33 (1H, m), 2.84-2.87 (2H, m); $^{13}$C NMR (150 MHz, $CDCl_3$) δ 161.8, 139.7, 139.1, 137.3, 136.0, 135.9, 134.1, 130.94, 130.85, 129.7, 128.5, 127.5, 113.5, 30.7, 30.0, 26.0; LCMS m/z 331.0404 ([M+H$^+$], $C_{17}H_{12}Cl_2N_2O$ requires 331.0399).

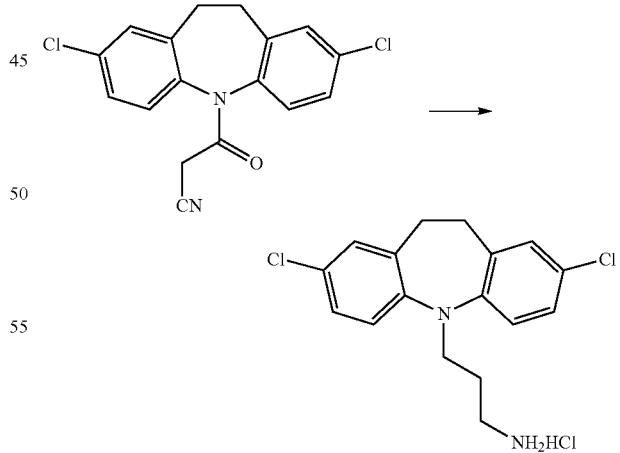

3-(2,8-Dichloro-10,11-dihydro-5H-dibenzo[b,f]azepin-5-yl)propan-1-amine hydrochloride. A solution of 3-(2,8-dichloro-10,11-dihydro-5H-dibenzo[b,f]azepin-5-yl)-3-oxopropanenitrile (1.30 g, 3.92 mmol) in THF (10.0 mL) was cooled to 0° C. and treated with a $BH_3$-THF (1 M solution in THF, 15.7 mL, 15.7 mmol). The flask was sealed, heated to 70° C. for 5 h, and then cooled to 0° C. The solution was treated slowly, dropwise with a solution of aqueous 1 M HCl (32 mL), stirred for an additional 0.5 h, and then heated to 70° C. for 1 h. The mixture was cooled to 25° C., treated with aqueous 4 M NaOH until pH>8, and then the mixture was extracted with ethyl acetate (3×200 mL). The combined extracts were washed with saturated aqueous NaCl (100 mL), dried (Na$_2$SO$_4$), and concentrated in vacuo. The residue was dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$:MeOH:NH$_4$OH to elute the product). The combined fractions of pure product were concentrated, dried azeotropically with toluene, and then suspended in Et$_2$O (100 mL) and treated dropwise with a 4 N HCl-dioxane solution (1.0 mL). The white solid that had precipitated was collected by filtration to afford the title compound (0.842 g, 60%). $^1$H NMR (600 MHz, CD$_3$OD) δ 7.13 (6H, m), 3.81 (2H, t, J=6.6 Hz), 3.11 (4H, s), 2.95 (2H, t, J=7.8 Hz), 1.90 (2H, quintet, J=7.2 Hz); $^{13}$C NMR (150 MHz, CD$_3$OD) δ 146.8, 136.5, 129.8, 128.4, 126.8, 121.7, 47.8, 38.0, 31.7, 26.0; LCMS m/z 321.1785 ([M+H$^+$], C$_{17}$H$_{19}$Cl$_2$N$_2$ requires 321.0920).

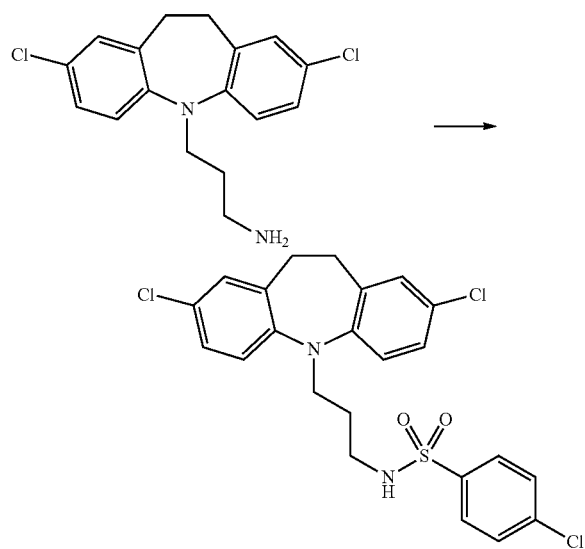

4-Chloro-N-(3-(2,8-dichloro-10,11-dihydro-5H-dibenzo[b,f]azepin-5-yl)propyl)benzenesulfonamide. A solution of 3-(2,8-dichloro-10,11-dihydro-5H-dibenzo[b,f]azepin-5-yl)propan-1-amine hydrochloride (0.080 g, 0.224 mmol) in DMF (1.0 mL) was cooled to 0° C., treated with triethylamine (65.0 μL, 0.474 mmol), and 4-chlorobenzenesulfonyl chloride (0.052 g, 0.246 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a white solid (0.0429 g, 39%). $^1$H NMR (600 MHz, CDCl$_3$) δ 7.87 (2H, d, J=8.8 Hz), 7.59 (2H, d, J=8.4 Hz), 7.25 (4H, m), 7.07 (2H, d, J=9.6 Hz), 5.19 (1H, t, J=6.0 Hz), 3.82 (2H, t, J=6.6 Hz), 3.19 (4H, s), 3.15 (2H, q, J=6.6 Hz), 1.88 (2H, quintet, J=6.0 Hz); $^{13}$C NMR (150 MHz, CDCl$_3$) δ 146.1, 139.3, 138.3, 135.8, 129.9, 129.5, 128.5, 128.2, 126.7, 121.2, 47.5, 41.0, 31.7, 27.5; LCMS m/z 495.0033 ([M+H$^+$], C$_{23}$H$_{21}$Cl$_3$N$_2$O$_2$S requires 495.0462).

Example 53

4-Trifluoromethoxy-N-(3-(2,8-dichloro-10,11-dihydro-5H-dibenzo[b,f]azepin-5-yl)propyl)benzenesulfonamide

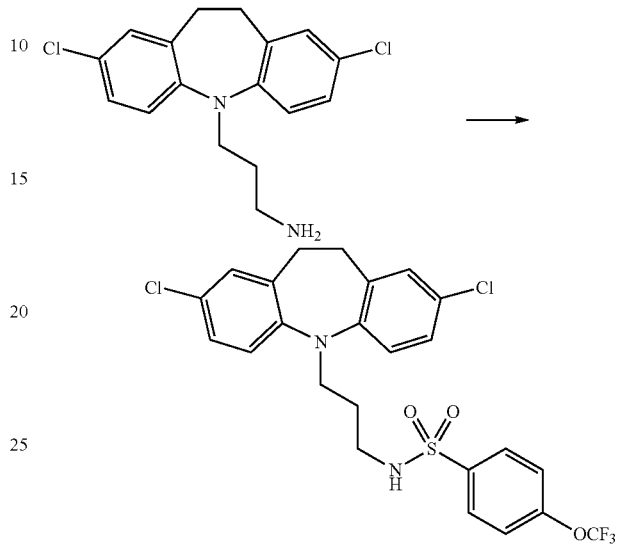

A solution of 3-(2,8-dichloro-10,11-dihydro-5H-dibenzo[b,f]azepin-5-yl)propan-1-amine hydrochloride (0.080 g, 0.224 mmol) in DMF (1.0 mL) was cooled to 0° C., treated with triethylamine (65.0 μL, 0.474 mmol), and 4-trifluoromethoxybenzenesulfonyl chloride (0.064 g, 0.246 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a white solid (0.0489 g, 40%). $^1$H NMR (600 MHz, CDCl$_3$) δ 7.99 (2H, d, J=8.4 Hz), 7.46 (2H, d, J=8.4 Hz), 7.27 (4H, m), 7.09 (2H, d, J=9.6 Hz), 5.13 (1H, t, J=6.0 Hz), 3.85 (2H, t, J=6.0 Hz), 3.19 (4H, s), 3.17 (2H, q, J=6.0 Hz), 1.89 (2H, quintet, J=6.6 Hz); $^{13}$C NMR (150 MHz, CDCl$_3$) δ 152.3, 146.2, 138.2, 135.8, 129.9, 129.8, 129.3, 128.3, 126.7, 121.2, 121.1, 47.6, 41.2, 31.7, 27.5; LCMS m/z 545.0211 ([M+H$^+$], C$_{24}$H$_{21}$Cl$_2$F$_3$N$_2$O$_3$S requires 545.0675).

Example 54

Synthesis of N-(3-(3-chloro-10,11-dihydro-5H-dibenzo[b,f]azepin-5-yl)propyl)-3-(trifluoromethoxy)benzenesulfonamide

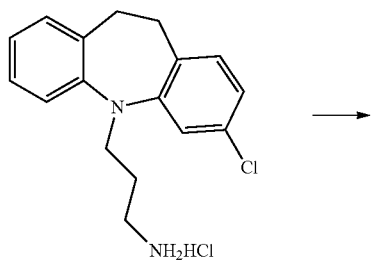

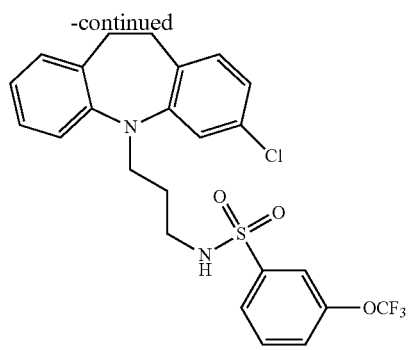

A solution of 3-(3-chloro-10,11-dihydro-5H-dibenzo[b,f]azepin-5-yl)propan-1-amine hydrochloride (0.0700 g, 0.217 mmol) in DMF (1.0 mL) was cooled to 0° C., treated with Et$_3$N (63.0 μL, 0.455 mmol), and 3-trifluoromethoxybenzenesulfonyl chloride (0.58 mL, 3.40 mmol). The mixture was warmed to 25° C., and stirred for 2 h. The mixture was partitioned between saturated aqueous NaCl (100 mL), and CH$_2$Cl$_2$ (300 mL). The organic layer was washed with saturated aqueous NaCl (2×100 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a clear film (0.104 g, 94%). $^1$H NMR (600 MHz, CDCl$_3$) δ 7.67 (2H, br s), 7.46 (1H, t, J=8.4 Hz), 7.39 (1H, d, J=8.4 Hz), 7.12 (2H, m), 6.96 (3H, m), 6.96 (1H, m), 6.88 (1H, d, J=7.2 Hz), 5.02 (1H, t, J=5.4 Hz), 3.68 (2H, t, J=6.0 Hz), 3.05 (4H, br s), 3.00 (2H, q, J=6.6 Hz), 1.73 (2H, quintet, J=6.6 Hz); $^{13}$C NMR (600 MHz, CDCl$_3$) δ 149.4, 148.8, 147.4, 142.1, 135.1, 131.8, 131.7, 131.5, 131.0, 129.8, 126.8, 125.3, 125.0, 123.8, 122.6, 121.3, 120.3, 119.8, 119.7, 47.3, 41.2, 32.0, 31.4, 27.5; LCMS m/z 511.0821 ([M+H$^+$], C$_{24}$H$_{22}$ClF$_3$N$_2$O$_3$S requires 511.1065).

Example 55

Synthesis of 4-Chloro-N-(2-((10,11-dihydro-5H-dibenzo[a,d][7]annulen-5-yl)amino)ethyl)benzenesulfonamide

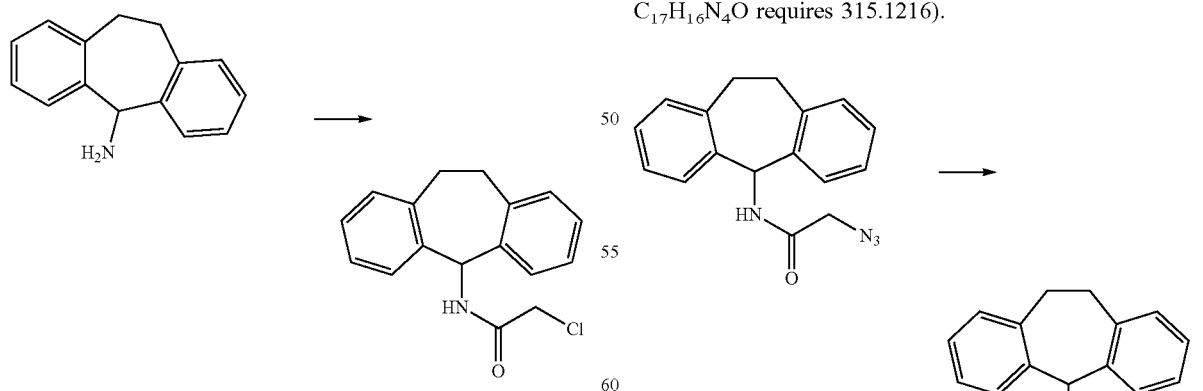

2-Chloro-N-(10,11-dihydro-5H-dibenzo[a,d][7]annulen-5-yl)acetamide. A solution of 10,11-dihydro-5H-dibenzo[a,d][7]annulen-5-amine (0.600 g, 4.07 mmol) in toluene (10.0 mL) was treated with chloroacetyl chloride (0.360 mL, 4.48 mmol) and a white solid formed. The mixture was heated to 100° C. for 1 h. The mixture was cooled to 25° C., treated with hexanes to further precipitate the product. The white solid was collected by suction filtration to afford the title compound as a white solid (0.716 g, 79%). $^1$H NMR (600 MHz, CD$_3$OD) δ (mixture of rotamers) 7.37 (2H, d, J=6.6 Hz), 7.17 (6H, m), 6.21 (1H, br s), 4.06 (2H, br s), 3.37 (2H, t, J=6.6 Hz), 3.10 (2H, t, J=6.0 Hz); $^{13}$C NMR (150 MHz, CD$_3$OD) δ 164.8, 138.7, 138.6, 132.8, 130.1, 127.6, 125.9, 55.6, 42.6, 31.6; LCMS m/z 308.0810 ([M+Na$^+$], C$_{17}$H$_{16}$ClNO requires 308.0813).

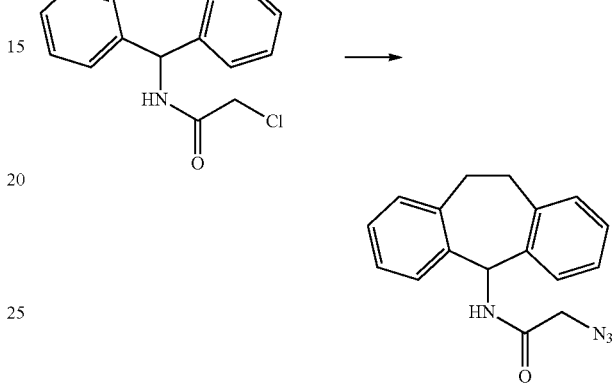

2-Azido-N-(10,11-dihydro-5H-dibenzo[a,d][7]annulen-5-yl)acetamide. A solution of 2-chloro-N-(10,11-dihydro-5H-dibenzo[a,d][7]annulen-5-yl)acetamide (0.681 g, 2.38 mmol) in DMF (10.0 mL) was treated with sodium azide (0.329 g, 4.78 mmol) and stirred for 14 h at 25° C. The solution was diluted with CH$_2$Cl$_2$ (100 mL) and the organic layer was washed with H$_2$O (3×100 mL), saturated aqueous NaCl (100 mL), dried (Na$_2$SO$_4$), and concentrated in vacuo. The residue was taken up in a minimal amount of CH$_2$Cl$_2$ and purified by flash chromatography (SiO$_2$, 0-20% ethyl acetate-hexanes) to afford the title compound as a white solid (0.661 g, 95%). $^1$H NMR (600 MHz, DMSO-d$_6$) δ 7.37 (2H, d, J=7.2 Hz), 7.17 (6H, m), 6.27 (1H, d, J=8.4 Hz), 3.93 (2H, br s), 3.27 (2H, m), 3.10 (2H, m); $^{13}$C NMR (150 MHz, DMSO-d$_6$) δ 166.5, 138.8, 138.6, 130.1, 127.8, 127.6, 125.9, 55.6, 50.4, 31.7; LCMS m/z 315.1191 ([M+Na$^+$], C$_{17}$H$_{16}$N$_4$O requires 315.1216).

N$^1$-(10,11-dihydro-5H-dibenzo[a,d][7]annulen-5-yl)ethane-1,2-diamine. A solution of 2-azido-N-(10,11-dihydro-5H-dibenzo[a,d][7]annulen-5-yl)acetamide (0.580 g, 1.98 mmol) in THF (10.0 mL) was cooled to 0° C. and treated with a BH$_3$-THF (1 M solution in THF, 8.00 mL, 8.00 mmol). The flask was sealed, heated to 70° C. for 5 h, and then cooled to 0° C. The solution was treated slowly, dropwise with a solution of aqueous 1 M HCl (16.0 mL), stirred for an additional 0.5 h, and then heated to 70° C. for 1 h. The mixture was cooled to 25° C., treated with aqueous 4 M NaOH until pH>8, and then the mixture was extracted with ethyl acetate (3×200 mL). The combined extracts were washed with saturated aqueous NaCl (100 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes to remove nonpolar impurities followed by 17:2:1 CH$_2$Cl$_2$:MeOH:NH$_4$OH to elute the product). The combined fractions of pure product were concentrated, dried azeotropically with toluene, and then suspended in Et$_2$O (100 mL) and treated dropwise with a 4 N HCl-dioxane solution (0.50 mL). The white solid that had precipitated was collected by filtration to afford the title compound (0.362 g, 73%). $^1$H NMR (600 MHz, CDCl$_3$) δ 7.18 (2H, m), 7.09 (2H, m), 7.04 (4H, m), 4.74 (1H, s), 3.65 (2H, d, J=6.6 Hz), 2.89 (2H, q, J=7.8 Hz), 2.66 (2H, t, J=5.4 Hz), 2.54 (2H, t, J=5.4 Hz), 1.34 (2H, br s); $^{13}$C NMR (150 MHz, CDCl$_3$) δ 140.6, 140.1, 130.6, 129.4, 127.7, 126.1, 60.9, 51.5, 42.4, 32.6; LCMS m/z 253.1682 ([M+H$^+$], C$_{17}$H$_{20}$N$_2$ requires 253.1699).

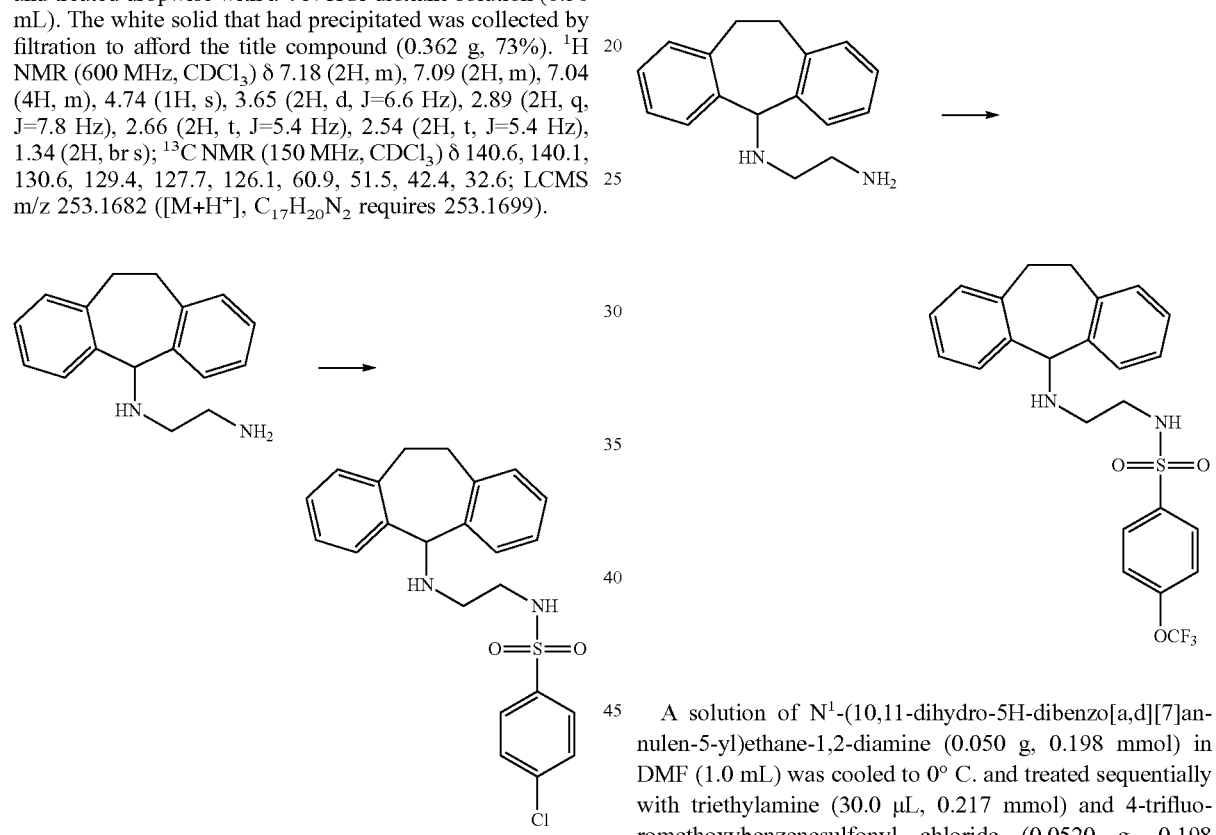

4-Chloro-N-(2-((10,11-dihydro-5H-dibenzo[a,d][7]annulen-5-yl)amino)ethyl)benzenesulfonamide. A solution of N$^1$-(10,11-dihydro-5H-dibenzo[a,d][7]annulen-5-yl)ethane-1,2-diamine (0.050 g, 0.198 mmol) in DMF (1.0 mL) was cooled to 0° C. and treated sequentially with triethylamine (30.0 μL, 0.217 mmol) and 4-chlorobenzenesulfonyl chloride (0.0420 g, 0.198 mmol). The solution was warmed to 25° C. and stirred for 2 h. The mixture was poured over saturated aqueous NaCl (20 mL) and extracted with CH$_2$Cl$_2$ (3×50 mL). The combined organic layers were washed with saturated aqueous NaCl (3×50 mL), dried (Na$_2$SO$_4$), concentrated in vacuo, and the residue was purified by flash chromatography (SiO$_2$, 0-20% ethyl acetate-hexanes) to afford the title compound as a clear film (0.0581 g, 69%). $^1$H NMR (600 MHz, CDCl$_3$) δ 7.66 (2H, d, J=9.0 Hz), 7.39 (2H, d, J=8.4 Hz), 7.19 (2H, t, J=6.6 Hz), 7.17 (2H, d, J=6.6 Hz), 5.07 (1H, br s), 4.66 (1H, s), 3.62 (2H, d, J=6.0 Hz), 2.92 (4H, q, J=6.0 Hz), 2.65 (2H, t, J=5.4 Hz), 1.62 (1H, br s); $^{13}$C NMR (150 MHz, CDCl$_3$) δ 140.0, 139.5, 139.1, 138.4, 130.7, 129.6, 129.5, 128.6, 127.9, 126.2, 60.6, 47.0, 43.1, 32.6; LCMS m/z ([M+H$^+$], C$_{23}$H$_{23}$ClN$_2$O$_2$S requires).

Example 56

Synthesis of 4-Trifluoromethoxy-N-(2-((10,11-dihydro-5H-dibenzo[a,d][7]annulen-5-yl)amino)ethyl)benzenesulfonamide A solution of N$^1$-(10,11-dihydro-5H-dibenzo[a,d][7]annulen-5-yl)ethane-1,2-diamine (0.050 g, 0.198 mmol) in DMF (1.0 mL) was cooled to 0° C. and treated sequentially with triethylamine (30.0 μL, 0.217 mmol) and 4-trifluoromethoxybenzenesulfonyl chloride (0.0520 g, 0.198 mmol). The solution was warmed to 25° C. and stirred for 2 h. The mixture was poured over saturated aqueous NaCl (20 mL) and extracted with CH$_2$Cl$_2$ (3×50 mL). The combined organic layers were washed with saturated aqueous NaCl (3×50 mL), dried (Na$_2$SO$_4$), concentrated in vacuo, and the residue was purified by flash chromatography (SiO$_2$, 0-20% ethyl acetate-hexanes) to afford the title compound as a clear film (0.0584 g, 62%). $^1$H NMR (600 MHz, CDCl$_3$) δ 7.79 (2H, d, J=9.0 Hz), 7.25 (2H, d, J=9.0 Hz), 7.19 (2H, m), 7.12 (2H, m), 5.11 (1H, br s), 4.67 (1H, s), 3.62 (2H, d, J=6.0 Hz), 2.92 (4H, q, J=5.4 Hz), 2.68 (2H, t, J=5.4 Hz), 1.63 (1H, br s); $^{13}$C NMR (150 MHz, CDCl$_3$) δ 152.11, 152.10, 140.1, 139.5, 138.3, 130.8, 129.7, 129.3, 128.0, 126.2, 121.1, 69.9, 47.0, 43.1, 32.6; LCMS m/z 477.1399 ([M+H$^+$], C$_{24}$H$_{23}$F$_3$N$_2$O$_3$S requires 477.1454).

Example 57

Synthesis of 4-Chloro-N-(3-(3-chloro-10,11-dihydro-5H-dibenzo[b,f]azepin-5-yl)-2-hydroxypropyl)benzenesulfonamide

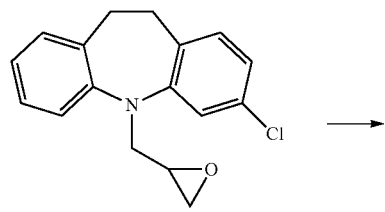

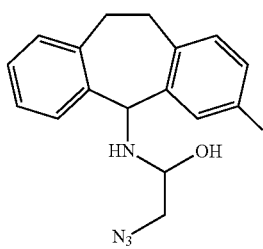

1-Azido-3-(3-chloro-10,11-dihydro-5H-dibenzo[b,f]azepin-5-yl)propan-2-ol. A solution of 3-chloro-5-(oxiran-2-ylmethyl)-10,11-dihydro-5H-dibenzo[V]azepine (0.772 g, 2.70 mmol) in methanol (10.0 ml) was treated with sodium azide (0.351, 5.40 mmol) and heated to 70° C. for 14 h. The mixture was cooled to 25° C., concentrated in vacuo, resuspended in EtOAc (100 mL). This organic layer was washed with saturated aqueous NaCl (3×50 mL), dried (Na$_2$SO$_4$), concentrated in vacuo, and the residue was purified by flash chromatography (SiO$_2$, 0-20% ethyl acetate-hexanes) to afford the title compound as a clear film (0.425 g, 48%). $^1$H NMR (600 MHz, CDCl$_3$) δ 7.18 (1H, t, J=7.8 Hz), 7.15 (1H, d, J=7.8 Hz), 7.09 (1H, d, J=7.8 Hz), 7.07 (1H, d, J=1.8 Hz), 7.07 (1H, d, J=1.8 Hz), 7.02 (2H, d, J=7.8 Hz), 6.93 (1H, dd, J=8.4, 2.4 Hz), 3.97 (1H, m), 3.88 (1H, dd, J=13.2, 4.8 Hz), 3.73 (1H, dd, J=13.2, 7.8 Hz), 3.47 (1H, dd, J=13.2, 4.2 Hz), 3.35 (1H, dd, J=12.6 5.4 Hz), 3.17 (2H, m), 3.17 (2H, m), 3.14 (2H, m); $^{13}$C NMR (150 MHz, CDCl$_3$) δ 148.8, 147.4, 135.1, 132.02, 131.97, 131.7, 130.1, 127.1, 124.4, 123.3, 120.4, 120.0, 67.9, 54.8, 54.4, 32.1, 31.7; LCMS m/z 321.1037 ([M+H$^+$], C$_{17}$H$_{17}$ClN$_4$O requires 329.1164).

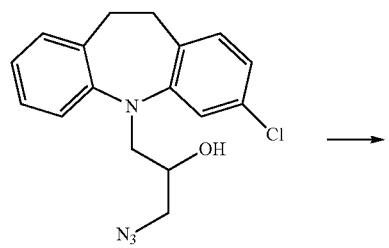

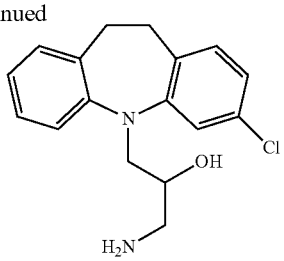

1-Amino-3-(3-chloro-10,11-dihydro-5H-dibenzo[b,f]azepin-5-yl)propan-2-ol. A solution of 1-azido-3-(3-chloro-10,11-dihydro-5H-dibenzo[b,f]azepin-5-yl)propan-2-ol (0.590 g, 2.06 mmol) in THF (5.0 mL) was cooled to 0° C., treated with PPh$_3$ (0.595 g, 0.227 mmol), 3 drops of H$_2$O, and stirred for 14 h at 25° C. The solution was concentrated to dryness, dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$:MeOH:NH$_4$OH to elute the product). The combined fractions of pure product were concentrated, dried azeotropically with toluene. The residue was dissolved in a minimal amount of ethyl ether and precipitated with the addition of hexanes to afford the title compound as a white solid (0.380 g, 61%). $^1$H NMR (600 MHz, CDCl$_3$) δ 7.17 (1H, t, J=7.8 Hz), 7.14 (1H, d, J=5.4 Hz), 7.11 (1H, d, J=4.8 Hz), 7.09 (2H, m), 6.99 (2H, m), 6.89 (1H, d, J=7.8 Hz), 3.19 (2H, q, J=6.0 Hz), 3.13 (4H, s), 2.85 (1H, br s), 2.64 (1H, br s), 1.94 (2H, br s); $^{13}$C NMR (150 MHz, CDCl$_3$) δ 149.1, 147.9, 135.1, 131.8, 131.5, 129.8, 126.9, 123.91, 123.90, 122.8, 120.6, 120.1, 68.8, 55.0, 45.5, 32.2, 31.7; LCMS m/z 303.1382 ([M+H$^+$], C$_{17}$H$_{19}$Cl$_2$NO requires 303.1259).

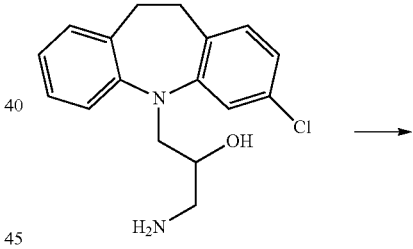

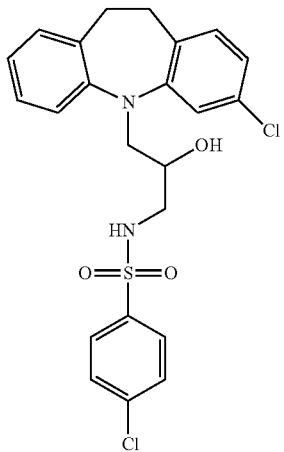

4-Chloro-N-(3-(3-chloro-10,11-dihydro-5H-dibenzo[b,f]azepin-5-yl)-2-hydroxypropyl)benzenesulfonamide. A solution of 1-amino-3-(3-chloro-10,11-dihydro-5H-dibenzo[b,f]azepin-5-yl)propan-2-ol (0.0732 g, 0.242 mmol) in DMF (1.0 mL) was cooled to 0° C. and treated sequentially with triethylamine (37.0 μL, 0.266 mmol) and 4-chlorobenzenesulfonyl chloride (0.0540 g, 0.254 mmol). The solution was warmed to 25° C. and stirred for 2 h. The mixture was poured over saturated aqueous NaCl (20 mL) and extracted with CH$_2$Cl$_2$ (3×50 mL). The combined organic layers were washed with saturated aqueous NaCl (3×50 mL), dried (Na$_2$SO$_4$), concentrated in vacuo, and the residue was purified by flash chromatography (SiO$_2$, 0-20% ethyl acetate-hexanes) to afford the title compound as a clear film (0.103 g, 89%). $^1$H NMR (600 MHz, CDCl$_3$) δ 7.71 (2H, d, J=8.4 Hz), 7.41 (2H, d, J=9.0 Hz), 7.15 (1H, t, J=7.8 Hz), 7.13 (1H, d, J=8.4 Hz), 7.02 (2H, m), 6.99 (2H, d, J=7.8 Hz), 6.92 (1H, dd, J=8.4, 1.8 Hz), 5.03 (1H, t, J=6.0 Hz), 3.82 (1H, br s), 3.76 (1H, dd, J=12.6, 4.8 Hz), 3.64 (1H, dd, J=13.2, 7.8 Hz), 3.22 (1H, m), 3.09 (4H, m), 2.95 (1H, quintet, J=6.0 Hz), 2.39 (1H, br s); $^{13}$C NMR (150 MHz, CDCl$_3$) δ 148.6, 147.3, 139.5, 138.3, 134.9, 132.1, 131.9, 131.8, 130.2, 129.7, 128.6, 127.2, 124.5, 123.5, 120.3, 119.9, 67.0, 54.3, 46.6, 32.1, 31.6; LCMS m/z 477.0708 ([M+H$^+$], C$_{23}$H$_{22}$Cl$_2$N$_2$O$_3$S requires 477.0801).

Example 58

Synthesis of 4-Trifluoromethoxy-N-(3-(3-chloro-10, 11-dihydro-5H-dibenzo[b,f]azepin-5-yl)-2-hydroxypropyl)benzenesulfonamide

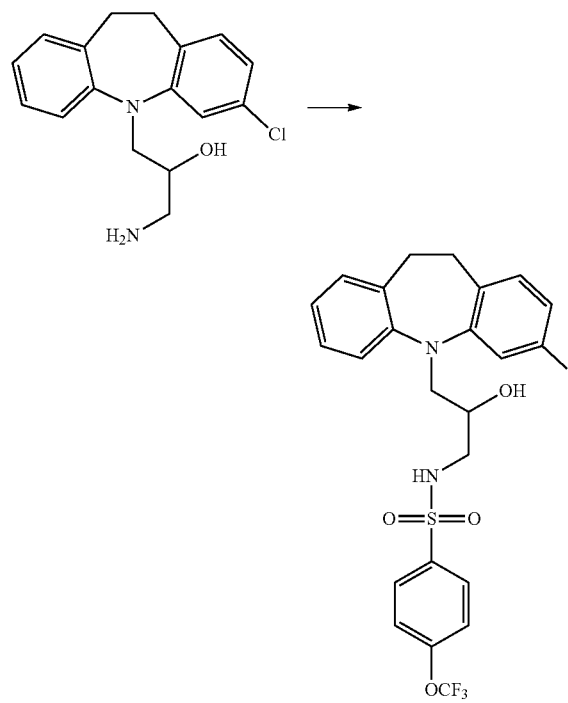

A solution of 1-amino-3-(3-chloro-10,11-dihydro-5H-dibenzo[b,f]azepin-5-yl)propan-2-ol (0.100 g, 0.330 mmol) in DMF (1.0 mL) was cooled to 0° C. and treated sequentially with triethylamine (45.0 μL, 0.330 mmol) and 4-trifluoromethoxybenzenesulfonyl chloride (0.0860 g, 0.330 mmol). The solution was warmed to 25° C. and stirred for 2 h. The mixture was poured over saturated aqueous NaCl (20 mL) and extracted with CH$_2$Cl$_2$ (3×50 mL). The combined organic layers were washed with saturated aqueous NaCl (3×50 mL), dried (Na$_2$SO$_4$), concentrated in vacuo, and the residue was purified by flash chromatography (SiO$_2$, 0-20% ethyl acetate-hexanes) to afford the title compound as a clear film (0.155 g, 89%). $^1$H NMR (600 MHz, CDCl$_3$) δ 7.95 (2H, d, J=7.2 Hz), 7.40 (2H, d, J=8.4 Hz), 7.28 (1H, t, J=7.2 Hz), 7.26 (1H, d, J=7.8 Hz), 7.13-7.17 (4H, m), 7.05 (1H, d, J=7.8 Hz), 5.21 (1H, br s), 3.97 (1H, br s), 3.91 (1H, dd, J=12.6, 3.6 Hz), 3.78 (1H, dd, J=12.6, 7.8 Hz), 3.36 (1H, m), 3.22 (4H, d, J=4.8 Hz), 3.09 (1H, quintet, J=6.6 Hz), 2.56 (1H, br s); $^{13}$C NMR (150 MHz, CDCl$_3$) δ 152.3, 148.6, 147.3, 141.2, 138.1, 134.9, 132.0, 131.9, 131.8, 130.2, 129.3, 127.2, 124.5, 123.5, 121.2, 120.3, 119.9, 67.0, 54.3, 46.6, 32.0, 31.6; LCMS m/z 527.1056 ([M+H$^+$], C$_{24}$H$_{22}$ClF$_3$N$_2$O$_4$S requires 527.1014).

Example 59

Synthesis of 4-Chloro-N-(3-(10,11-dihydro-5H-dibenzo[b,f]azepin-5-yl)-2-hydroxypropyl)benzenesulfonamide

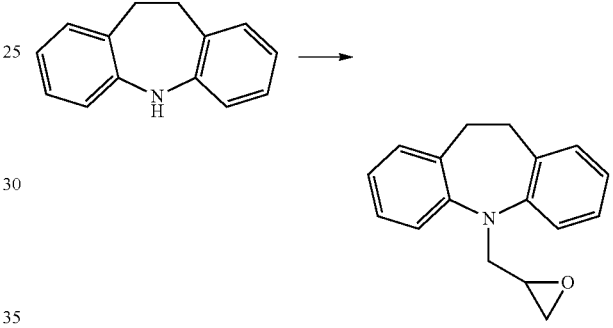

5-(Oxiran-2-ylmethyl)-10,11-dihydro-5H-dibenzo[b,f]azepine. A solution of 10,11-dihydro-5H-dibenzo[b,f]azepine (3.00 g, 15.4 mmol) in toluene (20.0 mL) was treated with a solution of sodium amide in toluene (50% by weight, 2.28 g, 29.2 mmol) and epichlorohydrin (2.41 mL, 30.7 mmol). The vial was sealed, heated to 80° C. for 6 h. The mixture was cooled to 25° C. treated with a solution of aqueous 1 M HCl (10.0 mL), and then filtered. The mixture was extracted with CH$_2$Cl$_2$ (3×100 mL), and the combined organic layers were washed with saturated aqueous NaCl (100 mL), dried (Na$_2$SO$_4$), concentrated in vacuo, and the residue was purified by flash chromatography (SiO$_2$, 0-5% ethyl acetate-hexanes) to afford the title compound as a white solid (1.00 g, 26%). $^1$H NMR (600 MHz, CDCl$_3$) δ 7.16-7.18 (2H, m), 7.14 (4H, br s), 6.98 (2H, t, J=7.2 Hz), 3.95 (2H, qd, J=10.8, 4.2 Hz), 3.20-3.28 (4H, m), 3.13 (1H, br s), 2.74 (1H, t, J=4.2 Hz), 2.61 (1H, t, J=2.4 Hz); $^{13}$C NMR (150 MHz, CDCl$_3$) δ 148.2, 134.6, 130.1, 126.7, 123.1, 120.5, 54.2, 51.1, 46.9, 32.5; LCMS m/z 252.1356 ([M+H$^+$], C$_{17}$H$_{17}$NO requires 252.1383).

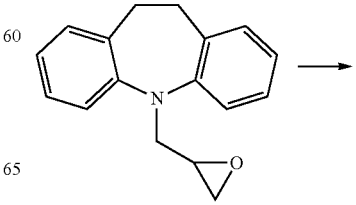

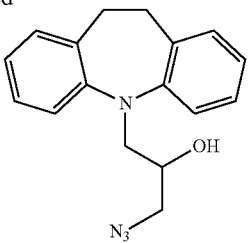

1-Azido-3-(10,11-dihydro-5H-dibenzo[b,f]azepin-5-yl)propan-2-ol. A solution of 5-(oxiran-2-ylmethyl)-10,11-dihydro-5H-dibenzo[b,f]azepine (1.00 g, 3.98 mmol) in 4:1 ethanol:H$_2$O (10.0 ml) was treated with sodium azide (0.192, 2.95 mmol), ammonium chloride (0.158 g, 2.95 mmol) and heated to 80° C. for 14 h. The mixture was cooled to 25° C., concentrated in vacuo, resuspended in EtOAc (100 mL). This organic layer was washed with saturated aqueous NaCl (3×50 mL), dried (Na$_2$SO$_4$), concentrated in vacuo, and the residue was purified by flash chromatography (SiO$_2$, 0-20% ethyl acetate-hexanes) to afford the title compound as a beige oil (0.7472 g, 64%). $^1$H NMR (600 MHz, CDCl$_3$) δ 7.17 (2H, t, J=7.8 Hz), 7.14 (2H, d, J=8.4 Hz), 7.11 (2H, d, J=8.4 Hz), 6.99 (2H, t, J=7.2 Hz), 3.98 (1H, m), 3.93 (1H, dd, J=13.2, 4.8 Hz), 3.75 (1H, dd, J=12.6, 7.8 Hz), 3.48 (1H, dd, J=12.6, 3.0 Hz), 3.34 (1H, dd, J=12.6, 5.4 Hz), 3.20 (4H, m), 2.38 (1H, d, J=3.0 Hz); $^{13}$C NMR (150 MHz, CDCl$_3$) δ 147.9, 134.4, 130.4, 126.9, 123.7, 119.9, 68.0, 54.8, 54.3, 32.3; LCMS m/z 295.1775 ([M+H$^+$], C$_{17}$H$_{18}$N$_4$O requires 295.1553).

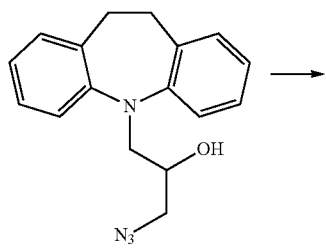

1-Amino-3-(10,11-dihydro-5H-dibenzo[b,f]azepin-5-yl)propan-2-ol. A solution of 1-azido-3-(10,11-dihydro-5H-dibenzo[b,f]azepin-5-yl)propan-2-ol (0.747 g, 2.54 mmol) in THF (5.0 mL) was cooled to 0° C., treated with PPh$_3$ (0.732 g, 2.79 mmol), 3 drops of H$_2$O, and stirred for 14 h at 25° C. The solution was concentrated to dryness, dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$: MeOH:NH$_4$OH to elute the product). The combined fractions of pure product were concentrated, dried azeotropically with toluene. The residue was dissolved in a minimal amount of ethyl ether and precipitated with the addition of hexanes to afford the title compound as a white solid (0.612 g, 90%). $^1$H NMR (600 MHz, CDCl$_3$) δ 7.10-7.16 (6H, m), 6.95 (2H, dt, J=7.2, 1.8 Hz), 3.76 (3H, m), 3.19 (4H, m), 2.89 (1H, dd, J=13.2, 3.0 Hz), 2.68 (1H, dd, J=12.6, 5.4 Hz), 1.80 (2H, br s); $^{13}$C NMR (150 MHz, CDCl$_3$) δ 148.3, 134.4, 130.2, 126.8, 123.3, 120.1, 69.1, 54.8, 45.5, 32.3; LCMS m/z 269.2340 ([M+H$^+$], C$_{17}$H$_{20}$N$_2$O requires 269.1648).

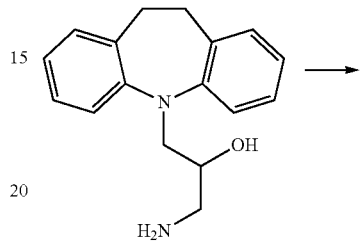

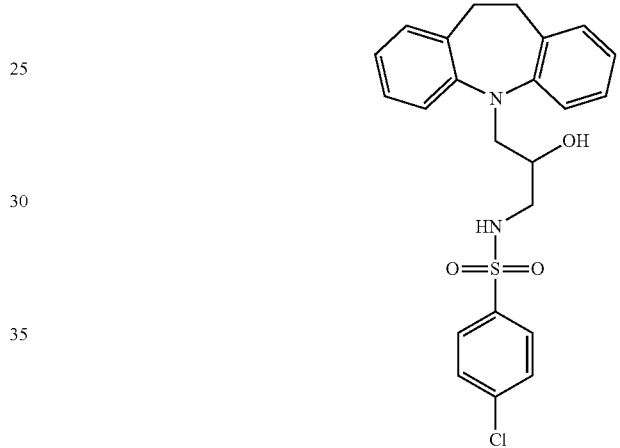

4-Chloro-N-(3-(10,11-dihydro-5H-dibenzo[b,f]azepin-5-yl)-2-hydroxypropyl)benzenesulfonamide. A solution of 1-amino-3-(10,11-dihydro-5H-dibenzo[b,f]azepin-5-yl)propan-2-ol (0.100 g, 0.373 mmol) in DMF (1.0 mL) was cooled to 0° C. and treated sequentially with triethylamine (52.0 µL, 0.373 mmol) and 4-chlorobenzenesulfonyl chloride (0.0780 g, 0.373 mmol). The solution was warmed to 25° C. and stirred for 2 h. The mixture was poured over saturated aqueous NaCl (20 mL) and extracted with CH$_2$Cl$_2$ (3×50 mL). The combined organic layers were washed with saturated aqueous NaCl (3×50 mL), dried (Na$_2$SO$_4$), concentrated in vacuo, and the residue was purified by flash chromatography (SiO$_2$, 0-20% ethyl acetate-hexanes) to afford the title compound as a clear film (0.148 g, 90%). $^1$H NMR (600 MHz, CDCl$_3$) δ 7.71 (2H, d, J=8.4 Hz), 7.41 (2H, d, J=7.8 Hz), 7.13 (2H, t, J=7.8 Hz), 7.12 (2H, d, J=6.6 Hz), 7.01 (2H, d, J=7.8 Hz), 6.98 (2H, d, J=7.2 Hz), 5.14 (1H, br s), 3.80 (1H, br s), 3.79 (1H, d, J=4.2 Hz), 3.67 (1H, dd, J=12.0, 7.2 Hz), 3.22 (1H, m), 3.12 (4H, m), 2.94 (1H, m); $^{13}$C NMR (150 MHz, CDCl$_3$) δ 147.8, 139.3, 138.4, 134.3, 130.4, 129.6, 128.6, 126.9, 123.7, 119.8, 67.0, 54.2, 46.7, 32.2; LCMS m/z 443.1492 ([M+H$^+$], C$_{23}$H$_{23}$ClN$_2$O$_3$S requires 443.1191).

Example 60

Synthesis of 4-Trifluoromethoxy-N-(3-(10,11-dihydro-5H-dibenzo[b,f]azepin-5-yl)-2-hydroxypropyl)benzenesulfonamide

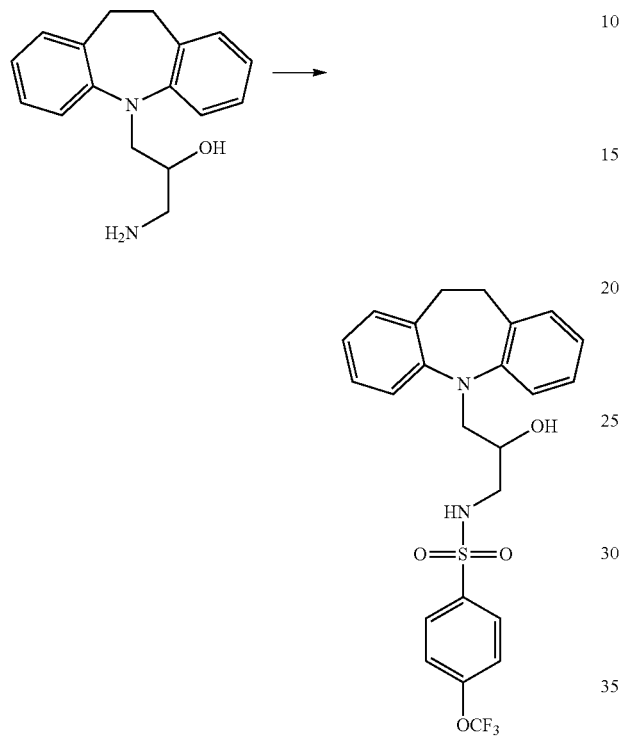

A solution of 1-amino-3-(10,11-dihydro-5H-dibenzo[b,f]azepin-5-yl)propan-2-ol (0.100 g, 0.373 mmol) in DMF (1.0 mL) was cooled to 0° C. and treated sequentially with triethylamine (52.0 µL, 0.373 mmol) and 4-trifluoromethoxybenzenesulfonyl chloride (0.0970 g, 0.373 mmol). The solution was warmed to 25° C. and stirred for 2 h. The mixture was poured over saturated aqueous NaCl (20 mL) and extracted with $CH_2Cl_2$ (3×50 mL). The combined organic layers were washed with saturated aqueous NaCl (3×50 mL), dried ($Na_2SO_4$), concentrated in vacuo, and the residue was purified by flash chromatography ($SiO_2$, 0-20% ethyl acetate-hexanes) to afford the title compound as a clear film (0.166 g, 91%). Mp. 102-103° C. (white needles, ether-hexanes); $^1$H NMR (600 MHz, $CDCl_3$) δ 7.95 (2H, d, J=8.4 Hz), 7.39 (2H, d, J=8.4 Hz), 7.25 (2H, t, J=7.8 Hz), 7.24 (2H, d, J=6.0 Hz), 7.16 (2H, d, J=7.8 Hz), 7.10 (2H, t, J=6.6 Hz), 5.22 (1H, br s), 3.98 (1H, br s), 3.96 (1H, d, J=4.8 Hz), 3.81 (1H, dd, J=12.0, 7.2 Hz), 3.36 (1H, m), 3.26 (4H, m), 3.10 (1H, q, J=7.2 Hz), 2.66 (1H, br s); $^{13}$C NMR (150 MHz, $CDCl_3$) δ 152.3, 150.6, 147.8, 138.2, 134.3, 130.4, 129.3, 127.0, 123.8, 121.2, 119.8, 67.0, 54.2, 46.6, 32.2; LCMS m/z 443.1492 ([M+H$^+$], $C_{23}H_{23}ClN_2O_3S$ requires 443.1191). Anal. Calcd for $C_{23}H_{23}ClN_2O_3S$: C, 58.53; H, 4.71; N, 5.69; S, 6.51. Found: C, 58.41; H, 4.87; N, 6.01; S, 7.01.

Example 61

Synthesis of 4,5-dichloro-N-(3-(3-chloro-10,11-dihydro-5H-dibenzo[b,f]azepin-5-yl)propyl)thiophene-2-sulfonamide

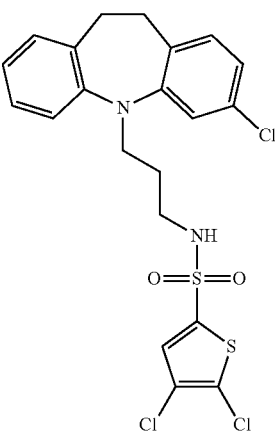

A solution of 3-(3-chloro-10,11-dihydro-5H-dibenzo[b,f]azepin-5-yl)propan-1-amine hydrochloride (0.0700 g, 0.216 mmol) in DMF (1.0 mL) was cooled to 0° C., treated with triethylamine (62 µL, 0.454 mmol), and 4,5-dichlorothiophene-2-sulfonyl chloride (0.0600 g, 0.238 mmol). The mixture was warmed to 25° C., and stirred for 2 h. The mixture was partitioned between saturated aqueous NaCl (50 mL), and $CH_2Cl_2$ (100 mL). The organic layer was washed with saturated aqueous NaCl (2×50 mL), dried ($Na_2SO_4$), and concentrated in vacuo. The residue was dissolved in a minimal amount of $CH_2Cl_2$ and purified by flash chromatography ($SiO_2$, 0-20% ethyl acetate-hexanes) to afford the title compound as a clear film (0.102 g, 94%). $^1$H NMR (600 MHz, $CDCl_3$) δ 7.28 (1H, m), 7.19 (1H, t, J=7.8 Hz), 7.16 (1H, d, J=7.8 Hz), 7.04 (4H, m), 6.92 (1H, d, J=8.4 Hz), 4.88 (1H, t, J=5.4 Hz), 3.77 (2H, t, J=6.0 Hz), 3.12 (6H, br s), 1.84 (2H, quintet, J=6.0 Hz); $^{13}$C NMR (150 MHz, $CDCl_3$) δ 148.8, 147.4, 137.4, 135.1, 131.9, 131.8, 131.6, 131.5, 131.1, 130.0, 126.9, 124.9, 124.0, 122.9, 120.3, 119.7, 47.5, 41.6, 32.1, 31.5, 27.4; LCMS m/z 503.0177 ([M+H$^+$], $C_{21}H_{19}Cl_3N_2O_2S_2$ requires 502.9997).

Example 62

Synthesis of 2,5-dichloro-N-(3-(3-chloro-10,11-dihydro-5H-dibenzo[b,f]azepin-5-yl)propyl)thiophene-3-sulfonamide

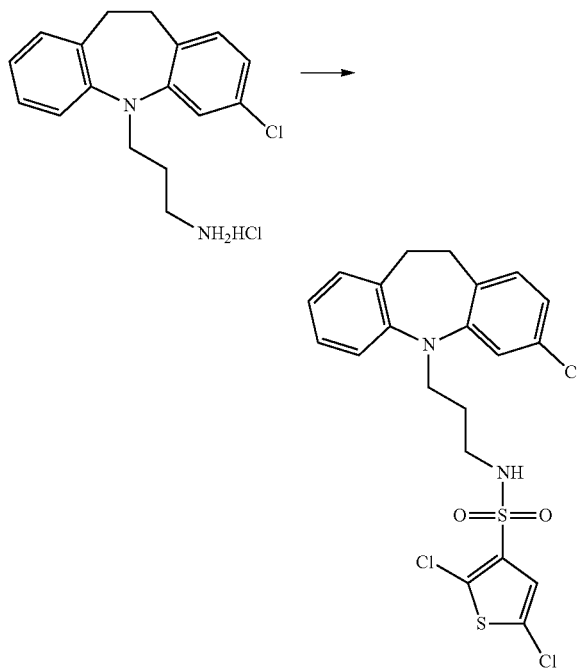

A solution of 3-(3-chloro-10,11-dihydro-5H-dibenzo[b,f]azepin-5-yl)propan-1-amine hydrochloride (0.0700 g, 0.216 mmol) in DMF (1.0 mL) was cooled to 0° C., treated with triethylamine (62 μL, 0.454 mmol), and 2,5-dichlorothiophene-3-sulfonyl chloride (0.0600 g, 0.238 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a clear film (0.101 g, 93%). $^1$H NMR (600 MHz, CDCl$_3$) δ 7.15 (1H, t, J=7.2 Hz), 7.12 (1H, d, J=8.4 Hz), 7.03 (1H, m), 7.00 (3H, m), 6.89 (1H, dd, J=8.4, 1.2 Hz), 5.00 (1H, t, J=5.4 Hz), 3.72 (2H, t, J=6.6 Hz), 3.06 (6H, br m), 1.78 (2H, quintet, J=6.6 Hz); $^{13}$C NMR (150 MHz, CDCl$_3$) δ 148.8, 147.4, 136.3, 135.2, 131.8, 131.7, 131.6, 129.9, 129.5, 127.6, 126.9, 126.8, 123.9, 122.7, 120.3, 119.7, 47.4, 41.2, 32.1, 31.5, 27.5; LCMS m/z 503.0176 ([M+H$^+$], C$_{21}$H$_{19}$Cl$_3$N$_2$O$_2$S$_2$ requires 502.9997).

Example 63

Synthesis of 5-Bromo-6-chloro-N-(3-(3-chloro-10,11-dihydro-5H-dibenzo[b,f]azepin-5-yl)propyl)pyridine-3-sulfonamide

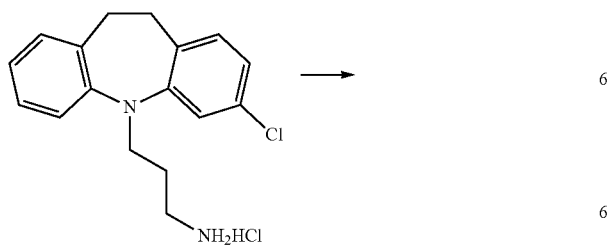

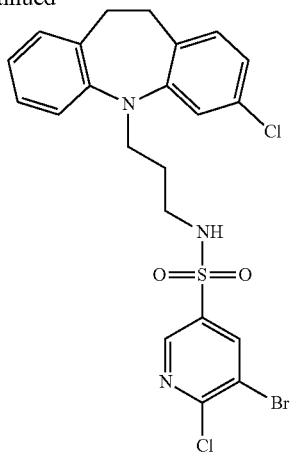

A solution of 3-(3-chloro-10,11-dihydro-5H-dibenzo[b,f]azepin-5-yl)propan-1-amine hydrochloride (0.0700 g, 0.216 mmol) in DMF (1.0 mL) was cooled to 0° C., treated with triethylamine (62 μL, 0.454 mmol), and 5-bromo-6-chloropyridine-3-sulfonyl chloride (0.0690 g, 0.238 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes). The purified fractions were combined, concentrated, and the residue dissolved in minimal amount of ethyl ether and precipitated by the addition of hexanes to afford the title compound as a white solid (0.103 g, 88%). $^1$H NMR (600 MHz, CDCl$_3$) δ 8.65 (1H, br s), 8.23 (1H, br s), 7.14 (1H, t, J=7.8 Hz), 7.11 (1H, t, J=7.8 Hz), 6.99 (4H, m), 6.89 (1H, dd, J=7.8, 1.8 Hz), 4.93 (1H, t, J=6.0 Hz), 3.70 (2H, t, J=5.4 Hz), 3.06 (6H, br s), 1.78 (2H, quintet, J=6.6 Hz); $^{13}$C NMR (150 MHz, CDCl$_3$) δ 155.0, 148.6, 147.3, 146.1, 140.5, 140.4, 136.5, 135.0, 131.9, 131.7, 130.0, 127.0, 124.1, 122.9, 121.1, 120.3, 119.7, 47.3, 41.3, 31.2, 31.5, 27.6; LCMS m/z 542.0093 ([M+H$^+$], C$_{22}$H$_{20}$BrCl$_2$N$_3$O$_2$S requires 541.9880).

Example 64

Synthesis of N-(3-(10,11-dihydro-5H-dibenzo[b,f]azepin-5-yl)-2-oxopropyl)-4-(trifluoromethoxy)benzenesulfonamide

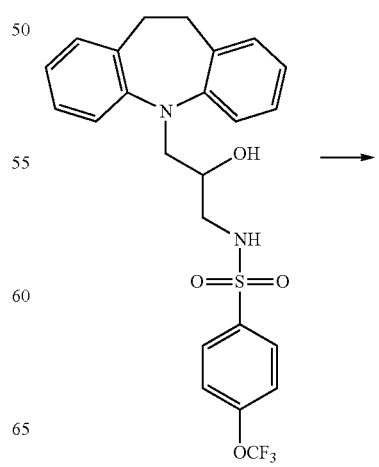

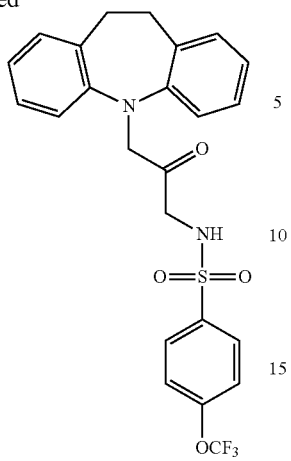

A solution of N-(3-(10,11-dihydro-5H-dibenzo[b,f]azepin-5-yl)-2-hydroxypropyl)-4-(trifluoromethoxy)benzenesulfonamide (0.133 g, 0.579 mmol) in DMSO (procedure from JACS 2011, 133, 1428-1437) (2.0 mL) was treated with triethylamine (0.480 mL, 3.47 mmol) and stirred for 0.5 h at 25° C. The mixture was then treated with sulfur trioxide pyridine complex (0.189 g, 1.19 mmol) and stirred for an additional 14 h. The mixture was partitioned between saturated aqueous NaCl (50 mL), and ethyl acetate (100 mL). The organic layer was washed with $H_2O$ (2×50 mL), saturated aqueous NaCl (2×50 mL), dried ($Na_2SO_4$), and concentrated in vacuo. The residue was dissolved in a minimal amount of $CH_2Cl_2$ and purified by flash chromatography ($SiO_2$, 0-20% ethyl acetate-hexanes) to afford the title compound as a yellow film (0.068 g, 24%). $^1$H NMR (600 MHz, $CDCl_3$) δ 7.58 (2H, t, J=8.4 Hz), 7.12 (2H, d, J=8.4 Hz), 7.04 (2H, d, J=7.2 Hz), 6.96 (2H, t, J=7.8 Hz), 6.86 (2H, t, J=7.2 Hz), 6.74 (2H, d, J=7.8 Hz), 5.19 (1H, br s), 4.40 (2H, s), 3.90 (2H, d, J=4.2 Hz), 3.12 (4H, s), 2.94 (4H, s), 2.77 (1H, dd, J=16.2, 3.0 Hz), 2.67 (1H, dd, J=16.8, 6.6 Hz); $^{13}$C NMR (150 MHz, $CDCl_3$) δ 202.4, 152.2, 147.2, 137.5, 134.0, 130.7, 129.3, 128.3, 127.2, 124.0, 121.0, 118.7, 60.5, 50.4, 32.3; LCMS m/z 491.1578 ([M+H$^+$], $C_{24}H_{21}F_3N_2O_4S$ requires 491.1247).

Example 65

Synthesis of N-(2-cyano-3-(10,11-dihydro-5H-dibenzo[b,f]azepin-5-yl)propyl)-4-(trifluoromethoxy)benzenesulfonamide

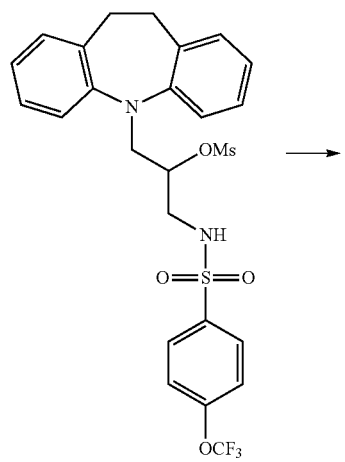

A solution of 1-(10,11-dihydro-5H-dibenzo[b,f]azepin-5-yl)-3-(4-(trifluoromethoxy)phenylsulfonamido)propan-2-yl methanesulfonate (0.0837 g, 0.147 mmol) in DMF (1.0 mL) was treated with pulverized sodium cyanide (0.0220 g, 0.440 mmol) and stirred for 14 h at 25° C. The mixture was partitioned between saturated aqueous NaCl (50 mL), and $CH_2Cl_2$ (100 mL). The organic layer was washed with saturated aqueous NaCl (2×50 mL), dried ($Na_2SO_4$), and concentrated in vacuo. The residue was dissolved in a minimal amount of $CH_2Cl_2$ and purified by flash chromatography ($SiO_2$, 0-20% ethyl acetate-hexanes) to afford the title compound as a clear film (0.0470 g, 64%). $^1$H NMR (600 MHz, $CDCl_3$) δ 7.64 (2H, t, J=9.0 Hz), 7.11 (2H, t, J=8.4 Hz), 6.99 (2H, t, J=7.8 Hz), 6.94 (2H, t, J=8.4 Hz), 6.86 (2H, t, J=7.2 Hz), 6.82 (2H, d, J=8.4 Hz), 5.17 (1H, t, J=4.2 Hz), 3.92 (1H, dd, J=13.2, 6.0 Hz), 3.65 (1H, t, J=8.4 Hz), 3.57 (1H, br s), 2.94 (4H, s), 2.77 (1H, dd, J=16.2, 3.0 Hz), 2.67 (1H, dd, J=16.8, 6.6 Hz); $^{13}$C NMR (150 MHz, $CDCl_3$) δ 152.5, 146.8, 139.6, 137.4, 134.0, 130.6, 129.3, 127.1, 124.2, 121.0, 119.2, 116.6, 53.1, 48.0, 32.1; LCMS m/z 502.1705 ([M+H$^+$], $C_{25}H_{22}F_3N_3O_3S$ requires 502.1407).

Example 66

Synthesis of N-(3-(10,11-dihydro-5H-dibenzo[b,f]azepin-5-yl)propyl)pyridine-3-sulfonamide

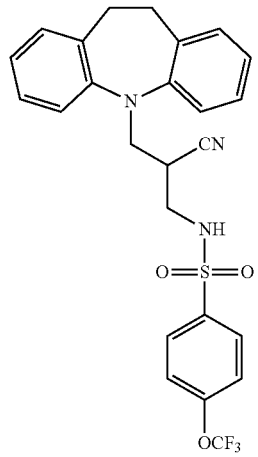

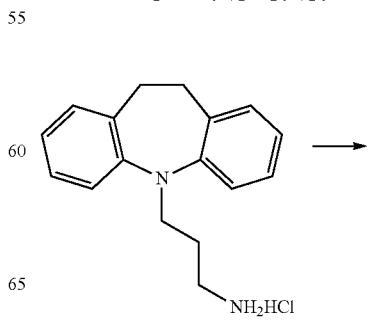

-continued

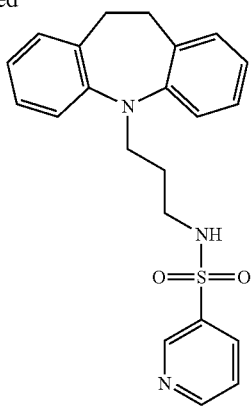

A solution of 3-(10,11-dihydro-5H-dibenzo[b,f]azepin-5-yl)propan-1-amine hydrochloride (0.100 g, 0.346 mmol) in DMF (1.0 mL) was cooled to 0° C., treated with triethylamine (150 μL, 1.07 mmol), and pyridine-3-sulfonyl chloride hydrochloride (0.0820 g, 0.381 mmol). The mixture was warmed to 25° C., and stirred for 2 h. The mixture was partitioned between saturated aqueous NaCl (20 mL), and CH$_2$Cl$_2$ (20 mL). The organic layer was washed with a H$_2$O (2×20 mL), saturated aqueous NaCl (20 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes). The purified fractions were concentrated in vacuo, the residue was suspended in a minimal amount of ethyl ether and then precipitated with the addition of hexanes to afford the title compound as a white solid (0.0939 g, 69%). $^1$H NMR (600 MHz, CDCl$_3$) δ 8.98 (1H, s), 8.74 (1H, d, J=3.0 Hz), 7.96 (1H, d, J=7.8 Hz), 7.33 (1H, q, J=4.8 Hz), 7.12 (2H, t, J=6.6 Hz), 7.09 (2H, d, J=7.8 Hz), 6.99 (2H, d, J=7.8 Hz), 6.94 (2H, d, J=7.2 Hz), 4.84 (1H, br s), 3.73 (2H, t, J=5.4 Hz), 3.08 (4H, s), 3.05 (2H, m), 1.76 (2H, quintet, J=6.0 Hz); $^{13}$C NMR (150 MHz, CDCl$_3$) δ 153.3, 148.2, 147.9, 136.8, 134.8, 134.4, 130.3, 126.8, 123.9, 123.2, 119.8, 47.4, 41.5, 32.2, 27.7; LCMS m/z 394.2885 ([M+H$^+$], C$_{22}$H$_{23}$N$_3$O$_2$S requires 394.1584).

Example 67

Synthesis of N-(3-(10,11-dihydro-5H-dibenzo[b,f]azepin-5-yl)-2-methylpropyl)-4-(trifluoromethoxy)benzenesulfonamide

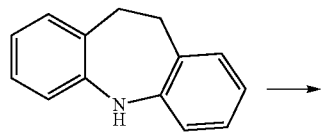

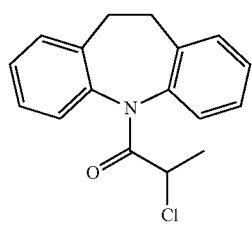

2-Chloro-1-(10,11-dihydro-5H-dibenzo[b,f]azepin-5-yl)propan-1-one. A solution of 10,11-dihydro-5H-dibenzo[b,f]azepine (2.00 g, 10.24 mmol) in toluene (10.0 mL) was treated with chloroacetyl chloride (1.04 mL, 10.75 mmol) and heated to 100° C. for 1 h. The mixture was cooled to 25° C., concentrated under N$_2$ stream, taken up in a minimal amount of toluene and purified by flash chromatography (SiO$_2$, 5-20% ethyl acetate-hexanes) to afford the title compound as beige oil (1.60 g, 55%). $^1$H NMR (600 MHz, CDCl$_3$) δ (mixture of rotamers) 7.52 (1H, d, J=7.2 Hz), 7.40 (1H, d, J=7.2 Hz), 7.25-7.30 (2H, comp), 7.16-7.24 (3H, comp), 7.12-7.14 (1H, m), [1H, 4.67 (q, J=6.6 Hz), 4.40 (q, J=6.6 Hz)], [1H, 3.55-3.63 (m), 3.41-3.50 (m)], 3.25-3.33 (1H, m), 2.78-2.90 (2H, m), [3H, 1.71 (d, J=6.6 Hz), 1.59 (d, J=6.0 Hz)]; LCMS m/z 286.2355 ([M+H$^+$], C$_{17}$H$_{16}$ClNO requires 286.0993).

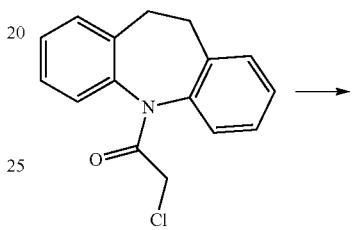

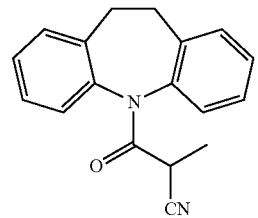

3-(10,11-dihydro-5H-dibenzo[b,f]azepin-5-yl)-2-methyl-3-oxopropanenitrile. A solution of 2-chloro-1-(10,11-dihydro-5H-dibenzo[b,f]azepin-5-yl)propan-1-one (g, 6.72 mmol) (ref) in DMF (5.0 mL) was cooled to 0° C. and treated with sodium cyanide (0.411 g, 8.40 mmol). The mixture was warmed to 25° C. and stirred for 14 h. The solution was diluted with CH$_2$Cl$_2$ (200 mL) and the organic layer was washed with H$_2$O (2×100 mL), saturated aqueous NaCl (100 mL), dried (Na$_2$SO$_4$), and concentrated in vacuo. The residue was taken up in a minimal amount of CH$_2$Cl$_2$ and purified by flash chromatography (SiO$_2$, 10-30% ethyl acetate-hexanes) to afford the title compound as a beige oil (1.45 g, 94%). $^1$H NMR (600 MHz, CDCl$_3$) δ (as a mixture of rotamers) 7.46 (1H, d, J=7.2 Hz), 7.39 (1H, d, J=7.8 Hz), 7.28-7.36 (2H, m), 7.25 (1H, m), 7.18-7.23 (2H, m), 7.14 (1H, d, J=7.2 Hz), [1H, 3.81 (q, J=6.6 Hz), 3.38-3.44 (m)], 3.55-3.60 (1H, m), 3.26-3.36 (1H, m), 2.81-2.94 (2H, m), [3H, 1.58 (d, J=7.2 Hz), 1.46 (d, J=6.6 Hz); LCMS m/z 277.2268 ([M+H$^+$], C$_{18}$H$_{16}$N$_2$O requires 277.1335).

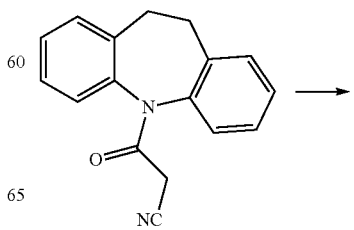

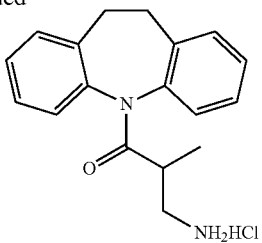

3-(10,11-dihydro-5H-dibenzo[b,f]azepin-5-yl)-2-methylpropan-1-amine hydrochloride. A solution of 3-(10,11-dihydro-5H-dibenzo[b,f]azepin-5-yl)-2-methyl-3-oxopropanenitrile (1.45 g, 5.26 mmol) in THF (10.0 mL) was cooled to 0° C. and treated with a BH$_3$-THF (1 M solution in THF, 21.0 mL, 21.0 mmol). The flask was sealed, heated to 70° C. for 5 h, and then cooled to 0° C. The solution was treated slowly, dropwise with a solution of aqueous 1 M HCl (42 mL), stirred for an additional 0.5 h, and then heated to 70° C. for 1 h. The mixture was cooled to 25° C., treated with aqueous 4 M NaOH until pH>8, and then the mixture was extracted with ethyl acetate (3×200 mL). The combined extracts were washed with saturated aqueous NaCl (100 mL), dried (Na$_2$SO$_4$), and concentrated in vacuo. The residue was dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$:MeOH:NH$_4$OH to elute the product). The combined fractions of pure product were concentrated, dried azeotropically with toluene, and then suspended in Et$_2$O (100 mL) and treated dropwise with a 4 N HCl-dioxane solution (1.32 mL). The white solid that had precipitated was collected by filtration to afford the title compound (1.52 g, 96%). $^1$H NMR (600 MHz, CD$_3$OD) δ 7.13 (4H, m), 7.09 (2H, d, J=7.2 Hz), 6.91-6.93 (2H, m), 3.68-3.71 (1H, m), 3.61-3.64 (1H, m), 3.15 (4H, s), 3.13 (1H, m), 2.73 (1H, t, J=12.0 Hz), 2.16 (1H, br s), 1.06 (3H, d, J=6.6 Hz); $^{13}$C NMR (150 MHz, CD$_3$OD) δ 148.7, 134.5, 130.2, 126.8, 123.2, 119.9, 54.6, 43.9, 32.3, 30.4, 15.0; LCMS m/z 267.2566 ([M+H$^+$], C$_{18}$H$_{22}$N$_2$ requires 267.1856).

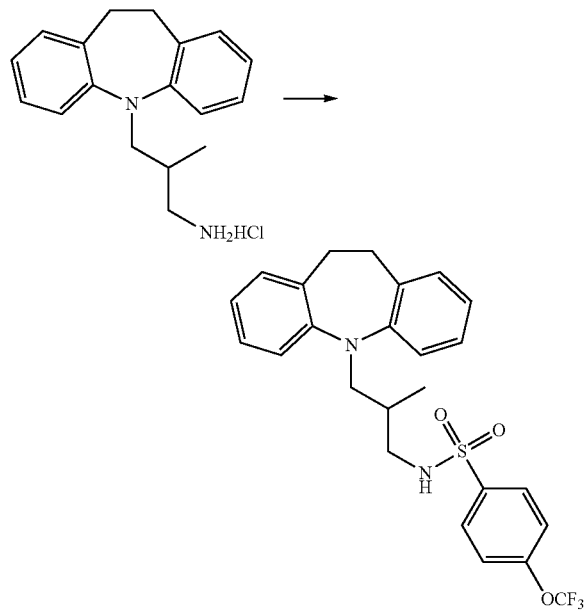

N-(3-(10,11-dihydro-5H-dibenzo[b,f]azepin-5-yl)-2-methylpropyl)-4-(trifluoromethoxy)benzenesulfonamide. A solution of 3-(10,11-dihydro-5H-dibenzo[b,f]azepin-5-yl)-2-methylpropan-1-amine hydrochloride (0.100 g, 0.330 mmol) in DMF (1.0 mL) was cooled to 0° C., treated with triethylamine (96.1 μL, 0.693 mmol), and 4-trifluoromethoxybenzenesulfonyl chloride (61.4 μL, 0.363 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a clear film (0.0948 g, 59%). $^1$H NMR (600 MHz, CDCl$_3$) δ 7.74 (2H, d, J=9.0 Hz), 7.24 (2H, d, J=8.4 Hz), 7.10-7.13 (4H, m), 6.99 (2H, d, J=7.8 Hz), 6.95 (2H, d, J=7.2 Hz), 4.94 (1H, t, J=6.6 Hz), 3.66 (1H, dd, J=13.2, 6.0 Hz), 3.40 (1H, dd, J=13.2, 8.4 Hz), 3.10 (4H, s), 3.07 (1H, q, J=5.4 Hz), 2.85 (1H, quintet, J=6.6 Hz), 1.94 (1H, sextet, J=6.0 Hz), 0.93 (3H, d, J=6.6 Hz); $^{13}$C NMR (150 MHz, CDCl$_3$) δ 152.11, 152.10, 148.2, 138.5, 134.2, 130.3, 129.3, 126.7, 123.2, 121.1, 119.7, 54.8, 47.8, 32.1, 31.1, 25.5; LCMS m/z 491.2506 ([M+H$^+$], C$_{25}$H$_{25}$F$_3$N$_2$O$_3$S requires 491.1611).

Example 68

Synthesis of 4-Chloro-N-(3-(10,11-dihydro-5H-dibenzo[b,f]azepin-5-yl)-2-methylpropyl)benzenesulfonamide

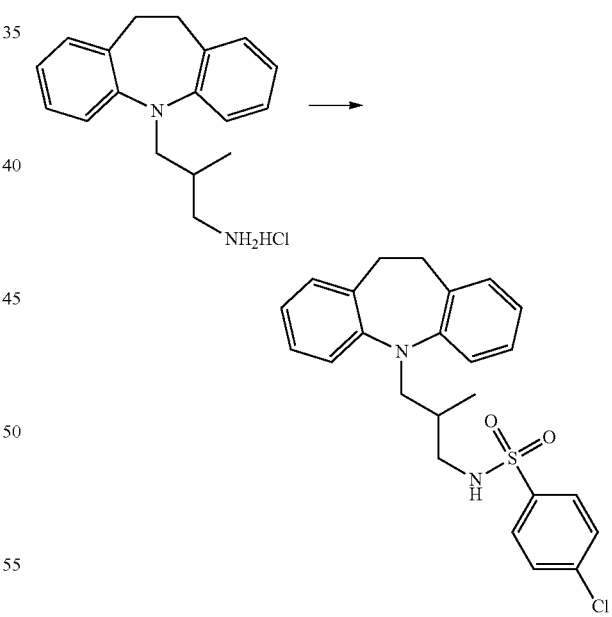

A solution of 3-(10,11-dihydro-5H-dibenzo[b,f]azepin-5-yl)-2-methylpropan-1-amine hydrochloride (0.100 g, 0.330 mmol) in DMF (1.0 mL) was cooled to 0° C., treated with triethylamine (96.1 μL, 0.693 mmol), and 4-chlorobenzenesulfonyl chloride (0.0945 g, 0.363 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of $CH_2Cl_2$ and purified by flash chromatography ($SiO_2$, 0-20% ethyl acetate-hexanes) to afford the title compound as a white foam (0.089 g, 61%). $^1$H NMR (600 MHz, $CDCl_3$) δ 7.62 (2H, d, J=8.4 Hz), 7.37 (2H, d, J=8.4 Hz), 7.10-7.13 (4H, m), 6.98 (2H, d, J=8.4 Hz), 6.96 (2H, d, J=7.2 Hz), 4.77 (1H, t, J=6.0 Hz), 3.65 (1H, dd, J=12.6, 5.4 Hz), 3.38 (1H, dd, J=12.6, 8.4 Hz), 3.09 (4H, m), 3.03 (1H, q, J=6.0 Hz), 2.84 (1H, quintet, J=6.6 Hz), 1.92 (1H, sextet, J=6.0 Hz), 0.92 (3H, d, J=7.2 Hz); $^{13}$C NMR (150 MHz, $CDCl_3$) δ 148.2, 139.2, 138.6, 134.3, 130.4, 129.5, 128.6, 126.8, 123.2, 119.7, 54.8, 47.7, 32.1, 31.0, 16.4; LCMS m/z 441.1575 ([M+H$^+$], $C_{24}H_{25}ClN_2O_2S$ requires 441.1398).

Example 69

Synthesis of N-(3-(4-chloro-10,11-dihydro-5H-dibenzo[b,f]azepin-5-yl)propyl)-4-(trifluoromethoxy)benzenesulfonamide

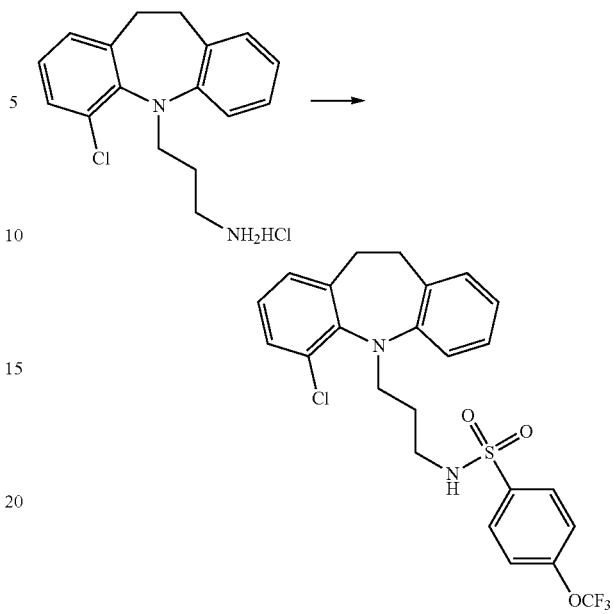

3-(4-chloro-5H-dibenzo[b,f]azepin-5-yl)-3-oxopropanenitrile. A solution of 2-chloro-1-(4-chloro-5H-dibenzo[b,f]azepin-5-yl)ethanone (1.18 g, 3.85 mmol) in DMF (5.0 mL) was cooled to 0° C. and treated with sodium cyanide (0.207 g, 4.23 mmol). The mixture was warmed to 25° C. and stirred for 14 h. The solution was diluted with $CH_2Cl_2$ (200 mL) and the organic layer was washed with $H_2O$ (2×100 mL), saturated aqueous NaCl (100 mL), dried ($Na_2SO_4$), and concentrated in vacuo. The residue was taken up in a minimal amount of $CH_2Cl_2$ and purified by flash chromatography ($SiO_2$, 10-30% ethyl acetate-hexanes) to afford the title compound as a white solid (0.928 g, 82%). $^1$H NMR (600 MHz, $CDCl_3$) δ (as a mixture of rotamers) [2H, 3.45 (s), 3.34 (t, J=18.6 Hz), 3.00 (dd, J=27.0, 18.6, Hz)]; LCMS m/z 295.1097 ([M+H$^+$], $C_{17}H_{11}ClN_2O$ requires 295.0633).

N-(3-(4-chloro-10,11-dihydro-5H-dibenzo[b,f]azepin-5-yl)propyl)-4-(trifluoromethoxy)benzenesulfonamide. A solution of 3-(4-chloro-10,11-dihydro-5H-dibenzo[b,f]azepin-5-yl)propan-1-amine hydrochloride (0.085 g, 0.263 mmol) in DMF (1.0 mL) was cooled to 0° C., treated with triethylamine (76.6 µL, 0.552 mmol), and 4-trifluoromethoxybenzenesulfonyl chloride (0.0752 g, 0.289 mmol). The mixture was warmed to 25° C., and stirred for 2 h. The mixture was partitioned between saturated aqueous NaCl (50 mL), and $CH_2Cl_2$ (100 mL). The organic layer was washed with saturated aqueous NaCl (2×50 mL), dried ($Na_2SO_4$), and concentrated in vacuo. The residue was dissolved in a minimal amount of $CH_2Cl_2$ and purified by flash chromatography ($SiO_2$, 0-20% ethyl acetate-hexanes) to afford the title compound as a clear film (0.0346 g, 26%). $^1$H NMR (600 MHz, $CDCl_3$) δ 7.82 (2H, d, J=8.4 Hz), 7.28 (2H, d, J=8.4 Hz), 7.18 (1H, d, J=7.8 Hz), 7.13 (1H, t, J=8.4 Hz), 7.09 (1H, t, J=6.0 Hz), 7.06 (1H, d, J=5.4 Hz), 7.03 (1H, t, J=7.2 Hz), 6.98 (1H, d, J=7.8 Hz), 6.86 (1H, t, J=6.0 Hz), 4.53 (1H, t, J=6.0 Hz), 3.97-4.02 (1H, m), 3.61-3.65 (1H, m), 3.47 (1H, td, J=13.8, 3.6 Hz), 3.19 (1H, dt, J=17.4, 3.6 Hz), 3.00 (2H, app. q, J=6.6 Hz), 2.80-2.86 (1H, m), 2.65 (1H, dt, J=9.0, 4.2 Hz), 1.63-1.71 (2H, m); $^{13}$C NMR (150 MHz, $CDCl_3$) δ 152.3, 145.1, 144.8, 143.5, 138.5, 132.1, 131.7, 130.9, 130.5, 129.4, 128.7, 128.1, 126.72, 126.66, 122.0, 121.3, 121.2, 50.0, 41.6, 33.7, 31.5, 29.1; LCMS m/z 511.1387 ([M+H$^+$], $C_{24}H_{22}ClF_3N_2O_3S$ requires 511.1065).

Example 70

Synthesis of 4-Chloro-N-(3-(4-chloro-10,11-dihydro-5H-dibenzo[b,f]azepin-5-yl)propyl)benzenesulfonamide

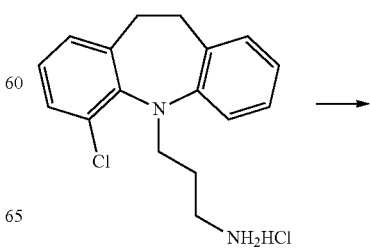

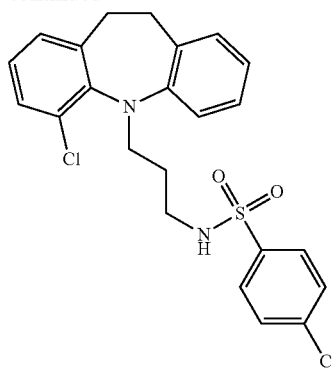

A solution of 3-(4-chloro-10,11-dihydro-5H-dibenzo[b,f]azepin-5-yl)propan-1-amine hydrochloride (0.085 g, 0.263 mmol) in DMF (1.0 mL) was cooled to 0° C., treated with triethylamine (76.6 µL, 0.552 mmol), and 4-chlorobenzenesulfonyl chloride (0.0610 g, 0.289 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a clear film (0.0354 g, 29%). $^1$H NMR (600 MHz, CDCl$_3$) δ 7.71 (2H, d, J=7.8 Hz), 7.41 (2H, d, J=7.8 Hz), 7.18 (1H, d, J=7.8 Hz), 7.10-7.13 (2H, m), 7.08 (1H, d, J=7.2 Hz), 7.03 (1H, t, J=7.2 Hz), 6.98 (1H, d, J=7.8 Hz), 6.84 (1H, t, J=7.2 Hz), 4.64 (1H, t, J=6.0 Hz), 3.96 (1H, quintet, J=6.6 Hz 3.60 (1H, quintet, J=6.6 Hz), 3.45 (1H, td, J=13.2, 3.0 Hz), 3.19 (1H, d, J=16.8 Hz), 2.98 (2H, app. q, J=6.6 Hz), 2.81 (1H, t, J=13.8 Hz), 2.67 (1H, dt, J=13.2, 3.6 Hz), 1.59-1.68 (2H, m); $^{13}$C NMR (150 MHz, CDCl$_3$) δ 145.1, 144.8, 143.5, 139.3, 138.6, 132.1, 131.6, 130.4 129.62, 129.57, 128.8, 128.6, 126.7, 126.6, 122.0, 121.3, 49.9, 41.5, 33.7, 31.4, 29.0; LCMS m/z 461.1034 ([M+H$^+$], C$_{23}$H$_{22}$Cl$_2$N$_2$O$_2$S requires 461.0852).

Example 71

Synthesis of N-(3-(10,11-dihydro-5H-dibenzo[a,d][7]annulen-5-ylidene)propyl)-4-cyanobenzenesulfonamide

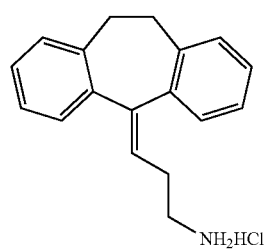

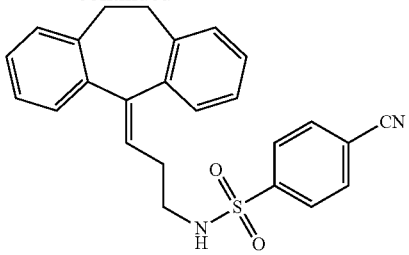

A solution of 3-(10,11-dihydro-5H-dibenzo[a,d][7]annulen-5-ylidene)propan-1-amine hydrochloride (0.080 g, 0.280 mmol) in DMF (1.0 mL) was cooled to 0° C., treated with triethylamine (81.4 µL, 0.587 mmol), and 4-cyanobenzenesulfonyl chloride (0.0612 g, 0.308 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a white foam (0.0694 g, 60%). $^1$H NMR (600 MHz, CDCl$_3$) δ 7.85 (2H, d, J=7.8 Hz), 7.67 (2H, d, J=7.8 Hz), 7.20-7.26 (2H, m), 7.18-7.20 (2H, m), 7.13-7.16 (2H, m), 7.07 (1H, d, J=7.2 Hz), 7.00 (1H, t, J=7.2 Hz), 5.63 (1H, t, J=7.2 Hz), 4.47 (1H, t, J=6.0 Hz), 3.29 (2H, br s), 3.04-3.18 (2H, m), 2.92-3.03 (1H, m), 2.75-2.84 (1H, m), 2.21-2.36 (2H, m); $^{13}$C NMR (150 MHz, CDCl$_3$) δ 146.6, 144.5, 140.6, 139.39, 139.36, 137.1, 133.1, 130.4, 128.6, 128.3, 128.1, 127.8, 127.74, 127.73, 126.4, 126.2, 117.5, 116.5, 43.3, 33.9, 32.3, 29.9; LCMS m/z 415.1632 ([M+H$^+$], C$_{25}$H$_{22}$N$_2$O$_2$S requires 415.1475).

Example 72

Synthesis of N-(3-(10,11-dihydro-5H-dibenzo[a,d][7]annulen-5-ylidene)propyl)-4-fluorobenzenesulfonamide

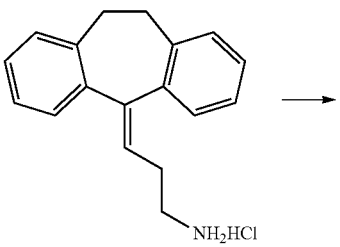

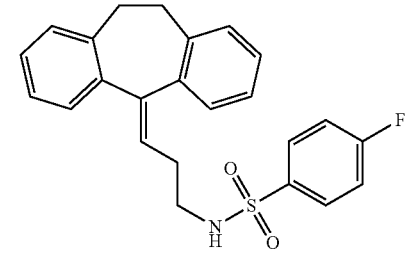

A solution of 3-(10,11-dihydro-5H-dibenzo[a,d][7]annulen-5-ylidene)propan-1-amine hydrochloride (0.080 g, 0.280 mmol) in DMF (1.0 mL) was cooled to 0° C., treated with triethylamine (81.4 µL, 0.587 mmol), and 4-fluorobenzenesulfonyl chloride (0.0600 g, 0.308 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound as a white solid (0.105 g, 92%). $^1$H NMR (600 MHz, CDCl$_3$) δ 7.79-7.82 (2H, m), 7.18-7.23 (3H, m), 7.12-7.17 (3H, m), 7.07-7.10 (2H, m), 7.05 (1H, t, J=7.2 Hz), 7.03 (1H, d, J=7.2 Hz), 5.70 (1H, t, J=7.2 Hz), 4.73 (1H, t, J=6.0 Hz), 3.25-3.39 (2H, m), 3.01-3.11 (2H, m), 2.92-3.01 (1H, m), 2.79 (1H, br s), 2.22-2.36 (2H, br s); $^{13}$C NMR (150 MHz, CDCl$_3$) δ 165.1 (d, J=253.5 Hz), 146.0, 140.7, 139.5, 139.3, 137.1, 136.1 (d, J=3.0 Hz), 130.2, 129.8 (d, J=9.0 Hz), 128.6, 128.4, 128.2, 127.9, 127.5, 126.7, 126.2, 126.0, 116.4 (d, J=24.0 Hz), 43.1, 33.8, 32.2, 29.7; LCMS m/z 408.1587 ([M+H$^+$], C$_{24}$H$_{22}$FNO$_2$S requires 408.1428).

Example 73

Synthesis of N-(3-(10,11-dihydro-5H-dibenzo[b,f] azepin-5-yl)cyclohexyl)-4-(trifluoromethoxy)benzenesulfonamide

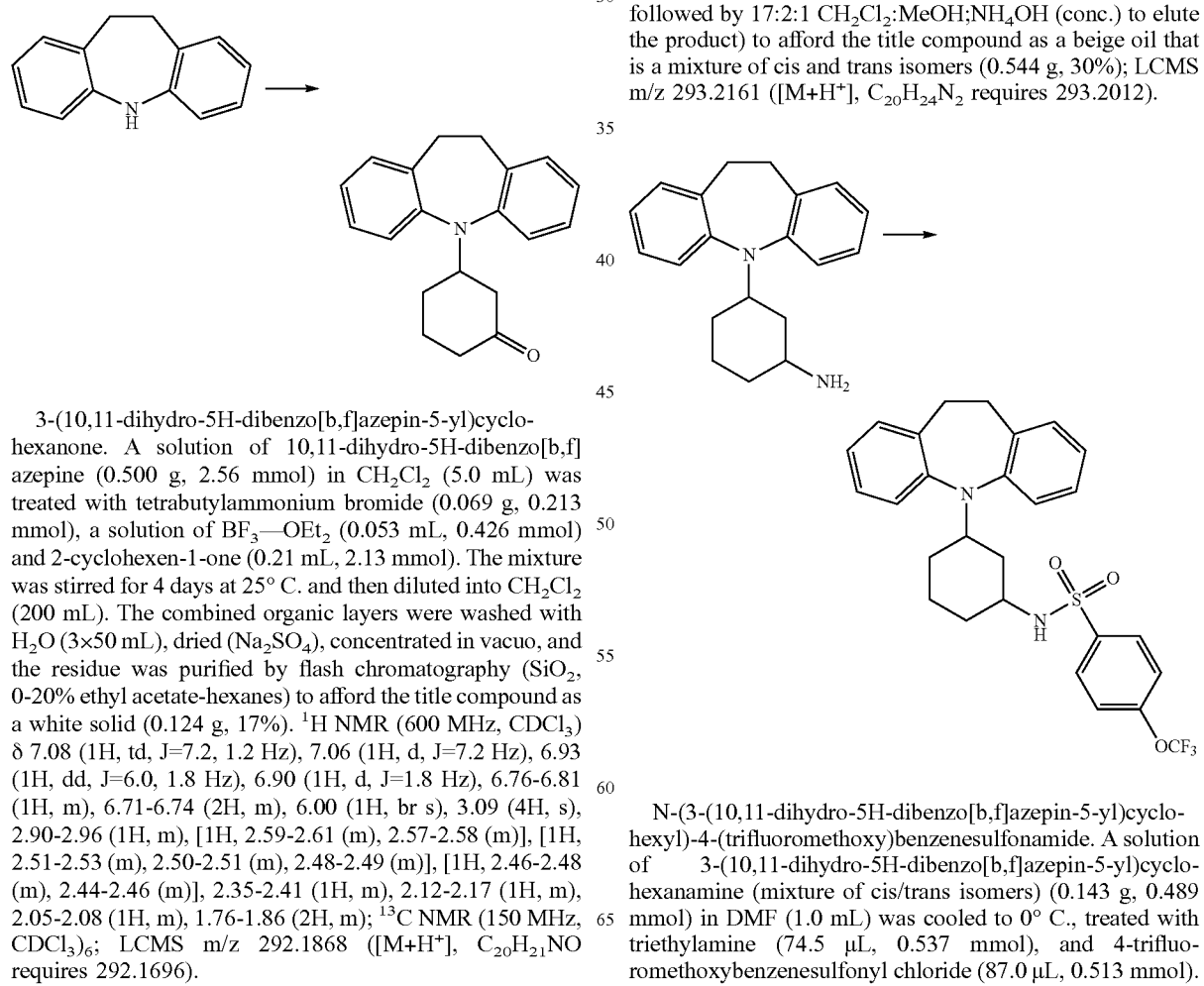

3-(10,11-dihydro-5H-dibenzo[b,f]azepin-5-yl)cyclohexanone. A solution of 10,11-dihydro-5H-dibenzo[b,f]azepine (0.500 g, 2.56 mmol) in CH$_2$Cl$_2$ (5.0 mL) was treated with tetrabutylammonium bromide (0.069 g, 0.213 mmol), a solution of BF$_3$—OEt$_2$ (0.053 mL, 0.426 mmol) and 2-cyclohexen-1-one (0.21 mL, 2.13 mmol). The mixture was stirred for 4 days at 25° C. and then diluted into CH$_2$Cl$_2$ (200 mL). The combined organic layers were washed with H$_2$O (3×50 mL), dried (Na$_2$SO$_4$), concentrated in vacuo, and the residue was purified by flash chromatography (SiO$_2$, 0-20% ethyl acetate-hexanes) to afford the title compound as a white solid (0.124 g, 17%). $^1$H NMR (600 MHz, CDCl$_3$) δ 7.08 (1H, td, J=7.2, 1.2 Hz), 7.06 (1H, d, J=7.2 Hz), 6.93 (1H, dd, J=6.0, 1.8 Hz), 6.90 (1H, d, J=1.8 Hz), 6.76-6.81 (1H, m), 6.71-6.74 (2H, m), 6.00 (1H, br s), 3.09 (4H, s), 2.90-2.96 (1H, m), [1H, 2.59-2.61 (m), 2.57-2.58 (m)], [1H, 2.51-2.53 (m), 2.50-2.51 (m), 2.48-2.49 (m)], [1H, 2.46-2.48 (m), 2.44-2.46 (m)], 2.35-2.41 (1H, m), 2.12-2.17 (1H, m), 2.05-2.08 (1H, m), 1.76-1.86 (2H, m); $^{13}$C NMR (150 MHz, CDCl$_3$)$_6$; LCMS m/z 292.1868 ([M+H$^+$], C$_{20}$H$_{21}$NO requires 292.1696).

3-(10,11-dihydro-5H-dibenzo[b,f]azepin-5-yl)cyclohexanamine. A pressure vessel was charged with a solution of 3-(10,11-dihydro-5H-dibenzo[b,f]azepin-5-yl)cyclohexanone (1.836 g, 6.30 mmol) in MeOH (10.0 mL) and treated with 10% Pd/C (0.670 g) and ammonium formate (2.35 g, 37.80 mmol). The solution was stirred at 25° C. for 14 h and then filtered through a pad of celite. The solution was concentrated in vacuo, and the residue was purified by flash chromatography (SiO$_2$, 0-20% ethyl acetate-hexanes followed by 17:2:1 CH$_2$Cl$_2$:MeOH:NH$_4$OH (conc.) to elute the product) to afford the title compound as a beige oil that is a mixture of cis and trans isomers (0.544 g, 30%); LCMS m/z 293.2161 ([M+H$^+$], C$_{20}$H$_{24}$N$_2$ requires 293.2012).

N-(3-(10,11-dihydro-5H-dibenzo[b,f]azepin-5-yl)cyclohexyl)-4-(trifluoromethoxy)benzenesulfonamide. A solution of 3-(10,11-dihydro-5H-dibenzo[b,f]azepin-5-yl)cyclohexanamine (mixture of cis/trans isomers) (0.143 g, 0.489 mmol) in DMF (1.0 mL) was cooled to 0° C., treated with triethylamine (74.5 µL, 0.537 mmol), and 4-trifluoromethoxybenzenesulfonyl chloride (87.0 µL, 0.513 mmol).

The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford two compounds of similar but distinguishable Rf, compound 1 the trans isomer (0.0955 g, 38%) and compound 2, the cis isomer (0.0355 g, 14%).

1$^{st}$ Spot, Trans Product $^1$H NMR (600 MHz, CDCl$_3$) δ 8.06 (2H, d, J=8.4 Hz), 7.37 (2H, d, J=8.4 Hz), 7.10 (1H, t, J=7.8 Hz), 7.07 (1H, J=7.8 Hz), 6.79 (1H, t, J=7.8 Hz), 6.78 (1H, s), 6.74 (1H, d, J=7.8 Hz), 6.66 (1H, d, J=7.8 Hz), 6.02 (1H, br s), 5.76 (1H, d, J=6.6 Hz), 3.74 (1H, d, J=3.0 Hz), 3.04-3.08 (4H, m), 2.68 (1H, t, J=11.4 Hz), 1.83-1.89 (1H, m), 1.68-1.74 (1H, m), 1.64-1.68 (1H, m), 1.57-1.64 (2H, m), 1.51 (1H, tt, J=12.8, 3.8 Hz), 1.42 (1H, qd, J=12.6, 3.5 Hz); $^{13}$C NMR (150 MHz, CDCl$_3$) δ 152.1, 142.8, 140.9, 139.5, 137.0, 130.8, 129.3, 129.1, 128.6, 126.9, 125.1, 121.1, 119.53, 119.45, 118.2, 118.0, 117.8, 50.1, 38.9, 36.9, 35.1, 35.0, 33.1, 30.8, 20.8; LCMS m/z 517.2372 ([M+H$^+$], C$_{27}$H$_{27}$F$_3$N$_2$O$_3$S requires 517.1767). TOCSY Spectra, No cross peaks between 3.74 (1H, d, J=3.0 Hz), 2.68 (1H, t, J=11.4 Hz)

2$^{nd}$ Spot, Cis Product $^1$H NMR (600 MHz, CDCl$_3$) δ 7.96 (2H, d, J=8.4 Hz), 7.34 (2H, d, J=8.4 Hz), 7.18 (1H, t, J=7.8 Hz), 7.04 (1H, J=7.2 Hz), 7.08 (1H, d, J=7.2 Hz), 6.82 (1H, d, J=8.4 Hz), 6.80 (1H, s), 6.68 (1H, t, J=7.8 Hz), 6.72 (1H, d, J=7.8 Hz), 6.66 (1H, d, J=7.8 Hz), 5.97 (1H, s), 4.78 (1H, d, J=7.8 Hz), 3.26-3.31 (1H, m), 3.06-3.09 (4H, m), 2.43 (1H, tt, J=11.7, 2.6 Hz), 2.03 (1H, d, J=12.6 Hz), 1.92 (1H, d, J=12.6 Hz), 1.84 (1H, dt, J=13.8, 2.7 Hz), 1.79 (1H, d, J=12.6 Hz), 1.40 (1H, qt, J=13.3, 3.3 Hz), 1.30 (1H, q, J=12.0 Hz), 1.22-1.28 (1H, m), 1.18 (1H, qd, J=12.7, 3.7 Hz); $^{13}$C NMR (150 MHz, CDCl$_3$) δ 152.2, 142.8, 141.0, 140.1, 136.8, 130.9, 129.2, 129.1, 128.73, 128.70, 127.0, 125.0, 121.3, 121.1, 119.6, 118.2, 118.0, 53.7, 42.4, 42.1, 35.1, 35.0, 34.1, 33.2, 25.2; LCMS m/z 517.2189 ([M+H$^+$], C$_{27}$H$_{27}$F$_3$N$_2$O$_3$S requires 517.1767). TOCSY Spectra, Cross peaks between 3.26-3.31 (1H, m), 2.43 (1H, tt, J=11.7, 2.6 Hz)

Example 74

Synthesis of (S)—N-(3-(10,11-dihydro-5H-dibenzo [b,f]azepin-5-yl)-2-hydroxypropyl)-4-(trifluoromethoxy)benzenesulfonamide

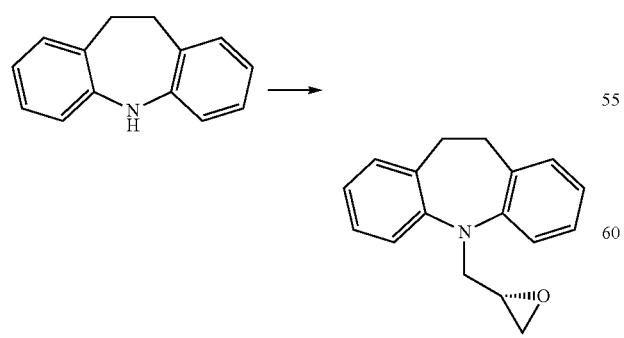

(S)-5-(Oxiran-2-ylmethyl)-10,11-dihydro-5H-dibenzo[b,f]azepine. A solution of 10,11-dihydro-5H-dibenzo[b,f]azepine (1.00 g, 5.12 mmol) in toluene (10.0 mL) was treated with a solution of sodium amide in toluene (50% by weight, 0.600 g, 7.68 mmol) and (R)-epichlorohydrin (0.400 mL, 5.12 mmol). The vial was sealed, heated to 80° C. for 6 h. The mixture was cooled to 25° C. treated with a solution of aqueous 1 M HCl (10.0 mL), and then filtered. The mixture was extracted with CH$_2$Cl$_2$ (3×100 mL), and the combined organic layers were washed with saturated aqueous NaCl (100 mL), dried (Na$_2$SO$_4$), concentrated in vacuo, and the residue was purified by flash chromatography (SiO$_2$, 0-5% ethyl acetate-hexanes) to afford the title compound as a white solid (0.757 g, 14%).

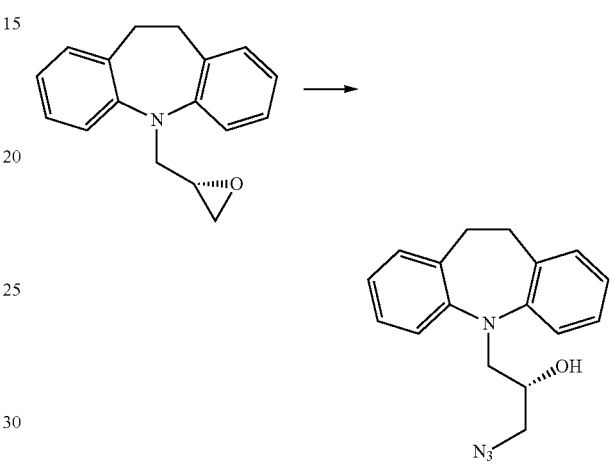

(S)-1-Azido-3-(10,11-dihydro-5H-dibenzo[b,f]azepin-5-yl)propan-2-ol. A solution of (S)-5-(oxiran-2-ylmethyl)-10,11-dihydro-5H-dibenzo[b,f]azepine (0.732 g, 2.91 mmol) in 4:1 ethanol:H$_2$O (10.0 ml) was treated with sodium azide (0.246, 3.79 mmol), ammonium chloride (0.203 g, 3.79 mmol) and heated to 80° C. for 14 h. The mixture was cooled to 25° C., concentrated in vacuo, and then resuspended in ethyl acetate (100 mL). This organic layer was washed with saturated aqueous NaCl (3×50 mL), dried (Na$_2$SO$_4$), concentrated in vacuo, and the residue was purified by flash chromatography (SiO$_2$, 0-20% ethyl acetate-hexanes) to afford the title compound as a beige oil (0.787 g, 92%).

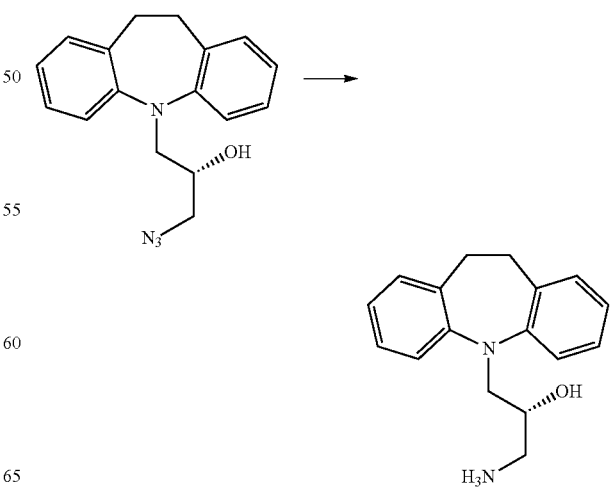

(R)-1-Amino-3-(10,11-dihydro-5H-dibenzo[b,f]azepin-5-yl)propan-2-ol. A solution of (S)-1-azido-3-(10,11-dihydro-5H-dibenzo[b,f]azepin-5-yl)propan-2-ol (0.767 g, 2.61 mmol) in THF (5.0 mL) was cooled to 0° C., treated with PPh$_3$ (0.717 g, 2.74 mmol), 5 drops of H$_2$O, and stirred for 14 h at 25° C. The solution was concentrated to dryness, dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$:MeOH:NH$_4$OH to elute the product). The combined fractions of pure product were concentrated and dried azeotropically with toluene. The residue was dissolved in a minimal amount of ethyl ether and precipitated with the addition of hexanes to afford the title compound as a white solid (0.614 g, 88%).

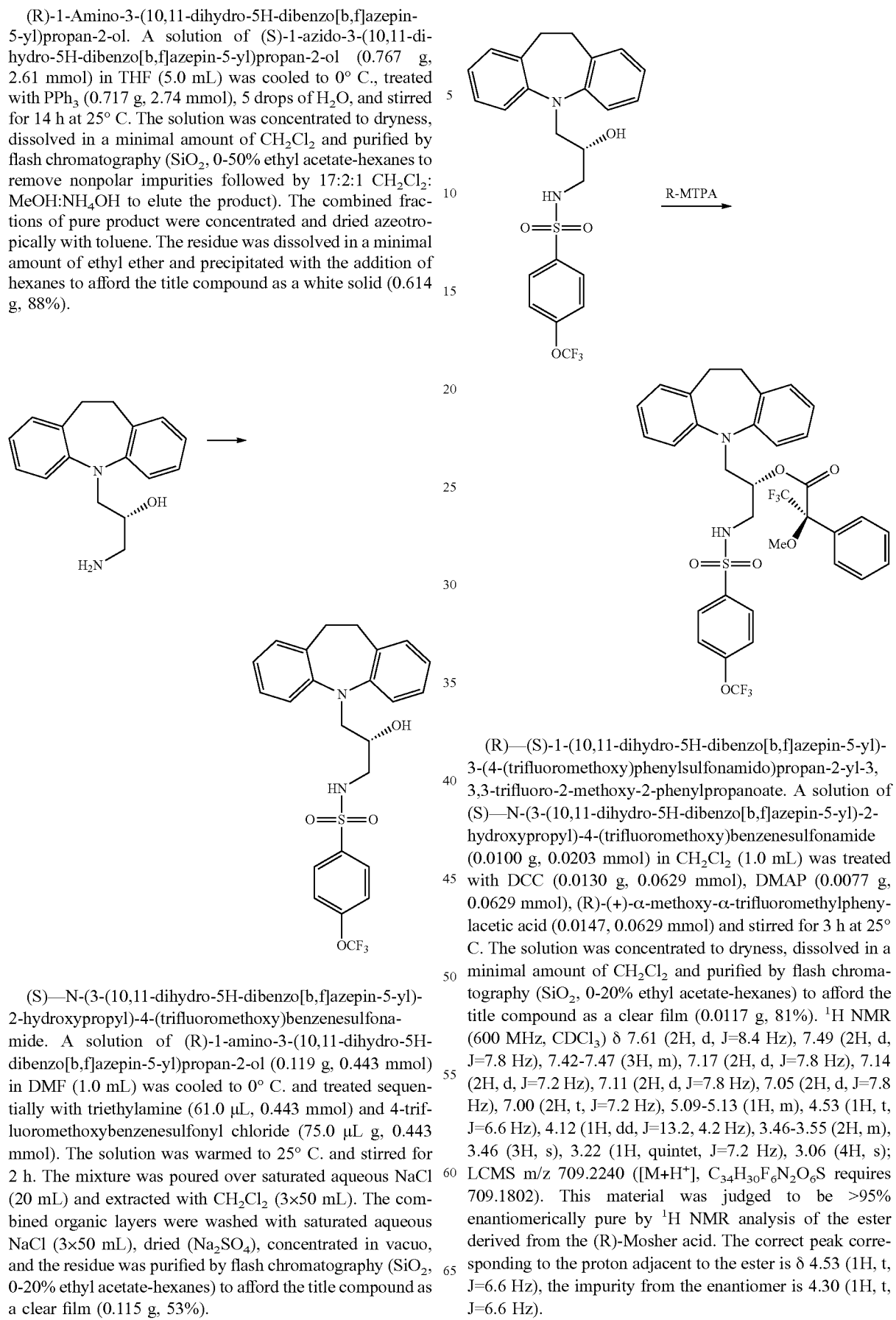

(S)—N-(3-(10,11-dihydro-5H-dibenzo[b,f]azepin-5-yl)-2-hydroxypropyl)-4-(trifluoromethoxy)benzenesulfonamide. A solution of (R)-1-amino-3-(10,11-dihydro-5H-dibenzo[b,f]azepin-5-yl)propan-2-ol (0.119 g, 0.443 mmol) in DMF (1.0 mL) was cooled to 0° C. and treated sequentially with triethylamine (61.0 μL, 0.443 mmol) and 4-trifluoromethoxybenzenesulfonyl chloride (75.0 μL g, 0.443 mmol). The solution was warmed to 25° C. and stirred for 2 h. The mixture was poured over saturated aqueous NaCl (20 mL) and extracted with CH$_2$Cl$_2$ (3×50 mL). The combined organic layers were washed with saturated aqueous NaCl (3×50 mL), dried (Na$_2$SO$_4$), concentrated in vacuo, and the residue was purified by flash chromatography (SiO$_2$, 0-20% ethyl acetate-hexanes) to afford the title compound as a clear film (0.115 g, 53%).

(R)—(S)-1-(10,11-dihydro-5H-dibenzo[b,f]azepin-5-yl)-3-(4-(trifluoromethoxy)phenylsulfonamido)propan-2-yl-3,3,3-trifluoro-2-methoxy-2-phenylpropanoate. A solution of (S)—N-(3-(10,11-dihydro-5H-dibenzo[b,f]azepin-5-yl)-2-hydroxypropyl)-4-(trifluoromethoxy)benzenesulfonamide (0.0100 g, 0.0203 mmol) in CH$_2$Cl$_2$ (1.0 mL) was treated with DCC (0.0130 g, 0.0629 mmol), DMAP (0.0077 g, 0.0629 mmol), (R)-(+)-α-methoxy-α-trifluoromethylphenylacetic acid (0.0147, 0.0629 mmol) and stirred for 3 h at 25° C. The solution was concentrated to dryness, dissolved in a minimal amount of CH$_2$Cl$_2$ and purified by flash chromatography (SiO$_2$, 0-20% ethyl acetate-hexanes) to afford the title compound as a clear film (0.0117 g, 81%). $^1$H NMR (600 MHz, CDCl$_3$) δ 7.61 (2H, d, J=8.4 Hz), 7.49 (2H, d, J=7.8 Hz), 7.42-7.47 (3H, m), 7.17 (2H, d, J=7.8 Hz), 7.14 (2H, d, J=7.2 Hz), 7.11 (2H, d, J=7.8 Hz), 7.05 (2H, d, J=7.8 Hz), 7.00 (2H, t, J=7.2 Hz), 5.09-5.13 (1H, m), 4.53 (1H, t, J=6.6 Hz), 4.12 (1H, dd, J=13.2, 4.2 Hz), 3.46-3.55 (2H, m), 3.46 (3H, s), 3.22 (1H, quintet, J=7.2 Hz), 3.06 (4H, s); LCMS m/z 709.2240 ([M+H$^+$], C$_{34}$H$_{30}$F$_6$N$_2$O$_6$S requires 709.1802). This material was judged to be >95% enantiomerically pure by $^1$H NMR analysis of the ester derived from the (R)-Mosher acid. The correct peak corresponding to the proton adjacent to the ester is δ 4.53 (1H, t, J=6.6 Hz), the impurity from the enantiomer is 4.30 (1H, t, J=6.6 Hz).

Example 75

Synthesis of (R)—N-(3-(10,11-dihydro-5H-dibenzo[b,f]azepin-5-yl)-2-hydroxypropyl)-4-(trifluoromethoxy)benzenesulfonamide

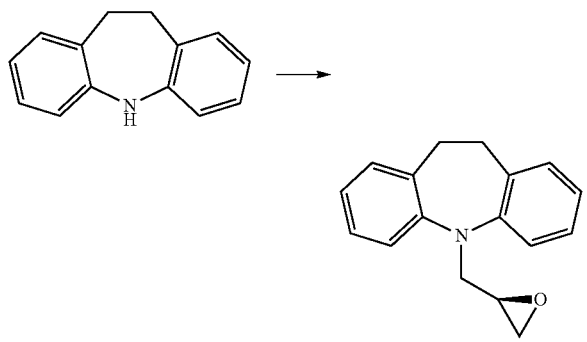

(R)-5-(Oxiran-2-ylmethyl)-10,11-dihydro-5H-dibenzo[b,f]azepine. A solution of 10,11-dihydro-5H-dibenzo[b,f]azepine (1.00 g, 5.12 mmol) in toluene (10.0 mL) was treated with a solution of sodium amide in toluene (50% by weight, 0.600 g, 7.68 mmol) and (S)-epichlorohydrin (0.400 mL, 5.12 mmol). The vial was sealed, heated to 80° C. for 6 h. The mixture was cooled to 25° C. treated with a solution of aqueous 1 M HCl (10.0 mL), and then filtered. The mixture was extracted with $CH_2Cl_2$ (3×100 mL), and the combined organic layers were washed with saturated aqueous NaCl (100 mL), dried ($Na_2SO_4$), concentrated in vacuo, and the residue was purified by flash chromatography ($SiO_2$, 0-5% ethyl acetate-hexanes) to afford the title compound as a white solid (0.758 g, 29%).

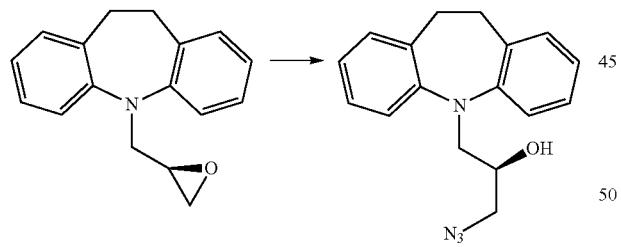

(R)-1-Azido-3-(10,11-dihydro-5H-dibenzo[b,f]azepin-5-yl)propan-2-ol. A solution of (R)-5-(oxiran-2-ylmethyl)-10,11-dihydro-5H-dibenzo[b,f]azepine (0.727 g, 2.89 mmol) in 4:1 ethanol:$H_2O$ (10.0 ml) was treated with sodium azide (0.244 g, 3.76 mmol), ammonium chloride (0.201 g, 3.76 mmol) and heated to 80° C. for 14 h. The mixture was cooled to 25° C., concentrated in vacuo, resuspended in ethyl acetate (100 mL). This organic layer was washed with saturated aqueous NaCl (3×50 mL), dried ($Na_2SO_4$), concentrated in vacuo, and the residue was purified by flash chromatography ($SiO_2$, 0-20% ethyl acetate-hexanes) to afford the title compound as a beige oil (0.787 g, 92%).

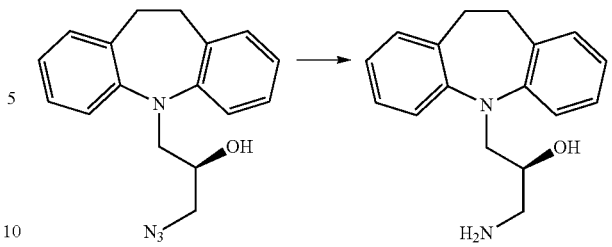

(S)-1-Amino-3-(10,11-dihydro-5H-dibenzo[b,f]azepin-5-yl)propan-2-ol. A solution of (R)-1-azido-3-(10,11-dihydro-5H-dibenzo[b,f]azepin-5-yl)propan-2-ol (0.782 g, 2.66 mmol) in THF (5.0 mL) was cooled to 0° C., treated with $PPh_3$ (0.767 g, 2.92 mmol), 5 drops of $H_2O$, and stirred for 14 h at 25° C. The solution was concentrated to dryness, dissolved in a minimal amount of $CH_2Cl_2$ and purified by flash chromatography ($SiO_2$, 0-50% ethyl acetate-hexanes to remove nonpolar impurities followed by 17:2:1 $CH_2Cl_2$:MeOH:$NH_4OH$ to elute the product). The combined fractions of pure product were concentrated and dried azeotropically with toluene. The residue was dissolved in a minimal amount of ethyl ether and precipitated with the addition of hexanes to afford the title compound as a white solid (0.435 g, 61%).

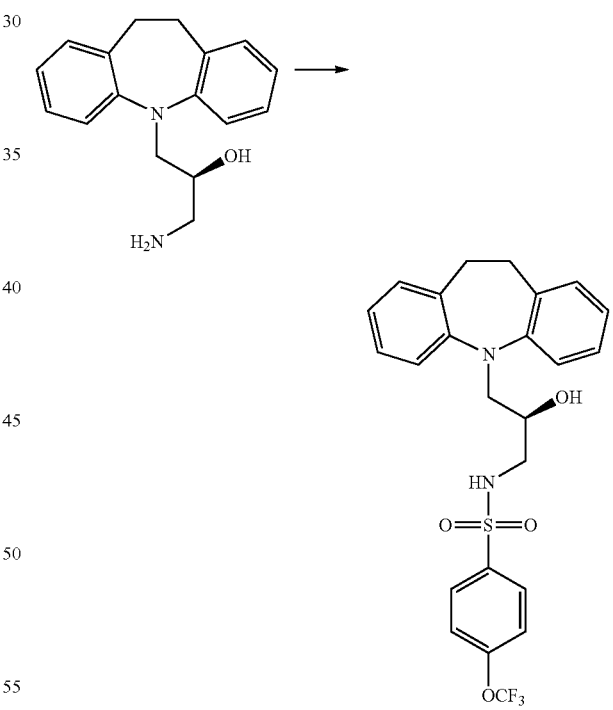

(R)—N-(3-(10,11-dihydro-5H-dibenzo[b,f]azepin-5-yl)-2-hydroxypropyl)-4-(trifluoromethoxy)benzenesulfonamide. A solution of (S)-1-amino-3-(10,11-dihydro-5H-dibenzo[b,f]azepin-5-yl)propan-2-ol (0.100 g, 0.373 mmol) in DMF (1.0 mL) was cooled to 0° C. and treated sequentially with triethylamine (52.0 µL, 0.373 mmol) and 4-trifluoromethoxybenzenesulfonyl chloride (0.0970 g, 0.373 mmol). The solution was warmed to 25° C. and stirred for 2 h. The mixture was poured over saturated aqueous NaCl (20 mL) and extracted with $CH_2Cl_2$ (3×50 mL). The combined organic layers were washed with saturated aqueous NaCl (3×50 mL), dried (Na₂SO₄), concentrated in vacuo, and the residue was purified by flash chromatography (SiO₂, 0-20% ethyl acetate-hexanes) to afford the title compound as a clear film (0.166 g, 91%).

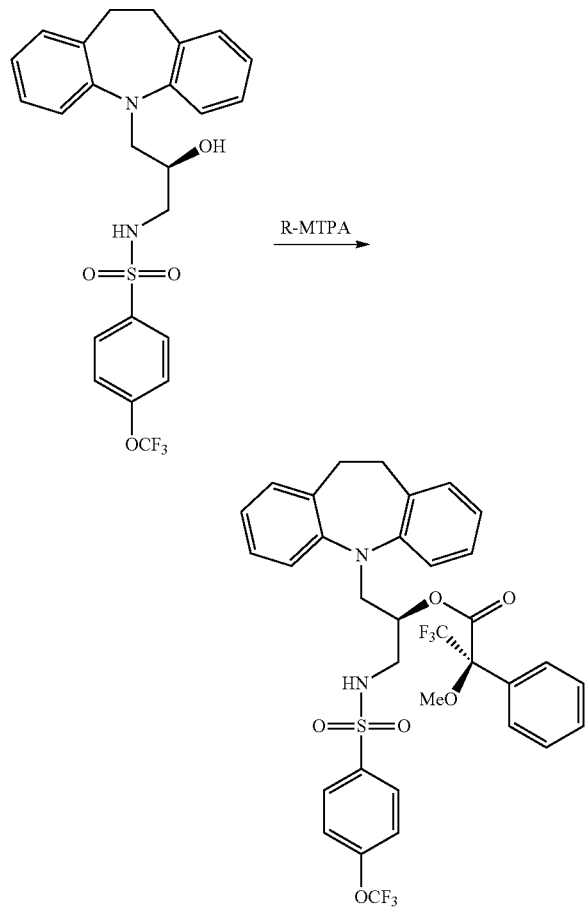

(R)—(R)-1-(10,11-dihydro-5H-dibenzo[b,f]azepin-5-yl)-3-(4-(trifluoromethoxy)phenylsulfonamido)propan-2-yl-3,3,3-trifluoro-2-methoxy-2-phenylpropanoate. A solution of (R)—N-(3-(10,11-dihydro-5H-dibenzo[b,f]azepin-5-yl)-2-hydroxypropyl)-4-(trifluoromethoxy)benzenesulfonamide (0.0100 g, 0.0203 mmol) in CH₂Cl₂ (1.0 mL) was treated with DCC (0.0130 g, 0.0629 mmol), DMAP (0.0077 g, 0.0629 mmol), (R)-(+)-α-methoxy-α-trifluoromethylphenylacetic acid (0.0147, 0.0629 mmol) and stirred for 3 h at 25° C. The solution was concentrated to dryness, dissolved in a minimal amount of CH₂Cl₂ and purified by flash chromatography (SiO₂, 0-20% ethyl acetate-hexanes) to afford the title compound as a clear film (0.0140 g, 97%). ¹H NMR (600 MHz, CDCl₃) δ 7.58 (2H, d, J=9.0 Hz), 7.44-7.48 (3H, m), 7.38 (2H, t, J=7.8 Hz), 7.17 (4H, t, J=8.4 Hz), 7.13 (2H, d, J=7.2 Hz), 7.08 (2H, d, J=8.4 Hz), 7.01 (2H, t, J=7.8 Hz), 5.12-5.12 (1H, m), 4.30 (1H, t, J=6.6 Hz), 4.17 (1H, dd, J=13.2, 4.8 Hz), 3.68 (1H, dd, J=7.8, 13.2 Hz), 3.50 (3H, s), 3.44-3.48 (1H, d, m), 3.16 (1H, quintet, J=6.6 Hz), 3.09 (4H, br s); LCMS m/z 709.2240 ([M+H⁺], C₃₄H₃₀F₆N₂O₆S requires 709.1802). This material was judged to be >95% enantiomerically pure by ¹H NMR analysis of the ester derived from the (R)-Mosher acid. The correct peak corresponding to the proton adjacent to the ester is a δ 4.30 (1H, t, J=6.6 Hz), the impurity from the enantiomer is δ 4.53 (1H, t, J=6.6 Hz).

Repeat of Example 75

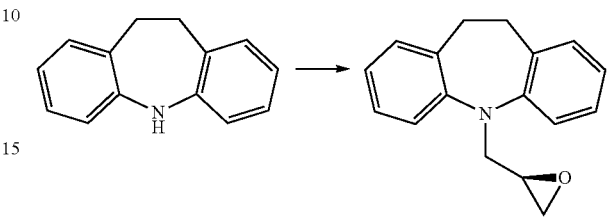

(R)-5-(oxiran-2-ylmethyl)-10,11-dihydro-5H-dibenzo[b,f]azepine. A solution of 10,11-dihydro-5H-dibenzo[b,f]azepine (10.00 g, 51.2 mmol) in toluene (100.0 mL) was treated with a solution of sodium amide in toluene (50% by weight, 6.00 g, 76.8 mmol) and (S)-epichlorohydrin (6.83 mL, 87.1 mmol). The flask was sealed and heated to 80° C. for 6 h. The mixture was cooled to 25° C. treated with a solution of aqueous 1 M HCl (100.0 mL), and then filtered to remove a brown precipitate which was washed with CH₂Cl₂ and discarded. The filtrate was extracted with CH₂Cl₂ (3×100 mL), and the combined organic layers were washed with saturated aqueous NaCl (100 mL), dried (Na₂SO₄), and concentrated in vacuo. At this stage, the material contains a mixture of the product and starting material, and is taken on crude to the next step (11.3 grams, 73% recovered material).

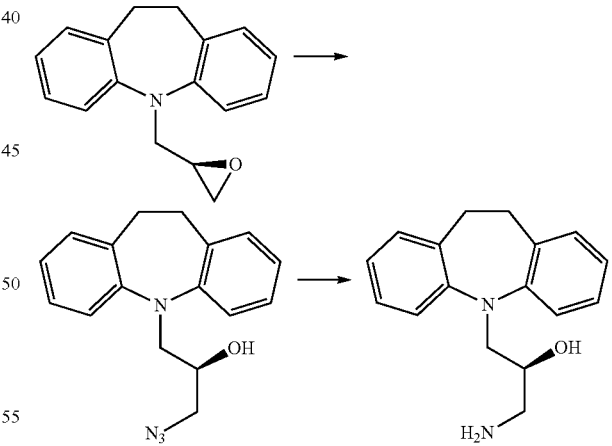

(S)-1-amino-3-(10,11-dihydro-5H-dibenzo[b,f]azepin-5-yl)propan-2-ol. A solution of (R)-5-(oxiran-2-ylmethyl)-10,11-dihydro-5H-dibenzo[b,f]azepine (11.3 g, 45.0 mmol) in 4:1 ethanol:H₂O (80.0 ml) was treated with sodium azide (3.80 g, 58.5 mmol), ammonium chloride (3.13 g, 58.5 mmol) and heated to 80° C. for 14 h. The mixture was cooled to 25° C., concentrated in vacuo, resuspended in EtOAc (300 mL). This organic layer was washed with saturated aqueous NaCl (3×50 mL), dried (Na₂SO₄), and concentrated in vacuo. At the stage, the crude rxn mixture was dissolved in THF (50 mL), treated with PPh$_3$ (12.97 g, 49.5 mmol), H$_2$O (1.0 mL), and stirred for 14 h at 25° C. The solution was concentrated to dryness, dissolved in a minimal amount of CH$_2$Cl$_2$ and purified by flash chromatography (SiO$_2$, 0-50% ethyl acetate-hexanes to remove nonpolar impurities followed by 17:2:1 CH$_2$Cl$_2$:MeOH:NH$_4$OH to elute the product). The combined fractions of pure product were concentrated, dried azeotropically with toluene. The residue was dissolved in a minimal amount of ethyl ether and precipitated with the addition of hexanes to afford the title compound as a white solid (4.23 g, 31%, 3 steps).

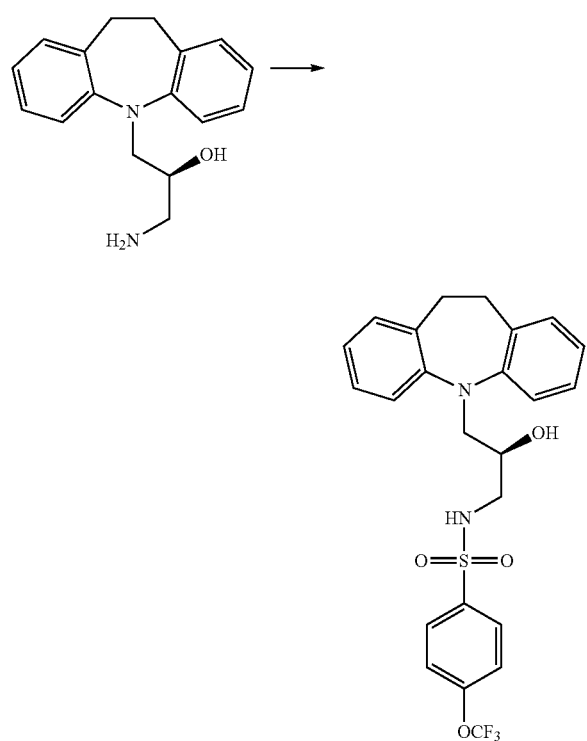 [SMILES: NC[C@H](O)CN1c2ccccc2CCc2ccccc21 ; O=S(=O)(NC[C@H](O)CN1c2ccccc2CCc2ccccc21)c1ccc(OC(F)(F)F)cc1]

(R)—N-(3-(10,11-dihydro-5H-dibenzo[b,f]azepin-5-yl)-2-hydroxypropyl)-4-(trifluoromethoxy)benzenesulfonamide. A solution of (S)-1-amino-3-(10,11-dihydro-5H-dibenzo[b,f]azepin-5-yl)propan-2-ol (3.57 g, 13.3 mmol) in DMF (1.0 mL) was cooled to 0° C. and treated sequentially with triethylamine (1.84 mL, 0.373 mmol) and 4-trifluoromethoxybenzenesulfonyl chloride (2.25 mL, 13.3 mmol). The solution was warmed to 25° C. and stirred for 2 h. The mixture was poured over saturated aqueous NaCl (20 mL) and extracted with CH$_2$Cl$_2$ (3×50 mL). The combined organic layers were washed with saturated aqueous NaCl (3×50 mL), dried (Na$_2$SO$_4$), concentrated in vacuo, and the residue was purified by flash chromatography (SiO$_2$, 0-40% ethyl acetate-hexanes). The purified fractions were concentrated, dissolved in a minimal amount of ether and precipitated with the addition of hexanes to afford the title compound as a white solid (6.23 g, 95%). This material was judged to be >95% enantiomerically pure by $^1$H NMR analysis of the ester derived from the (R)-Mosher acid.

Example 76

Synthesis of N-(3-(10,11-dihydro-5H-dibenzo[b,f] azepin-5-yl)cyclopentyl)-4-(trifluoromethoxy)benzenesulfonamide

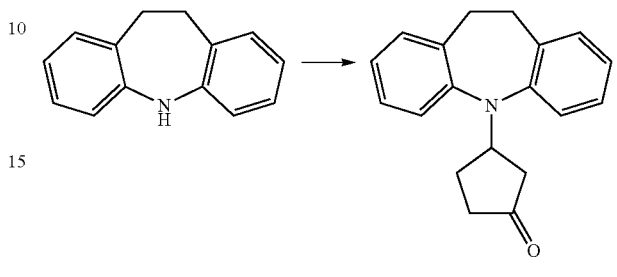

3-(10,11-dihydro-5H-dibenzo[b,f]azepin-5-yl)cyclopentanone. A solution of 10,11-dihydro-5H-dibenzo[b,f]azepine (4.00 g, 20.5 mmol) in 2-cyclopenten-1-one (4.0 mL) was treated with tetrabutylammonium bromide (0.550 g, 1.71 mmol), a solution of BF$_3$—OEt$_2$ (0.43 mL, 3.41 mmol) and the mixture was stirred for 6 hours at 25° C. The mixture was applied to the column directly and purified by flash chromatography (SiO$_2$, 0-20% ethyl acetate-hexanes) to afford the title compound as a white solid (1.83 g, 32%). $^1$H NMR (600 MHz, CDCl$_3$) δ 7.10 (1H, t, J=7.8 Hz), 7.06 (1H, d, J=7.2 Hz), 6.98 (1H, dd, J=7.8, 1.8 Hz), 6.94 (1H, br s), 6.80 (1H, t, J=7.2 Hz), 6.74 (2H, t, J=8.4 Hz), 6.05 (1H, s), 3.32-3.35 (1H, m), 3.10 (4H, br s), 2.64 (1H, dd, J=18.0, 7.8 Hz), 2.47 (1H, dd, J=18.6, 8.4 Hz), 2.40-2.42 (1H, m), 2.27-2.34 (2H, m), 1.94-1.99 (1H, m); $^1$H NMR (600 MHz, CDCl$_3$) δ 219.0, 142.6, 141.4, 134.1, 130.9, 129.2, 128.8, 128.7, 127.0, 125.2, 119.7, 118.4, 118.1, 46.2, 41.6, 39.1, 35.2, 35.0, 31.6; LCMS m/z 278.1837 ([M+H$^+$], C$_{19}$H$_{19}$NO requires 278.1539).

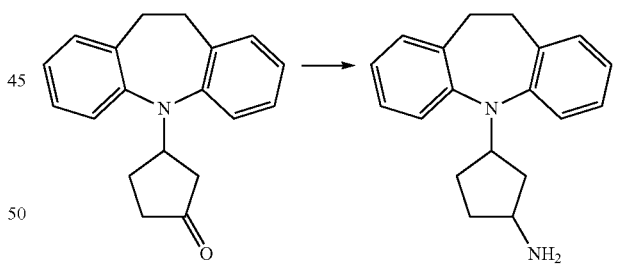

3-(10,11-dihydro-5H-dibenzo[b,f]azepin-5-yl)cyclopentanamine. A glass pressure vessel was charged with a solution of 3-(10,11-dihydro-5H-dibenzo[b,f]azepin-5-yl) cyclopentanone (1.18 g, 4.25 mmol) in MeOH (10.0 mL), treated with 10% Pd/C (0.425 g), and ammonium formate (1.58 g, 25.5 mmol). The solution was stirred at 25° C. for 14 h and then filtered through a pad of Celite. The solution was concentrated in vacuo, and the residue was purified by flash chromatography (SiO$_2$, 0-20% ethyl acetate-hexanes followed by 17:2:1 CH$_2$Cl$_2$:MeOH;NH$_4$OH (conc.) to elute the product) to afford the title compound as a white solid that is a mixture of diastereomers (0.428 g, 36%); LCMS m/z ([M+H$^+$], C$_{19}$H$_{22}$N$_2$ requires 279.1856).

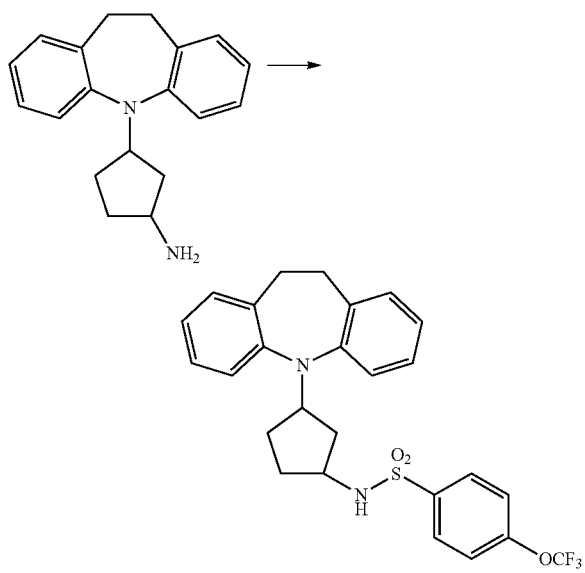

N-(3-(10,11-dihydro-5H-dibenzo[b,f]azepin-5-yl)cyclopentyl)-4-(trifluoromethoxy)benzenesulfonamide. A solution of 3-(10,11-dihydro-5H-dibenzo[b,f]azepin-5-yl)cyclopentanamine (0.208 g, 0.748 mmol) in DMF (1.0 mL) was cooled to 0° C., treated with triethylamine (109 µL, 0.748 mmol), and 4-trifluoromethoxybenzenesulfonyl chloride (127.0 µL, 0.748 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound (0.0669 g, 18%) as a white solid and mix of diastereomers. $^1$H NMR (600 MHz, CDCl$_3$) δ 7.96 (2H, d, J=8.4 Hz), 7.35 (2H, d, J=8.4 Hz), 7.07 (1H, t, J=7.8 Hz), 7.04 (1H, d, J=7.2 Hz), 6.86 (1H, d, J=8.4 Hz), 6.84 (1H, m), 6.81 (1H, s), 6.78 (1H, t, J=7.2 Hz), 6.72 (1H, t, J=8.4 Hz), 6.66 (1H, dd, J=7.8, 1.8 Hz), 4.74-4.77 (1H, m), 3.88 (0.5H, sextet, J=6.0 Hz), 3.78 (0.5H, sextet, J=7.2 Hz), 3.05-3.08 (4H, m), 2.87-2.93 (0.5H, m), 2.31 (0.5H, m), 2.08-2.16 (1H, m), 1.97-2.03 (1H, m), 1.89-1.94 (0.5H, m), 1.84-1.88 (0.5H, m), 1.69-1.72 (1H, m), 1.58-1.63 (1H, m), 1.50-1.55 (1H, m), 1.46-1.49 (1H, m); LCMS m/z 503.2494 ([M+H$^+$], C$_{26}$H$_{25}$F$_3$N$_2$O$_3$S requires 503.1611).

Example 77

Synthesis of N-(3-(10,11-dihydro-5H-dibenzo[a,d][7]annulen-5-ylidene)cyclohexyl)-4-(trifluoromethoxy)benzenesulfonamide

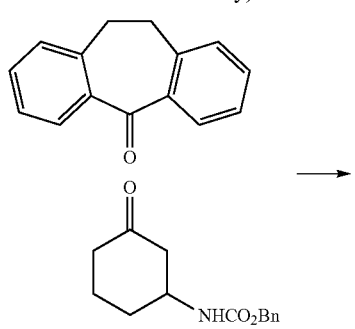

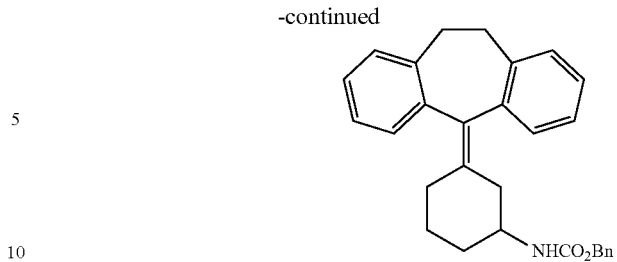

Benzyl (3-(10,11-dihydro-5H-dibenzo[a,d][7]annulen-5-ylidene)cyclohexyl)carbamate. A solution of dibenzosuberone (0.44 mL, 2.45 mmol) and benzyl (3-oxocyclohexyl)carbamate (prepared according to methods detailed in From WO9838166A1-1) (0.668 g, 2.70 mmol) in THF (10.0 mL), was treated with Zn powder (0.721 g, 11.0 mmol), cooled to 0° C., and treated slowly and dropwise with TiCl$_4$ (0.61 mL, 5.51 mmol). The mixture was warmed to 25° C., stirred for 30 min, heated to 75° C. for 90 minutes, and then cooled to 25° C. The mixture was treated with 1 M aqueous HCl (5.0 mL), and extracted into ethyl acetate (3×50 mL). The combined organic layers were washed with saturated aqueous NaCl (100 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound (0.488 g, 47%) as a white solid. The $^1$H NMR is a complex mixture of rotamers. LCMS m/z 424.2594 ([M+H$^+$], C$_{29}$H$_{29}$NO$_2$ requires 424.2271).

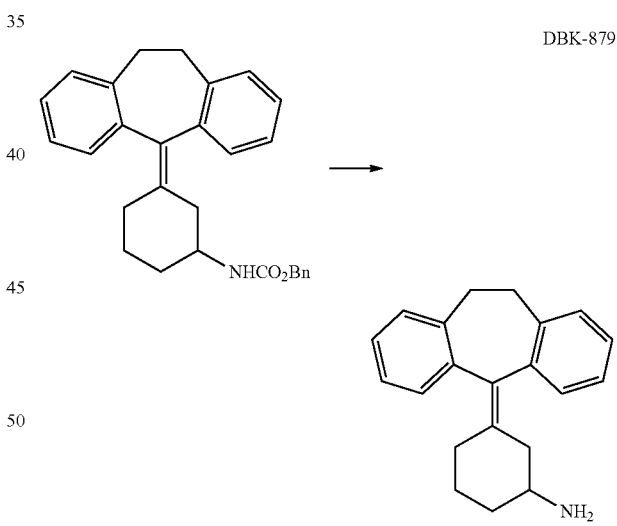

DBK-879

3-(10,11-dihydro-5H-dibenzo[a,d][7]annulen-5-ylidene)cyclohexanamine. A solution of benzyl (3-(10,11-dihydro-5H-dibenzo[a,d][7]annulen-5-ylidene)cyclohexyl)carbamate (0.388 g, 0.916 mmol) in 2:1:1 ethyl acetate-methanol-acetic acid (6.0 mL) was treated with 10% Pd/C (0.050 g), placed under one atmosphere of H$_2$ (g) and stirred for 3 h at 25° C. The mixture was filtered through a pad of Celite, concentrated in vacuo, and dried azeotropically with toluene (2×). The residue was dissolved in a minimal amount of ethyl acetate and precipitated with the addition of hexanes to afford the title compound as a white solid (0.326 g, 99%); $^1$H NMR (600 MHz, CDCl$_3$) δ 7.25 (2H, br s), 7.11-7.16 (4H, m), 7.04-7.07 (1H, m), 7.00-7.03 (1H, m), 5.31 (1H, s), 3.35-3.39 (1.5H, m), 3.10-3.16 (0.5H, m), 2.87-2.92 (0.5H, m), 2.74-2.85 (2H, m), 2.61 (0.5H, d, J=13.2 Hz), 2.12 (1H, d, J=10.2 Hz), 2.04 (0.5H, t, J=12.0 Hz), 1.99 (0.5H, d, J=12.0 Hz, 1.91-1.95 (0.5H, m), 1.87 (0.5H, t, J=12.0 Hz), 1.72-1.78 (0.5H, m), 1.68 (2H, s), 1.48-1.58 (0.5H, m), 1.42 (0.5H, q, J=11.4 Hz), 1.22 (0.5H, q, J=13.2 Hz); LCMS m/z 290.2083 ([M+H$^+$], C$_{21}$H$_{23}$N requires 290.1903).

m), 1.22-1.28 (1H, m); LCMS m/z 514.1958 ([M+H$^+$], C$_{28}$H$_{26}$F$_3$NO$_3$S requires 514.1658).

Example 78

Synthesis of N-(3-(10,11-dihydro-5H-dibenzo[a,d][7]annulen-5-ylidene)cyclohexyl)-4-chlorobenzenesulfonamide

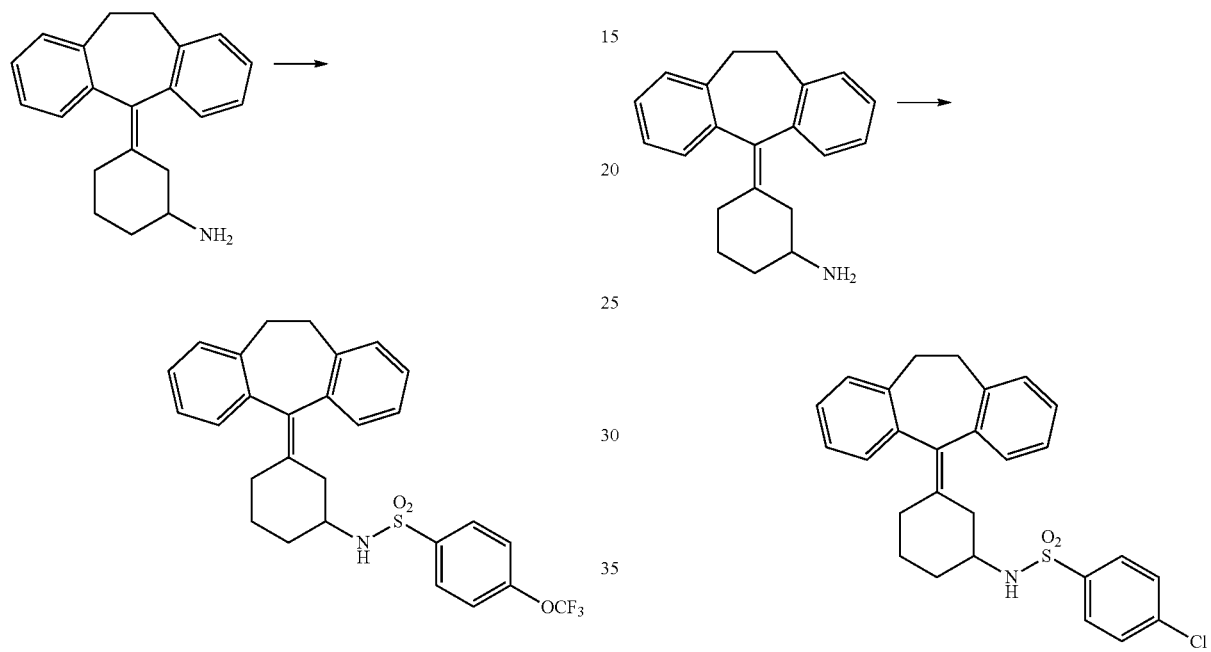

N-(3-(10,11-dihydro-5H-dibenzo[a,d][7]annulen-5-ylidene)cyclohexyl)-4-(trifluoromethoxy)benzenesulfonamide. A solution of 3-(10,11-dihydro-5H-dibenzo[a,d][7]annulen-5-ylidene)cyclohexanamine (0.0500 g, 0.173 mmol) in DMF (1.0 mL) was cooled to 0° C., treated with triethylamine (23.0 µL, 0.173 mmol), and 4-trifluoromethoxybenzenesulfonyl chloride (29.0 µL, 0.173 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound (0.023 g, 26%) as a clear film. $^1$H NMR (600 MHz, CDCl$_3$) δ (as a mixture of rotamers) [2H, 7.65 (d, J=8.4 Hz), 7.61 (d, J=9.0 Hz), 7.17-7.22 (2H, m), 7.13-7.17 (3H, m), 7.08-7.13 (2H, m), 7.03-7.05 (1H, m), 6.99-7.03 (1H, m), 6.88 (1H, t, J=5.4 Hz), [1H, 4.67 (d, J=7.2 Hz), 4.62 (d, J=7.2 Hz)], 3.43-3.47 (1H, m), 3.35-3.42 (1H, m), 3.26-3.34 (1H, m), 3.10-3.18 (0.5H, m), 2.84-2.93 (1H, m), 2.74-2.83 (1H, m), 2.58-2.62 (0.5H, m), 2.47-2.51 (0.5H, m), 2.41 (0.5H, dd, J=13.2, 3.6 Hz), 2.24-2.28 (0.5H, m), 2.11-2.16 (0.5H, m), 1.94-2.02 (1H, m), 1.83-1.92 (1H, m), 1.69-1.76 (1H, m), 1.56-1.67 (1H, m), 1.37-1.42 (0.5H, A solution of 3-(10,11-dihydro-5H-dibenzo[a,d][7]annulen-5-ylidene)cyclohexanamine (0.0500 g, 0.173 mmol) in DMF (1.0 mL) was cooled to 0° C., treated with triethylamine (23.0 µL, 0.173 mmol), and 4-chlorobenzenesulfonyl chloride (0.0365 g, 0.173 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound (0.026 g, 32%) as a clear film. $^1$H NMR (600 MHz, CDCl$_3$) δ (as a mixture of rotamers) 7.43-7.47 (2H, m), 7.22-7.24 (1H, m), 7.17-7.19 (1H, m), 7.09-7.12 (1H, m), 7.07-7.09 (1H, m), 7.03-7.06 (2H, m), 6.99-7.02 (1H, m), 6.93-6.98 (1H, m), 6.91 (1H, t, J=7.2 Hz), 6.76 (1H, d, J=7.8 Hz), [1H, 4.60 (d, J=7.8 Hz), 4.54 (d, J=7.8 Hz)], 3.27-3.34 (2H, m), 3.18-3.23 (1H, m), 2.95-3.02 (0.5H, m), 2.45-2.48 (0.5H, m), 2.38-2.40 (0.5H, m), 2.32 (0.5H, dd, J=13.2, 3.6 Hz), 2.15-2.22 (0.5H, m), 1.99-2.02 (0.5H, m), 1.88-1.91 (1H, m), 1.76-1.82 (1H, m), 1.72-1.74 (0.5H, m), 1.60-1.64 (1H, m), 1.51-1.54 (1H, m), 1.44-1.51 (1H, m), 1.24-1.32 (0.5H, m), 1.12-1.16 (1H, m); LCMS m/z 464.1802 ([M+H$^+$], C$_{27}$H$_{26}$ClNO$_2$S requires 464.1446).

Example 79

Synthesis of N-(4-(10,11-dihydro-5H-dibenzo[a,d][7]annulen-5-ylidene)cyclohexyl)-4-(trifluoromethoxy)benzenesulfonamide

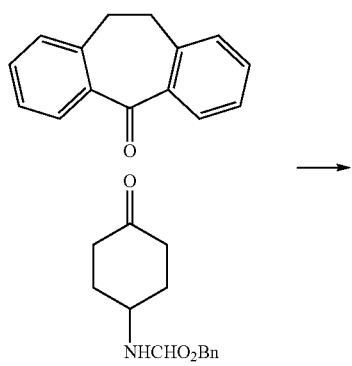

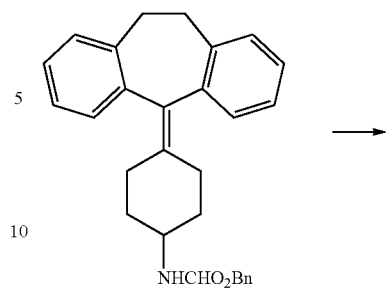

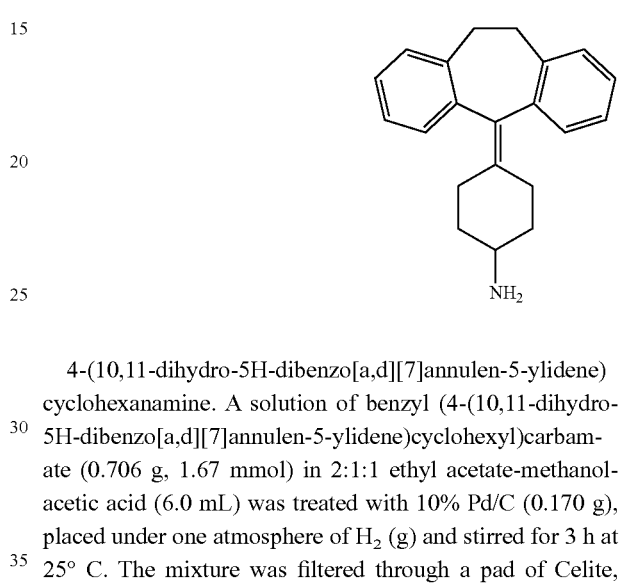

Benzyl (4-(10,11-dihydro-5H-dibenzo[a,d][7]annulen-5-ylidene)cyclohexyl)carbamate. A solution of dibenzosuberone (0.88 mL, 4.90 mmol) and benzyl (4-oxocyclohexyl)carbamate (1.34 g, 5.40 mmol) in THF (10.0 mL), was treated with Zn powder (1.44 g, 22.1 mmol), cooled to 0° C., and treated slowly and dropwise with $TiCl_4$ (1.22 mL, 11.0 mmol). The mixture was warmed to 25° C., stirred for 30 min, heated to 75° C. for 90 minutes, and then cooled to 25° C. The mixture was treated with 1 M aqueous HCl (5.0 mL), and extracted into ethyl acetate (3×50 mL). The combined organic layers were washed with saturated aqueous NaCl (100 mL), dried ($Na_2SO_4$), and concentrated in vacuo. The residue was dissolved in a minimal amount of $CH_2Cl_2$ and purified by flash chromatography ($SiO_2$, 0-20% ethyl acetate-hexanes) to afford the title compound (0.706 g, 34%) as a white solid. $^1$H NMR (600 MHz, $CDCl_3$) δ 7.40-7.43 (2H, m), 7.36-7.39 (3H, m), 7.15-7.19 (5H, m), 7.12-7.14 (1H, m), 7.08-7.12 (2H, m), [2H, 5.29 (s), 5.13 (d, J=24.0 Hz), 4.92 (0.5H, d, J=6.6 Hz), 4.72 (0.5H, d, J=7.2 Hz), 3.84 (1H, br s), 3.78 (1H, br s), 3.38-3.47 (2H, m), 2.82-2.86 (2H, m), 2.60-2.66 (2H, m), 2.19 (1H, t, J=12.0 Hz), 2.05-2.12 (1H, m), 2.02 (1H, t, J=11.4 Hz), 1.52 (1H, qd, J=10.2, 3.0 Hz), 1.18 (1H, qd, J=12.0, 3.6 Hz); LCMS m/z 424.2608 ([M+H$^+$], $C_{29}H_{29}NO_2$ requires 424.2271).

4-(10,11-dihydro-5H-dibenzo[a,d][7]annulen-5-ylidene)cyclohexanamine. A solution of benzyl (4-(10,11-dihydro-5H-dibenzo[a,d][7]annulen-5-ylidene)cyclohexyl)carbamate (0.706 g, 1.67 mmol) in 2:1:1 ethyl acetate-methanol-acetic acid (6.0 mL) was treated with 10% Pd/C (0.170 g), placed under one atmosphere of $H_2$ (g) and stirred for 3 h at 25° C. The mixture was filtered through a pad of Celite, concentrated in vacuo, and dried azeotropically with toluene (2×). The residue was dissolved in a minimal amount of ethyl acetate and precipitated with the addition of hexanes to afford the title compound as a white solid (0.445 g, 92%).

$^1$H NMR (600 MHz, $CDCl_3$) δ 7.13-7.15 (6H, m), 7.10-7.13 (1H, m), 7.09 (1H, t, J=7.2 Hz), 3.43-3.47 (1H, m), 3.37-3.42 (1H, m), 2.86-2.89 (1H, m), 2.79-2.86 (2H, m), 2.64-2.66 (2H, m), 2.09 (1H, td, J=13.2, 3.6 Hz), 1.97-2.00 (1H, m), 1.91 (1H, td, J=13.2, 3.6 Hz), 1.83-1.85 (1H, m), 1.42 (1H, qd, J=12.6, 3.6 Hz), 1.35 (2H, br s), 1.10 (1H, qd, J=12.6, 3.6 Hz); LCMS m/z 290.4011 ([M+H$^+$], $C_{21}H_{23}N$ requires 290.1903).

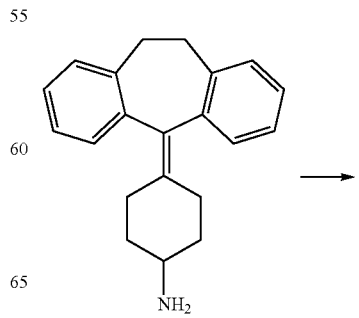

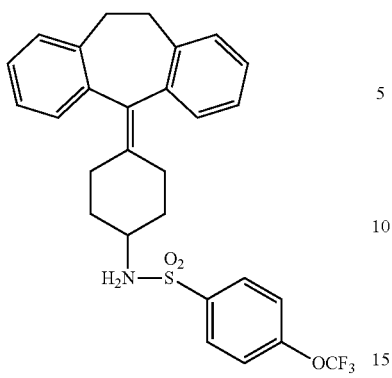

N-(4-(10,11-dihydro-5H-dibenzo[a,d][7]annulen-5-ylidene)cyclohexyl)-4-(trifluoromethoxy)benzenesulfonamide. A solution of 4-(10,11-dihydro-5H-dibenzo[a,d][7]annulen-5-ylidene)cyclohexanamine (0.0800 g, 0.276 mmol) in DMF (1.0 mL) was cooled to 0° C., treated with triethylamine (38.0 μL, 0.276 mmol), and 4-trifluoromethoxybenzenesulfonyl chloride (46.0 μL, 0.276 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound (0.113 g, 80%) as a white solid. $^1$H NMR (600 MHz, CDCl$_3$) δ (as a mixture of rotamers) [2H, 8.03 (dd, J=8.4, 1.8 Hz), 7.98 (dd, J=9.0, 2.4 Hz)], [2H, 7.35 (d, J=8.4 Hz), 7.34 (d, J=9.0, 2.4 Hz)], 7.14-7.16 (4H, m), 7.09 (2H, m), 7.04 (2H, t, J=7.8 Hz), [1H, 5.36 (t, J=7.2 Hz), 5.09 (t, J=9.0, 2.4 Hz)], 3.47 (1H, br s), 3.34-3.39 (2H, m), 2.81-2.85 (2H, m), 2.52-2.58 (2H, m), 2.08 (1H, t, J=12.4 Hz), 1.96 (1H, t, J=13.0 Hz), 1.85-1.91 (1H, m), 1.81 (1H, d, J=9.4 Hz), 1.55 (1H, q, J=11.0 Hz), 1.20 (1H, q, J=11.4 Hz); LCMS m/z 514.2000 ([M+H$^+$], C$_{28}$H$_{26}$F$_3$NO$_3$S requires 514.1658).

Example 80

Synthesis of N-(4-(10,11-dihydro-5H-dibenzo[a,d][7]annulen-5-ylidene)cyclohexyl)-4-chlorobenzenesulfonamide A solution of 4-(10,11-dihydro-5H-dibenzo[a,d][7]annulen-5-ylidene)cyclohexanamine (0.800 g, 0.276 mmol) in DMF (1.0 mL) was cooled to 0° C., treated with triethylamine (38 μL, 0.276 mmol), and 4-chlorobenzenesulfonyl chloride (0.0583 g, 0.276 mmol). The mixture was warmed to 25° C., and stirred for 2 h. The mixture was partitioned between saturated aqueous NaCl (50 mL), and CH$_2$Cl$_2$ (100 mL). The organic layer was washed with saturated aqueous NaCl (2×50 mL), dried (Na$_2$SO$_4$), and concentrated in vacuo. The residue was dissolved in a minimal amount of CH$_2$Cl$_2$ and purified by flash chromatography (SiO$_2$, 0-20% ethyl acetate-hexanes) to afford the title compound (0.104 g, 81%) as a white solid. $^1$H NMR (600 MHz, CDCl$_3$) δ (as a mixture of rotamers) [2H, 7.88 (dd, J=9.0, 1.8 Hz), 7.84 (dd, J=8.4, 1.8 Hz)], [2H, 7.50 (dd, J=9.0, 1.8), 7.47 (dd, J=8.4, 1.8 Hz), 7.11-7.14 (4H, m), 7.08-710 (2H, m), 7.02 (2H, t, J=7.2 Hz), [1H, 5.21 (d, J=7.2 Hz), 4.95 (d, J=7.8 Hz), 3.40-3.45 (1H, m), 3.34-3.39 (2H, m), 2.78-2.83 (2H, m), 2.50-2.56 (2H, m), 1.47 (1H, td, J=13.8, 4.2 Hz), 1.94 (1H, td, J=14.4, 3.6 Hz), 1.84-1.89 (1H, m), 1.77-1.80 (1H, m), 1.50 (1H, q, J=10.8 Hz), 1.16 (1H, qd, J=11.4, 3.6 Hz); LCMS m/z 464.1779 ([M+H$^+$], C$_{28}$H$_{26}$ClNO$_2$S requires 464.1446).

Example 81

Synthesis of 5-bromo-6-chloro-N-(3-(10,11-dihydro-5H-dibenzo[V]azepin-5-yl)propyl)pyridine-3-sulfonamide

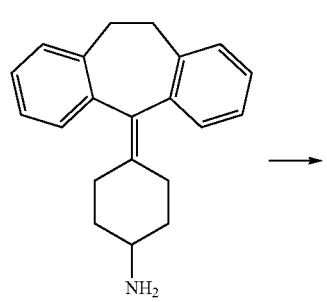

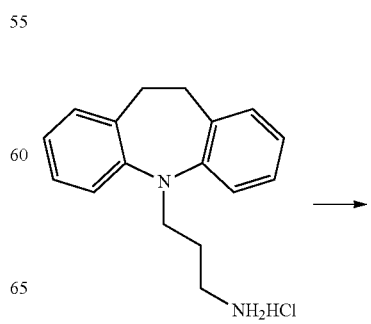

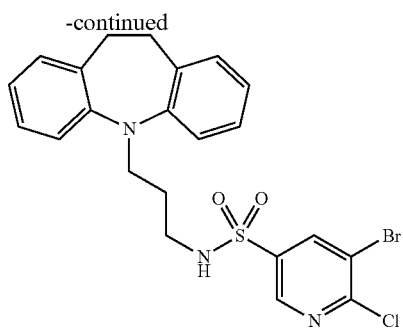

A solution of 3-(10,11-dihydro-5H-dibenzo[b,f]azepin-5-yl)propan-1-amine hydrochloride (0.075 g, 0.259 mmol) in DMF (0.85 mL) was cooled to 0° C., treated with Et$_3$N (0.076 mL, 0.544 mmol), and 5-bromo-6-chloropyridine-3-sulfonyl chloride (0.083 g, 0.285 mmol). The mixture was warmed to 25° C., and stirred for 2 h. The mixture was partitioned between water (50 mL) and CH$_2$Cl$_2$ (50 mL). The organic layer was washed with saturated aqueous NaCl (5×30 mL), dried (Na$_2$SO$_4$), and concentrated in vacuo. The residue was dissolved in a minimal amount of CH$_2$Cl$_2$ and purified by flash chromatography (SiO$_2$, 13-16% ethyl acetate-hexanes) to afford the title compound (0.042 g, 32%) as a white solid. $^1$H NMR (600 MHz, DMSO-d$_6$) δ 8.66 (1H, s), 8.40 (1H, s), 7.94 (1H, br s), 7.09-7.02 (6H, m), 6.89-6.87 (2H, m), 3.63 (2H, t, J=6.0 Hz), 2.99 (4H, br s), 2.86 (2H, J=6.6 Hz), 1.56 (2H, quintet, J=6.0 Hz); $^{13}$C NMR (150 MHz, DMSO-d$_6$) δ 153.6, 148.5, 146.4, 140.9, 137.7, 134.1, 130.3, 126.9, 123.1, 120.9, 120.3, 47.2, 41.0, 32.0, 27.8; LCMS m/z 508.0469 ([M+H$^+$], C$_{22}$H$_{24}$BrClN$_3$O$_2$S requires 508.0279).

Example 82

Synthesis of N-(5-(N-(3-(10,11-dihydro-5H-dibenzo[b,f]azepin-5-yl)propyl)sulfamoyl)-4-methylthiazol-2-yl)acetamide

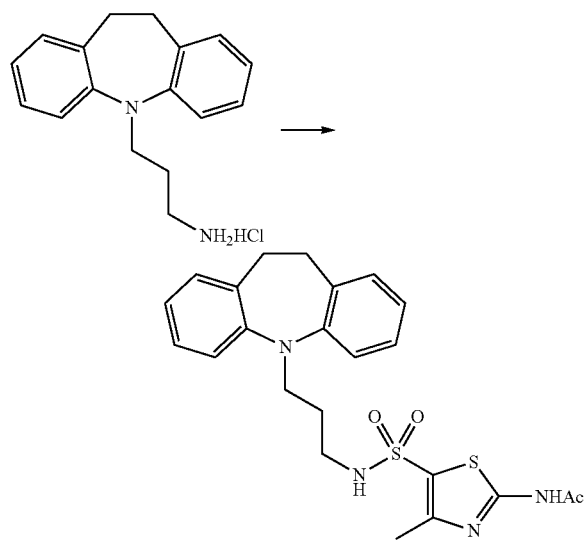

A solution of 3-(10,11-dihydro-5H-dibenzo[b]azepin-5-yl)propan-1-amine hydrochloride (0.075 g, 0.259 mmol) in DMF (0.85 mL) was cooled to 0° C., treated with Et$_3$N (0.144 mL, 1.03 mmol), and 2-acetamido-4-methylthiazole-5-sulfonyl chloride (0.073 g, 0.285 mmol). The mixture was warmed to 25° C. and stirred for 2 h. The mixture was partitioned between water (50 mL) and CH$_2$Cl$_2$ (50 mL). The organic layer was washed with saturated aqueous NaCl (5×30 mL), dried (Na$_2$SO$_4$), and concentrated in vacuo. The residue was dissolved in a minimal amount of CH$_2$Cl$_2$ and purified by flash chromatography (SiO$_2$, 2-5% ethyl acetate-hexanes) to afford the title compound (0.032 g, 26%) as a white solid. $^1$H NMR (600 MHz, CD$_3$OD) δ 7.10-7.01 (6H, m), 6.88-6.85 (2H, m), 3.71 (2H, t, J=6.6 Hz), 3.02 (3H, br s), 2.99 (2H, J=6.6 Hz), 2.36 (3H, s), 2.23 (3H, s), 1.71 (2H, quintet, J=6.6 Hz); $^{13}$C NMR (150 MHz, CD$_3$OD) δ 169.8, 159.2, 151.7, 148.2, 134.2, 129.5, 126.1, 12.4, 119.6, 119.5, 46.9, 40.5, 31.9, 27.2, 21.2, 15.0; LCMS m/z 471.2135 ([M+H$^+$], C$_{23}$H$_{27}$N$_4$O$_3$S$_2$ requires 471.1519).

The following additional compounds were made by methods analogous to those described above and were tested in the screens that follow:

Example 83

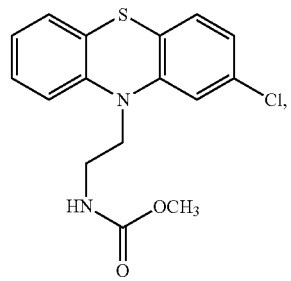

Example 84

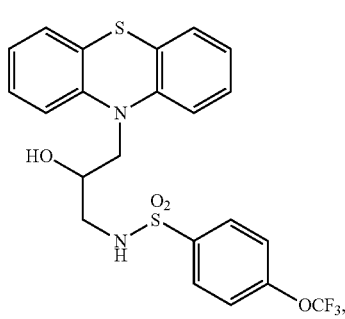

Example 85

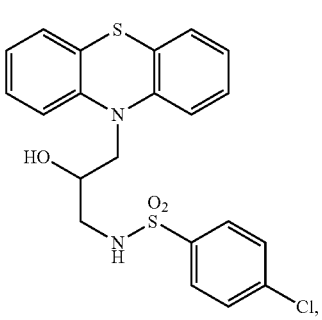

-continued

Example 86
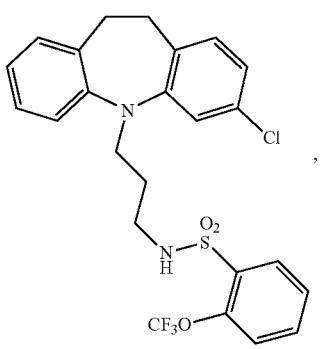

Example 87
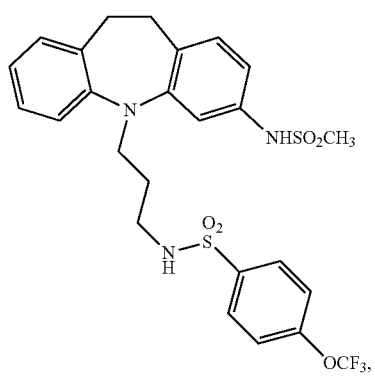

Example 88
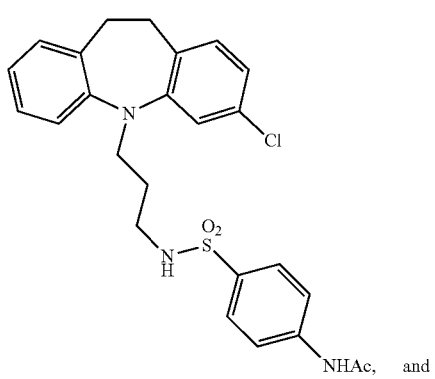

Example 89
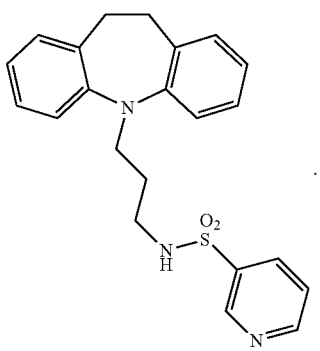

Cell Viability Assays (IC$_{50}$ Determination)

Cell viability assays were performed according to Denizot, F. and R. Lang, Journal of Immunological Methods, 1986. 89(22): p. 271-277. H1650 lung cancer cells were plated at 150,000 cells per well in a 12 well plate. Twenty-four hours after plating, cells were treated as described with increasing concentrations of drug and control. Forty-eight hours after drug treatment, cells were treated with 100 μL of 3-(4,5-Dimethylthiazol-2-yl)-2,5-diphenyltetrazolium bromide (MTT) and incubated for 2 hours at 37 C. The MTT solution was subsequently replaced with 300 μL of n-propyl alcohol and re-aliquoted to a 96 well plates. Spectrophotometric analysis of each solution was performed using a 96 well plate reader at 600 nm in triplicate. Results are shown in Table 1:

TABLE 1

Cell Viability Data

| Example # | IC$_{50}$ (μM) |
|---|---|
| 3 | 20 |
| 4 | 10 |
| 8 | 20 |
| 9 | 30 |
| 10 | 20 |
| 11 | INACTIVE |
| 13 | 18 μM |
| 14 | 40 μM |
| 15 | 20 μM |
| 17 | >50 |
| 19 | 24.4 μM |
| 20 | >40 μM |
| 21 | 15.3 μM |
| 22 | 11.1 μM |
| 23 | ~25 μM |
| 24 | 15.1 μM |
| 25 | <40 μM |
| 26 | >40 μM |
| 27 | 20 μM |
| 28 | INACTIVE |
| 29 | ~25 μM |
| 30 | 12.6 μM |
| 33 | ~20 μM |
| 34 | ~20 μM |
| 35 | ~20 μM |
| 36 | ~15 μM |
| 37 | ~25 μM |
| 38 | ~10 μM |
| 39 | ~10 μM |
| 40 | ~15 μM |
| 41 | ~25 μM |
| 42 | ~25 μM |
| 43 | ~35 |
| 44 | ~30 |
| 45 | ~25 μM |
| 46 | ~30 μM |
| 47 | ~30 μM |
| 50 | ~15 μM |
| 51 | ~20 μM |
| 52 | ~10 μM |
| 53 | ~10 μM |
| 54 | ~15 μM |
| 55 | ~25 μM |
| 56 | ~25 μM |
| 57 | ~10 μM |
| 58 | ~5 μM |
| 59 | ~25 μM |
| 60 | ~15 μM |
| 61 | ~20 μM |
| 62 | ~25 μM |
| 63 | 65% @ 20 μM |
| 64 | ~35 μM |
| 65 | ~15 μM |
| 66 | N/A |
| 67 | ~20 μM |
| 68 | ~20 μM |
| 69 | ~20 μM |
| 70 | ~20 μM |
| 71 | 25 |
| 72 | 20 |
| 73 trans | 15 |
| 73 cis | 5 |
| 74 | ~15 μM |
| 75 | ~15 μM |
| 75 | ~15 μM |
| 76 | 20 |

TABLE 1-continued

Cell Viability Data

| Example # | IC$_{50}$ (µM) |
|---|---|
| 77 | 15 |
| 78 | 15 |
| 79 | ~20 |
| 80 | ~20 |
| 81 | INACTIVE |
| 82 | INACTIVE |
| 83 | INACTIVE |
| 84 | ~25 µM |
| 85 | ~15 µM |
| 86 | INACTIVE |
| 87 | ~15 µM |
| 88 | ~20 µM |
| 89 | 50% @ 40 µM |

Colony Formation Assay

Protocol for clonogenic assay follows Sangodkar et al. J Clin Invest 2012; 122:2637-51.

Cell culture and staining: For both A549luc and H292 cells, 500 cells were seeded into each well of a 6-well plate and allowed to attach for 24 hours before drug treatment. The following day, cells were treated with either the appropriate dose of drug or an equivalent volume of DMSO (two replicates were treated for each condition). For each condition, depleted media was replaced with fresh media containing the equivalent drug dose four days after initial treatment. Cells were harvested either 7 (A549luc) or 8 (H292) days after initial treatment. Briefly, media was aspirated from each well and the cells were washed twice with ice-cold PBS, then plates were allowed to dry at room temperature for 4 hours. Cells were fixed for one hour in a fixing solution consisting of 10% methanol and 10% glacial acetic acid in distilled water, then stained overnight in 1% (w/v) crystal violet dissolved in methanol. The next day, staining solution was aspirated from the wells and plates were washed gently with distilled water to remove excess stain before colony counting. Colonies were imaged on a ChemiDoc XRS+ (Bio-Rad) and images were exported as 8-bit TIFF files. Colonies were counted using the Colony Counter plugin in ImageJ, with colony size defined as between 4 and 400 square pixels, and minimum circularity set at 0.6. Duplicate wells were averaged to obtain a single value for each condition. Results (number of colonies) for A549luc cells are shown in Table 2 and results (number of colonies) for H292 cells are shown in Table 3:

TABLE 2

| Example # | 5 µM | 7.5 µM | 10 µM |
|---|---|---|---|
| DMSO blank | 146 | 159 | 161.5 |
| 30 | 116 | 111.5 | 67.5 |
| 60 | 126.5 | 118.5 | 56 |
| 74 | 135.5 | 118.5 | 96 |
| 75 | 133.5 | 105 | 63.5 |
| 73 | 2 | 0 | 0 |

TABLE 3

| Example # | 5 µM | 7.5 µM | 10 µM |
|---|---|---|---|
| DMSO blank | 111 | 108 | 120 |
| 30 | 95 | 74.5 | 61 |
| 60 | 107 | 105 | 42 |
| 74 | 85.5 | 65.5 | 46.5 |

TABLE 3-continued

| Example # | 5 µM | 7.5 µM | 10 µM |
|---|---|---|---|
| 75 | 109.5 | 80 | 47 |
| 73 | 40.5 | 16.5 | 7 |

In Vivo Cancer Model

The in vivo lung cancer model is described in Politi et al., Genes Dev. Jun. 1, 2006 20: 1496-1510. EGFR-L858R/CCSP mice were fed doxycycline-impregnanted food pellets to induce tumor formation. After 8-12 weeks, mice were imaged in a Bruker 4.7T Biospec scanner to confirm lung nodule development. After tumor confirmation, the compound of Example 30 was prepared in DMSO (Sigma) and administered i.p. at 100 mg/kg every other day for two weeks. After treatment, the mice were re-imaged by MRI, and pre-treatment and post-treatment lung volumes were calculated by visible lung opacity present in each axial image using Osirix 4.1.1. DMSO control animals show a 20% increase in tumor volume over two week treatment period. Animals treated with the compound of Example 30 show a 60% decrease in tumor volume over two week treatment period.

As mentioned above, CD4+ Foxp3+ regulatory T cells (Tregs) are required for self-tolerance and are essential for induction of allograft tolerance in animals. Immunosuppressive medications required for treating autoimmunity and preventing transplant rejection, including calcineurin inhibitors, nonspecifically inhibit all T cells including Treg. Such pharmacological inhibition of Treg prevents, rather than promotes, allograft tolerance, subjecting the individual to the toxicities of long term immunosuppression, including an increased risk of developing malignancy because anti-tumor immune surveillance is blocked. Thus, immunosuppressants capable of facilitating Treg induction and function, and simultaneously preventing malignancy could be transformative in the care of patients with immune mediated diseases, including transplant rejection.

Example 30 has been tested for its ability to induce Treg from naïve CD4 T cells. These experiments revealed that Example 30 facilitated upregulation of Foxp3 in naïve polyclonal treated with TGFβ and TCR transgenic T cells stimulated in vivo during costimulatory blockade, and the induced Tregs functionally suppressed alloreactive T cells in a suppression assay. Fifty thousand CD4 naïve cells (CD62Lhi, CD25 low, CD4 positive) were incubated with 2 ng/mL TGFβ, 1 ug/mL anti-CD3, 100 ng/mL IL-2, 50000 APCs per well and the compounds 10 µM, 5 µM and 2.5 µM concentrations. The cells were incubated for 3 days and then stained for CD4 and Foxp3 expression. Results were expressed as fold increase over the % induced in control (DMSO) wells (typically 20-25% Foxp3+). AKTi, a small molecule AKT inhibitor, was used as a positive control; it induced about a 4-fold increase. Haloperidol was used as a specificity control; it did not induce a statistically significant increase. Example 30 exhibited a greater than 2 fold increase in iTreg at 2.5 µM. Example 27 exhibited a 2 fold increase in iTreg at 5 µM. The effects of Example 30 on iTreg induction are amplified as the TGFβ concentration decreases. Results of suppression assays using iTreg induced with or without Example 30 demonstrate equivalent suppressive capacity, presented as % inhibition of maximal proliferation induced in the absence of Treg.

To test for a clinically relevant in vivo effect, BALB/c hearts were transplanted into fully allogeneic B6 recipients. While untreated animals rejected their grafts by day 8 n=4,

The invention claimed is:
1. A compound of formula (I):

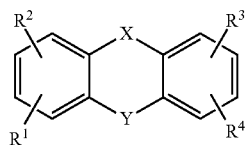

wherein:
X is selected from the group consisting of: —(CH$_2$—CH$_2$)—, and —CH=CH—;
Y is

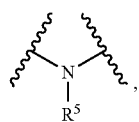

$R^1$, $R^2$, $R^3$, and $R^4$ are independently selected from the group consisting of: H, halo, —N$_3$, —NR$^6$R$^7$, (C$_1$-C$_6$)alkyl, (C$_1$-C$_6$)haloalkyl, —OR$^6$, —C(O)R$^6$, —OC(O)R$^6$, —C(O)NR$^6$R$^7$, —C(O)OR$^6$, —SR$^6$, —SO$_2$R$^6$, and —SO$_2$NR$^6$R$^7$;
$R^5$ is —(CR$^{15}$R$^{16}$)$_p$-Q$_q$-(CR$^{15}$R$^{16}$)$_{n-p}$—Z or

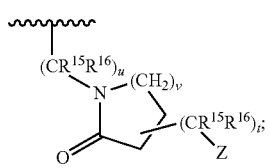

Q is chosen from —O—, —NR$^{14}$— and

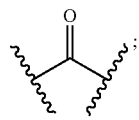

each $R^6$ and $R^7$ is independently selected from the group consisting of: H and (C$_1$-C$_6$)alkyl;
$R^{14}$ is H or (C$_1$-C$_3$)alkyl;
$R^{15}$ and $R^{16}$, in each occurrence are chosen independently from H, OH, cyano, amino, (C$_1$-C$_3$)alkylamino, (C$_1$-C$_3$)dialkylamino, (C$_1$-C$_3$)alkyl, (C$_1$-C$_3$)haloalkyl, (C$_1$-C$_3$)haloalkoxy, and (C$_1$-C$_3$)alkoxy, or, taken together, two of $R^{14}$, $R^{15}$ and $R^{16}$ may form a three to seven membered non-aromatic carbocycle or heterocycle wherein said three to seven membered carbocycle or heterocycle may be additionally substituted with one or two substituents chosen from OH, F, cyano, amino, (C$_1$-C$_3$)alkylamino, (C$_1$-C$_3$)dialkylamino, (C$_1$-C$_3$)alkyl, (C$_1$-C$_3$)haloalkyl, (C$_1$-C$_3$)haloalkoxy, and (C$_1$-C$_3$)alkoxy;
n is an integer from 2 to 4;
p is zero, 1 or 2;
q is zero or 1;
t is zero, 1 or 2;
u is 2;
v is 1, 2 or 3;
with the proviso that when q is zero and $R^{15}$ and $R^{16}$, in all of their occurrences are H, n is not 4;
Z is selected from the group consisting of: —NHSO$_2$R$^{17}$, —NHC(O)NR$^8$R$^9$, —S(O)$_2$NR$^8$R$^9$, substituted or unsubstituted cyclic carbamate; substituted or unsubstituted cyclic urea, cyanoguanidine;
$R^8$ and $R^9$ are independently selected from H, substituted or unsubstituted (C$_1$-C$_6$)alkyl, and substituted or unsubstituted (C$_3$-C$_7$) cycloalkyl; and
$R^{17}$ is chosen from phenyl and monocyclic heteroaryl, said phenyl and monocyclic heteroaryl optionally substituted with one or two substituents chosen from OH, halogen, cyano, nitro, (C$_1$-C$_3$)alkylamino, (C$_1$-C$_3$)dialkylamino, (C$_1$-C$_3$)acylamino, (C$_1$-C$_3$)alkylsulfonyl, (C$_1$-C$_3$)alkylthio, (C$_1$-C$_3$)alkyl, (C$_1$-C$_3$)haloalkyl, (C$_1$-C$_3$)haloalkoxy, and (C$_1$-C$_3$)alkoxy.

2. A compound according to claim 1, wherein Z is selected from the group consisting of: —NHSO$_2$R$^{17}$ and —NHC(O)NR$^8$R$^9$.

3. A compound according to claim 2 wherein Z is —NHSO$_2$R$^{17}$.

4. A compound according to claim 3 of formula:

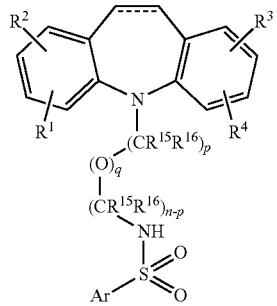

wherein Ar is a substituted or unsubstituted phenyl, thienyl, furanyl or pyrrolyl, and the dotted line represents an optional double bond.

5. A compound according to claim 4 wherein p and q are both zero, $R^{15}$ is H and $R^{16}$ is chosen from H and OH.

6. A compound according to claim 5 of formula (ID) or (ID'):

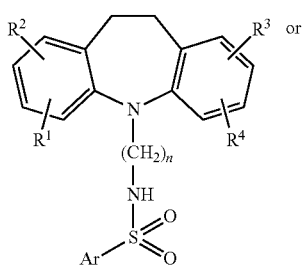

-continued

ID'

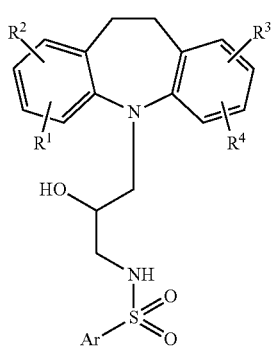

wherein:
R[1] and R[3] are independently selected from the group consisting of: H and halo; and
R[2] and R[4] are H.

7. A compound according to claim 6 wherein Ar is phenyl or thienyl, optionally substituted with one or two substituents chosen from $(C_1$-$C_3)$alkyl, halogen, cyano, nitro, $(C_1$-$C_3)$haloalkyl, $(C_1$-$C_3)$alkylsulfonyl, $(C_1$-$C_3)$haloalkoxy, and acetylamino.

8. A compound according to claim 4 wherein two R[15] or R[16] taken together form a three to seven membered non-aromatic carbocycle or heterocycle B, wherein said three to seven membered carbocycle or heterocycle B may be additionally substituted with one or two substituents chosen from OH, F, cyano, amino, $(C_1$-$C_3)$alkylamino, $(C_1$-$C_3)$dialkylamino, $(C_1$-$C_3)$alkyl, $(C_1$-$C_3)$haloalkyl, $(C_1$-$C_3)$haloalkoxy, and $(C_1$-$C_3)$alkoxy, said compound being of formula:

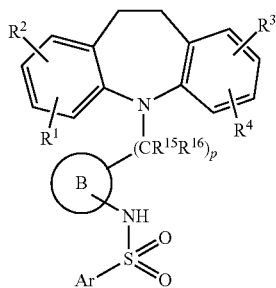

wherein
p is zero, 1 or 2; and
Ar is a substituted or unsubstituted phenyl, thienyl, furanyl or pyrrolyl.

9. A compound according to claim 8 wherein
(a) B is a five-membered ring of formula:

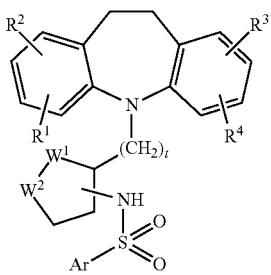

wherein:
W[1] and W[2] are both —CH$_2$—; or
one of W[1] and W[2] is —O— and the other is —CH$_2$—; or
one of W[1] and W[2] is —CH(OH)— and the other is —CH$_2$—; or
(b) B is a six-membered ring of formula:

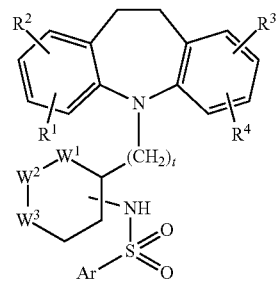

wherein:
all of W[1] W[2] and W[3] are —CH$_2$—; or
one of W[1] W[2] and W[3] is —O— and the other two are —CH$_2$—; or
one of W[1] W[2] and W[3] is —CH(OH)— and the other two are —CH$_2$—.

10. A compound according to claim 4 wherein two R[15] or R[16] taken together form a three to seven membered non-aromatic carbocycle or heterocycle B, wherein said three to seven membered carbocycle or heterocycle B may be additionally substituted with one or two substituents chosen from OH, F, cyano, amino, $(C_1$-$C_3)$alkylamino, $(C_1$-$C_3)$dialkylamino, $(C_1$-$C_3)$alkyl, $(C_1$-$C_3)$haloalkyl, $(C_1$-$C_3)$haloalkoxy, and $(C_1$-$C_3)$alkoxy, said compound being of formula:

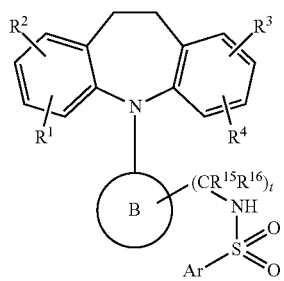

wherein
k is zero, 1 or 2; and
Ar is a substituted or unsubstituted phenyl, thienyl, furanyl or pyrrolyl.

11. A compound according to claim 10 wherein
(a) B is a five-membered ring of formula:

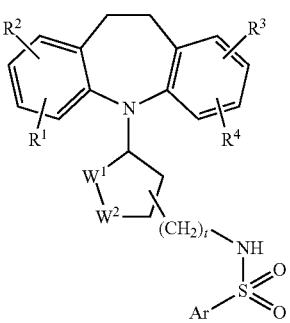

wherein:
W¹ and W² are both —CH₂—; or
one of W¹ and W² is —O— and the other is —CH₂—; or
one of W¹ and W² is —CH(OH)— and the other is —CH₂—; or
(b) B is a six-membered ring of formula:

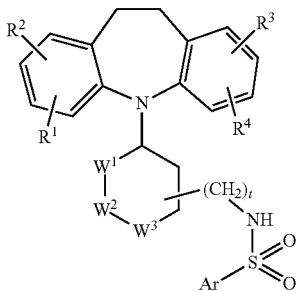

wherein:
all of W¹ W² and W³ are —CH₂—; or
one of W¹ W² and W³ is —O— and the other two are —CH₂—; or
one of W¹ W² and W³ is —CH(OH)— and the other two are —CH₂—.

12. A compound according to claim 9 wherein p is zero.

13. A compound according to claim 4 wherein Ar is phenyl or thienyl, optionally substituted with one or two substituents chosen from methyl, halogen, cyano, nitro, trifluoromethyl, methyl sulfonyl, trifluoromethoxy, and acetyl amino.

14. A compound according to claim 13 wherein said one or two substituents are located at positions that are not adjacent to the point of attachment of Ar to the sulfonamide.

15. A compound according to claim 4 wherein
Ar is phenyl, optionally substituted at the 3, 4 or 5 positions with one or two substituents chosen from methyl, halogen, cyano, trifluoromethyl and trifluoromethoxy;
R¹ and R³ are independently selected from the group consisting of H and halo; and
R² and R⁴ are H.

16. A compound according to claim 2 wherein Z is —NHC(O)NR⁸R⁹.

17. A compound according to claim 16 of formula (1C):

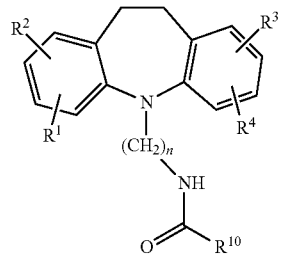

wherein:
R² and R⁴ are H;
R¹⁰ is NHR¹¹;
R¹¹ is selected from the group consisting of: substituted or unsubstituted (C₁-C₆)alkyl, and substituted or unsubstituted (C₃-C₇) cycloalkyl.

18. A compound according to claim 17 wherein is (C₁-C₆)alkyl.

19. A method for the treatment of a disease chosen from:
(a) lung tumors;
(b) solid organ transplant rejection; and
(c) graft vs host disease,
comprising administering to a patient in need of such treatment a therapeutically effective amount of a compound according to claim 1.

20. A pharmaceutical composition comprising a pharmaceutically acceptable carrier and a compound according to claim 1.

* * * * *

UNITED STATES PATENT AND TRADEMARK OFFICE
CERTIFICATE OF CORRECTION

PATENT NO. : 9,540,358 B2
APPLICATION NO. : 14/238511
DATED : January 10, 2017
INVENTOR(S) : Ohlmeyer et al.

Page 1 of 2

It is certified that error appears in the above-identified patent and that said Letters Patent is hereby corrected as shown below:

Column 135, Line 55: Claim 9,

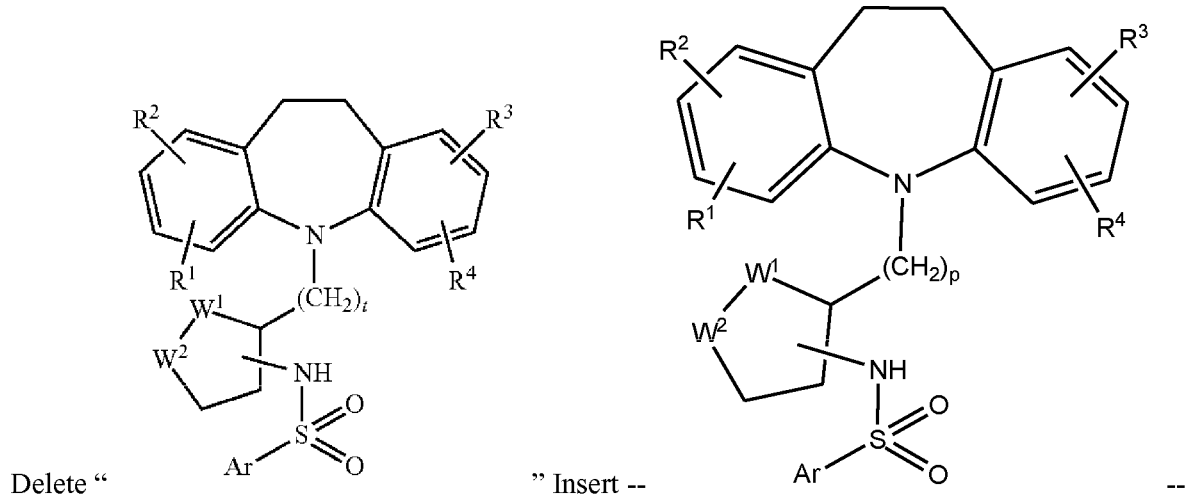

Delete "                            " Insert --                            --

Column 136, Line 10: Claim 9,

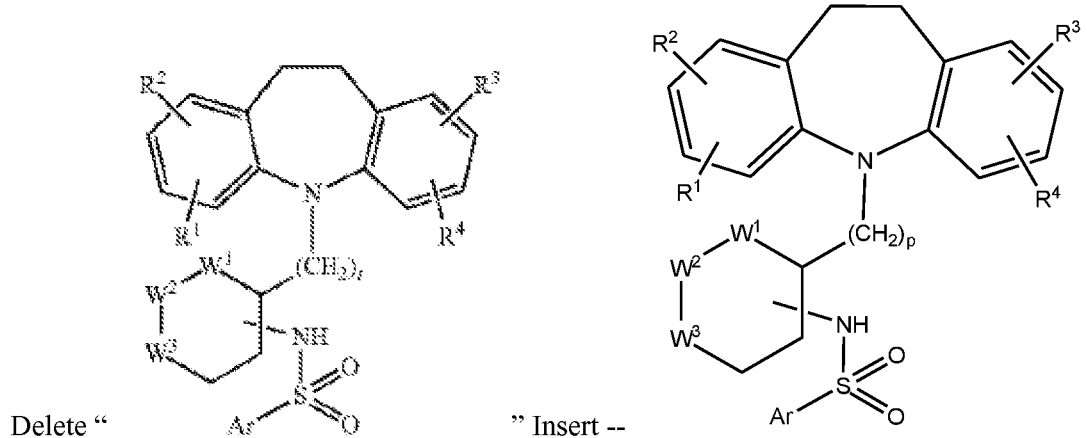

Delete "                            " Insert --                            --

Signed and Sealed this
Fourteenth Day of March, 2017

Michelle K. Lee
*Director of the United States Patent and Trademark Office*

CERTIFICATE OF CORRECTION (continued)
U.S. Pat. No. 9,540,358 B2

Column 136, Line 35: Claim 10,

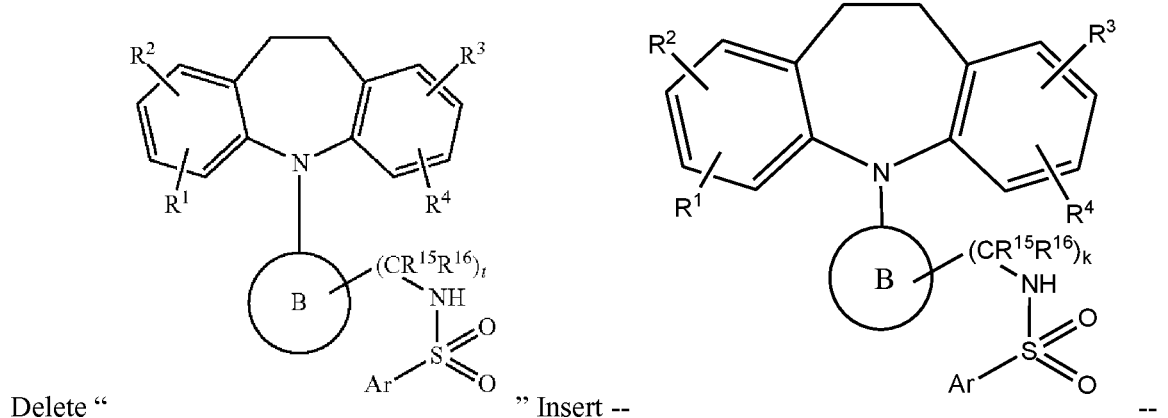

Delete " " Insert -- --

Column 136, Line 55: Claim 11,

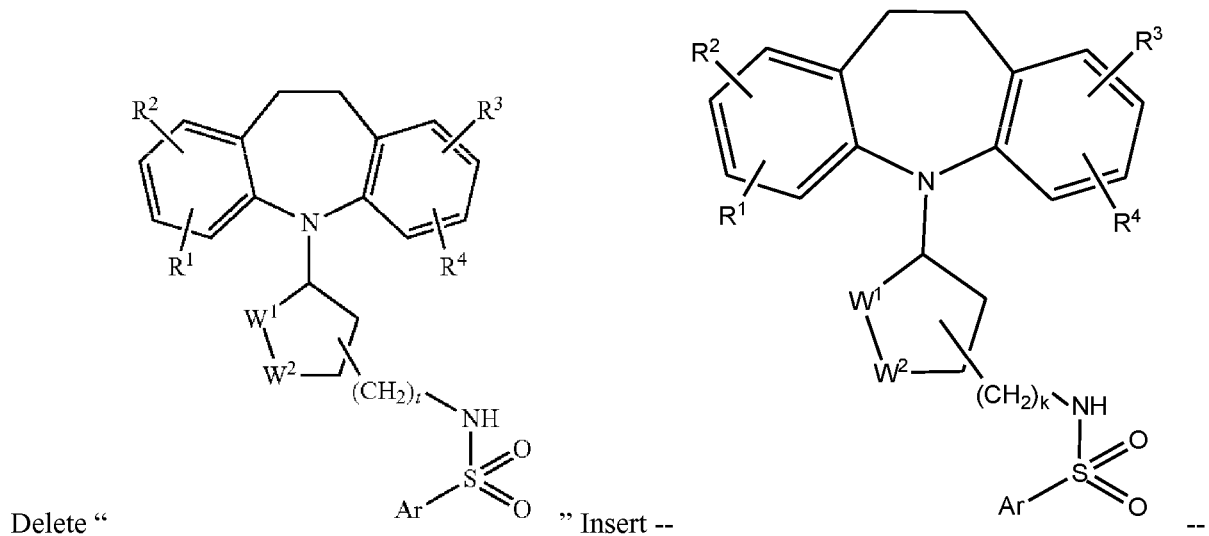

Delete " " Insert -- --

Column 137, Line 10: Claim 11,

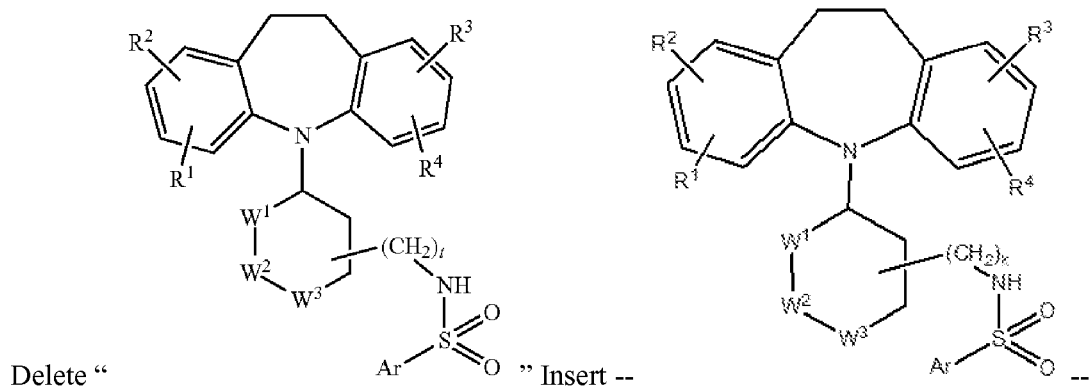

Delete " " Insert -- --

Column 137, Line 31: Claim 13, Delete "methyl sulfonyl" and insert -- methylsulfonyl --

Column 137, Line 32: Claim 13, Delete "acetyl amino" and insert -- acetylamino --